(12) United States Patent
Marsais et al.

(10) Patent No.: US 9,376,387 B2
(45) Date of Patent: Jun. 28, 2016

(54) OXIDISABLE PYRIDINE DERIVATIVES, THEIR PREPARATION AND USE AS ANTI-ALZHEIMER AGENTS

(71) Applicants: INSA (INSTITUT NATIONAL DES SCIENCES APPLIQUEES) DE ROUEN, Saint Etienne du Rouvray (FR); CENTRE NATIONAL DE LA RECHERCHE SCIENTIFIQUE (CNRS), Paris (FR); UNIVERSITE DE ROUEN, Mont Saint Aignan (FR); VFP THERAPIES, Rouen (FR)

(72) Inventors: Francis Marsais, Rouen (FR); Vincent Levacher, Fontaine sous Preaux (FR); Cyril Papamicael, Bois Guillaume (FR); Pierre Bohn, Rouen (FR); Ludovic Peauger, Rouen (FR); Vincent Gembus, Rouen (FR); Nicolas Le Fur, Lille (FR); Marie-Laurence Dumartin-Lepine, Rouen (FR)

(*) Notice: Subject to any disclaimer, the term of this patent is extended or adjusted under 35 U.S.C. 154(b) by 0 days.

(21) Appl. No.: 14/763,222

(22) PCT Filed: Jan. 24, 2014

(86) PCT No.: PCT/EP2014/051392
§ 371 (c)(1),
(2) Date: Jul. 24, 2015

(87) PCT Pub. No.: WO2014/114742
PCT Pub. Date: Jul. 31, 2014

(65) Prior Publication Data
US 2015/0353493 A1 Dec. 10, 2015

(30) Foreign Application Priority Data
Jan. 25, 2013 (EP) .................................. 13305088

(51) Int. Cl.
| | | |
|---|---|---|
| C07D 211/84 | (2006.01) |
| C07D 213/61 | (2006.01) |
| C07D 401/06 | (2006.01) |
| C07D 405/06 | (2006.01) |
| C07D 213/50 | (2006.01) |
| C07D 213/56 | (2006.01) |
| C07D 213/80 | (2006.01) |
| C07D 213/803 | (2006.01) |
| C07D 213/71 | (2006.01) |
| C07D 213/70 | (2006.01) |
| C07D 213/57 | (2006.01) |
| C07D 213/82 | (2006.01) |
| C07D 213/85 | (2006.01) |
| C07D 211/82 | (2006.01) |
| C07D 211/90 | (2006.01) |

(52) U.S. Cl.
CPC ............ *C07D 213/50* (2013.01); *C07D 211/82* (2013.01); *C07D 211/84* (2013.01); *C07D 211/90* (2013.01); *C07D 213/56* (2013.01); *C07D 213/57* (2013.01); *C07D 213/61* (2013.01); *C07D 213/70* (2013.01); *C07D 213/71* (2013.01); *C07D 213/80* (2013.01); *C07D 213/803* (2013.01); *C07D 213/82* (2013.01); *C07D 213/85* (2013.01); *C07D 401/06* (2013.01); *C07D 405/06* (2013.01)

(58) Field of Classification Search
None
See application file for complete search history.

(56) References Cited

FOREIGN PATENT DOCUMENTS

| | | |
|---|---|---|
| EP | 0296560 A2 | 12/1988 |
| WO | 9708146 A1 | 3/1997 |
| WO | 9836749 A1 | 8/1998 |
| WO | 9936405 A1 | 7/1999 |
| WO | 2006103120 A2 | 10/2006 |

OTHER PUBLICATIONS

Hur et al, Chemistry & Biology (2010), 17(5), pp. 537-547.*
European Patent Office—PCT International Search Report regarding corresponding PCT Application No. PCT/EP2014/051392 issued Mar. 13, 2014, pp. 1-4.
Rongyuan Xie et al., "Selective A3 Adenosine Receptor Antagonists: Water-Soluble3, 5-Diacyl-1,2,4-Trialkylpyridinium Salts and Their Oxidative Generation From Dihydropyridine Precursors," Journal of Medicinal Chemistry, vol. 42, No. 20, 1999, pp. 4232-4238, XP000877112.

* cited by examiner

*Primary Examiner* — Zinna Northington Davis
(74) *Attorney, Agent, or Firm* — Duane Morris LLP

(57) ABSTRACT

A compound of formula (I) in which the dotted lines indicate the presence of at least one double bond; n=0 to 4; $R_3$ and $R_4$ are H, or when n=1, $R_3$ and $R_4$ can also form together a double bond between the carbon atoms, and m=0, 1 or 2, Z is CH or N or Z is C and —$CHR_3$— is =CH— linked by the double bond to cyclopentanone; or –(–)$_m$- is absent, and Z is NH, >N-alkyl, >N-phenyl, >N-benzyl or >N heteroaryl; $R_8$ is alkyl, aryl or heteroaryl which can be optionally substituted; EWG represents an electron withdrawing group selected from the group comprising COOR, COSR, CONRR', CN, COR, $CF_3$, SOR, $SO_2R$, SONRR', $SO_2NRR'$, $NO_2$, halogen, heteroaryl; and the pharmaceutical salts and stereisomers thereof. The compounds of formula (I) are potent in the treatment of neurodegenerative diseases such as Alzheimer's disease.

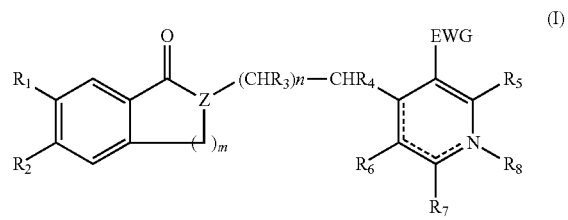

25 Claims, No Drawings

OXIDISABLE PYRIDINE DERIVATIVES, THEIR PREPARATION AND USE AS ANTI-ALZHEIMER AGENTS

CROSS-REFERENCE TO RELATED APPLICATIONS

The present application is a U.S. national phase application filed under 35 U.S.C. §371 of International Application No. PCT/EP2014/051392, which was filed Jan. 24, 2011 and which claims priority to European Application No. 13305088.0 filed on Jan. 25, 2013, both of which are incorporated herein by reference in their entirety.

FIELD OF THE INVENTION

The invention relates to oxidisable pyridine derivatives which are useful in the treatment of neurodegenerative diseases such as Alzheimer disease. The present invention thus relates to these compounds per se, their preparation, pharmaceutical compositions comprising them as well as their use as a medicament, i.e. for the treatment of neurodegenerative diseases.

BACKGROUND OF THE INVENTION

The present invention relates to the prevention, treatment and amelioration of neurodegenerative or Alzheimer's disease, and more particularly to the prevention, treatment and amelioration of Alzheimer's disease with new donepezil like compounds which act as inhibitors of central cholinesterase enzyme following the indirect cholinomimetic pathway.

Alzheimer's disease (AD) is a progressive and neurodegenerative disease in the brain characterized by abnormal clumps and tangled bundles of fibers composed of misplaced proteins. Age is the most important factor for AD since the number of people afflicted with the disease doubles every 5 years in those over 65 years old. Symptoms of AD include memory loss, language deterioration and impaired ability to memory loss, language deterioration, and impaired ability to mentally manipulate visual information, poor judgment, confusion, restlessness, and mood swings. Eventually AD destroys cognition, personality, and the ability to function. The early symptoms of AD, which include forgetfulness and loss of concentration, are often missed because they resemble natural signs of aging.

Acetylcholine is involved in sending many types of messages throughout the brain, including those involving memory and learning. It carries a message once released into the synapse of a neuron towards a specific sites located on the next neuron. This message is sent until another enzyme (acetylcholinesterase, AChE) enters the synapse to break down acetylcholine. Damages to the cholinergic system in the brain, i.e. a decrease in the choline acetyltransferase activity, has been suggested to play a role in the memory losses that are associated with AD. Therefore, it has been established that the inhibition of AChE allows preventing a too early break down of the few amount of acetylcholine that is still formed in the patients afflicted with AD.

The patent application WO 97/08146 discloses a series of carbamates based on the structure of pyridostigmine as potential drugs for the treatment of cognitive impairments associated with cholinergic perturbances such as in AD. However the document is directed to compounds which differ from that of the present invention and have the drawback of being unstable and of being rapidly deactivated.

Similarly, Wuest et al (JACS Vol. 73, 1951 pp 1210-1216) discloses positively charged pyridine carbamates; Wang et al. (Nuclear Medicine and Biology 31 (2004)), discloses pyridostigmine, edrophonium and neostigmine agents as AChE. However none of the reported compounds have the same structure as the compounds of the instant invention and these are deprived of the withdrawing electron group attached to the ring.

In fact there are only few acetylcholinesterase inhibitors (AChEi) that have been useful in the treatment of neurodegenerative diseases. For example, donepezil, tacrine, rivastigmine and galantamine are indicated. Donepezil, also known as 1-benzyl-4-(5,6-dimethoxy-1-oxoindan-2-ylmethyl)piperidine, is disclosed in the European patent EP 296 560. EP 296 560 describes 1,4-substituted piperidines and several structures derived from indanyl or indanonyl among others, and linked to the piperidine through a organic group X having lots of significations, including carbamoyl groups, carbamates, esters. Said compounds are active against CNS diseases. However, nowhere are described compounds having an unsaturated nitrogen containing-heterocycle such as pyridine or dihydropyridine.

However, the manifestation of peripheral activity in the course of the treatment causes serious adverse effects on peripheral organs, which limits the therapeutic potential of these cholinesterase inhibitors. In addition, it is known that these drugs loose their therapeutical efficacy with time which requires increased daily dosages with the associated side effects.

There is thus a need for new cholinesterase inhibitors agent which could act against neurodegenerative diseases having a higher affinity for inhibiting central AChE instead of peripheral AChE. These agents should also be able to cross the Blood Brain Barrier (BBB) which protects the brain from harmful substances in the blood stream, while at the same time supplying the brain with the required nutrients for proper function. The BBB strictly limits passages to the brain through both physical and metabolic barriers and is often the rate limiting factor in determining permeation of therapeutic drugs into the brain.

Patent application WO 2006/103120 provides prodrugs which appeared to be particularly efficient in the treatment of neurodegenerative diseases. In their oxidizable and non protonable (neutral nitrogen) forms, the prodrugs are deprived of activity against central or peripheral acetylcholinesterase but have the ability to easily pass through the blood brain barrier into the central nervous system (CNS) where they become active upon oxidation. These prodrugs have the further advantage of being entrapped into the CNS once in their oxidized form, which avoids any side effect into the peripherical nervous system (PNS). After having completed their anticholinesterase activity, the molecules are inactivated and degraded in situ, which allows their degradation. Nevertheless, the document focuses on carbamate prodrugs and thus differs from the compounds of the instant invention.

The patent application WO 99/36405 discloses quaternary salts of donepezil derivatives which are however different from the compounds within the scope of the invention since they do not comprise an electronic withdrawing group on the pyridine moiety. In addition, this application is concerned with the use of quaternary salts as intermediate materials in the synthesis of donezepil to afford improved yields rather than on their therapeutical use.

SUMMARY OF THE INVENTION

It has now been discovered that donepezil like drugs could be afforded into a prodrug form which travels efficiently through the blood brain barrier. Once into the brain, the prodrug form can be easily transformed (through an oxidative activation step) into amore active compound (at least 10-fold more active than the prodrug form). Thus, these new AChE inhibitors are expected to display less peripheral side effects. This improves their therapeutical efficiency and patient compliance.

Furthermore, not only did the prodrugs of the instant invention exhibit improved travelling into the brain, but they also exhibited a substantial improved stability and efficacy over the marketed drug and the existing prodrugs that could not have been envisaged from the prior art documents.

In contrast to compounds presented in WO 2006/103120 which act mainly at the esterasic site by carbamylation of the enzyme, compounds of the instant invention act at both the midgorge and more importantly at the peripheral active site (PAS) which has been identified as playing a key role in the pathological process of the β-amyloid peptide aggregation. Thus, compounds of the present invention may not only restore the cholinergic balance but may also prevent the β-amyloid peptide aggregation.

DETAILED DESCRIPTION OF THE INVENTION

An object of the invention is a pyridine derivative which should be considered as a prodrug when it is in its oxidisable and non protonable or neutral nitrogen form. This prodrug per se has no activity against central or peripheral acetylcholinesterase, because the oxidisable nitrogen atom is non protonable at physiological pH.

Oxidation of the prodrugs in CNS, induce the recognition by CNS receptors and the central activity, therefore inducing enhanced bioavailability. As a consequence the prodrugs can be administered in lower dose, inducing less side effects, and they can be easier to formulate into solid dosage forms and thus facilitate their administration to the patients in need thereof.

The pyridine derivatives of the invention are represented by the following formula (I):

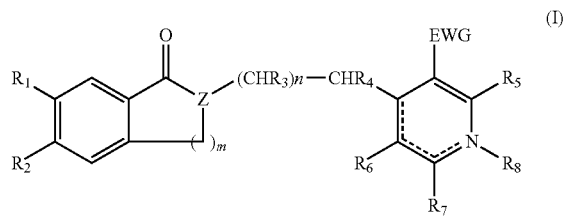

wherein:
the dotted lines in the pyridine cycle indicate the presence of at least one double bond,
$R_1$ and $R_2$ are independently chosen between a hydrogen atom, a halogen atom, hydroxy, CN, $CF_3$, a ($C_1$-$C_8$) alkyl, an aryl, a ($C_1$-$C_8$) alkoxy or $R_1$ and $R_2$ form together a dioxolyl group;
n is an integer from 0 to 4 and
$R_3$ and $R_4$ are a hydrogen atom, or
n=1 and $R_3$ and $R_4$ can also form together a double bond between the carbon atoms to which they are attached so that the radical —$CHR_3$—$CHR_4$— form a vinylenyl group —CH=CH—, and either m is 0, 1 or 2, and
Z is CH or N; or >Z—($CHR_3$)—$CHR_4$— is >C=CH—($CH_2$)$_n$—;
or --(--)$_m$--- is absent and Z is NH, >N-alkyl ($C_1$-$C_8$), >N-phenyle, >N-benzyle or >N-heteroaryle;
$R_5$ is chosen from a hydrogen atom, a halogen atom, hydroxy, CN, $CF_3$, a ($C_1$-$C_8$) alkyl, an aryl, a ($C_1$-$C_8$) alkoxy; and
$R_6$ and $R_7$ which may be identical or different are hydrogen, OH, ($C_1$-$C_8$) alkyl, aryl, heteroaryl, ($C_1$-$C_8$) alkylaryl, aryl ($C_1$-$C_8$) alkyl, ($C_1$-$C_8$) alkoxy, hydroxyl ($C_1$-$C_8$) alkyl, ($C_1$-$C_8$) alkoxy ($C_1$-$C_8$) alkyl, —($CH_2$)$_q$—COOH wherein q is comprised between 1 and 4, Z', $Z_1$; or
$R_6$ and $R_7$ taken together with the carbon atoms to which they are attached form a ($C_5$-$C_{10}$) cycloalkenyl, a 6-membered aromatic ring or a 5- or 10-membered heterocyclic ring comprising 1 to 4 heteroatoms identical or different chosen between N, S and O, being optionally substituted by one or more identical or different group defined as OH, ($C_1$-$C_8$) alkyl, aryl, heteroaryl, ($C_1$-$C_8$) alkyl-aryl, aryl ($C_1$-$C_8$) alkyl, ($C_1$-$C_8$) alkoxy, hydroxyl ($C_1$-$C_8$) alkyl, ($C_1$-$C_8$) alkoxy ($C_1$-$C_8$) alkyl, ($CH_2$)$_q$—COOH wherein q is comprised between 1 and 4, Z', $Z_1$;
Z' is a group defined by formula (L)p-Z1, L is ($C_1$-$C_8$)alkyl, an aryl, ($C_5$-$C_{10}$)heteroaryl, ($C_r$-$C_8$)alkyl-aryl, aryl-($C_1$-$C_8$) alkyl and p is comprised between 1 and 6;
$Z_1$ is defined by formula: —X—C(Y)—$NR_9R_{10}$ wherein X and Y, are O or S, $R_9$ and $R_{10}$ may be identical or different and represent hydrogen, ($C_1$-$C_8$)alkyl, an aryl, ($C_5$-$C_{10}$)heteroaryl, ($C_1$-$C_8$)alkyl-aryl, cyclopropyl, —($CH_2$)$_{p'}$—COOH; and wherein p' is comprised between 1 and 4;
$R_8$ is a ($C_1$-$C_8$)alkyl, an aryl, ($C_5$-$C_{10}$)heteroaryl, an aryl-($C_1$-$C_8$)alkyl or a ($C_1$-$C_8$)alkyl-aryl radical, which can be optionally substituted by at least one group from OH, $NO_2$, $CF_3$, halogen, ($C_1$-$C_8$)alkyl, ($C_1$-$C_8$)alkoxy, or ($C_1$-$C_8$) alkoxy-aryl or sulfonyle;
EWG represents an electron withdrawing group selected from the group comprising COOR, COSR, CONRR', CN, COR, $CF_3$, SOR, $SO_2R$, SONRR', $SO_2NRR'$, $NO_2$, halogen, heteroaryl, wherein R and R' are independently chosen from H, alkyl, cycloalkyl, arylalkyl, heteroarylalkyl, hydroxyalkyl, alkoxyalkyl, aryloxyalkyl, alkylaminoalkyl, aminoalkyl, heteroaryloxyalkyl, halogenoalkyl, mercaptoalkyle HS-alk, alkylthioalkyl, aryl, alkylaryl, hydroxyaryl, alkoxyaryl, aryloxyaryl, aminoaryl, alkylaminoaryl, halogenoaryl, heteroaryl, alkylheteroaryl, alkoxyheteroaryl, aminoheteroaryl, alkylaminoheteroaryl, halogenoheteroaryl, or
R and R' taken together with the nitrogen atom to which they are attached either form an heterocyclic ring of at least 3 members, preferably a 5 or 6 membered heterocyclic ring, optionally substituted by one or more groups being as defined for $R_5$, or form a fused polyheterocyclic system, preferably tetrahydroisoquinoline, indoline, isoindoline, optionally substituted by one or more group being as defined for $R_5$,
and the pharmaceutical salts and stereoisomers thereof if any
or the quaternarized oxidized forms of said family of prodrugs, it being understood that when the nitrogen atom of formula (I) is quaternarized, there is a counter ion $X^-$.

Unless more limited, the "alkyl" radicals or alkyl portions are linear or branched and contain 1 to 8 carbon atoms. More specifically, the alkyl radicals are chosen from methyl, ethyl, propyl, isopropyl, as well as butyl, pentyl or hexyl radicals. Preferably the alkyl radicals have 1 to 4 carbon atoms.

As used herein, "aryl" is intended to mean any stable monocyclic to tricyclic carbon ring having from 6 to 14 carbon atoms, wherein at least one ring is aromatic, and provided that the attachment is made via the aromatic ring when a non-aromatic ring is present. Examples of such aryl elements include, but are not limited to, phenyl, naphthyl, tetrahydronaphthyl, indanyl, biphenyl, phenanthryl, anthryl or acenaphthyl.

The terms "aryl alkyl" or "alkyl aryl" radical, include an alkyl portion where alkyl is as defined above and include an aryl portion where aryl are as defined above. Examples of aryl alkyl include, but are not limited to: benzyl, halobenzyl, phenylethyl, phenylpropyl, halophenylethyl, thienylethyl, thienylpropyl. Examples of alkylaryl include toluene, ethylbenzene, propylbenzene.

By "halo" or "halogen" radical or by halogen atom is intended to mean in a non limited manner; fluorine, chlorine, bromine or iodine.

"Cycloalkyl" as used herein is intended to include non-aromatic cyclic hydrocarbon groups, having the specified number of carbon atoms, which may or may not be bridged or structurally constrained. Examples of such cycloalkyls include, but are not limited to, cyclopropyl, cyclobutyl, cyclopentyl, cyclohexyl, adamantyl, cyclooctyl, cycloheptyl.

"Alkoxy" represents either a cyclic or non-cyclic alkyl group of indicated number of carbon atoms, linear or branched, and attached through an oxygen bridge. "Alkoxy" therefore encompasses the definitions of alkyl and cycloalkyl above. Alkyl portions are linear or branched and contain 1 to 8 carbon atoms. Preferably the alkyl portions have 1 to 4 carbon atoms.

"Heteroaryl" means a mono or polycyclic system of at least 5 members by cycle combining aliphatic and aromatic rings and may be selected among thienyle, furyle, pyrrolyle, imidazolyle, thiazolyle, thiazolinyl, oxazolyle, oxazolinyl, thiadiazolyle, oxadiazolyle, tetrazolyle, pyridyle, pyridazinyle, pyrazinyle, pyrimidinyle, indolyle, benzothienyle, benzofuranyle indazolyle, benzothiazolyle, naphtyridinyle, quinolyle, isoquinolyle, cinnolyle, quinazolyle, quinoxalyle, benzoxazolyle, benzimidazolyle, or triazolyl, optionally substituted by one or more groups as defined above.

When the pyridine derivative of the formula (I) is quaternarized, the counter ion $X^-$ can be chosen from a halogen atom, or sulphate, triflate, carboxylate, tosylate, or mesylate ion. More specifically, it can be chosen through chloride, bromide or iodide ions.

This prodrug comprises at least one electron withdrawing group (EWG). The presence of the EWG increases the stability of the prodrug form. Moreover the ability of the uncharged or oxidisable nitrogen of being non protonable is enhanced by the presence in the compound of the invention of this electron withdrawing group (EWG) which draws electrons away from a reaction center. This results in a non protonable compound with an enhanced stability in vivo and specifically in the PNS before the passage through the BBB towards the CNS. Preferably EWG is COOR, CONRR', CN, COR, $SO_2R$, $SO_2N'$, halogen.

The dotted line in formula (I) indicates the presence of double bonds. In the non-protonated form, one double bond may be localized either between the carbon bearing $R_7$ and the carbon bearing $R_6$ or between the carbon bearing $R_6$ and the carbon bearing the linkage to the rest of the molecule. Thus, the prodrug according to the present invention may be represented by any of the following chemical formula (Ia) or (Ib):

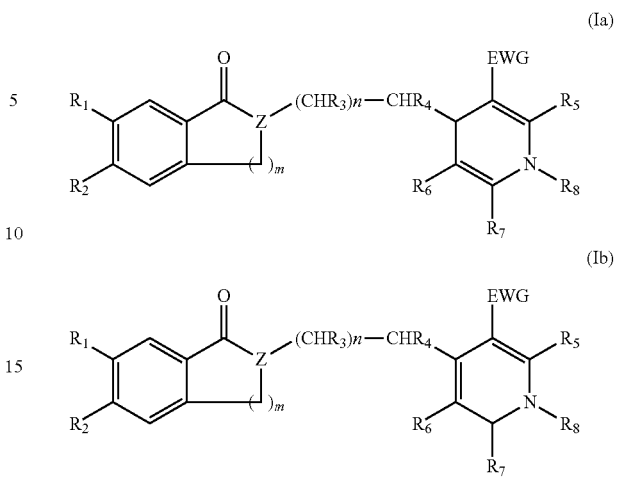

An object of the present invention is directed to the quaternarized oxidized forms of the above family of prodrugs, represented by the following structure:

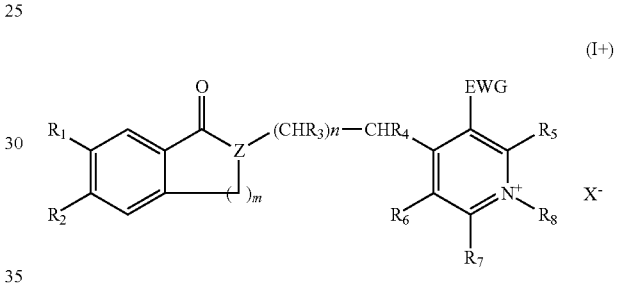

wherein $R_1$, $R_2$, $R_3$, $R_4$, $R_5$, $R_6$, $R_7$, $R_8$, Z, m, n and EWG have the same meaning as above. $X^-$ represents a counterion.

The counterion can be chosen from a chloride, bromide or iodide, sulphate, triflate, carboxylate, tosylate, mesylate ion.

Among preferred compounds are compounds of formula (I) where $R_1$ and $R_2$ are independently a ($C_1$-$C_8$)alkoxy, preferably a ($C_1$-$C_4$) alkoxy, or more preferably ethoxy or methoxy. Also preferred are compounds in which $R_8$ is an aryl-($C_1$-$C_8$)alkyl, preferably an aryl-($C_1$-$C_4$)alkyl, or phenyl-($C_1$-$C_4$)alkyl preferably benzyl.

According to a preferred embodiment EWG can be chosen from COOR, CONRR' in which R and R' are defined as in formula (I) or from CN radicals.

These oxidized compounds are active in vivo into the Central Nervous System. Once oxidized, they cannot go back to the peripheral system and are thus devoid of the side effects usually associated with the prior art cholinesterase inhibitors compounds. In addition, these oxidized compounds appeared to be particularly efficient.

Although it appeared that the EWG group plays a role in the prodrug stability, it has further been discovered that the compounds wherein EWG is replaced by hydrogen also proved to be particularly efficient in the inhibition of acetylcholinesterase. Their use as a medicament is also comprised within the scope of the invention.

These compounds are either the starting product for obtaining the prodrug of formula (I) by a step of reduction or the active drug which is liberated in vivo in the CNS.

The compounds of the invention are potent central or peripheral acetylcholinesterase inhibitors, that can be used in the treatment of neurodegenerative diseases such as Alzheimer's disease or in the prevention of cardiovascular diseases or in the treatment of myasteny disease.

The biological activities of the products encompassed by the general formulae (I) and (I+) have been tested. The acetylcholinesterase (AChE) activity was determined by a modification of the Ellman method (Ellman, G. L., Courtney, K. D., Andres, V., Featherstone, R. M. *A new and rapid colorimetric determination of acetylcholinesterase activity*. Biochem. Pharmacol. 7: 88-95, 1961) using acetylthiocholine iodide as substrate. The assay mixture (Phosphate buffer, pH=7.4, 52 mM, 3 mL) contained 5,5'-dithiobis-(2-nitro) benzoic acid (0.5 mM), human erythrocyte membranes as a AChE source and compounds at various concentrations. The 10.0 minutes incubation time at room temperature was selected for the enzyme assay after preliminary experiments performed to ensure that the enzyme activity is linear with respect to the reaction time and the enzyme concentration employed. The blank was also run at the same conditions and with the same components except that the enzyme was omitted. An apparent IC50 can be determined for compounds and expressed by comparison to that of Donepezil ($IC_{50}$=60 nM).

The compounds according to the invention can also inhibit the butyrylcholinesterase activity following the description of J. Med. Chem., 52(22), 7255, (2009).

Considering the determined activity as acetylcholinesterase inhibitors, and according to Current Medicinal Chemistry, 7, 303-339, (2000) there is a correlation between the in vitro test and the in vivo activity on central cholinergic activity: "A wide range of evidence shows that acetylcholinesterase (AChE) inhibitors can interfere with the progression of Alzheimer's disease (AD)". This is predictive of the in vivo activity of the compounds of the invention, particularly on the progression of Alzheimer's disease.

According to an embodiment of the invention, the compounds of the invention are acetylcholinesterase inhibitors, at least 10 times, preferably at least 100 times, more active in central nervous system CNS under their oxidized form than in peripheral nervous system PNS under their non oxidized form.

According to a preferred embodiment of the invention, the compounds of the invention are compounds of formula (I) where,
the dotted lines in the pyridine cycle indicate the presence of at least one double bond,
$R_1$ and $R_2$ are independently chosen between a hydrogen atom, a halogen atom, a (C1-C8) alkyl, a (C1-C8) alkoxy or $R_1$ and $R_2$ form together a dioxolyl group;
n is an integer from 0 to 2; and
$R_3$ and $R_4$ are a hydrogen atom, and
either m is 1 or 2, and Z is CH or N; or >Z—$(CHR_3)_n$—$CHR_4$— is >C=CH—$(CH_2)_n$—;
or --(--)$_m$--- is absent and Z is >N-phenyle;
$R_5$ is chosen from a hydrogen atom, a ($C_1$-$C_8$) alkyl; and
$R_6$ and $R_7$ are hydrogen;
$R_8$ is a (C1-C8)alkyl or an aryl-($C_1$-$C_8$)alkyl radical, which can be optionally substituted by at least one group from $NO_2$, $CF_3$, halogen, ($C_1$-$C_8$)alkyl or sulfonyle;
EWG represents an electron withdrawing group selected from the group comprising COOR, COSR, CONRR', CN, COR, $CF_3$, SOR, $SO_2R$, SONRR', $SO_2NRR'$, $NO_2$, halogen, wherein R and R' are independently chosen from H, alkyl,
and the pharmaceutical salts and stereoisomers thereof if any,
or the quaternarized oxidized forms of said pyridine derivatives, it being understood that when the nitrogen atom of formula (I) is quaternarized, there is a counter ion $X^-$.

According to an embodiment of the invention, more preferred compounds are compounds of formula (Ia)

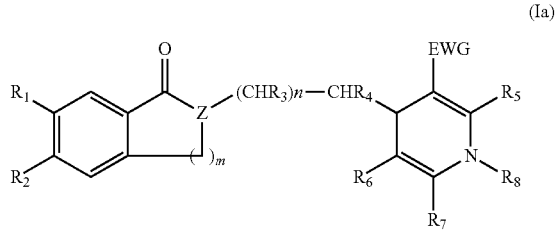

where
$R_3$ and $R_4$ are hydrogen,
$R_5$ is chosen from a hydrogen atom, $CF_3$, a ($C_1$-$C_8$) alkyl, a ($C_1$-$C_8$) alkoxy;
$R_6$ and $R_7$ are hydrogen;
$R_8$ is a ($C_1$-$C_8$)alkyl, an aryl-($C_1$-$C_8$)alkyl or a ($C_1$-$C_8$) alkyl-aryl radical which can be optionally substituted by at least one group from OH, $NO_2$, halogen, ($C_1$-$C_8$)alkyl, ($C_1$-$C_8$)alkoxy, or ($C_1$-$C_8$)alkoxy-aryl;
Z and m are defined as above for formula (I) and when –(–)$_m$- is absent, Z is NH, >N-alkyl($C_1$-$C_8$), or >N-phenyle;
$R_1$, $R_2$, n and EWG are defined as above for formula (I);
and the pharmaceutical salts thereof and stereoisomers thereof if any.

More preferred compounds within the scope of the present invention are the prodrugs and oxidized forms of donepezil, as in the following formula (IIa) and related quaternarized oxidized form of formula (II+) wherein EWG has the same meaning as above.

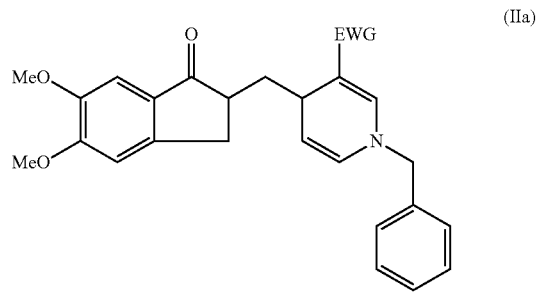

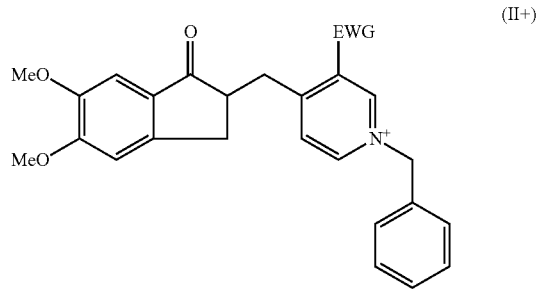

Additionally to the advantage of being deprived of side effects, the compounds of the invention provide substantially higher activity for inhibiting acetylcholinesterase in comparison to the existing donepezil and some prodrugs mentioned in the art.

Compounds of the invention of the formulae (Ia) and (Ib) exhibit acetylcholinesterase inhibition (hAChE inhibition)

between 6 and 62% at 1 µM. They also exhibit butyrylcholinesterase inhibition (eqBuChE inhibition) between 17 and 92% at 10 µM.

Compounds of the invention of the formula (I+) exhibit acetylcholinesterase inhibition (hAChE inhibition) between 62 and 100% at 1 µM. They also exhibit butyrylcholinesterase inhibition (eqBuChE inhibition) between 4 and 97% at 10 µM.

Inhibitory concentration IC$_{50}$ of compounds (I) and (I+) has not been determined when acetylcholinesterase inhibition and butyrylcholinesterase inhibition were inferior to 50% at 1 µM and 10 µM respectively.

For example the data below reports the inhibitory concentration IC$_{50}$ of some compounds of the invention, as measured according to the modified Ellman method described above.

| Compound No (structure hereafter described) | hAChE IC$_{50}$ (nM) | Binding to the PAS measured by propidium iodide displacement | EqBuChE IC$_{50}$ (nM) |
| --- | --- | --- | --- |
| Donepezil | 6 | 24% | nd |
| 24 (Example 4.2) | 11.5 | nd | nd |
| 26 (Example 4.4) | 11.3 | nd | nd |
| 33 (Example 6) | 18 | 23% | nd |
| 32 (Example 8) | nd | nd | 6205 |
| 36 (Example 9) | nd | nd | 4595 |
| 55 (Example 18) | nd | nd | 6010 |
| 59 (Example 20) | nd | nd | 8270 |
| 61 (Example 21) | nd | nd | 4020 |
| 67 (Example 24) | nd | nd | 3050 |
| 77 (Example 29) | 543 | 18 | 13500 |
| 82 (Example 32) | 76 | 22 | 371 |
| 117 (Example 38.1) | 20 | 20 | 447 |
| 118 (Example 38.2) | 16.5 | 19 | 664 |
| 119 (Example 38.3) | 71 | 23 | 412 |
| 120 (Example 38.4) | 110 | 27 | 596 |
| 121 (Example 38.5) | 10 | 24 | 433 |
| 122 (Example 38.6) | 71 | 20 | 496 |
| 123 (Example 38.7) | 78.6 | 22 | 1325 |
| 124 (Example 38.8) | 307.5 | 25 | 2170 |
| 125 (Example 38.9) | 57.7 | 23 | 592 |
| 126 (Example 38.10) | 29 | 22 | 256 |
| 127 (Example 38.11) | 43 | 21 | 489 |
| 128 (Example 38.12) | 55 | 23 | 412 |
| 129 (Example 38.13) | 141 | 22 | 171 |
| 130 (Example 38.14) | 556 | 23 | 4140 |
| 131 (Example 38.15) | 568 | 19 | 6090 |
| 132 (Example 38.16) | 24.2 | 24 | nd |
| 133 (Example 38.17) | 9.1 | 18 | 508 |
| 136 (Example 38.20) | 262 | 20 | 3630 |
| 138 (Example 38.22) | 30 | 23 | 2990 |
| 139 (Example 38.23) | 60 | 19 | 1615 |
| 140 (Example 38.24) | 0.255 | 21 | 984 |
| 141 (Example 38.25) | 0.053 | 20 | 2285 |
| 142 (Example 38.27) | 8.8 | 18 | 5930 |
| 144 (Example 38.29) | 3.2 | 16 | 3340 |
| 145 (Example 38.30) | 0.36 | 16 | 1790 |
| 146 (Example 38.31) | 0.465 | 18 | 3865 |
| 149 (Example 38.34) | 20.1 | 23 | nd |
| 152 (Example 38.37) | 37.7 | 18 | 262 |
| 155 (Example 39.3) | nd | nd | 2270 |
| 156 (Example 39.4) | nd | 26 | 4400 |
| 157 (Example 39.5) | nd | 15 | 5775 |
| 160 (Example 39.8) | nd | nd | 8270 |
| 160-B (Example 39.8) | nd | nd | 5645 |
| 160-C (Example 39.8) | nd | nd | 4700 |
| 162 (Example 39.10) | 415 | 16 | 3970 |
| 163 (Example 39.11) | nd | nd | 4820 |
| 164 (Example 39.12) | nd | nd | 5435 |
| 165 (Example 39.13) | nd | nd | 4615 |
| 166 (Example 39.14) | 653 | nd | 1255 |
| 169 (Example 39.17) | 428 | 17 | nd | nd: not determined (% inhibition hAChE < 50% at 1 µM)

Among the hereabove mentioned compounds, more particularly potent compounds are the compounds of formula (I) wherein the dotted lines in the pyridine cycle indicate the presence of at least one double bond, $R_1$ and $R_2$ are independently chosen between a hydrogen atom, a halogen atom, a methyl, a methoxy radical or $R_1$ and $R_2$ form together a dioxolyl group;

n is an integer from 0 to 2; and $R_3$ and $R_4$ are a hydrogen atom, and either m is 1 or 2, and Z is CH or N; or >Z—(CHR$_3$)$_n$—C is >C=CH—;

or --(--)$_m$--- is absent and Z is >N-phenyle;

$R_5$ is chosen from a hydrogen atom, a methyl; and $R_6$ and $R_7$ are hydrogen;

$R_8$ is a (C$_1$-C$_4$)alkyl or a benzyl radical, which can be optionally substituted by a group chosen from NO$_2$, CF$_3$, chloro, fluoro, methyl or sulfonyle;

EWG represents an electron withdrawing group selected from the group comprising COOR, CONRR', CN, COMe, SO$_2$Me, SO$_2$NRR', fluoro, chloro, bromo, wherein R and R' are independently chosen from H, (C$_1$-C$_3$)alkyl, and the pharmaceutical salts and stereoisomers thereof if any, or the quaternarized oxidized forms of said pyridine derivatives, it being understood that when the nitrogen atom of formula (I) is quaternarized, there is a counter ion X$^-$.

The compounds of the present invention include the conventional pharmaceutically acceptable salts and isomers thereof.

According to another aspect, the invention is directed to a process for the preparation of the prodrugs and oxidized compounds within the scope of the invention.

According to the invention, compounds of formula (I) and (I+) can be prepared through the following schemes:

route A: is illustrative of the process for the preparation of the compounds where Z is CH: the quaternisation of a compound of the structure

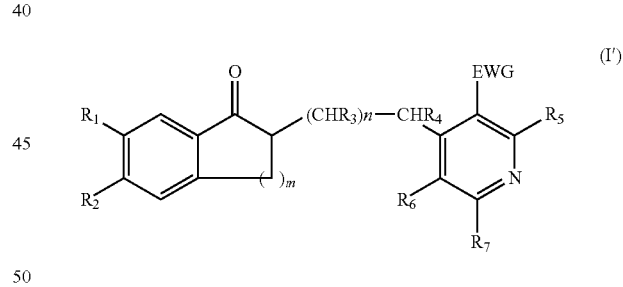

(I')

where radicals $R_1$ to $R_7$, m, n and EWG are defined as above, is made for the preparation of a compound of the formula (I+), followed if desired by regioselective reduction, for the preparation of compounds of formula (I);

The quaternization involves the reaction of an alkylating agent on the compound of formula (I').

Route A

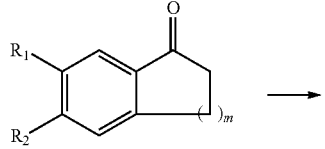

-continued

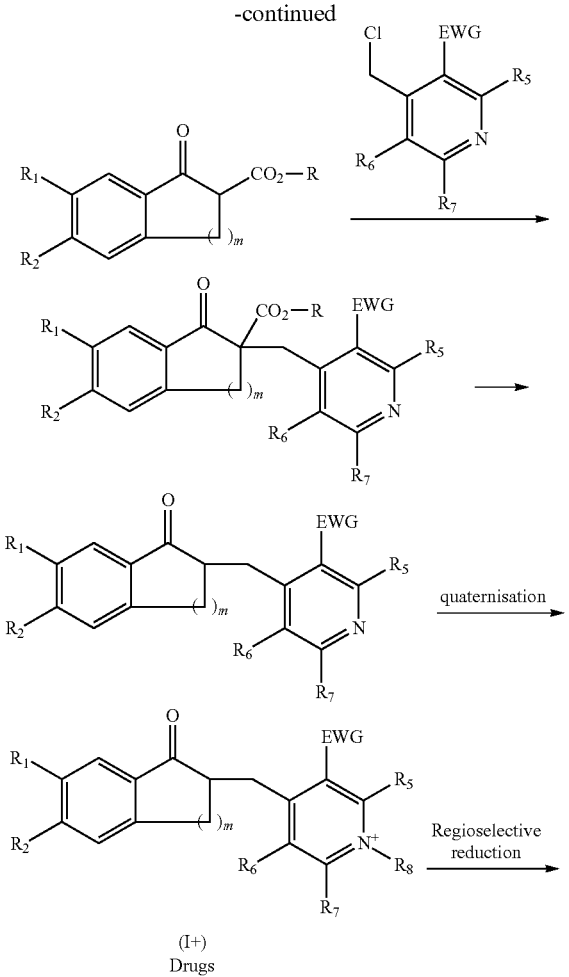

(I+)
Drugs (I)
Prodrugs

It being understood that in route A above the group "CH$_2$—" between the indanone and the pyridine means indifferently CH$_2$— (when n=0) or —(CHR$_3$)$_n$—CHR$_4$—, or route B: is illustrative of the process for the preparation of the compounds where Z is CH or N, and where a compound of the formula having radicals R$_1$, R$_2$, R$_6$ and R$_7$ and m defined as above, is submitted to a dihydropyridine construction, leading to a compound of formula (I), and if desired, subsequently to the corresponding drug of formula (I+) by oxidation of said compound.

Route B

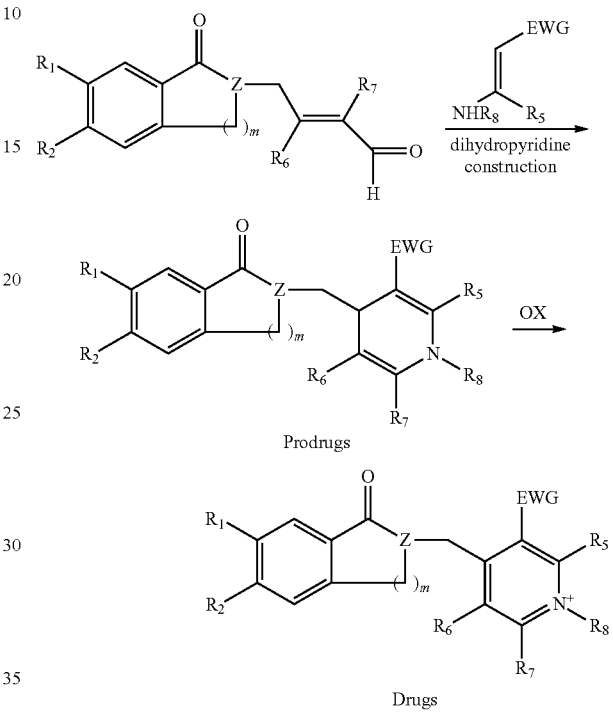

it being understood that in the scheme of route B above, the group —CH$_2$— between the indanone and either the ethylenyle chain or the pyridine group, can be understood as meaning indifferently —CH$_2$— (when n=0) or —(CHR$_3$)—CHR$_4$—.

Route C: is illustrative of process for the preparation of the compounds where Z is CH and n=0:

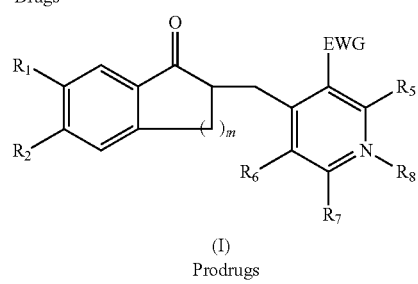

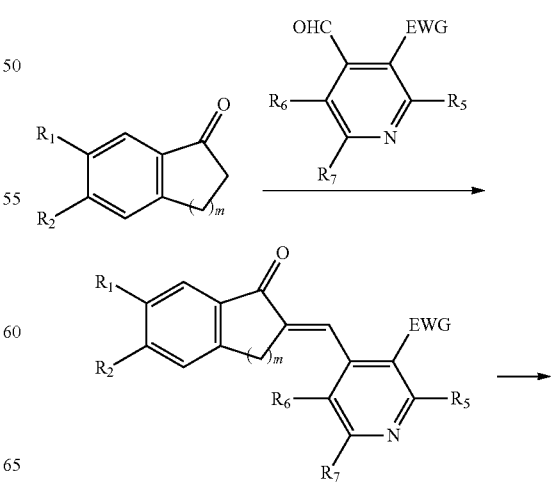

-continued

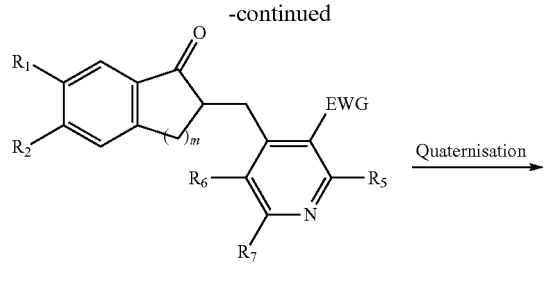

(I+)
Drugs

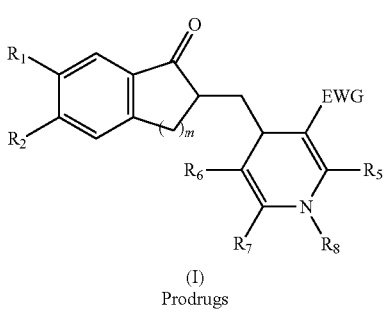

(I)
Prodrugs

It being understood that in route C depicted above, the quaternisation and regioselective reduction steps are identical to route A.

The prodrug forms may be reached using elements of synthesis that are reported in the literature having radicals $R_1$ to $R_8$, m, n and EWG defined as above.

It is also understood that in route C depicted above, when a compound having EWG=COOR, COR or CN is intended to be prepared, the corresponding pyridine having EWG=bromo is firstly reacted and before the step of quaternisation, the intermediate compound is converted into a compound having EWG=COOR, COR or CN According to Route A, the oxidized compounds may be obtained starting from a prodrug form with a step of quaternization involving an alkylating agent in an appropriate solvent to provide the compounds of formula (I+). Appropriate alkylating agents are of the type Rx-W, wherein Rx is ($C_1$-$C_8$) alkyl, aryl, ($C_1$-$C_8$) alkylaryl, aryl ($C_1$-$C_8$) alkyl, alkoxy, hydroxy ($C_1$-$C_8$) alkyl, alkoxy ($C_1$-$C_8$) alkyl, phenyl, ($CH_2$) n-COOH; W being a leaving group, preferably selected from halogen, O-triflate, carboxylate, sulfate, tosylate, mesylate.

The prodrug forms may be reached using elements of synthesis that are reported in the literature. For instance, 2-carbethoxy-5,6-dimethoxyindanone 2 may be prepared as a first starting material from commercial indanone material 1 according to the following scheme by carbethoxylation using diethylcarbonate under basic conditions (as described in Haadsma-Svensson et al. *J. Med Chem.*, 2001, 44(26), 4716-4732 and Kaspi et al., *Eur. Pat. Appl.*, 2004).

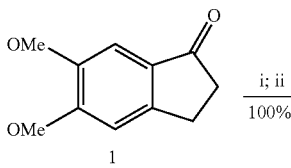

1

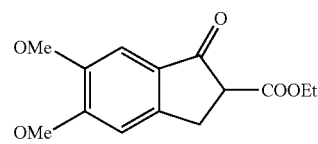

2 i: NaH/THF/reflux/1 h 30
ii: Diethylcarbonate/reflux/3 h

On the second hand, several 3-substituted 4-chloromethylpyridines may also be prepared as the second starting material. For instance, 3-bromo-4-chloromethylpyridine 5 may be obtained quantitatively according to the following scheme by reduction of commercial 3-bromo-4-pyridinecarboxaldehyde 3 using sodium borohydride in methanol quantitatively afforded 3-bromo-4-hydroxymethylpyridine 4. Treatment of 4 by thionyl chloride in dichloromethane gave the expected chloromethylpyridine which could be isolated as its hydrochloride salt.

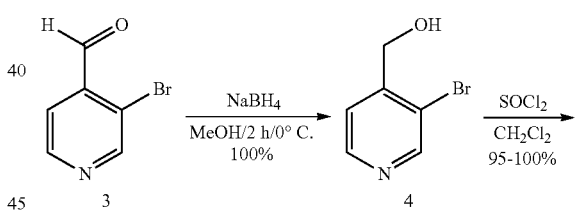

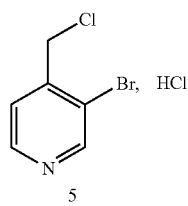

5

Alternatively, N,N-diisopropyl-4-chloromethylnicotinamide 9 may be prepared according to the following scheme by formylation of N,N-diisopropylnicotinamide 6 (obtained from nicotinamide in 2 steps as taugh by Broussy et al., *Org. Biomol. Chem.*, 2005, 3, 666) following a metalation strategy. The resulting aldehyde 7 was reduced to the hydroxymethyl pyridine 8 which could be conveniently transformed into the 4-chloromethyl compound 9 isolated as its hydrochloride salt.

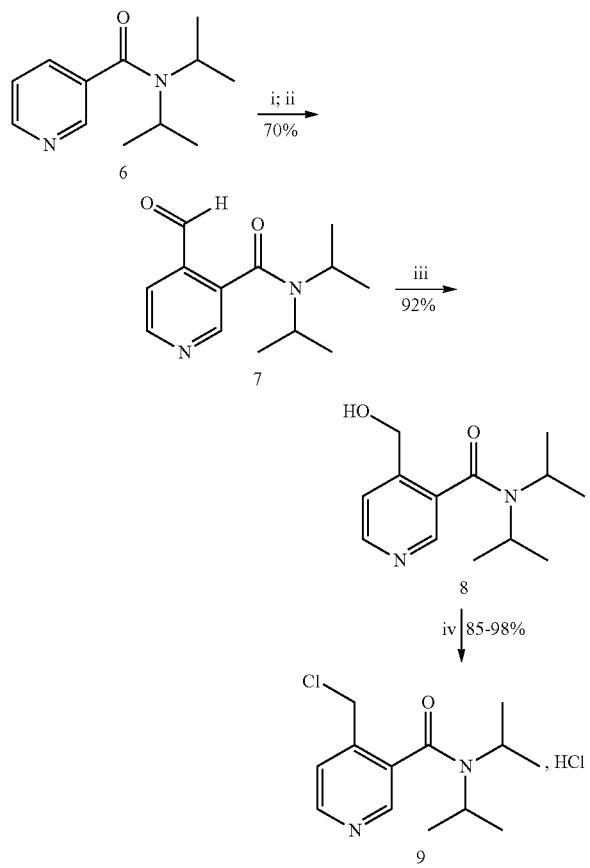

i: LiTMP/THF/-78° C.
ii: DMF/rt
iii: NaBH₄/MeOH
iv: SOCl₂/CH₂Cl₂

Still alternatively, 3-cyano-4-chloromethylpyridine 13 may be prepared according to the following scheme by silylation of the hydroxymethyl group of 4 using tertio-butyldimethylsilylchloride allowed the further substitution of the 3-bromo atom by a cyano function following the Rutan and Heldrich procedure (J. Org. Chem., 1995, 60, 2948). Deprotection of the silylether 11 and treatment of 12 with thionyl chloride led to the hydrochloride salt of 3-cyano-4-chloromethylpyridine 13.

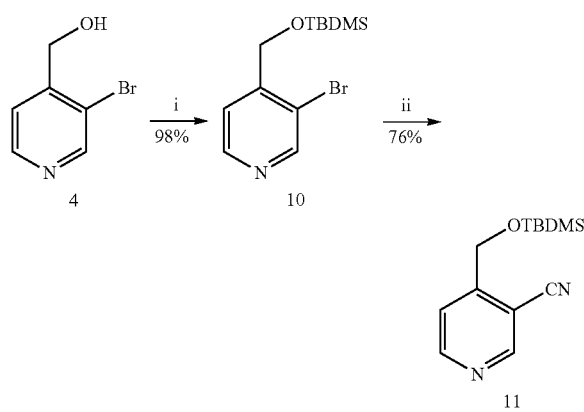

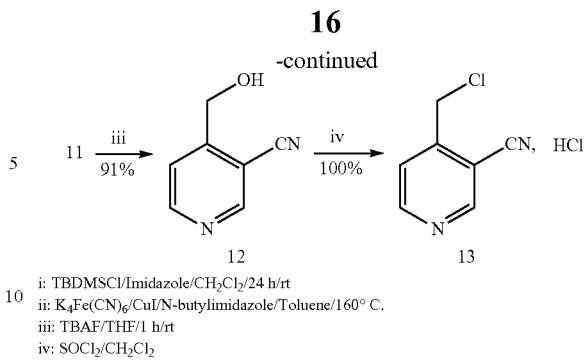

i: TBDMSCl/Imidazole/CH₂Cl₂/24 h/rt
ii: K₄Fe(CN)₆/CuI/N-butylimidazole/Toluene/160° C.
iii: TBAF/THF/1 h/rt
iv: SOCl₂/CH₂Cl₂

Starting from these above 4-chloromethylpyridine alkylating agents, the 2-(4-pyridylmethyl)indanones compounds can be afforded. Alkylation of 2-carbethoxyindanone 2 by the hydrochloride salt of 4-chloromethylpyridines using potassium carbonate in the presence of sodium iodide led to the corresponding 2-carbethoxy-2-(4-pyridylmethyl)indanones 14-16 which were decarboxylated by treatment with potassium hydroxyde in ethanol-water to give compounds 18-20. The reaction is illustrated as follows:

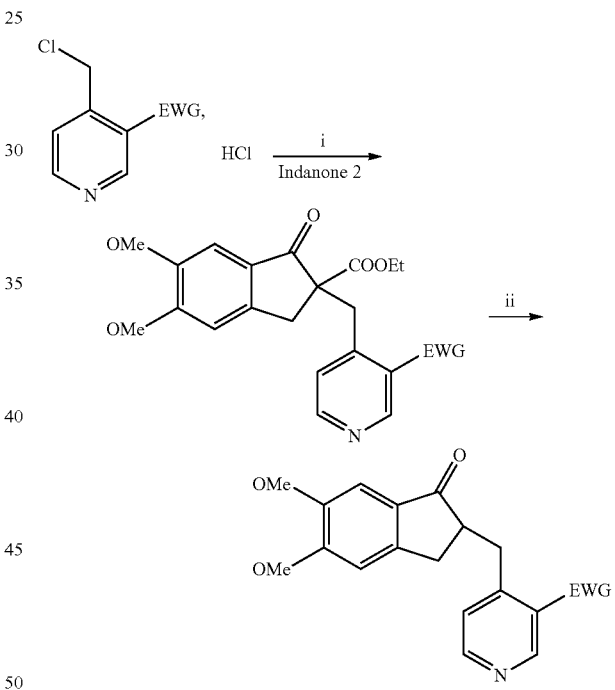

EWG = H, Br and CON(i-Pr)₂
i: K₂CO₃/NaI/Acetone/6 h/reflux
ii: KOH/EtOH — H₂O/40'/reflux
14: EWG = H - 100%
15: EWG = Br - 80%
16 EWG = CON(i-Pr)₂ - 81%
18 EWG = H - 29%
19 EWG = Br - 36%
20 EWG = CON(i-Pr)₂ - 41%

The 2-(3-cyano-4-pyridylmethyl)indanone 21 may be afforded using the 3-cyano-4-chloromethylpyridine 13 prepared above. The ethyl ester 2 is transesterified to the corresponding allyl ester 22 which is then alkylated with the hydrochloride salt of 4-chloromethyl-3-cyanopyridine 13 using potassium carbonate in the presence of sodium iodide. This leads to the corresponding 2-allyloxycarbonyl-2-(4-pyridylmethyl)indanones 17 that may be further decarboxylated by treatment with potassium hydroxide in ethanol-water to give compounds 21. The reaction is summarized in the following scheme.

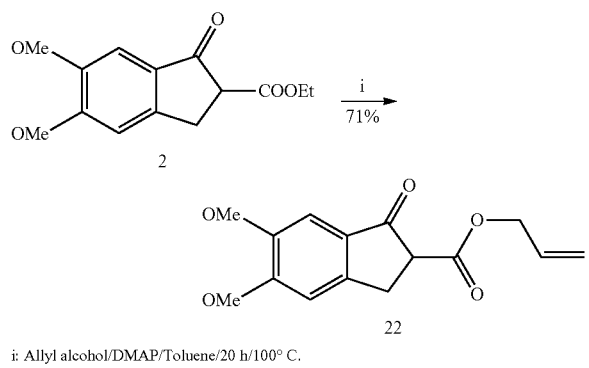

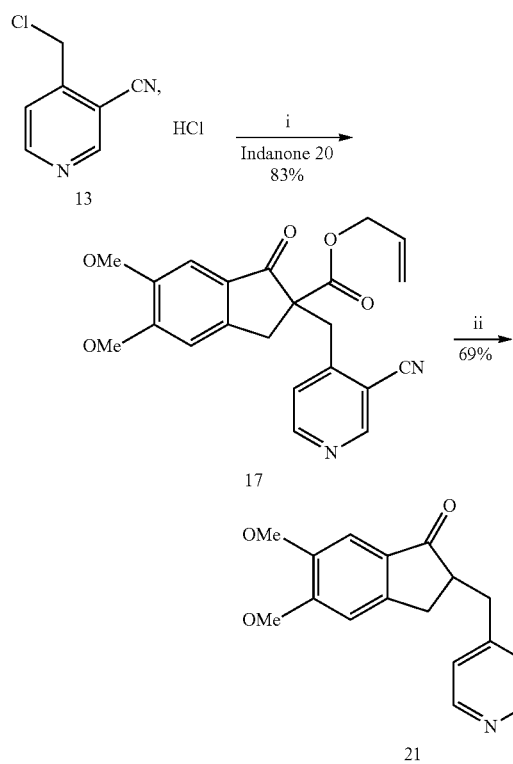

i: K₂CO₃/NaI/Acetone/6 h/reflux
ii: Pd(OAc)₂/PPh₃/HCO₂H/Et₃N/THF/rt

Compound 32 was prepared by palladium-catalysed cross-coupling reaction from the 3-bromopyridine 19 and 1-(ethoxyvinyl)tri(n-butyl)stannane following the method taught in Legros et al.; Tetrahedron, 2001, 2507.

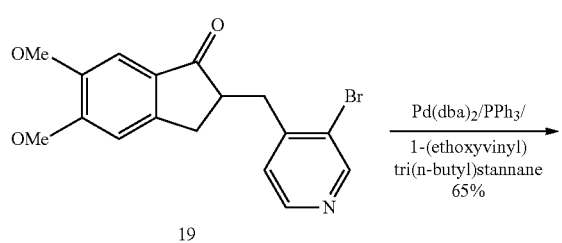

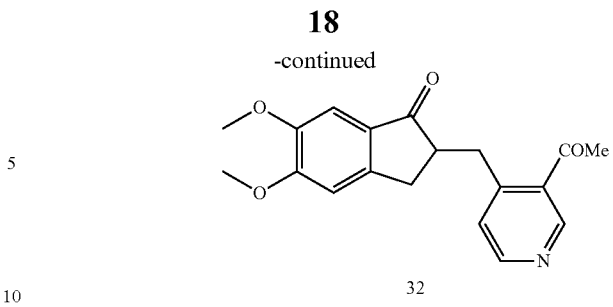

Once prepared, the indanone derivatives may finally be transformed into the desired prodrugs. Substituted 2-(4-pyridylmethyl)indanones 18-21, 32 may be quaternized according to the following scheme using the method taught in Rama et al., *Synthetic Communication*, 2007, 37, 2847 by reaction of benzyl bromide in the presence of sodium iodide to afford the corresponding iodides of N-benzylpyridinium 23-26, 33. The salts are isolated by crystallization after addition of pentane. Compound 22 has been already described by Limura et al. in WO 99/36405: Clark et al., Bioorganic & Medicinal Chemistry Letters, 2002, 256.

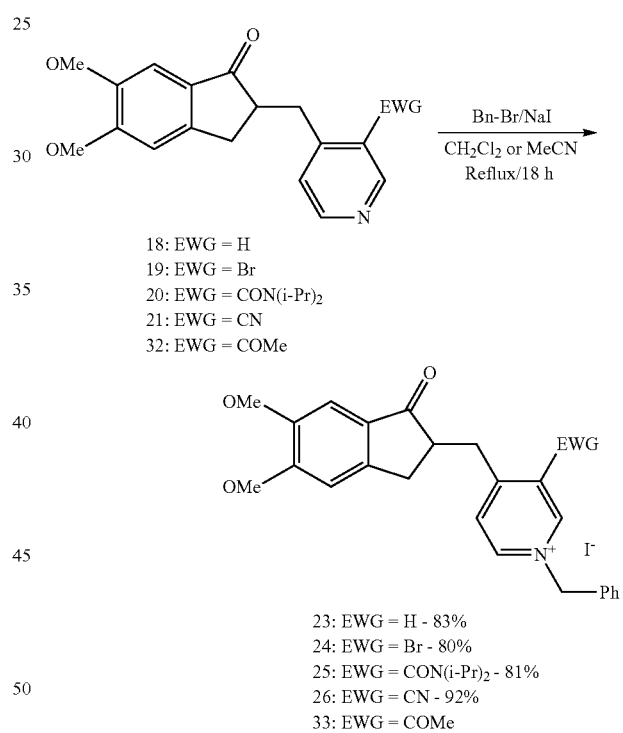

Another object of the invention is the preparation of the prodrugs of the invention starting from the oxidized compounds (I+).

These may be reduced regioselectively to afford prodrugs (Ia). For instance, the reduction of pyridinium salts into 1,4-dihydropyridines could be achieved according to the following scheme using either N-benzyl-1,4-dihydronicotinamide (BNAH) or sodium dithionite (Na₂S₂O₄) as already disclosed in Gaillard et al. *Synlett*, 2005, 3, 441; Carelli et al. Tetrahedron, 2005, 61, 10331; Gomez et al. Tet. Lett., 2005, 46, 3513 and Lavilla at al. J. Org. Chem., 2001, 66, 1487. BNAH was previously prepared by reduction of N-benzylpyridinium chloride with sodium dithionite in a Na₂CO₃/H₂O solution, see Mauzerall et al., *J. Am. Chem. Soc.*, 1955, 77, 2261.

Alternatively, these pyridinium salts may be reduced by NaBH₄ to give rise to a mixture of prodrugs (Ia) and (Ib).

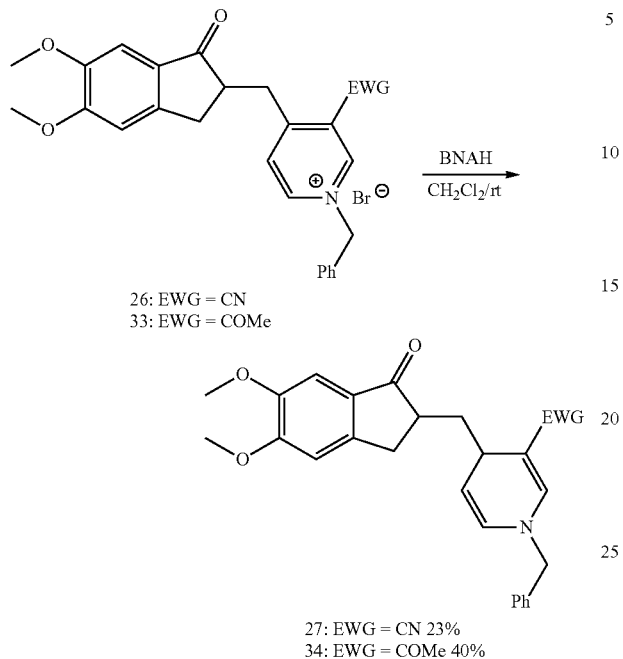

26: EWG = CN
33: EWG = COMe

27: EWG = CN 23%
34: EWG = COMe 40%

According to route B, the prodrugs compounds of formula (I) may be obtained by dihydropyridine construction, from unsaturated aldehydes and enamines involving a catalyst in an appropriate solvent. The oxidized compounds of formula (I⁺) may be eventually obtained from the corresponding prodrug forms of the formula (I) via an oxidation step involving an oxidant in an appropriate solvent.

The prodrug forms of the formula (I) may be reached by using elements of synthesis that are reported in the literature. The required unsaturated compounds can be prepared from the commercially available 3,4-dimethoxy-N-phenylbenzamide using the methods disclosed by Li et al.; *Organic Letters*, 2012, 14, 214, Kumar et al.; *Tetrahedron* 2011, 67, 4093 and Padwa et al, *Journal of Organic Chemistry*, 1998, 63, 3986. From 6-methoxy-3,4-dihydro-2H-isoquinolin-1-one [prepared as described by Plobeck et al., *Journal of Medicinal Chemistry*, 2000, 3878], the synthesis of N-substituted lactams can be achieved in the presence of NaH in dimethylformamide (DMF) and subsequent addition of allyl iodide as taught by Zhou et al, *Journal of Medicinal Chemistry*, 2012, 55, 2452 or in the presence of KOH in DMSO and reaction with but-3-enyl 4-methylbenzenesulfonate [prepared as described by Clive et al. in *Journal of American Chemical Society*, 2009, 6003] as taught by Kumar et al.; *Tetrahedron*, 2011, 67, 4093. Alternatively, commercially available 6-methoxy-1-tetralone and 5,6-dimethoxy-indanone may also be alkylated with allyl bromide or 4-bromo-1-butene by using a procedure reported by Ahmad at al, WO 98/36749.

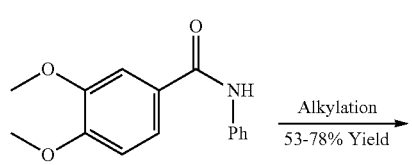

Alkylation
53-78% Yield

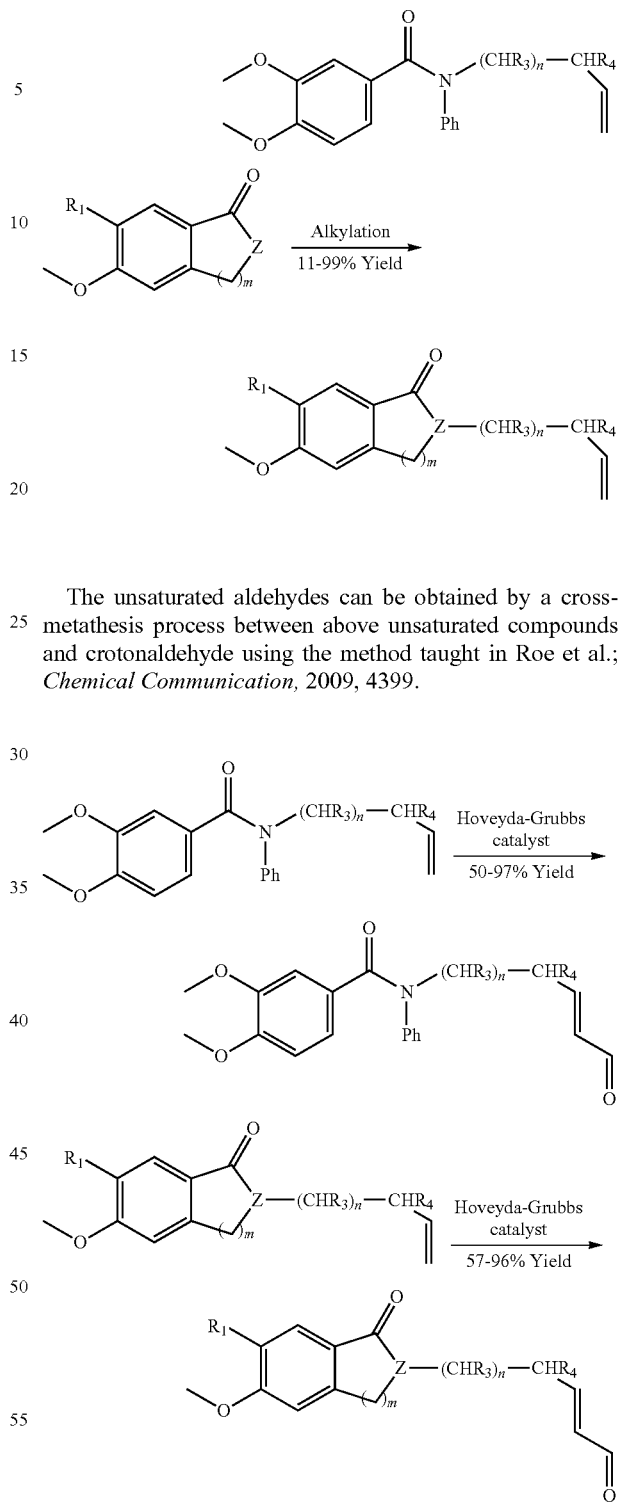

The unsaturated aldehydes can be obtained by a cross-metathesis process between above unsaturated compounds and crotonaldehyde using the method taught in Roe et al.; *Chemical Communication*, 2009, 4399.

The synthesis of a variety of enamines can be achieved by reaction of the corresponding methoxyvinylcarbonyl derivatives and amines as taught by Girling et al. in *Chemical Communication*, 2012, 48, 4893 or reaction of amines with commercial β-ketoesters, β-ketosulfones, β sulfonamides, β-ketoketones using the method reported by Liu et al. in *Applied Organomettalic Chemistry*, 2010, 685.

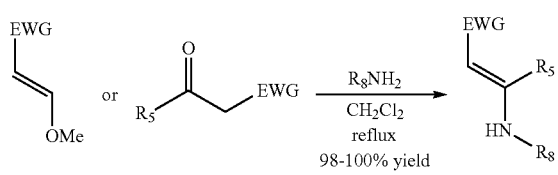
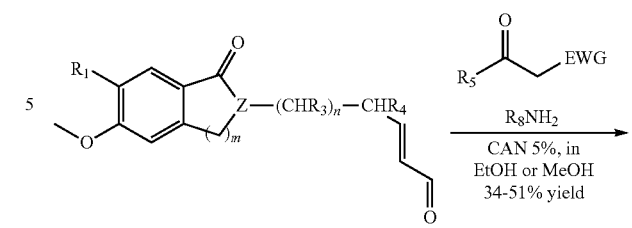

Thereafter, racemic 1,4-dihydropyridines may be prepared by condensation of synthesized enamine and unsaturated aldehydes as disclosed by Bartoli et al, *Synlett,* 2007, 18, 2897 or Vohra at al, *Adv. Synth. Catal,* 2006, 348, 2571. Thus, the present methodology, derivated from the classical Hantzsch condensation, led to unsymmetrical 1,4-dihydropyridines under mild reaction conditions. An asymmetric synthesis could also be envisaged by using different types of catalysts able to induce stereoselectivity at CA of functionalized 1,4-dihydropyridines as taught by Noole et al, *J. Org. Chem.,* 2011, 75, 1538 or Yoshida et al, *Synlett,* 2010, 12, 1865 or Buchanan et al, *Org. Lett.,* 2011, 13(16), 4402, or Franke et al., *Chemistry an Asian. Journal,* 2008, 3, 216.

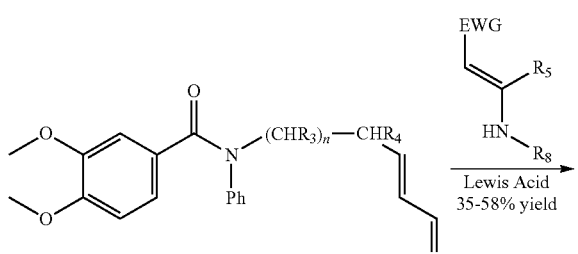

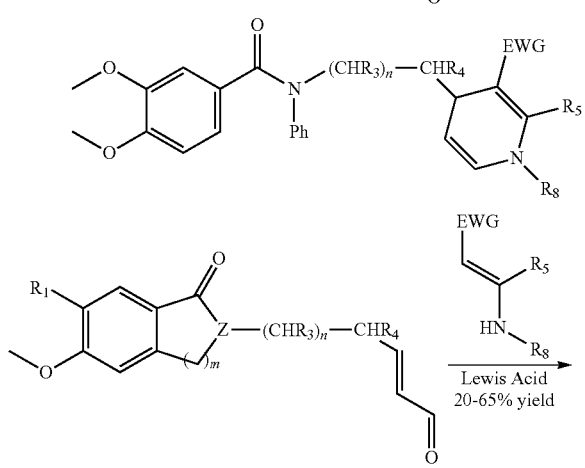

The synthesis of racemic 1,4-diydropyridines derivatives (I) can also be achieved using the method described by Menéndez in *Chem. Eur. J.,* 2013, 13207.

Among the numerous reagents developed in the aromatization process of 1,4-dihydropyridinesto pyridinium salts, DDQ or iodine can be used as taught by Tao et al, *Tetrahedron,* 2011, 67(30), 5469 and Vanden Eynde, *Tetrahedron,* 1995, 51(23), 6511. The so-obtained counter-ion can be readily exchanged if desired by means of an amberlite ion exchange resin.

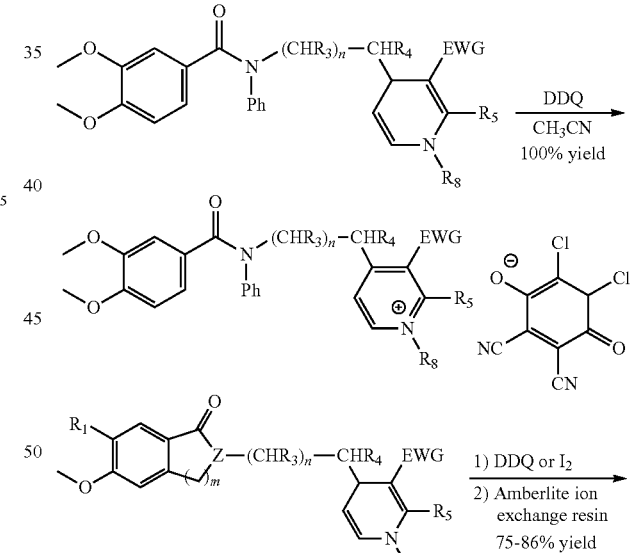

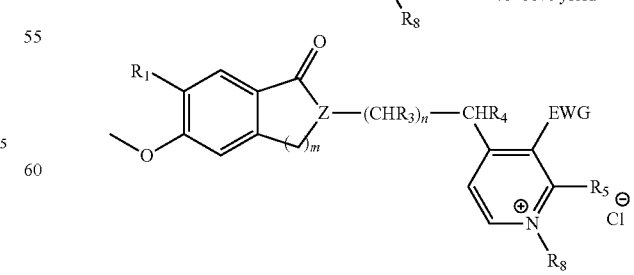

As an example of route B, the desired compound 29 was obtained by a cross-metathesis process between compound 28 and crotonaldehyde using the method taught in Roe et al.; *Chemical Communication*, 2009, 4399. The required allyl benzamide 28 was prepared using the method disclosed by Li at al.; *Organic Letters*, 2012, 14, 214.

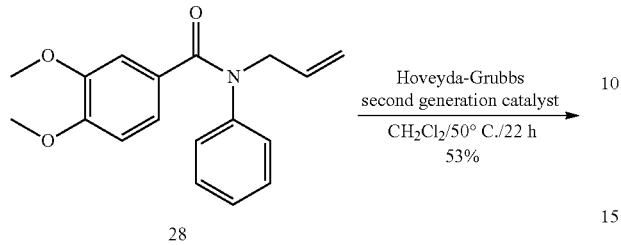

28

The enamide 30 was obtained from 4-methoxybut-3-en-2-one and benzylamine using the method taught in Girling et al.; *Chemical Communication*, 2012, 48, 4893. The 1,4-dihydropyridine 31 was obtained by reacting both compounds 29 and 30 in the presence of a Lewis acid under the reaction conditions developed by Bartoli et al. *SYNLETT*, 2007, 2897; Renaud and al., *Advanced Synthesis and Catalalysis*, 2006, 2571. Alternatively, the 1,4-dihydropyridine 31 may be obtained enantioenriched by reacting compounds 29 and 30 under the reaction conditions reported by Jergensen et al., Chemistry: an Asian Journal, 2008, 3, 216; Kanger et al, *The journal of Organic Chemistry*, 2011, 76, 1538; Takemoto et al. *SYNLETT*, 2010, 1865.

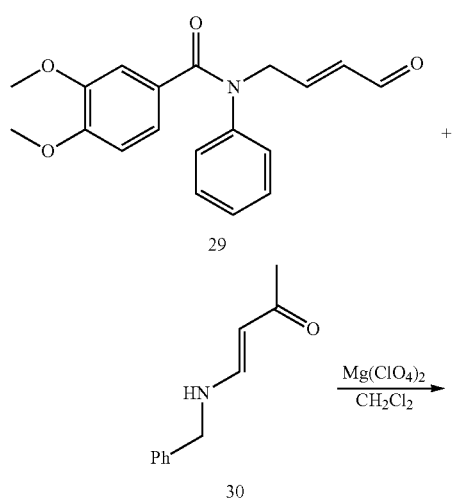

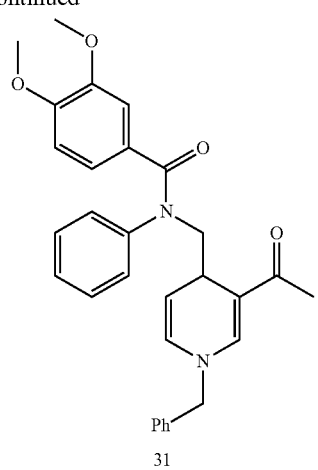

31

According to route C, compounds of formula (I⁺) may be obtained by an aldolisation-crotonisation step with ketones and 3-substituted 4-carboxaldehyde pyridine compounds. The prodrug compounds (I) may be eventually obtained from the drugs compounds (I) as described in route A.

Condensation of ketones on pyridine-4-carboxaldehyde derivatives can afford the corresponding unsaturated ketone as taught by Huang et al *J. Med. Chem.*, 2012, (55), 8483, by Potter et al. in *J. Med Chem.*, 2006, 1325 and by Li et al. in *Bioorganic & Medicinal Chemistry Letters*, 2012, 4462. Several 3-substituted 4-carboxaldehyde pyridine compounds used are commercially available or may be prepared either by oxidation as taught by Li, Xiao-Qiang et al *Synthesis*, 1999, (7), 1163 or reduction to aldehyde as taught by Munoz, Juan de M. et al *Eur. J. Org. Chem.*, 2012, 2, 260 or regioselective functionalization as taught by Shlecker et al *J. Org. Chem.*, 1995, 60(26), 8414 and Epsztajn et al *J. Chem. Res.-S*, 1986, (1), 18. For instance, the synthesis of α,β-unsaturated indanones or tetralones with a pyridine moiety can be achieved by reaction of commercial indanones or tetralones with 3-halogeno-4-carboxaldehyde pyridine as depicted below.

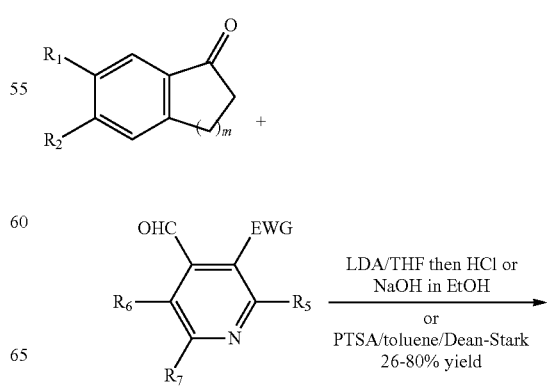

-continued

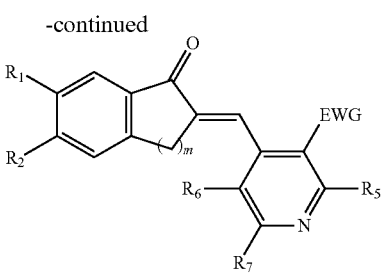

Reduction of the so-obtained conjugated double bond can be conducted by using a reducing agent. For instance, Hantzsch ester in the presence of $TiCl_4$ affords the desired derivatives in conditions as described by Lam et al. in *Synlett,* 2010, 2415. The reduction reaction can be also conducted by hydrogenolysis in the presence of platinum on carbon.

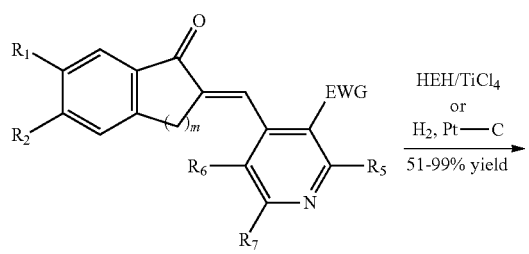

Unsaturated and saturated 3-bromo-pyridine derivatives can be engaged in a large variety of coupling reactions. For instance, various 3-acetylpyridine derivatives can be also prepared by reacting (1-ethoxyvinyl)tri-(n-butyl) stannane in the presence of $PPh_3$ and $Pd(dba)_2$ as taught by Kosugi et al, *Bull. Chem. Soc. Japan,* 1987, 60(2), 767 or littke et al, *J. Am. Chem. Soc.,* 2002, 124, 6343. As well, 3-iodo-pyridine derivatives can be obtained by a copper-catalyzed halogen exchange as disclosed by Klapars et al, *J. Am. Chem. Soc.,* 2002, 14844. A subsequent coupling reaction leads to 3-cyano-pyridine derivatives as described by Anderson et al. in *Journal of Organic Chemistry,* 1998, 8224. Furthermore, a coupling reaction with Xantphos, $Pd(OAc)_2$ and 2,4,6-trichlorophenylformate as disclosed by Konishi et al, *Org. Synth.,* 2014, 90, 39 leads to a 2,4,6-trichlorophenylcarboxylate derivatives. In addition, 3-carboxamide, 3-thioester and 3-alkyl ester pyridine derivatives can be prepared from 2,4,6-trichlorophenylcarboxylate derivatives as disclosed by Manabe et al. in *Organic Letters,* 2012, 5370.

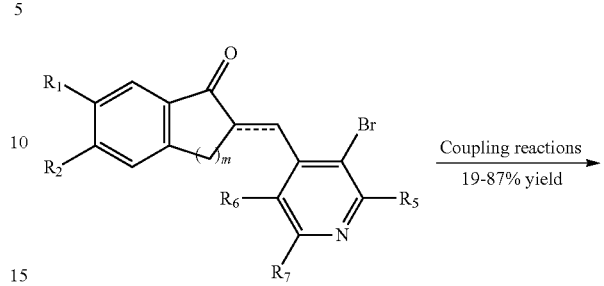

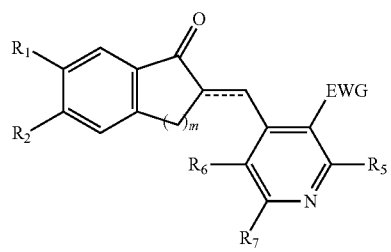

The following quaternisation is conducted as described in route A. For instance, a large variety of pyridium derivatives is synthesized from unsaturated and saturated 3-substituted-pyridine derivatives.

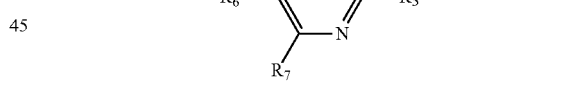

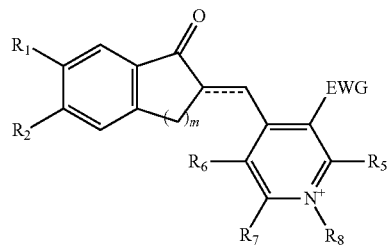

Regioselective reduction step with BNAH or sodium dithionite is also performed as reported in route A. Additionally, 1,2-dihydropyridine derivatives can also be obtained by reaction with sodium borohydride as disclosed by Kreevoy et al. in *Journal of Organic Chemistry,* 1983, 2053.

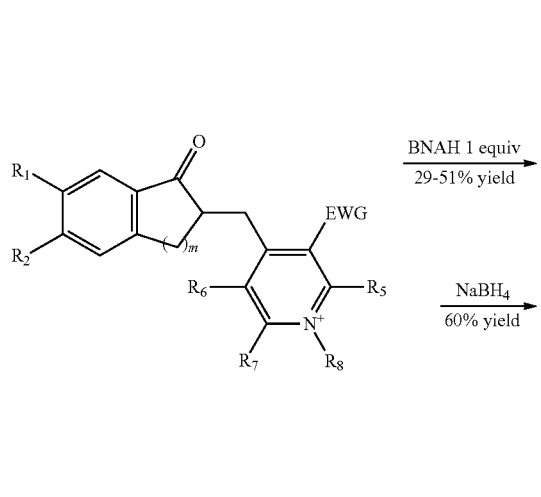 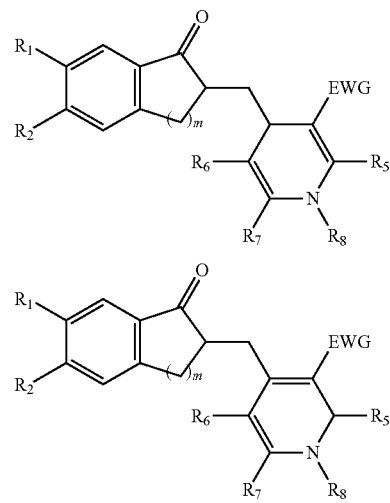

An object of the invention is also the pharmaceutical compositions comprising at least one of the compounds of formula (I) or (I+) according to the invention and/or their salts or tautomers or isomers, as active ingredient, in a safe and effective amount, in the pure state or in a combined form with one or more compatible and pharmaceutically acceptable diluents or adjuvants. Due to their specific structural design, the compounds of the invention and more particularly those of formula (II) are very convenient and stable enough to be formulated and stored.

These compositions can be administered by oral, rectal, parenteral or by local route such as a topical application on the skin and the mucous membranes. The compositions according to the invention can be solids or liquids. The solid compositions, are for example in the form of tablets, coated tablets, of pills, gelatine capsules, powders to be placed in solution or in suspension, or granules. The liquid compositions are for example injectable solutions or suspensions, drinkable solutions or suspensions, syrups, emulsions, elixirs containing diluents such as water or paraffin oil or in the form of suppositories, creams, ointments and lotions or also in the form of spray compositions.

The rectal compositions are suppositories or rectal capsules, containing, apart from the active ingredient, excipients such as cocoa butter, semi-synthetic glycerides or polyethylene glycols.

The compositions for topical administration can be for example patches transdermal patches creams, gels, containing compatible excipients such as silicone oil, paraffin, as well as the active ingredient.

These pharmaceutical forms are prepared according to the usual methods. Depending upon the composition, the active ingredient(s) can be incorporated with excipients usually used in pharmaceutical compositions, such as talc, arabic gum, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives. The compounds of the invention can also be formulated in the form of inclusion complex into beta-cyclodextrines, for instance into hydroxypropyl-betacyclodextrine. The inclusion complexes comprise at least one compound according to the invention with a beta-cyclodextrine.

The dose administered is variable according to the condition treated, the patient in question, the administration route and the product considered. A safe an effective amount can be, for example, comprised between 0.01 mg and 300 mg, preferably between 0.1 mg and 100 mg per day by oral, intramuscular or intravenous route in adults or also comprised between 0.01 mg and 1 mg per hour by percutaneous route.

The compounds of the present invention have been prepared according to the procedures described below in the examples section.

EXAMPLES

Example 1

Synthesis of 2-carbethoxy-5,6-dimethoxyindanone 2 ($C_{11}H_{12}O_3$—MW 192.21 g·mol$^{-1}$)

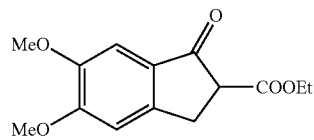 [SMILES: CCOC(=O)C1Cc2cc(OC)c(OC)cc2C1=O]

To a suspension of NaH 60% (1.37 g, 34.2 mmol) in THF (50 mL) was added diethylcarbonate (4.15 mL, 34.2 mmol). The mixture was stirred at reflux for 1 h 30 before indanone (3.29 g, 17.1 mmol) in THF (100 mL) was added at room temperature. The reaction was further stirred at reflux under argon for 3 h. At room temperature, ethyl acetate was then added, and the mixture was washed with a solution of acetic acid. The organic layer was dried over $Na_2SO_4$. Filtration and evaporation of the solvent under reduced pressure gave a residue, which was purified by flash silica chromatography ($CH_2Cl_2$/MeOH: 99.5/0.5). Evaporation of the solvent gave compound 2 as a white solid (3.5 g, 78%).

$^1$H NMR (CDCl$_3$, 300 MHz, 298 K, δ ppm): 7.17 (s, 1H), 6.90 (s, 1H), 4.23 (q, J=7.2 Hz, 2H), 3.97 (s, 3H), 3.89 (s, 3H), 3.69 (m, 1H), 3.48-3.22 (m, 2H), 1.3 (t, J=7.2 Hz, 3H).

[^13]C NMR (CDCl$_3$, 75.5 MHz, 298 K, δ ppm): 198.26, 169.62, 156.17, 149.87, 149.42, 128.14, 107.38, 104.94, 61.83, 56.47, 56.28, 53.73, 30.19, 14.36.

Example 2

Synthesis of 3-substituted 4-chloromethylpyridines

Example 2.1

Synthesis of 3-bromo-4-(hydroxymethyl)pyridine (C$_6$H$_6$BrNO—MW 188.02 g·mol$^{-1}$)

To a solution of 3-bromo-4-pyridinecarboxaldehyde 3 (3.0 g, 16.2 mmol) in absolute methanol (40 mL) was added NaBH$_4$ (0.736 g 19.5 mmol) at 0° C. The mixture was stirred at 0° C. for 2 hours under nitrogen. The solvent was then removed under vacuum. Water and ethyl acetate were added and the organic layer was washed with water, dried over Na$_2$SO$_4$ and evaporated under vacuum to afford the compound 4 (3.021 g, 100%) as a white powder.

[^1]H NMR (CDCl$_3$, 300 MHz, 298 K, δ ppm): 8.61 (s, 1H), 8.51 (d, 1H, J=4.8 Hz), 7.55 (d, 1H, J=4.8 Hz), 4.76 (s, 2H), 2.89 (s, 1H).

[^13]C NMR (CDCl$_3$, 75.5 MHz, 298 K, δ ppm): 151.14, 149.45, 148.54, 122.47, 119.90, 63.47.

GC/MS (m/z): 188

IR (KBr, ν, cm$^{-1}$): 3152, 2894, 2829, 1593, 1447, 1401, 1333, 1223, 1170, 1070, 1024, 834, 705, 599

Example 2.2

Synthesis of 3-bromo-4-(chloromethyl)pyridine hydrochloride 5 (C$_6$H$_6$BrCl$_2$N—MW 242.93 g·mol$^{-1}$)

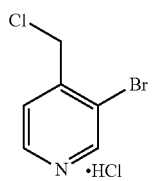

To a solution of 3-bromo-4-(hydroxymethyl)pyridine (1.6 g, 8.4 mmol) in methylene chloride (90 mL) was added thionyl dichloride (1.6 mL, 22.0 mmol) dropwise over at 0° C. The reaction was stirred at room temperature for 2 h and then concentrated. The yellow solid was dried in a vacuum to afford the compound 5 (2.05 g, 100%).

[^1]H NMR (CDCl$_3$, 300 MHz, 298 K, δ ppm): 8.96 (s, 1H), 8.88 (d, 1H, J=6 Hz), 8.17 (d, 1H, J=6 Hz), 4.81 (s, 2H).

[^13]C NMR (CDCl$_3$, 75.5 MHz, 298 K, δ ppm): 155.56, 143.52, 140.61, 127.14, 123.20, 43.88

Example 2.3

Synthesis of 4-formyl-N,N-diisopropylnicotinamide 7 (C$_{13}$H$_{18}$N$_2$O$_2$—MW 234.29 g·mol$^{-1}$)

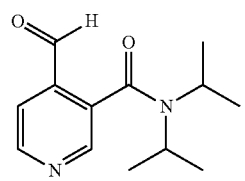

To a LiTMP solution prepared from BuLi (hexane solution, 5.02 mL, 10 mmol) and TMPH (1.7 mL, 10 mmol) in THF (24 mL) at −78° C. for 1 hour under an argon atmosphere, was slowly added N,N-diisopropylnicotinamide 6 (0.691 g, 3.3 mmol) and the mixture was stirred at −78° C. for 1 hour. After addition of DMF (1.03 mL, 13.3 mmol) the mixture was stirred for 1 hour. The mixture was allowed to warm at room temperature and stirred for an additional 30 mn. Saturated aqueous NH$_4$Cl solution was added and the mixture was extracted with DCM. The DCM extract was washed with brine and dried (Na$_2$SO$_4$). The residue was purified by silica gel column chromatography using EtOAc/Petroleum ether (3/7) as eluent to afford 7 (0.55 g, 70%).

[^1]H NMR (CDCl$_3$, 300 MHz, 298 K, δ ppm): 10.03 (s, 1H), 8.74 (d, 1H, J=4.8 Hz), 8.57 (s, 1H), 7.65 (d, 1H, J=4.8 Hz), 1.50 (d, 6H, J=6.7 Hz), 1.05 (d, 6H, J=6.7 Hz).

[^13]C NMR (CDCl$_3$, 75.5 MHz, 298 K, δ ppm): 189.77, 165.33, 150.40, 147.23, 137.42, 133.38, 121.67, 5124, 46.04, 20.24, 19.97.

Example 2.4

Synthesis of 3-(N,N-diisopropyl)-4-hydroxymethylnicotinamide 8 (C$_{13}$H$_{20}$N$_2$O$_2$—MW 236.31 g·mol$^{-1}$)

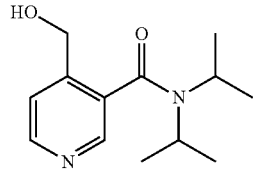 [SMILES: CC(C)N(C(=O)c1cnccc1CO)C(C)C]

To a solution of 7 (1.43 g, 6.1 mmol) in absolute methanol (15 mL) was added NaBH$_4$ (0.278 g, 7.3 mmol) at 0° C. The mixture was stirred at 0° C. for 2 hours under nitrogen. The solvent was then removed under vacuum. Water and CH$_2$Cl$_2$ were added and the organic layer was washed with water, dried over Na$_2$SO$_4$ and evaporated under vacuum to afford 8 (1.33 g, 92%) as a white powder.

¹H NMR (CDCl₃, 300 MHz, 298 K, δ ppm): 8.35 (d, 1H, J=5.1 Hz), 8.16 (s, 1H), 7.28 (d, 1H, J=8.4 Hz), 4.41 (m, 2H), 3.45 (m, 2H), 1.40 (s, 6H).

Example 2.5

Synthesis of 4-Chloromethyl-N,N-diisopropylnicotinamide hydrochloride 9 ($C_{13}H_{20}Cl_2N_2O$—MW 291.22 g·mol⁻¹)

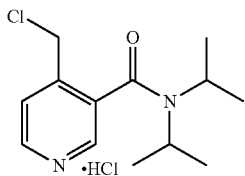 [SMILES: CC(C)N(C(=O)c1cnccc1CCl)C(C)C ; Cl]

To a solution of 8 (1.32 g, 5.6 mmol) in methylene chloride (90 mL) was added thionyl dichloride (1.06 mL, 14.6 mmol) dropwise over at 0° C. The reaction was stirred at room temperature for 2 h and then concentrated. The yellow solid was dried in a vacuum to afford 9 (1.59 g, 100%).

¹H NMR (CDCl₃, 300 MHz, 298 K, δ ppm): 8.50 (d, 1H, J=5.1 Hz), 8.36 (s, 1H), 7.32 (d, 1H, J=5.1 Hz), 4.54 (m, 2H), 3.55 (m, 2H), 1.47 (m, 6H), 1.09 (m, 6H).

¹³C NMR (CDCl₃, 75.5 MHz, 298 K, δ ppm): 149.64, 145.82, 142.78, 133.10, 124.10, 20.10, 51.02, 45.99, 41.16, 20.61, 21.16, 20.08

Example 2.6

Synthesis of 3-Bromo-4-tert-butyldimethylsilyloxymethylpridine 10 ($C_{12}H_{20}BrNOSi$—MW 302.28 g·mol⁻¹)

To a solution of 3-bromo-4-hydroxymethyl)pyridine 4 (1.593 g, 8.47 mmol) in dichloromethane (20 mL) was added imidazole (0.692 g, 10.17 mmol) and tert-butyldimethylsilyl chloride (1.534 g, 10.17 mmol) at 0° C. and the reaction mixture was stirred for 18 h at rt. The solution was extracted with DCM and the organic phase was washed with brine, dried and concentrated under vacuum. Purification by silica gel column chromatography using EtOAc/DCM (1/9) as eluent gave 10 (2.518 g, 98%).

¹H NMR (CDCl₃, 300 MHz, 298 K, δ ppm): 8.60 (s, 1H), 8.52 (d, 1H, J=4.8 Hz), 7.52 (d, 1H, J=4.8 Hz), 4.71 (s, 2H), 0.97 (s, 9H), 0.15 (s, 6H).

¹³C NMR (CDCl₃, 75.5 MHz, 298 K, δ ppm): 150.90, 149.67, 148.54, 122.19, 119.20, 63.78, 25.96, 18.43, −5.31.

GC/MS (m/z): [M-t-Butyl] 244.

IR (KBr, ν, cm⁻¹): 3046, 2953, 2887, 2857, 2709, 1926, 1789, 1737, 1587, 1472, 1445, 1397, 1373, 1360, 1261, 1172, 1114, 1079, 839, 778, 706, 673.

Example 2.7

Synthesis of 4-tert-Butyldimethylsilyloxymethylnicotinonitrile 11 ($C_{13}H_{20}N_2OSi$—MW 248.40 g·mol⁻¹)

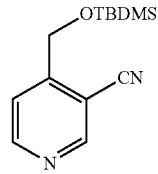 [SMILES: CC(C)(C)[Si](C)(C)OCc1ccncc1C#N]

First, $K_4[Fe(CN)_6]\cdot 3H_2O$ is grounded to a fine powder and dried under vacuum at 80° C. overnight. Then (0.366 g, 0.99 mmol) dry $K_4[Fe(CN)_6]$, (0.094 g, 0.49 mmol) copper iodide, (1.3 mL, 9.92 mmol) n-butylimidazole, toluene (7 mL) and (1.5 g, 4.96 mmol) 3-bromo-4-(tert-butyldimethylsilyloxy)methyl)pyridine 10 are placed in a pressure tube under argon. The pressure tube is sealed and heated at 160° C. for 3 days. After cooling to room temperature, $CH_2C_2$ and water are added. The solution is extracted with DCM and the organic phase is washed with EDTA, brine, dried on $Na_2SO_4$ and concentrated under vacuum. Purification by silica gel column chromatography using petroleum ether/DCM (3/7) as eluent gave 11 (0.937 g, 76%).

¹H NMR (CDCl₃, 300 MHz, 298 K, δ ppm): 8.81 (s, 2H), 7.64 (s, 1H), 4.90 (s, 2H), 0.95 (s, 9H), 0.14 (s, 6H).

¹³C NMR (CDCl₃, 75.5 MHz, 298 K, δ ppm): 15424, 153.28, 152.34, 120.99, 115.09, 25.88, 18.38, −5.38.

MS (ESI, MW g·mol⁻¹, m/z): [M+H⁺] 249.13

IR (KBr, ν, cm⁻¹): 2955, 2938, 2858, 2360, 2228, 1590, 1471, 1404, 1257, 1159, 1110, 1006, 842, 779.

Example 2.8

Synthesis of 4-Hydroxymethylnicotinonitrile 12 ($C_7H_6N_2O$—MW 134.14 g·mol⁻¹)

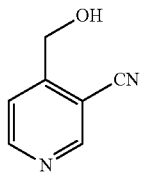

To a solution of 11 (1.161 g, 4.67 mmol) in THF (16 mL) was added a tetrabutylammonium fluoride solution in THF (7.01 mL, 7.01 mmol). After stirring for 1 h, ethyl acetate was added to the solution which was then washed with brine, dried on $Na_2SO_4$. Ethyl acetate was then removed under vacuum. Purification by silica gel column chromatography using DCM/MeOH (97/3) as eluent gave 12 (0.566 g, 91%).

¹H NMR (CDCl₃, 300 MHz, 298 K, δ ppm): 8.61 (s, 1H), 8.51 (d, 1H, J=5.1 Hz), 7.55 (d, 1H, J=5.1 Hz), 4.77 (s, 2H), 3.07 (s, 1H).

¹³C NMR (MeOH, 75.5 MHz, 298 K, δ ppm): 156.62, 153.89, 15331, 122.81, 115.86, 109.10, 61.89.
GC/MS (m/z): 134
IR (KBr, ν, cm⁻¹): 3152, 2894, 2829, 1593, 1447, 1401, 1333, 1223, 1170, 1070, 1024, 834.

Example 2.9

Synthesis of 4-Chloromethylnicotinonitrile hydrochloride 13 (C₇H₆Cl₂N₂—MW 189.04 g·mol⁻¹)

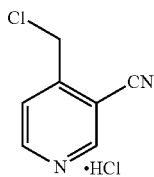

To a solution of 12 (1.06 g, 7.93 mmol) in methylene chloride (150 mL) was added thionyl chloride (1.5 mL, 20.6 mmol) dropwise over at 0° C. The reaction was stirred at room temperature for 18 h and then concentrated. The brown solid was dried under vacuum to afford 13 (1.47 g, 100%).

¹H NMR (MeOD, 300 MHz, 298 K, δ ppm): 9.44 (s, 1H), 9.17 (d, 1H, J=6 Hz), 8.37 (d, 1H, J=6 Hz), 5.10 (s, 2H).
¹³C NMR (MeOD, 75.5 MHz, 298 K, δ ppm): 159.52, 148.67, 148.29, 128.20, 113.65, 113.37, 42.62
GC/MS (m/z): [M–HCl] 152.
IR (KBr, ν, cm⁻¹): 3021, 2966, 2928, 2247, 2102, 1996, 1927, 1635, 1599, 1533, 1407, 1345, 1050, 840.

Example 3

Synthesis of (pyridyl)inden-1-one derivatives

Example 3.1

Synthesis of Ethyl 2-(3-bromopyridin-4-yl)methyl)-5,6-dimethoxy-1-oxo-2,3-dihydro-1H-indene-2-carbonylate 15 (C₂₀H₂₀BrNO₅—MW 434.28 g·mol⁻¹)

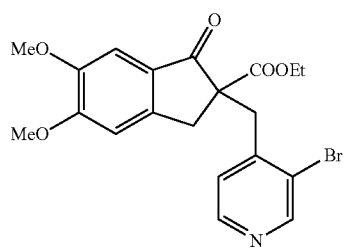 [SMILES: CCOC(=O)C1(Cc2ccncc2Br)Cc2cc(OC)c(OC)cc2C1=O]

A suspension of 2 (0.431 g, 1.64 mmol), potassium carbonate (0.614 g, 4.45 mmol), sodium iodide (0.123 g, 0.5 mmol) and 5 (0.480 g, 1.97 mmol) in 45 mL of acetone was refluxed for 6 hours and then diluted with ether at room temperature. After filtration over Celite, the filtrate was evaporated under vacuum to afford 15 (0.71 g, 100%)

¹H NMR (CDCl₃, 300 MHz, 298 K, δ ppm): 8.66 (s, 1H), 8.29 (d, 1H, J=5.1 Hz,), 7.18 (s, 1H), 7.14 (d, 1H, J=5.1 Hz), 6.80 (s, 1H), 4.20 (q, 2H, J=7.1 Hz), 3.95 (s, 3H), 3.92 (s, 3H), 3.75 (d, 1H, J=14.7 Hz), 3.60 (d, 1H, J=17.2 Hz), 3.42 (d, 1H, J=14.7 Hz), 2.97 (d, J=17.2 Hz, 1H), 1.22 (t, 3H, J=7.1 Hz).
¹³C NMR (CDCl₃, 75.5 MHz, 298 K, δ ppm): 199.97, 170.65, 156.45, 152.26, 149.95, 149.13, 148.29, 145.84, 128.47, 125.73, 124.73, 107.17, 103.96, 62.29, 61.10, 56.44, 56.25, 37.61, 35.23
MS (ESI⁺, MW g·mol⁻¹, m/z): [M+H⁺] 436

Example 3.2

Synthesis of Ethyl 2-(3-diisopropacarbamoylpyridin-4-yl)methyl-5,6-dimethoxy-1-oxo-2,3-dihydro-1H-indene-2-carboxylate 16 (C₂₇H₃₄N₂O₆—MW 482.57 g·mol⁻¹)

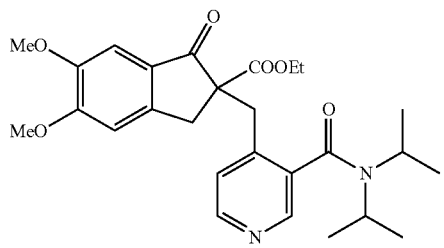 [SMILES: CCOC(=O)C1(Cc2ccncc2C(=O)N(C(C)C)C(C)C)Cc2cc(OC)c(OC)cc2C1=O]

A suspension of 2 (0.100 g, 0.38 mmol), potassium carbonate (0.142 g, 1.03 mmol), sodium iodide (0.028 g, 0.19 mmol) and 9 (0.133 g, 0.45 mmol) in 5 mL of acetone was refluxed for 6 hours and then diluted with ether at room temperature. After filtration over Celite, the filtrate was evaporated under vacuum to afford 16 (0.095 g, 51%)

¹H NMR (CDCl₃, 300 MHz, 298 K, δ ppm): 8.50-8.18 (m, 2H), 7.16 (m, 1H), 6.88 (m, 1H), 6.71 (s, 1H), 4.22-4.10 (m, 2H), 3.97 (s, 3H), 3.86 (s, 3H), 3.81-2.76 (m, 6H), 1.60-1.08 (m, 15H)
¹³C NMR (CDCl₃, 75.5 MHz, 298 K, δ ppm): 202.04, 199.51, 171.42, 170.50, 167.75, 167.47, 156.51, 156.22, 150.43, 149.86, 149.74, 149.67, 149.50, 149.07, 146.17, 146.01, 143.72, 141.50, 135.44, 128.68, 125.96, 124.31, 107.53, 107.29, 105.07, 104.44, 62.16, 61.90, 61.14, 60.46, 56.45, 56.28, 56.19, 56.15, 51.28, 46.30, 46.19, 35.82, 35.67, 35.20, 34.56, 20.97, 20.92, 20.88, 20.79, 20.71, 20.63, 20.35, 20.03, 14.13, 14.06
MS (ESI⁺, MW g·mol⁻¹, m/z): [M+H⁺] 483

Example 3.3

Synthesis of 2-(3-Bromopyridin-4-yl)methyl-5,6-dimethoxy-2,3-dihydro-1H-inden-1-one 19 (C₁₇H₁₆BrNO₃—MW 362.22 g·mol⁻¹)

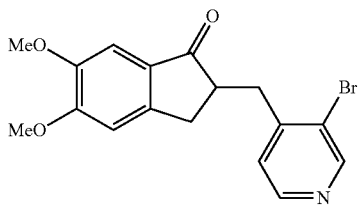 [SMILES: COc1cc2c(cc1OC)C(=O)C(Cc1ccncc1Br)C2]

Compound 15 (3.06 g, 7 mmol) was dissolved in 45 mL of ethanol, then 9 mL of water and (1.86 g, 28.15 mmol) of 85% potassium hydroxide were added hereinto, and was heated under reflux for 30 mn. The reaction mixture was cooled to room temperature, and was concentrated under reduced pressure, then 45 mL of water was added. Filtration of the precipitated solid and drying under vacuum afforded 19 (0.91 g, 36%).

$^1$H NMR (CDCl$_3$, 300 MHz, 298 K, δ ppm): 8.71 (s, 1H), 8.43 (d, 1H, J=5.0 Hz), 7.23 (d, 1H, J=5.0 Hz), 7.21 (s, 1H), 6.84 (s, 1H), 3.96 (s, 3H), 3.93 (s, 3H), 3.47 (m, 1H), 3.11 (m, 1H), 2.81 (m, 1H).

$^{13}$C NMR (CDCl$_3$, 75.5 MHz, 298 K, δ ppm): 205.13, 158.26, 152.15, 149.68, 148.51, 148.33, 128.89, 125.57, 107.41, 104.46, 56.33, 56.19, 46.78, 36.42, 31.80

MS (ESI$^+$, MW g·mol$^{-1}$, m/z): [M+H$^+$] 363

Example 3.4

Synthesis of 4-(5,6-Dimethoxy-1-oxo-2,3-dihydro-1H-inden-2-yl)methyl-N,N-diisopropylnicotinamide 20 (C$_{24}$O$_{30}$N$_2$O$_4$—MW 410.51 g·mol$^{-1}$)

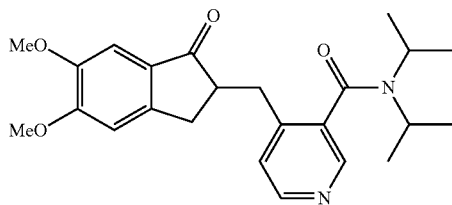 [SMILES: COc1cc2c(cc1OC)C(=O)C(Cc1ccncc1C(=O)N(C(C)C)C(C)C)C2]

Compound 16 (0.874 g, 1.8 mmol) was dissolved in 12 mL of ethanol, then 2.40 mL of water and (0.478 g, 7.24 mmol) of 85% potassium hydroxide were added hereinto, and was heated under reflux for 30 mn. The reaction mixture was cooled to room temperature, and was concentrated under reduced pressure, then 12 mL of water was added. Ethyl acetate was added to the solution which was then washed with brine, dried on Na$_2$SO$_4$. Ethyl acetate was then removed under vacuum. Purification by silica gel column chromatography using EtOAc/petroleum ether (90/10) as eluent gave 20 (0.301 g, 41%).

$^1$H NMR (CDCl$_3$, 300 MHz, 298 K, δ ppm): 8.57-8.34 (m, 2H), 7.36 (d, 0.5H, J=5.1 Hz), 7.18 (s, 1H): 7.12 (s, 0.5H, J=5.1 Hz), 6.83 (d, 1H, 15.9 Hz), 3.92 (m, 6H), 3.63-2.33 (m, 7H), 1.63-1.08 (m, 12H)

$^{13}$C NMR (CDCl$_3$, 75.5 MHz, 298 K, δ ppm): 205.75, 205.72, 167.65, 155.92, 155.72, 149.56, 149.48, 149.44, 148.96, 146.24, 146.16, 145.88, 144.77, 134.93, 134.87, 129.16, 128.53; 124.98, 123.76, 107.71, 107.48, 104.34, 56.33, 56.31, 56.15, 51.31, 51.26, 48.35, 47.62, 46.33, 46.21, 33.86, 33.37, 32.27, 31.62, 21.0, 20.88, 20.71, 20.59, 20.49, 20.41.

Example 3.5

Synthesis of 5,6-Dimethoxy-2-(pyridin-4-ylmethyl)-2,3-dihydro-1H-inden-1-one 18 (C$_{17}$H$_{17}$NO$_3$—283.32 g·mol$^{-1}$)

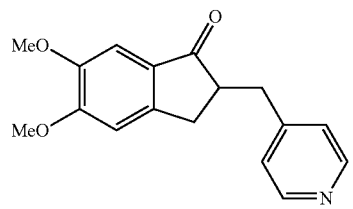 [SMILES: COc1cc2c(cc1OC)C(=O)C(Cc1ccncc1)C2]

Ethyl 2-(3-bromopyridin-4-yl)methyl)-5,6-dimethoxy-1-oxo-2,3-dihydro-1H-indene-2-carboxylate 14 (0.134 g, 0.37 mmol) was dissolved in 5 mL of ethanol, then 1 mL of water and (0.099 g, 1.51 mmol) of 85% potassium hydroxide were added hereinto, and was heated under reflux for 30 mn. The reaction mixture was cooled to room temperature, and was concentrated under reduced pressure, then 5 mL of water was added. Filtration of the precipitated crystal and drying afforded 18 (0.03 g, 29%).

$^1$H NMR (CDCl$_3$, 300 MHz, 298 K, δ ppm): 8.52 (s, 2H), 7.18 (s, 3H), 6.81 (s, 1H), 3.94 (s, 3H), 3.92 (s, 3H), 3.34 (m, 1H), 3.16-2.98 (m, 2H), 2.73-2.65 (m, 2H)

$^{13}$C NMR (CDCl$_3$, 75.5 MHz, 298 K, δ ppm): 205.66, 155.89, 149.97, 149.71, 148.91, 148.71, 129.06, 124.42, 107.44, 104.46, 56.22, 56.21, 48.03, 39.35, 36.59, 31.89.

Example 3.6

Synthesis of allyl 5,6-dimethoxy-1-oxo-2,3-dihydro-1H-indene-2-carboxylate 22 (C$_{15}$H$_{16}$rO$_5$—MW 276.28 g·mol$^{-1}$)

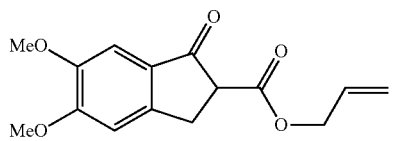 [SMILES: C=CCOC(=O)C1Cc2cc(OC)c(OC)cc2C1=O]

A solution 2 (1 g, 3.78 mmol), DMAP (46 mg, 0.37 mmol), and allyl alcohol (2.59 mL, 37.8 mmol) in dry toluene (20 mL) was heated at 100° C. for 24 h. The cooled solution was evaporated to dryness. Purification by silica gel column chromatography using petroleum ether/AcOEt (7/3) as eluent gave 22 (0.742 g, 71%).

$^1$H NMR (CDCl$_3$, 300 MHz, 298 K, δ ppm): 7.17 (s, 1H), 6.91 (s, 1H), 5.93 (m, 1H), 5.31 (m, 2H), 4.69 (m, 2H), 3.98 (s, 3H), 3.90 (s, 3H), 3.75 (m, 1H), 3.44 (m, 1H), 3.28 (m, 1H).

$^{13}$C NMR (CDCl$_3$, 75.5 MHz, 298 K, δ ppm): 197.89, 169.10, 156.10, 149.78, 149.26, 131.75, 127.95, 118.59, 107.29, 104.80, 66.13, 56.37, 56.15, 53.54, 30.08.

Example 3.7

Synthesis of allyl 2-(3-cyanopyridin-4-yl)methyl-5,6-dimethoxy-1-oxo-2,3-dihydro-1H-indene-2-carboxylate 17 (C$_{22}$H$_{20}$N$_2$O$_5$—MW 392.40 g·mol$^{-1}$)

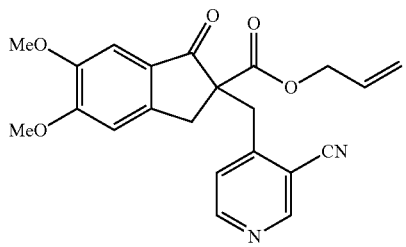 [SMILES: C=CCOC(=O)C1(Cc2ccncc2C#N)Cc2cc(OC)c(OC)cc2C1=O]

A suspension of 2 (0.670 g, 2.42 mmol), potassium carbonate (0.905 g, 6.54 mmol), sodium iodide (0.181 g, 1.21 mmol) and 13 (0.550 g, 2.9 mmol) in 97 mL of acetone was refluxed for 3 hours and then diluted with ether at room temperature. After filtration over Celite, the filtrate was evaporated under vacuum. Purification by silica gel column chromatography using petroleum ether/AcOEt (1/1) as eluent gave 17 (0.789 g, 83%).

$^1$H NMR (CDCl$_3$, 300 MHz, 298 K, δ ppm): 8.69 (s, 1H), 8.47 (d, 1H, J=5.4 Hz), 7.23 (d, 1H, J=5.4 Hz), 7.06 (s, 1H), 6.74 (s, 1H), 5.72 (m, 1H), 5.12 (m, 2H), 4.53 (d, 2H, J=5.4 Hz), 3.85 (s, 3H), 3.80 (s, 3H), 3.58 (m, 3H), 2.91 (d, 1H, J=17.4$^2$ Hz).

$^{13}$C NMR (CDCl$_3$, 75.5 MHz, 298 K, δ ppm): 198.82, 169.73, 156.43, 152.93, 152.46, 149.91, 149.57, 14837, 131.08, 127.13, 124.91, 118.67, 115.97, 111.77, 107.01, 104.73, 66.41, 60.91, 56.26, 56.02, 36.63, 35.44.

MS (ESI, MW g·mol$^{-1}$, m/z): [M+Na$^+$] 415.0

IR (KBr, ν, cm$^{-1}$): 3418, 2941, 2838, 2228, 1696, 1592, 1504, 1463, 1366, 1315, 1272, 1222, 1190, 1113, 1042, 996, 922, 866, 795, 516, 472.

Example 3.8

Synthesis of 4-(5,6-Dimethoxy-1-oxo-2,3-dihydro-1H-inden-2-yl)methylnicotinonitrile 21 (C$_{18}$H$_{16}$N$_2$O$_3$—MW 308.33 g·mol$^{-1}$)

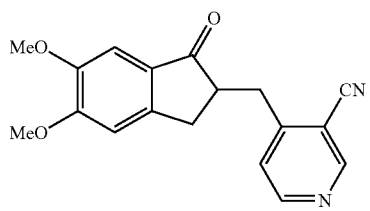 [SMILES: COc1cc2c(cc1OC)C(=O)C(Cc1ccncc1C#N)C2]

To a stirred solution of palladium acetate (3.136 mg, 0.014 mmol) and PPh$_3$ (7.3 mg, 0.028 mmol) in dry THF (1.2 mL) was added in one portion a mixture of formic acid (42.1 μL, 1.1 mmol) and Et$_3$N (0.194 mL, 1.39 mmol) in THF (0.6 mL) at room temperature under argon. The mixture was vigorously stirred and a solution of 17 (0.219 g, 0.55 mmol) in dry THF (0.3 mL) was added. The resulting mixture was stirred for additional 30 mn at rt and was heated at 70° C. for 2 h. The mixture was passed through a short SiO$_2$ column, followed by ether washing and EtOAc. After the filtrate was concentrated in vacuum, the residue was chromatographed on SiO$_2$ with EtOAc/petroleum ether (70/30) to afford 21 (0.116 g, 69%).

$^1$H NMR (CDCl$_3$, 300 MHz, 298 K, δ ppm): 8.84 (s, 1H), 8.69 (d, 1H, J=5.10 Hz), 7.38 d, 1H, J=5.10 Hz), 7.18 (s, 1H), 6.83 (s, 1H), 3.95 (s, 3H), 3.91 (s, 3H), 3.46 (m, 1H), 3.21 (m, 1H), 3.08 (m, 2H), 2.76 (m, 1H).

$^{13}$C NMR (CDCl$_3$, 75.5 MHz, 298 K, δ ppm): 204.28, 156.02, 153.13, 152.82, 152.68, 149.79, 148.24, 128.64, 124.48, 116.08, 110.98, 107.40, 104.44, 56.35, 56.17, 47.57, 34.92, 31.81

MS (ESI$^+$, MW g·mol$^{-1}$, m/z): [M+H$^+$] 309.2

IR (KBr, ν, cm$^{-1}$): 2932, 2837, 2227, 1690, 1590, 1502, 1463, 1319, 1264, 1220, 1118, 1036, 839.

Example 4

Synthesis of Quaternized Form

Example 4.1

Synthesis of 1-Benzyl-4-((5,6-dimethoxy-1-oxo-2,3-dihydro-1H-inden-2-yl)methyl)pyridinium iodide 23 (C$_{24}$H$_{24}$INO$_3$—MW 501.36 g·mol$^{-1}$)

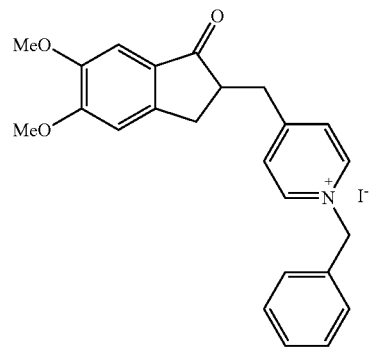

Compound 18 (0.030 g, 0.10 mmol) was dissolved in 6 mL of dichloromethane under reflux condition, (12.6 μL, 0.10 mmol) of benzyl bromide and (15.9 mg, 0.10 mmol) of sodium iodide were added hereinto. After keeping heating under reflux for 18 h, reaction mixture was cooled to room temperature, followed by concentration under reduced pressure. Pentane was added to the residue. Filtration of the precipitated crystal and drying afforded 23 (0.044 g, 83%).

$^1$H NMR (CDCl$_3$, 300 MHz, 298 K, δ ppm): 9.24 (s, 1H), 9.22 (s, 1H), 7.93 (s, 1H), 7.90 (s, 1H), 7.63 (m, 2H), 7.41 (m, 3H), 7.11 (s, 1H), 6.87 (s, 1H), 6.17 (s, 2H), 3.96 (s, 3H), 3.89 (s, 3H), 3.32 (m, 2H), 3.11 (m, 2H), 2.75 (m, 1H)

$^{13}$C NMR (CDCl$_3$, 75.5 MHz, 298 K, δ ppm): 204.23, 161.20, 156.37, 149.96, 148.56, 144.05, 132.37, 130.33, 129.94, 129.89, 129.84, 128.78, 128.37, 107.73, 104.37, 63.89, 58.68, 56.60, 56.26, 47.17, 37.20, 32.29.

MS (ESI$^+$, MW g·mol$^{-1}$, m/z): [M−I$^-$]$^+$ 374.2 ICs: 36.8 nM

Example 4.2

Synthesis of 1-Benzyl-3-bromo-4-(5,6-dimethoxy-1-oxo-2,3-dihydro-1H-inden-2-yl)methylpyridinium iodide 24 ($C_{24}H_{23}BrINO_3$—MW 580.25 g·mol$^{-1}$)

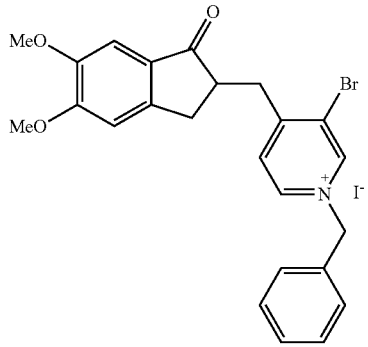

19 (0.290 g, 0.80 mmol) was dissolved in 41 mL of dichloromethane under reflux condition, (95.1 µL, 0.80 mmol) of benzyl bromide and (0.120 g, 0.80 mmol) of sodium iodide were added hereinto. After keeping heating under reflux for 18 h, reaction mixture was cooled to room temperature, followed by concentration under reduced pressure. Pentane was added to the residue. Filtration of the precipitated crystal and drying afforded 24 (0371 g, 80%).

$^1$H NMR (CDCl$_3$, 300 MHz, 298 K, δ ppm): 9.59 (s, 1H), 9.39 (d, 1H, J=6.3 Hz), 8.07 (d, 1H, J=6.3 Hz), 7.72 (s, 2H), 7.38 (s, 3H), 7.07 (s, 1H), 6.85 (s, 1H), 6.27 (s, 2H), 3.93 (s, 3H), 3.86 (s, 3H), 3.39 (m, 2H), 3.05 (m, 2H), 2.75 (d, 1H, J=16.5 Hz).

$^{13}$C NMR (CDCl$_3$, 75.5 MHz, 298 K, δ ppm): 203.84, 160.57, 156.17, 149.79, 148.43, 14533, 142.78, 132.11, 130.29, 129.76, 128.90, 128.15, 125.54, 107.62, 104.29, 63.34, 56.52, 56.18, 45.73, 37.65, 32.52.

MS (ESI$^+$, MW g·mol$^{-1}$, m/z): [M−I$^-$]$^+$ 454.3

IC$_{50}$: 11.5 nM

Example 4.3

Synthesis of 1-Benzyl-3-(N,N-diisopropylcarbamoyl)-4-(5,6-dimethoxy-1-oxo-2,3-dihydro-1H-inden-2-yl)methylpyridinium iodide 25 ($C_{31}H_{37}IN_2O_4$—MW 628.54 g·mol$^{-1}$)

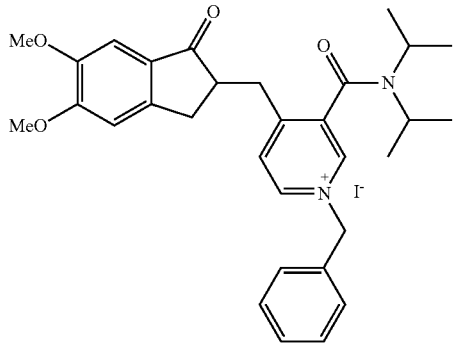

20 (0.150 g, 0.36 mmol) was dissolved in 19 mL of dichloromethane under reflux condition, (43.4 µL, 0.36 mmol) of benzyl bromide and (54.7 mg, 0.36 mmol) of sodium iodide were added hereinto. After keeping heating under reflux for 18 h, reaction mixture was cooled to room temperature, followed by concentration under reduced pressure. Pentane was added to the residue. Filtration of the precipitated crystal and drying afforded 25 (0.186 g, 81%).

$^1$H NMR (CDCl$_3$, 300 MHz, 298 K, δ ppm): 8.81 (s, 2H), 8.04 (dd, 1H, J=24.9 et 6.9 Hz), 7.51 (m, 5 Hz), 7.02 (m, 2H), 5.77 (s, 2H), 3.88 (s, 3H), 3.82 (s, 3H), 3.53-2.79 (m, 7H), 1.48 (m, 6H), 1.11 (m, 6H).

$^{13}$C NMR (CDCl$_3$, 75.5 MHz, 298 K, δ ppm): 204.80, 204.69, 163.39, 163.32, 159.23, 158.72, 157.04, 156.97, 150.68, 149.69, 149.58, 144.32, 144.17, 141.01, 139.48, 134.27, 134.22, 130.74, 130.53, 130.58, 130.36, 130.18, 129.18, 128.94, 108.87, 104.92, 64.31, 56.81, 56.44, 55.33, 52.51, 47.61, 47.47, 47.34, 47.28, 35.26, 34.90, 32.92, 32.62, 21.00, 20.79, 20.72, 20.61, 20.55, 20.39, 20.33.

MS (ESI$^+$, MW g·mol$^{-1}$, m/z): [M−I]$^+$ 501.4

Example 4.4

Synthesis of 1-Benzyl-3-cyano-4-(5,6-dimethoxy-1-oxo-2,3-dihydro-1H-inden-2-yl)methylpyridinium iodide 26 ($C_{25}H_{23}IN_2O_3$—MW 526.37 g·mol$^{-1}$)

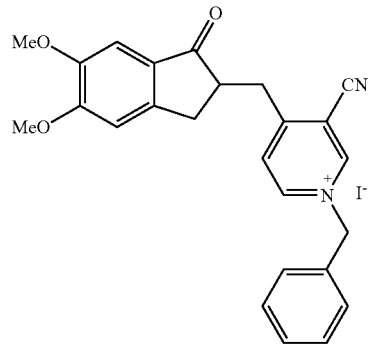

21 (0.050 g, 0.16 mmol) was dissolved in 8 mL of dichloromethane under reflux condition, (19.1 µL, 0.16 mmol) of benzyl bromide and (24.2 mg, 0.16 mmol) of sodium iodide were added hereinto. After keeping heating under reflux for 18 h, reaction mixture was cooled to room temperature, followed by concentration under reduced pressure. Pentane was added to the residue. Filtration of the precipitated crystal and drying afforded 26 (0.077 g, 92%).

$^1$H NMR (CDCl$_3$, 300 MHz, 298 K, δ ppm): 9.53 (s, 1H), 9.47 (s, 1H), 8.33 (s, 1H), 7.68 (s, 2H), 7.48 (s, 3H), 7.07 (s, 1H), 6.89 (s, 1H), 6.24 (s, 2H), 3.99 (s, 3H), 3.90 (s, 3H), 3.6-3.2 (m, 4H), 2.85 (m, 1H)

$^{13}$C NMR (CDCl$_3$, 75.5 MHz, 298 K, δ ppm): 203.79, 164.02, 156.37, 149.91, 148.51, 147.64, 147.32, 131.96, 130.51, 130.35, 129.97, 129.62, 128.02, 114.74, 112.52, 107.66, 104.40, 64.52, 56.56, 56.24, 46.99, 36.50, 32.70.

MS (ESI$^+$, MW g·mol$^{-1}$, m/z): [M−I$^-$]$^+$ 399.1

IR (KBr, ν, cm$^{-1}$): 3400, 2928, 2243, 1693, 1640, 1589, 1320, 1285, 1267, 1219, 1118, 1045, 1012, 722.

IC$_{50}$: 11.2 nM

Example 5

Reduction of Quaternized Forms

Example 5.1

Synthesis of 1-Benzyl-4-(5,6-dimethoxy-1-oxo-2,3-dihydro-1H-inden-2-yl)methyl-1,4-dihydropyridine-3-carbonitrile) 27 ($C_{25}H_{24}N_2O_3$—MW 400.47 g·mol$^{-1}$)

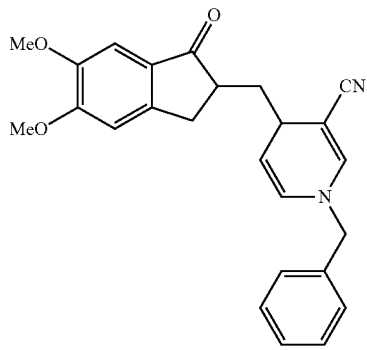 [SMILES: COc1cc2c(cc1OC)C(=O)C(CC1C=CN(Cc3ccccc3)C=C1C#N)C2]

To a solution of pyridinium salt 26 (0.100 g, 0.020 mmol) in dichloromethane (10 mL) was added N-benzyl-1,4-dihydronicotinamide (BNAH) (44.7 mg, 0.020 mmol) at room temperature under nitrogen and was stirred in darkness for 1 hour. The reaction mixture was then washed with water. After phase separation, the aqueous layer was extracted with dichloromethane. The combinated organic phases were dried over Na$_2$SO$_4$, filtered and evaporated under reduced pressure at room temperature. Purification by silica gel column chromatography using CH$_2$Cl$_2$/OEt-Ac (92/8) as eluent gave compound 27 (0.019 g, 23%).

$^1$H NMR (CDCl$_3$, 300 MHz, 298 K, δ ppm): 7.35 (m, 4H), 7.18 (m, 4H), 6.85 (s, 1H), 7.68 (d, 1H, J=5.4 Hz), 5.88 (m, 1H), 4.79 (m, 1H), 4.32 (d, 2H, J=3.6 Hz), 3.96 (s, 3H), 3.90 (s, 3H), 3.51 (m, 1H), 3.34 (m, 2H), 2.85 (m, 3H), 2.14 (m, 1H), 1.59 (m, 1H).

$^{13}$C NMR (CDCl$_3$, 75.5 MHz, 298 K, δ ppm): 207.70, 20731, 155.69, 155.63, 149.61, 149.54, 149.37, 148.96, 143.42, 143.00, 136.33, 129.27, 129.22, 128.99, 128.53, 128.41, 127.31, 127.29, 121.70, 121.29, 107.52, 107.49, 106.26, 105.12, 104.47, 104.41, 82.94, 82.61, 64.56, 57.68, 57.64, 56.39, 56.25, 44.38, 43.80, 41.65, 40.07, 33.95, 33.95, 33.18, 32.29, 32.07, 30.30, 30.17, 29.51, 29.46, 27.35, 24.92, 22.84, 22.48, 14.27, 14.21

IC$_{50}$: 175 nM

Example 5.2

Synthesis of I-benzyl-1,4-dihydropyridine-3-carboxamide ($C_{13}H_{14}N_2O$—MW 214.11 g·mol$^{-1}$)

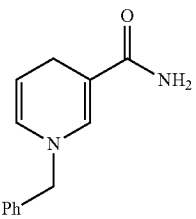

To a solution of 1-benzylpyridinium-3-carboxamide iodide (1 g, 3.41 mmol) in H$_2$O (15 mL) was added sodium carbonate (1.44 g, 13.64 mmol) and sodium dithionite (2.65 g, 12.96 mmol) at room temperature. The resulting solution was stirred under nitrogen in darkness for 15 mn. The reaction mixture was then extracted with dichloromethane. The combined organic phases were dried over Na$_2$SO$_4$, filtered and evaporated under reduced pressure at room temperature to afford N-benzyl-1,4-dihydronicotinamide (BNAH) (0.530 g, 73%).

$^1$H NMR (CDCl$_3$, 300 MHz, 298 K, δ ppm): 7.34 (m, 5H), 7.26 (s, 1H), 5.75 (d, 1H, J=8.10 Hz), 5.38 (s, 2H), 4.76 (m, 1H), 4.30 (s, 2H), 3.19 (s, 2H).

$^{13}$C NMR (CDCl$_3$, 75.5 MHz, 298 K, δ ppm): 140.15, 13737, 129.09, 128.95, 127.92, 127.29, 103.34, 98.75, 57.52, 22.97.

Example 6

Preparation of 1-Benzyl-4-(5,6-dimethoxy-1-oxo-2,3-dihydro-1H-inden-2-yl)methyl-1,4-dihydropyridine-3-acetyl (34)

Route A

Synthesis of 3-(1-acetyl-4-(5,6-Dimethoxy-1-oxo-2,3-dihydro-1H-inden-2-yl)methylpyridine (32)

This compound was prepared using the method taught in Legros et al.; *Tetrahedron*, 2001, 2507.

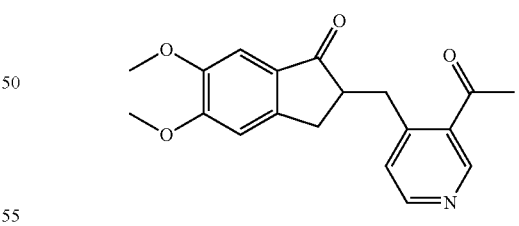

A solution of compound 19 (181 mg, 0.5 mmol) in toluene (1.5 mL), Pd(dba)$_2$ (12 mg, 0.02 mmol) and PPh$_3$ (11 mg, 0.04 mmol) was stirred at room temperature under argon for 15 min. (1-ethoxyvinyl)tri(n-butyl)stannane (180 mg, 0.5 mmol) in toluene (1 mL) was added and the resulting mixture was stirred at 110° C. for 2 h, cooled to room temperature, then 55 mL of HCl (0.1 N) were added. After 3 h stirring, the reaction mixture was neutralized with NaHCO$_3$ until pH=7-8 and extracted three times with AcOEt. The combined organic layers were dried (MgSO$_4$), filtered and concentrated. Purification on silica gel afforded the product 32 in 65% yield.

¹H NMR (300 MHz, CDCl₃, δ): 2.67 (s, 3H), 2.74-2.80 (m, 1H), 3.05-3.18 (m, 3H), 3.48-3.53 (s, 1H), 3.91 (s, 3H), 3.95 (s, 3H), 6.82 (s, 1H), 7.18 (s, 1H), 7.30 (d, 1H, J=5.1 Hz), 8.60 (d, 1H, J=5.1 Hz), 8.97 (s, 1H).

Synthesis of 1-Benzyl-3-actyl-4-(5,6-dimethoxy-1-oxo-2,3-dihydro-1H-inden-2-yl)methyl pyridinium bromide (33)

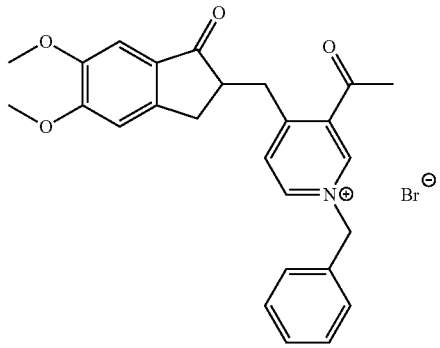 [SMILES: COc1cc2c(cc1OC)C(=O)C(Cc1cc[n+](Cc3ccccc3)cc1C(C)=O)C2 ; [Br-]]

The pyridine 32 (45 mg, 0.14 mmol) was dissolved in dichloromethane (1 mL). Benzyl bromide (17 μL, 0.14 mmol) was added and the solution was heated under reflux for 12 h. Concentration under reduced pressure and washings with n-pentane afforded the product 33 as a pale brown powder in 95% yield.

¹H NMR (300 MHz, CDCl₃, δ): 2.72-2.79 (m, 1H), 3.01-3.07 (m, 4H), 3.30-3.47 (m, 3H), 3.88 (s, 3H), 3.96 (s, 3H), 6.46 (s, 2H), 6.84 (s, 1H), 7.06 (s, 1H), 7.39-7.41 (m, 3H), 7.72-7.75 (m, 2H), 7.96 (d, 1H, J=6.4 Hz), 9.18 (d, 1H, J=6.2 Hz), 10.4 (s, 1H).

HRMS (ESI): calcd. For C₂H₂NO₄ 416.1862. found 416.1865.

IR: 1693, 1584, 1500, 1463, 1266, 1246, 1205, 1115, 04, 1018, 848, 799, 721, 697.

IC50: 18 nM.

Binding to the PAS: 23% of Propidium Iodide Displacement (donepezil 24%)

Measurement of Propidium Iodide Displacement from the Peripheral Anionic Site (PAS) of AChE was achieved according to the procedure reported in *Journal of Medicinal Chemistry*, 2009, 52, 7249.

Synthesis of 1-Benzyl-4-(5,6-dimethoxy-1-oxo-2,3-dihydro-1H-inden-2-yl methyl-1,4-dihydropyridine-3-acetyl

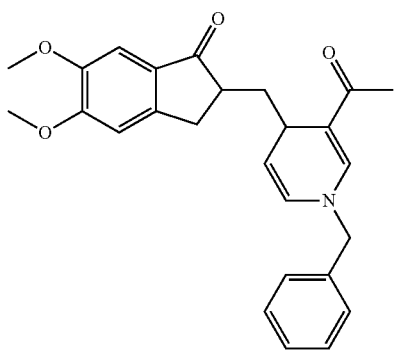 [SMILES: COc1cc2c(cc1OC)C(=O)C(CC1C=CN(Cc3ccccc3)C=C1C(C)=O)C2]

To a solution of pyridinium salt 33 (292 mg, 0.59 mmol) in CH₂Cl₂ (6 mL) was added N-benzyl-1,4-dihydronicotinamide (BNAH) (126 mg, 0.59 mmol) at room temperature under Argon. The resulting solution was stirred in darkness for 3 h. The reaction mixture was washed with H₂O, dried over MgSO₄, filtered and concentrated under reduced pressure. Flash chromatography on silica gel afforded the dihydropyridine 34 in 40% yield.

¹H NMR (300 MHz, CDCl₃, δ): 1.36-1.46 (m, 0.6H), 1.48-1.58 (m, 0.4H), 1.89-2.03 (m, 1H), 2.15 (s, 1.8H), 2.21 (s, 1.2H), 2.62-2.71 (m, 0.4H), 2.74-2.82 (m, 1H), 3.02-3.09 (m, 0.6H), 3.17-3.3 (m, 1H), 3.58-3.64 (m, 0.6H), 3.71-3.77 (m, 0.4H), 3.88 (m, 3H), 3.94-3.95 (m, 3H), 4.46 (s, 2H), 4.92-4.97 (m, 0.4H), 5.08-5.13 (m, 0.6H), 5.92-5.97 (m, 1H), 6.83 (s, 0.4H), 6.88 (s, 0.6H), 7.13-7.41 (m, 7H).

¹³C NMR (75 MHz, CDCl₃, δ): 24.49, 24.64, 29.18, 29.32, 29.72, 32.62, 33.89, 40.31, 41.16, 44.15, 45.11, 56.10, 56.24, 57.87, 57.96, 104.25, 104.28, 107.43, 107.63, 108.37, 109.99, 113.27, 113.89, 127.02, 128.12, 128.23, 129.07, 129.09, 129.39, 129.41, 136.70, 142.76, 143.25, 149.32, 149.60, 149.66, 155.36, 155.43, 194.87, 195.40, 208.26, 208.37.

HRMS (ESI): calcd. For C₂₆H₂NO₄ 418.2018. found 416.2014.

IR: 2857, 1679, 1573, 1504, 1308, 1261, 1185, 1174, 1119, 981.

IC50: 528 nM.

Example 7

Preparation of N-[(3-acetyl-1-benzyl-1,4-dihydropyridin-4-yl)methyl]-3,4-dimethoxy-N-phenylbenzamide (31)

Route B

Synthesis of N-allyl-N-phenyl-3,4-dimethoxybenzamide (28)

This compound was prepared using the method taught in Li at al.; *Organic Letters*, 2012, 14, 214.

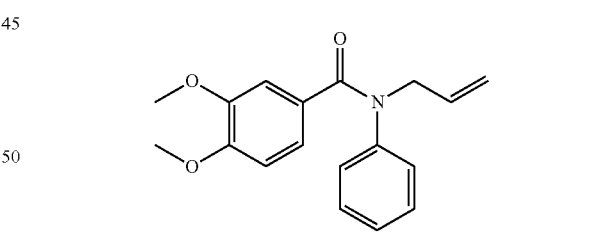

To a nitrogen flushed, three necked flask equipped with a dropping funnel was added N-allylaniline (2 mL, 15 mmol) and dry toluene (10 mL). To the solution was added a solution of trimethylaluminium (2M, 7.5 mL, 15 mmol) in toluene. The reaction was stirred at room temperature for 30 min. and 3,4-dimethoxybenzoic acid was added in one-portion. The reaction mixture was then heated at 80° C. for 18 hours. After the reaction mixture was quenched with MeOH (5 mL) dropwise followed by addition of a saturated NaHCO₃ solution (50 mL). The resulting slurry was then extracted with EtOAc and the combined organic extracts were washed with NaOH (1 N), HCl (2 N), brine (20 mL) and then concentrated in vacuo to give a reddish oil (0.57 g) which was subjected to a flash column using petroleum ether/EtOAc as eluent to give the desired N-allyl-N-phenyl-3,4-dimethoxybenzamide 28 in 78% yield.

$^1$H NMR (300 MHz, CDCl$_3$, δ): 3.65 (s, 3H), 3.81 (s, 3H), 4.53 (dt, 2H, J=6 Hz, J=1.5 Hz), 5.15-5.23 (m, 2H), 5.95-6.04 (m, 1H), 6.62 (d, 1H, J=8.4 Hz), 6.88 (d, 1H, J=2.1 Hz), 6.94 (dd, 1H, J=8.4 Hz, J=2.1 Hz), 7.03-7.06 (m, 2H), 7.15-7.17 (m, 1H), 7.21-7.26 (n, 2H).

$^{13}$C NMR (75 MHz, CDCl$_3$, δ): 53.57, 55.76, 55.85, 109.95, 112.59, 117.62, 122.97, 126.52, 127.47, 127.94, 129.19, 133.41, 144.38, 147.97, 150.34, 169.56.

Synthesis of 3,4-dimethoxy-N-(4-oxobut-2-enyl-N-phenylbenzamide (29)

This compound was prepared using the method taught in Roe et al.; *Chemical Communication*, 2009, 4399.

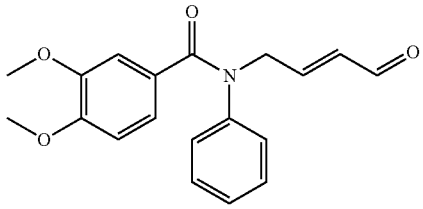 [SMILES: COc1ccc(C(=O)N(C/C=C/C=O)c2ccccc2)cc1OC]

To a solution of N-allyl-N-phenyl-3,4-dimethoxybenzamide 28 (567 mg, 1.91 mmol) in dichloromethane (15 mL) under argon was added sequentially crotonaldehyde (0.47 mL, 5.73 mmol) and Hoveyda-Grubbs second generation catalyst (31 mg, 0.05 mmol). The mixture was then heated at 50° C. and stirred for 22 hours. Then, the solution was filtered on a Celite pad and the solvent was evaporated under reduced pressure. The resulting oil was purified on silica gel (petroleum ether/EtOAc: 7/3 to 5/5) to afford the product 29 (330 mg, 53%).

$^1$H NMR (300 MHz, CDCl$_3$, δ): 3.65 (s, 3H), 3.82 (s, 3H), 4.79 (dd, 2H, J=5.4 Hz, J=1.8 Hz), 6.25 (ddt, 1H, J=15.9 Hz, J=7.8 Hz, J=1.5 Hz), 6.63 (d, 1H, J=8.4 Hz), 6.87 (d, 1H, J=1.8 Hz), 6.91-7.05 (m, 4H), 7.15-7.29 (m, 3H), 9.57 (d, 1H, J=7.8 Hz).

$^{13}$C NMR (75 MHz, CDCl$_3$, δ): 52.13, 55.73, 55.85, 109.96, 112.46, 123.18, 126.75, 126.98, 127.04, 129.56, 133.27, 143.95, 148.02, 150.71, 151.83, 169.70, 193.26.

Synthesis of 4-(benzylamino)but-3-en-2-one (30)

This compound was prepared using the method taught in Girling et al.; *Chemical Communication*, 2012, 48, 4893.

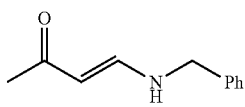

A mixture of benzylamine (1.1 mL, 10 mmol) and 4-methoxybut-3-en-2-one (1 mL, 10 mmol) in chloroform (100 mL) was stirred at room temperature until complete conversion. Then, the solvent was evaporated to afford the desired product 30 in 70% yield which was used without additional purification.

$^1$H NMR (300 MHz, CDCl$_3$, δ): 2.00 (s, 3H), 4.30 (d, 2H, J=6 Hz), 4.98 (d, 1H, J=7.5 Hz), 6.64 (dd, 1H, J=12.9 Hz, J=7.5 Hz), 7.23 (m, 6H).

HRMS (ESI$^+$), calcd for C$_{11}$H$_{14}$NO 176.10699 found 176.10685.

Synthesis of N-[(3-acetyl-1-benzyl-1,4-dihydropyridin-4-yl)methyl]-3,4-dimethoxy-N-phenylbenzamide (31)

This compound was prepared using the method taught in Bartoli et al.; *SYNLETT*, 2007, 2897

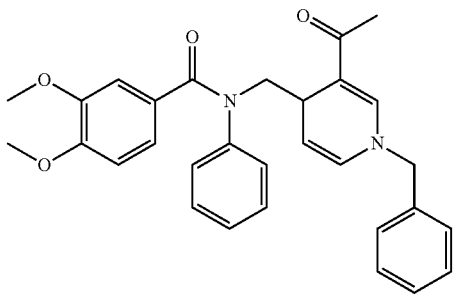 [SMILES: COc1ccc(C(=O)N(CC2C=CN(Cc3ccccc3)C=C2C(C)=O)c2ccccc2)cc1OC]

Mg(ClO$_4$)$_2$ (9 mg, 0.04 mmol), MgSO$_4$ (10 mg, 8 mmol) and 4-(benzylamino)but-3-en-2-one 30 (70 mg, 0.4 mmol) was suspended in dry dichloromethane (0.5 mL) and the aldehyde 29 (163 mg, 0.5 mmol) was added. The mixture was stirred at room temperature until completion of the reaction. The crude reaction mixture was filtered on celite and the solvent was removed by rotary evaporation. The dihydropyridine 31 was purified on silica gel (petroleum ether/EtOAc/ 5% Et$_3$N).

$^1$H NMR (300 MHz, CDCl$_3$, δ): 2.03 (s, 3H), 3.63 (s, 3H), 3.80 (s, 3H), 3.92 (t, 1H, J=5.1 Hz), 4.03-4.06 (m, 2H), 4.42 (s, 2H), 5.03 (dd, 114, J=7.8, 4.8 Hz), 5.97 (dd, 1H, J=7.8, 1.2 Hz), 6.62 (d, 1H, J=8.4 Hz), 6.80 (d, 1H, J=1.8 Hz), 6.90 (dd, 1H, J=8.4, 2.1 Hz), 6.98 (d, 1H, J=1.2 Hz), 7.06-7.42 (m, 10H).

$^{13}$C NMR (75 MHz, CDCl$_3$, δ): 24.5, 312, 54.0, 55.7, 55.8, 57.8, 108.0, 109.8, 111.3, 112.4, 122.7, 126.0, 127.12, 1273, 128.1, 128.4, 128.6, 128.8, 129.1, 136.7, 143.3, 144.3, 147.8, 149.9, 170.4, 195.4.

Example 8

Preparation of [N-[2-(3-acetyl-1-benzyl-4H-pyridin-4-yl)ethyl]-3,4-dimethoxy-N-phenyl-benzamide (32)

Step A: Synthesis of 3,4-dimethoxy-N-phenyl-benzamide (33)

The title compound is prepared as reported by Narasimhan et al. in *European Journal of Medicinal Chemistry*, 2009, 689.

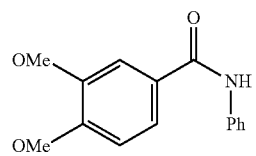 [SMILES: COc1ccc(C(=O)Nc2ccccc2)cc1OC]

$^1$H NMR (300 MHz, CDCl$_3$, δ): 3.94 (s, 3H), 3.95 (s, 3H), 6.91 (d, 1H, J=8.4 Hz), 7.11-7.17 (m, 1H), 7.34-7.41 (m, 3H), 7.50 (d, 1H, J=2.1 Hz), 7.60-7.65 (m, 2H), 7.79 (br s, 1H).

$^{13}$C NMR (75 MHz, CDCl$_3$, δ): 56.0, 56.1, 110.3, 110.7, 119.6, 120.3, 124.4, 127.5, 129.1, 138.2, 149.1, 152.0, 165.5.
MS (ESI$^+$): 258.11 (M+H$^+$)

Step B: Synthesis of N-but-3-enyl-3,4-dimethoxy-N-phenyl-benzamide (34)

This compound was prepared using the method described by Kumar et al. in *Tetrahedron* 2011, 67, 4093.

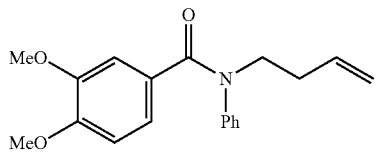 [SMILES: C=CCCN(C(=O)c1ccc(OC)c(OC)c1)c1ccccc1]

To a solution of 3,4-dimethoxybenzanilide 33 (771 mg, 3 mmol) and KOH (4 equiv) in DMSO (6 mL) was added but-3-enyl 4-methylbenzenesulfonate (2.85 g, 4 equiv) [prepared as reported in the Journal of the American Chemical Society 2009, 6003] at room temperature and the mixture was heated at 80° C. for 72 h. The mixture was cooled, taken up in EtOAc and washed twice with water. The organic layer was dried over magnesium sulfate, filtered and concentrated to dryness. The residue was purified by column chromatography on SiO$_2$ (gradient of diethylether in petroleum ether) to afford the title compound 34 (Yield 467 mg, 50%).

$^1$H NMR (300 MHz, CDCl$_3$, δ): 2.39-2.44 (m, 2H), 3.63 (s, 3H), 3.80 (s, 3H), 3.96-4.01 (m, 2H), 5.02-5.10 (m, 2H), 5.78-5.84 (m, 1H), 6.61 (d, 1H, J=8.4 Hz), 6.83 (d, 1H, J=2.1 Hz), 6.90 (dd, 1H, J=8.4 Hz, J=1.8 Hz), 7.03-7.06 (m, 2H), 7.15-7.28 (m, 3H).
MS (ESI$^+$): 312.16 (M+H$^+$)

Step C: Synthesis of 3,4-dimethoxy-N-[(E)-5-oxo-pent-3-enyl]-N-phenyl-benzamide (35)

This compound was prepared using the method described by Stockman et al. in *Chem. Commun.*, 2009, 4399.

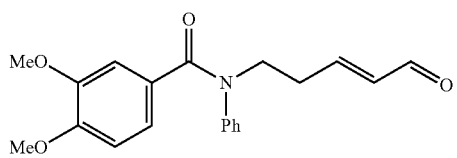 [SMILES: COc1ccc(C(=O)N(CC/C=C/C=O)c2ccccc2)cc1OC]

Crotonaldehyde (0.5 mL, 3 equiv) was added to a solution of compound 34 (608 mg, 1.95 mmol) in degassed CH$_2$Cl$_2$ (17 mL). Hoveyda-Grubbs' 2$^{nd}$ (31 mg, 2.5% mol) was added and the reaction mixture was heated to 40° C. under Ar atmosphere overnight. The reaction mixture was filtered over Celite and the filtrate was concentrated to dryness. The residue was purified by column chromatography on SiO$_2$ (Petroleum ether/EtOAc=2:3) to afford the title compound 35 as white solid (Yield 644 mg, 97%).

$^1$H NMR (300 MHz, CDCl$_3$, δ): 2.65-2.72 (m, 2H), 3.62 (s, 3H), 3.80 (s, 3H), 4.09-4.15 (m, 2H), 6.12 (dd, 1H, J=15.6 Hz, J=7.8 Hz), 6.61 (d, 1H, J=8, 4 Hz), 6.80-6.91 (m, 3H), 7.00-7.03 (m, 2H), 7.15-7.29 (m, 3H), 9.48 (d, 1H, J=7.8 Hz).
$^{13}$C NMR (75 MHz, CDCl$_3$, δ): 31.3, 48.7, 55.6, 55.8, 109.9, 112.3, 122.9, 126.8, 127.4, 127.6, 129.4, 1342, 143.5, 147.8, 150.3, 154.9, 169.9, 193.8.
MS (ESI$^+$): 340.15 (M+H$^+$)

Step D: Synthesis of N-[2-(3-acetyl-1-benzyl-4H-pyridin-4-yl)ethyl]-3,4-dimethoxy-N-phenyl-benzamide (32)

This compound was prepared using the method described by Renaud et al. in *Adv. Synth. Catal.*, 2006, 2571.

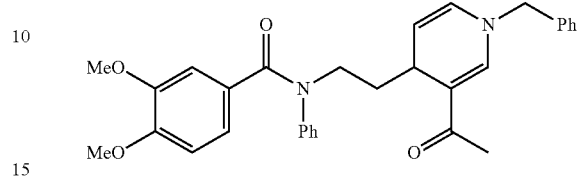

To a suspension of Sc(OTf)$_3$ (10% mol), Na$_2$SO$_4$ (3 equiv) in dry CH$_2$Cl$_2$ (15 mL) is added a solution of enamine 30 (332 mg, 1.9 mmol) and enal 35 (644 mg, 1.9 mmol) in dry CH$_2$Cl$_2$ (5 mL). The reaction mixture was stirred at room temperature for 48 h. The reaction solution is filtered on Celite and the solvent removed under pressure. The residue obtained is purified on SiO$_2$ (gradient of EtOAc in Petroleum ether) to afford the title compound 32 as a yellow oil (Yield 551 mg, 58%).

$^1$H NMR (300 MHz, CDCl$_3$, δ): 1.75-1.78 (m, 2H), 2.17 (s, 3H), 3.61-3.80 (m, 2H), 3.65 (s, 3H), 3.80 (s, 3H), 4.10-4.18 (m, 1H), 4.46 (s, 2H), 5.13 (dd, 1H, J=7.8 Hz, J=5.1 Hz), 5.95 (dd, 1H, J=7.2 Hz, J=1.2 Hz), 6.63 (d, 1H, J=8, 1 Hz), 6.86 (d, 1H, J=1.8 Hz), 6.93 (dd, 1H, J=8.4 Hz, J=2.1 Hz), 7.09-7.40 (m, 11H).
$^{13}$C NMR (75 MHz, CDCl$_3$, δ): 24.5, 28.7, 35.4, 47.2, 55.7, 55.8, 57.8, 109.3, 109.8, 112.3, 112.6, 122.6, 126.4, 127.0, 127.6, 127.7, 128.0, 128.1, 129.0, 129.1, 136.8, 143.3, 144.2, 147.7, 149.9, 169.6, 195.0.
MS (ESI$^+$): 497.24 (M+H$^+$)

Example 9

N-[3-(3-acetyl-1-benzyl-4H-pyridin-4-yl)propyl]-3,4-dimethoxy-N-phenyl-benzamide (36)

Step A: Synthesis of 3,4-dimethoxy-N-pent-4-enyl-N-phenyl-benzamide (37)

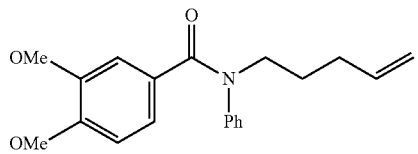 [SMILES: C=CCCCN(C(=O)c1ccc(OC)c(OC)c1)c1ccccc1]

To a solution of 3,4-dimethoxybenzanilide 33 (1.28 g, 5 mmol) and anhydrous cesium carbonate (4 equiv) in a mixture of anhydrous THF (14 mL) and DMF (56 mL) was added 5-bromo-pent-1-ene (2.85 g, 4 equiv) at room temperature and the mixture was heated at 80° C. for 72 h. The mixture was cooled, taken up in EtOAc and washed twice with water then brine. The organic layer was dried over magnesium sulfate, filtered and concentrated to dryness. The residue was purified by column chromatography on SiO$_2$ (gradient of diethyl ether in petroleum ether) to afford the title compound 37 as a yellow oil (Yield 1.0 g, 62%).

¹H NMR (300 MHz, CDCl₃, δ): 1.72-1.77 (m, 2H), 2.07-2.12 (m, 2H), 3.64 (s, 3H), 3.79 (s, 3H), 3.90-3.95 (m, 2H), 4.92-5.02 (m, 2H), 5.74-5.80 (m, 1H), 6.62 (d, 1H, J=8.4 Hz), 6.83 (d, 1H, J=1.8 Hz), 6.90 (dd, 1H, J=8.4 Hz, J=2.1 Hz), 7.03-7.06 (m, 2H), 7.15-7.28 (m, 3H).

¹³C NMR (75 MHz, CDCl₃, δ): 26.7, 31.1, 50.2, 55.6, 55.7, 109.7, 112.3, 114.9, 122.7, 126.4, 127.5, 128.1, 129.1, 137.7, 114.0, 147.7, 150.0, 169.5.

MS (ESI⁺): 326.17 (M+H⁺)

Step B: Synthesis of 3,4-dimethoxy-N-[(E)-6-oxo-hex-4-enyl]-N-phenyl-benzamide (38)

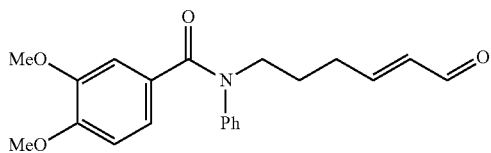 [SMILES: COc1ccc(C(=O)N(CCC/C=C/C=O)c2ccccc2)cc1OC]

The title compound 38 is prepared according to the procedure reported in step C of Example 8 with amide 33 (975 mg, 3 mmol) and crotonaldehyde (9 mmol, 3 equiv) as reactants. (Yield 1.02 g, 97%).

¹H NMR (300 MHz, CDCl₃, δ): 1.81-1.86 (m, 2H), 2.35-2.43 (m, 2H), 3.62 (s, 3H), 3.78 (s, 3H), 3.94-3.98 (m, 2H), 6.07 (dd, 1H, J=15.6 Hz, J=6.6 Hz), 6.60 (d, 1H, J=8, 4 Hz), 6.78-6.91 (m, 3H), 7.00-7.03 (m, 2H), 7.16-7.28 (m, 3H), 9.47 (d, 1H, J=8.1 Hz).

¹³C NMR (75 MHz, CDCl₃, δ): 25.6, 29.9, 49.7, 55.5, 55.6, 109.6, 112.1, 122.7, 126.5, 127.3, 127.5, 1292, 133.0, 143.6, 147.6, 150.0, 157.3, 169.6, 193.8.

MS (ESI⁺): 354.17 (M+H⁺)

Step C: Synthesis of N-[3-(3-acetyl-1-benzyl-4H-pyridin-4-yl)propyl]-3,4-dimethoxy-N-phenyl-benzamide (36)

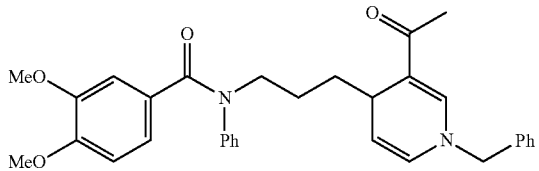 [SMILES: COc1ccc(C(=O)N(CCCC2C=CN(Cc3ccccc3)C=C2C(C)=O)c2ccccc2)cc1OC]

The title compound 36 is prepared according to the procedure reported in step D of Example 8 with aldehyde 38 (706 mg, 2 mmol) and enamine 30 (350 mg, 2 mmol) as reactants. (Yield 360 mg, 35%).

¹H NMR (300 MHz, CDCl₃, δ): 136-1.55 (m, 4H), 2.13 (s, 3H), 3.49-3.53 (m, 1H), 3.63 (s, 3H), 3.80 (s, 3H), 3.79-3.98 (m, 2H), 4.39 (s, 2H), 4.90 (dd, 1H, J=7.5 Hz, J=5.1 Hz), 5.85 (dd, 1H, J=8.4 Hz, J=1.5 Hz), 6.61 (d, 1H, J=7.2 Hz), 6.82 (d, 1H, J=1.8 Hz), 6.89 (dd, 1H, J=8.4 Hz, J=2.1 Hz), 7.00-7.38 (m, 11H).

¹³C NMR (75 MHz, CDCl₃, δ): 22.8, 24.1, 30.2, 34.0, 50.3, 55.3, 55.4, 57.3, 109.0, 109.5, 112.0, 112.5, 122.2, 126.0, 126.6, 127.3, 127.5, 127.6, 128.1, 128.5, 128.7, 136.7, 142.9, 143.6, 147.4, 149.6, 1692, 194.6.

MS (ESI⁺): 511.25 (M+H⁺)

Example 10

Preparation of N-[2-(3-acetyl-1-benzyl-pyridin-1-ium-4-yl)ethyl]-3,4-dimethoxy-N-phenyl-benzamide; 2,3-dichloro-5,6-dicyano-4-oxo-cyclohexa-1,5-dien-1-olate (39

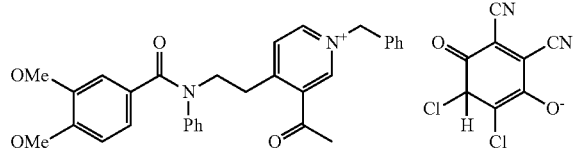 [SMILES: COc1ccc(C(=O)N(CCc2cc[n+](Cc3ccccc3)cc2C(C)=O)c2ccccc2)cc1OC ; N#CC1=C(C#N)C([O-])=C(Cl)C(Cl)C1=O]

To a solution of dihydropyridine 32 (100 mg, 0.2 mmol) in acetonitrile (4 mL) was added DDQ (1.5 equiv) in one portion at room temperature. After completion of the reaction, acetonitrile was removed under reduced pressure and the residue was taken up in diethyl ether (10 mL). The resulting precipitate was filtered off to give the title compound 39 as a red solid (120 mg, 83%).

¹H NMR (300 MHz, CD₃CN, δ): 2.65 (s, 3H), 3.36-3.40 (m, 2H), 3.48 (s, 3H), 3.71 (s, 4H), 4.21 (t, 2H, J=6.6 Hz), 5.75 (s, 2H), 6.64-6.69 (m, 2H), 6.99 (dd, 1H, J=8.4 Hz, J=1.8 Hz), 7.02-7.22 (m, 5H), 7.46-7.49 (m, 5H), 7.93 (d, 1H, J=6.3 Hz), 8.63 (d, 1H, J=6.3 Hz), 9.12 (s, 1H).

¹³C NMR (75 MHz, CD₃CN, δ): 30.2, 33.4, 50.7, 55.9, 56.0, 64.8, 102.3, 110.9, 113.0, 113.8, 121.4, 123.1, 127.6, 128.1, 128.4, 129.2, 129.4, 129.8, 129.9, 130.2, 130.6, 131.9, 133.7, 137.6, 138.0, 144.0, 145.4, 145.6, 145.9, 148.5, 151.1, 151.3, 160.9, 171.0, 172.4, 173.8, 175.9, 197.4.

MS (ESI⁺): 495.22 (M⁺)

Example 11

Preparation of N-[3-(3-acetyl-1-benzyl-pyridin-1-ium-4-yl)propyl]-3,4-dimethoxy-N-phenyl-benzamide; 2,3-dichloro-5,6-dicyano-4-oxo-cyclohexa-1,5-dien-1-olate

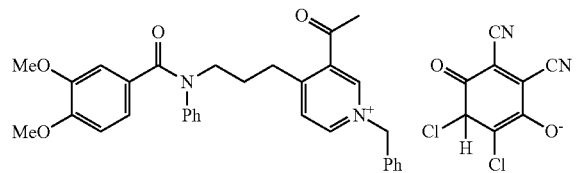 [SMILES: COc1ccc(C(=O)N(CCCc2cc[n+](Cc3ccccc3)cc2C(C)=O)c2ccccc2)cc1OC ; N#CC1=C(C#N)C([O-])=C(Cl)C(Cl)C1=O]

The title compound 40 is prepared according to the procedure reported in Example 10 with dihydropyridine 36 (51 mg, 0.1 mmol) and DDQ (1.5 equiv) as reactants. Red solid. (Yield 66.3 mg, 90%).

¹H NMR (300 MHz, CD₃CN, δ): 2.63 (s, 3H), 3.07-3.12 (m, 2H), 3.38-3.51 (m, 2H), 3.54 (s, 3H), 3.72 (s, 3H), 3.94 (t, 2H, J=7.2 Hz), 5.72 (s, 2H), 6.69-6.75 (m, 2H), 6.89 (dd, 1H, J=8.4 Hz, J=2.1 Hz), 7.11-7.28 (m, 6H), 7.46 (s, 5H), 7.96 (d, 1H, J=6.3 Hz), 8.63 (d, 1H, J=6.0 Hz), 9.06 (s, 1H).

¹³C NMR (75 MHz, CDCl₃, δ): 28.5, 30.4, 31.7, 50.2, 55.9, 56.0, 64.7, 66.1, 102.3, 111.0, 113.0, 113.8, 122.9, 127.6, 128.9, 129.1, 129.9, 130.0, 130.2, 130.6, 131.0, 133.6, 137.6, 137.9, 144.3, 145.4, 146.0, 148.6, 150.9, 151.3, 1633, 171.0, 172.4, 173.8, 176.0, 197.5.

MS (ESI⁺): 509.24 (M⁺)

Example 12

Preparation of 2-[[3-acetyl-1-[(2-chlorophenyl)methyl]-4H-pyridin-4-yl]methyl]-6-methoxy-3,4-dihydroisoquinolin-1-one (41)

Step A: Synthesis of 6-methoxy-3,4-dihydro-2H-isoquinolin-1-one (42)

The title compound is prepared as reported by Plobeck et al. in *J. Med Chem.*, 2000, 3878.

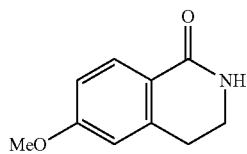

¹H NMR (300 MHz, CDCl₃, δ): 2.95 (t, 2H, J=6.6 Hz), 3.55 (dt, 2H, J=6.6 Hz, J=2.7 Hz), 3.78 (s, 3H), 6.60 (br s, 1H), 6.69 (d, 1H, J=1.8 Hz), 6.84 (dd, 1H, J=8.4 Hz, J=2.1 Hz), 7.98 (d, 1H, J=8.7 Hz).

Step B: Synthesis of 2-allyl-6-methoxy-3,4-dihydroisoquinolin-1-one (43)

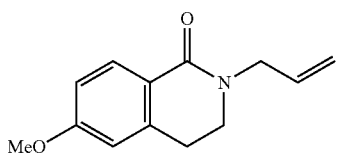 [SMILES: C=CCN1CCc2cc(OC)ccc2C1=O]

To a suspension of 95% NaH (1.2 equiv) in anhydrous DMF (2 mL) was slowly added a solution of amide 42 (198 mg, 1.12 mmol) at room temperature. The mixture was stirred at room temperature for 0.5 h after which time allyl iodide (1.2 equiv) was added. The resulting mixture was stirred for 4 hours at this temperature. After addition of water and extraction with EtOAc (3×), the resulting combined organic layers were dried over magnesium sulfate, filtered and concentrated to dryness. The residue was purified by column chromatography on SiO₂ (Petroleum ether/EtOAc=1:1) to afford the title compound 43 as a white solid (Yield 242.3 mg, 99%).

¹H NMR (300 MHz, CDCl₃, δ): 2.93 (t, 21H, J=6.6 Hz), 3.48 (t, 2H, J=6.6 Hz), 3.78 (s, 3H), 4.15-4.18 (m, 2H), 5.16-5.28 (m, 2H), 5.77-5.90 (m, 1H), 6.64 (d, 1H, J=2.4 Hz), 6.82 (dd, 1H, J=8.7 Hz, J=2.4 Hz), 8.01 (d, 1H, J=8.7 Hz).

¹³C NMR (75 MHz, CDCl₃, δ): 28.4, 45.3, 49.4, 55.4, 111.9, 112.4, 117.3, 122.2, 130.4, 133.3, 140.2, 162.2, 164.4.

MS (ESI⁺): 218.19 (M+H⁺)

Step C: Synthesis of (E)-4-(6-methoxy-1-oxo-3,4-dihydroisoquinolin-2-yl)but-2-enal (44)

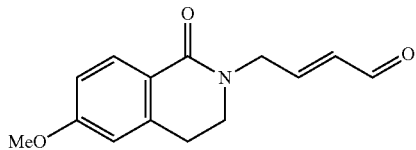 [SMILES: COc1ccc2c(c1)CCN(C/C=C/C=O)C2=O]

The title compound 44 is prepared according to the procedure reported in step C of Example 8 with amide 43 (222.4 mg, 1.03 mmol) and crotonaldehyde (4.12 mmol, 4 equiv) as reactants. Brown solid. (Yield 242.5 mg, 96%).

¹H NMR (300 MHz, CDCl₃, δ): 2.97 (t, 2H, J=6.6 Hz), 3.50 (t, 2H, J=6.6 Hz), 3.80 (s, 3H), 3.39-3.42 (m, 2H), 6.17 (dd, 1H, J=15.9 Hz, J=7.8 Hz), 6.64-6.69 (m, 1H), 6.78-6.86 (m, 2H), 7.98 (d, 1H, J=4.4 Hz), 9.54 (d, 1H, J=7.5 Hz).

¹³C NMR (75 MHz, CDCl₃, δ): 28.2, 46.3, 48.2, 55.3, 111.9, 112.6, 121.3, 130.3, 132.5, 140.1, 152.1, 162.4, 164.5, 193.1.

MS (ESI⁺): 246.11 (M+H⁺)

Step D: synthesis of 4-[(2-chlorophenyl)methylamino]but-3-en-2-one (45)

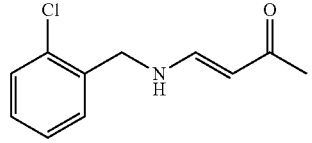

A solution of 4-methoxy-3-buten-2-one (100.1 mg, 1 mmol) and 2-chlorobenzylamine (141.6 mg, 1 mmol) in dry CH₂Cl₂ (5 mL) is stirred under reflux for 2 h. The solvent is evaporated under reduced pressure to afford the title compound 45 as a yellow oil (Yield 209 mg, 100%).

¹H NMR (300 MHz, CDCl₃, δ): 2.05 (s, 3H), 4.43 (d, J=6.3 Hz, 2H), 5.05 (d, J=7.2 Hz, 1H), 6.70 (dd, J=12.6, J=7.2 Hz, 1H), 7.21-7.37 (m, 4H), 10.04 (s, 1H).

Step E: Synthesis of 2-[[3-acetyl-1-[(2-chlorophenyl)methyl]-4H-pyridin-4-yl]methyl]-6-methoxy-3,4-dihydroisoquinolin-1-one (41)

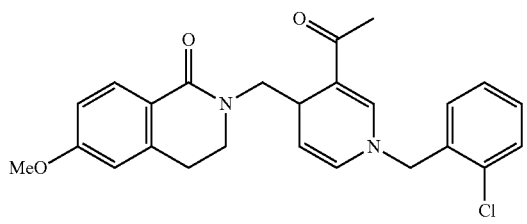 [SMILES: COc1ccc2c(c1)CCN(CC1C=CN(Cc3ccccc3Cl)C=C1C(C)=O)C2=O]

The title compound 41 is prepared according to the procedure reported in step D of Example 8 with aldehyde 44 (113 mg, 0.46 mmol) and enamine 45 (94 mg, 1 equiv) as reactants. (Yield 82.4 mg, 41%).

MS (ESI⁺): 437.16 (M+H⁺)

Example 13

Preparation of methyl 1-benzyl-4-[(6-methoxy-1-oxo-3,4-dihydroisoquinolin-2-yl)methyl]-2-methyl-4H-pyridine-3-carboxylate (46

This compound was prepared using the method described by Menendez et al. in *Chemistry an European Journal*, 2013, 13207.

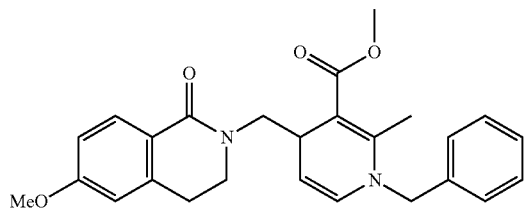 [SMILES: COC(=O)C1=C(C)N(Cc2ccccc2)C=CC1CN1CCc2cc(OC)ccc2C1=O]

To a solution of benzylamine (53 mg, 0.5 mmol) in methanol (4 mL) was added methyl acetoacetate (57.3 mg, 0.5 mmol) and CAN (13 mg, 5 mol %) at room temperature. The mixture was then heated to reflux for 30 minutes. Aldehyde 44 (121 mg, 0.49 mmol) was then added and the mixture was heated at reflux for further 30 minutes. After cooling to room temperature, the reaction mixture was diluted with dichloromethane and washed with water (3×). The organic layer was then dried over magnesium sulfate and concentrated to dryness. The crude residue was purified by column chromatography on SiO$_2$ (Petroleum Ether/EtOAc=2:1) to afford the title compound 46 as a yellow solid. (Yield 90.4 mg, 42%).

$^1$H NMR (300 MHz, CDCl$_3$, δ): 2.35 (s, 3H), 2.86 (t, 2H, J=6.9 Hz), 3.18 (dd, 1H, J=12.9 Hz, J=5.1 Hz), 3.50-3.56 (m, 2H), 3.61 (s, 3H), 3.83 (s, 3H), 3.80-3.87 (m, 1H), 4.58 (dd, 21, J=24.3 Hz, J=17.1 Hz), 4.96 (dd, 1H, J=7.2 Hz, J=5.7 Hz), 5.99 (d, 1H, J=7.5 Hz), 6.63 (d, 1H, J=2.4 Hz), 6.82 (dd, 1H, J=8.4 Hz, J=2.4 Hz), 7.14-7.30 (m, 6H), 8.02 (d, 1H, J=8.7 Hz).

$^{13}$C NMR (75 MHz, CDCl$_3$, δ): 16.1, 28.6, 332, 472, 50.9, 53.6, 53.7, 55.4, 97.1, 105.6, 111.9, 112.4, 122.7, 126.1, 127.4, 128.9, 130.3, 131.5, 137.9, 1402, 1512, 162.0, 164.8, 169.4.

MS (ESI$^+$): 433.21 (M+H$^+$)

Example 14

Preparation of ethyl 1-benzyl-4-[(6-methoxy-1-oxo-3,4-dihydroisoquinolin-2-yl)methyl]-2-methyl-4H-pyridin-3-carboxylate (471

This compound was prepared using the method described by Menendez et al. in *Chemistry an European Journal*, 2013, 13207.

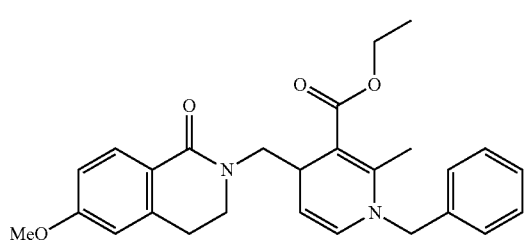 [SMILES: CCOC(=O)C1=C(C)N(Cc2ccccc2)C=CC1CN1CCc2cc(OC)ccc2C1=O]

To a solution of benzylamine (53 mg, 0.5 mmol) in ethanol (4 mL) was added ethyl acetoacetate (65 mg, 0.5 mmol) and CAN (13 mg, 5 mol %) at room temperature. The mixture was then heated to reflux for 30 minutes. The aldehyde 44 (121 mg, 0.49 mmol) was then added and the mixture was heated at reflux for further 30 minutes. After cooling to room temperature, the reaction mixture was diluted with dichloromethane and washed with water (3×). The organic layer was then dried over magnesium sulfate and concentrated to dryness. The crude residue was purified by column chromatography on SiO$_2$ (Petroleum Ether/EtOAc=2:1) to afford the title compound 47 as a yellow solid. (Yield 104 mg, 46%).

$^1$H NMR (300 MHz, CDCl$_3$, δ): 1.23 (t, 3H, J=6.9 Hz), 2.35 (s, 3H), 2.85-2.92 (m, 2H), 3.15 (dd, 1H, J=12.6 Hz, J=4.8 Hz), 3.48-3.61 (m, 3H), 3.83 (s, 3H), 3.78-3.99 (m, 1H), 4.05-4.11 (m, 2H), 4.59 (dd, 2H, J=24.1 Hz, J=16.8 Hz), 4.97 (dd, 1H, J=7.2 Hz, J=5.7 Hz), 5.99 (d, 1H, J=7.5 Hz), 6.64 (d, 1H, J=2.4 Hz), 6.82 (dd, 1H, J=8.4 Hz, J=2.4 Hz), 7.16-7.32 (m, 5H), 8.02 (d, 1H, J=8.4 Hz).

$^{13}$C NMR (75 MHz, CDCl$_3$, δ): 14.5, 16.1, 28.6, 33.3, 47.0, 53.5, 53.7, 55.4, 59.5, 97.3, 105.5, 111.9, 1123, 122.8, 126.1, 127.4, 128.9, 130.4, 131.5, 138.0, 140.2, 151.4, 162.0, 164.8, 169.0.

MS (ESI$^+$): 447.22 (M+H$^+$)

Example 15

Preparation of methyl 1-benzyl-4-[2-(6-methoxy-1-oxo-3,4-dihydroisoquinolin-2-yl)ethyl]-2-methyl-4H-pyridine-3-carboxylate (48)

Step A: Synthesis of 2-but-3-enyl-6-methoxy-3,4-dihydroisoquinolin-1-one (49)

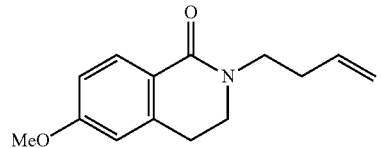

The title compound 49 is prepared according to the procedure reported in step B of Example 8 with amide 42 (0.32 g, 1.8 mmol) and but-3-enyl 4-methylbenzenesulfonate (1.63 g, 4 equiv) as reactants. Yellow oil. (Yield 0.29 g, 69%).

$^1$H NMR (300 MHz, CDCl$_3$, δ): 2.34-2.41 (m, 2H), 2.89-2.93 (m, 2H), 3.49-3.62 (m, 4H), 3.81 (s, 3H), 5.00-5.11 (m, 2H), 5.72-5.88 (m, 1H), 6.68 (s, 1H), 6.80-6.86 (m, 1H), 8.01 (d, 1H, J=5.7 Hz).

$^{13}$C NMR (75 MHz, CDCl$_3$, δ): 28.2, 32.2, 46.2, 46.7, 55.1, 111.6, 112.2, 116.6, 1222, 129.9, 135.3, 139.9, 161.9, 164.1.

MS (ESI$^+$): 232.13 (M+H$^+$)

Step B: Synthesis of (E)-5-(6-methoxy-1-oxo-3,4-dihydroisoquinolin-2-ylpent-2-enal (50)

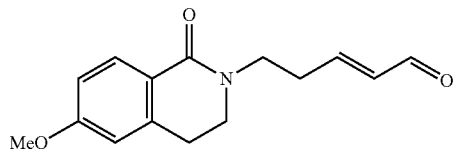 [SMILES: COc1ccc2c(c1)CCN(CC/C=C/C=O)C2=O]

The title compound 50 is prepared according to the procedure reported in step C of Example 8 with amide 49 (230.0 mg, 0.99 mmol) and crotonaldehyde (3.98 mmol, 4 equiv) as reactants. Yellow solid. (Yield 0.147 g, 57%).

$^1$H NMR (300 MHz, CDCl$_3$, δ): 2.64-2.72 (m, 2H), 2.94 (t, 2H, J=6.6 Hz), 3.53 (t, 2H, J=6.6 Hz), 3.73 (t, 2H, J=6.9 Hz), 3.83 (s, 3H), 6.11-6.19 (m, 1H), 6.64 (d, 1H, J=2.4 Hz), 6.81-6.92 (m, 2H), 7.98 (d, 1H, J=8.7 Hz), 9.49 (d, 1H, J=7.8 Hz).

$^{13}$C NMR (75 MHz, CDCl$_3$, δ): 28.2, 31.3, 45.6, 46.2, 55.2, 111.7, 112.4, 121.7, 130.0, 134.1, 139.9, 154.9, 162.1, 164.4, 193.7.

MS (ESI$^+$): 260.12 (M+H$^+$)

Step C: Synthesis of methyl 1-benzyl-4-[2-(6-methoxy-1-oxo-3,4-dihydroisoquinolin-2-yl)ethyl]-2-methyl-4H-pyridine-3-carboxylate (48)

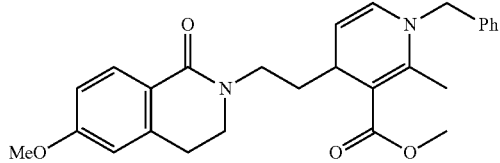 [SMILES: COC(=O)C1=C(C)N(Cc2ccccc2)C=CC1CCN1CCc2cc(OC)ccc2C1=O]

The title compound 48 is prepared according to the procedure reported in Example 13 with aldehyde 50 (50 mg, 0.19 mmol), benzylamine (20.6 mg, 1 equiv), methyl acetoacetate (22.4 mg, 1 equiv) and CAN (5.2 mg, 5 mol %) as reactants in MeOH. (Yield 18.9 mg, 21%).

$^1$H NMR (300 MHz, CDCl$_3$, δ): 233 (s, 3H), 2.91-2.96 (m, 2H), 3.30-3.42 (m, 1H), 3.44-3.55 (m, 4H), 3.64 (s, 3H), 3.83 (s, 3H), 3.87-3.96 (m, 1H), 4.57 (dd, 2H, J=30.0 Hz, J=16.8 Hz), 5.13 (dd, 1H, J=7.2 Hz, J=6.0 Hz), 5.96 (d, 1H, J=7.5 Hz), 6.66 (d, 1H, J=2.4 Hz), 6.83 (dd, 1H, J=8.4 Hz, J=2.4 Hz), 7.15-7.36 (m, 6H), 8.02 (d, 1H, J=8.7 Hz).

$^{13}$C NMR (75 MHz, CDCl$_3$, δ): 16.1, 28.6, 31.0, 36.4, 42.8, 45.4, 50.9, 53.6, 55.4, 99.0, 107.1, 111.9, 112.4, 122.8, 126.1, 127.5, 128.9, 1303, 130.9, 138.2, 140.1, 150.5, 162.1, 164.3, 169.5.

MS (ESI$^+$): 446.22 (M+H$^+$)

Example 16

Preparation of 2-[2-[3-acetyl-1-[(2-chlorophenyl)methyl]-4H-pyridin-4-yl]ethyl]-6-methoxy-3,4-dihydroisoquinolin-1-one (51)

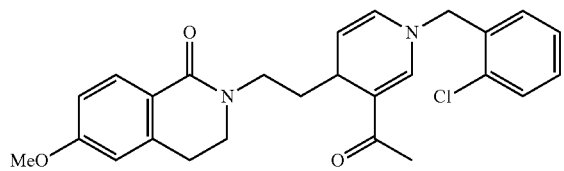 [SMILES: COc1ccc2c(c1)CCN(CCC1C=CN(Cc3ccccc3Cl)C=C1C(C)=O)C2=O]

The title compound 51 is prepared according to the procedure reported in step D of Example 8 with aldehyde 50 (100 mg, 0.386 mmol) and enamine 45 (73.1 mg, 1 equiv) as reactants. (Yield 28.5 mg, 16%).

$^1$H NMR (300 MHz, CDCl$_3$, δ): 1.52-1.68 (m, 1H), 1.71-1.83 (m, 1H), 2.16 (s, 3H), 2.89-2.96 (m, 1H), 2.97-3.12 (m, 1H), 3.13-3.25 (m, 1H), 3.49-3.68 (m, 3H), 3.81 (s, 3H), 3.97-4.11 (m, 1H), 4.50 (s, 2H), 5.23 (dd, 1H, J=7.8 Hz, J=5.1 Hz), 5.88 (dd, 1H, J=7.8 Hz, J=0.9 Hz), 6.64 (d, 1H, J=2.4 Hz), 6.81 (dd, 1H, J=8.7 Hz, J=2.4 Hz), 7.12 (d, 1H, J=1.2 Hz), 7.21-7.43 (m, 4H), 7.98 (d, 1H, J=8.7 Hz).

$^{13}$C NMR (75 MHz, CDCl$_3$, δ): 24.5, 28.4, 28.5, 35.0, 42.5, 45.2, 55.4, 55.5, 109.8, 111.8, 112.3, 113.0, 122.7, 127.5, 127.6, 128.6, 129.3, 130.0, 130.2, 133.1, 134.4, 140.4, 143.5, 162.0, 164.4, 195.1.

MS (ESI$^+$): 451.18 (M+H$^+$)

Example 17

Preparation of 2-[(3-acetyl-1-benzyl-4H-pyridin-4-yl)methyl]-6-methoxy-tetralin-1-one (52)

Step A: Synthesis of 2-allyl-6-methoxy-tetralin-1-one (53)

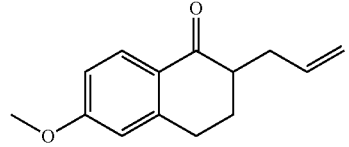 [SMILES: C=CCC1CCc2cc(OC)ccc2C1=O]

To a solution of LiHMDS (1.04 g, 6.24 mmol), in THF (40 mL) cooled at −78° C. is added slowly a solution of 6-methoxy-1-tetralone (1.0 g, 5.67 mmol) in anhydrous THF (40 mL). After the addition is complete, the solution is stirred at −78° C. for 30 minutes, then HMPA (1.97 mL, 11.3 mmol) is slowly added and the mixture is stirred for other 5 minutes followed by the addition of a solution of allyl bromide (0.74 mL, 8.5 mmol) in anhydrous THF (5 mL). The mixture is left to warm slowly to room temperature (2-3 h) and quenched at 0° C. with aqueous 1N HCl (20 mL), then extracted with diethylether. The organic phase is dried over MgSO$_4$ and concentrated to dryness. The residue is purified by column chromatography on SiO$_2$ (Petroleum Ether/EtOAc=95:5) to afford the title compound 53 as a colorless oil (Yield 0.56 g, 45%).

$^1$H NMR (300 MHz, CDCl$_3$, δ): 1.74-1.94 (m, 1H), 2.13-2.34 (m, 2H), 2.42-2.58 (m, 1H), 2.67-2.81 (m, 1H), 2.95 (dd, J=7.6 Hz, J=4.7 Hz, 2H), 3.85 (s, 3H), 5.16-4.98-5.16 (m, 2H), 5.73-5.97 (m, 1H), 6.68 (d, J=2.4 Hz, 1H), 6.82 (dd, J=8.7 Hz, J=2.5 Hz, 1H), 8.01 (d, J=8.8 Hz, 1H).

$^{13}$C NMR (75 MHz, CDCl$_3$, δ): 28.0, 29.0, 34.2, 46.9, 55.5, 112.5, 113.2, 116.8, 126.2, 130.0, 136.5, 146.6, 163.5, 198.4.

HRMS (ESI$^+$) calcd for [M+Na]$^+$ C$_{14}$H$_{16}$O$_2$Na m/z 239.1048 found 239.048.

Step B: Synthesis of (E)-4-(6-methoxy-1-oxo-tetralin-2-yl)but-2-enal (54)

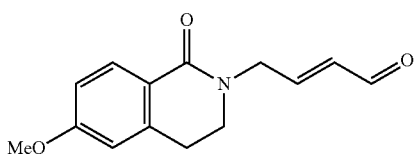 [SMILES: COc1ccc2c(c1)CCN(C/C=C/C=O)C2=O]

The title compound 54 is prepared according to the procedure reported in step C of Example 8 with tetralone 53 (1.1 g, 5.09 mmol) and crotonaldehyde (1.43 g, 20.34 mmol) as reactants. Purification by column chromatography on SiO$_2$ (Petroleum/EtOAc=4:1) afford the title compound 54 as an off-white solid. (Yield 0.95 g, 76%).

$^1$H NMR (300 MHz, CDCl$_3$, δ): 1.76-1.99 (m, 1H), 2.09-2.29 (m, 1H), 2.50-2.77 (m, 2H), 2.96-3.02 (m, 3H), 3.86 (s, 3H), 6.19 (dd, J=15.6 Hz, J=7.9 Hz, 1H), 6.69 (d, J=2.4 Hz, 1H), 6.84 (dd, J=8.8 Hz, J=2.5 Hz, 1H), 6.87-7.05 (m, 1H), 8.02 (d, J=8.8 Hz, 1H), 9.52 (d, J=7.9 Hz, 1H).

$^{13}$C NMR (75 MHz, CDCl$_3$, δ): 28.9, 29.4, 33.5, 46.6, 55.6, 112.6, 113.5, 125.9, 130.1, 134.7, 146.5, 156.7, 163.8, 194.0, 197.1.

HRMS (ESI$^+$) calcd for [M+Na]$^+$ C$_{15}$H$_{16}$O$_3$Na m/z 267.0997 found 267.1003.

Step C: Synthesis of 2-[(3-acetyl-1-benzyl-4H-pyridin-4-yl)methyl]-6-methoxy-tetralin-1-one (52)

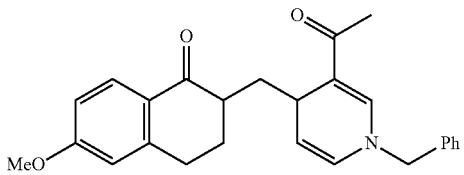 [SMILES: COc1ccc2c(c1)CCC(CC1C=CN(Cc3ccccc3)C=C1C(C)=O)C2=O]

The title compound 52 is prepared according to the procedure reported in step D of Example 8 with aldehyde 54 (100 mg, 0.41 mmol) and enamine 30 (70 mg, 0.4 mmol) as reactants. Purification by column chromatography on SiO$_2$ (Petroleum 4/EtOAc=4:1) afford the title compound 52 as a yellow oil. (Yield 55.0 mg, 35%).

$^1$H NMR (300 MHz, CDCl$_3$, δ): 1.24-1.37 (m, 0.54H), 1.42-1.54 (m, 0.46H), 1.66-2.32 (m, 3H), 2.07 (s, 1.5H), 2.10 (s, 1.5H), 2.37-2.49 (m, 0.54H), 2.51-2.63 (m, 0.46H), 2.71-2.88 (m, 1.54H), 2.99-3.11 (m, 0.46H), 3.50-3.64 (m, 1H), 3.74 (s, 3H), 4.36 (s, 2H), 4.90-4.99 (m, 1H), 5.79-5.88 (m, 1H), 6.54-6.62 (m, 1H), 6.65-6.74 (m, 1H), 7.05-7.33 (m, 6H), 7.83-7.90 (m, 1H).

$^{13}$C NMR (75 MHz, CDCl$_3$, δ): 24.5, 24.7, 27.0, 27.7, 28.1, 28.3, 28.9, 29.2, 37.7, 38.1, 42.7, 43.9, 55.4, 57.8, 57.9, 108.3, 110.2, 112.3, 113.0, 113.1, 113.3, 113.8, 126.0, 126.2, 126.9, 127.0, 127.9, 128.0, 128.1, 129.0, 129.0, 129.8, 136.8, 136.9, 142.9, 143.1, 146.6, 146.7, 163.2, 163.3, 195.0, 195.6, 199.8, 199.9.

MS (ESI$^+$): 402.20 (M+H$^+$)

Example 18

Preparation of 2-[[3-acetyl-1-[(2-fluorophenyl)methyl]-4H-pyridin-4-yl]methyl]-6-methoxy-tetralin-1-one (55)

Step A: synthesis of 4-[(2-fluorophenyl)methylamino]but-3-en-2-one (56)

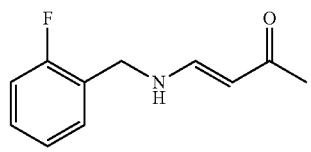

A solution of 4-methoxy-3-buten-2-one (0.1 g, 1 mmol) and 2-fluorobenzylamine (0.125 g, 1 mmol) in dry CH$_2$Cl$_2$ (5 mL) is stirred under reflux for 2 h. The solvent is evaporated under pressure to afford the title compound 56 as a yellow oil (Yield 0.19 g, 100%).

$^1$H NMR (300 MHz, CDCl$_3$, δ): 2.06 (s, 3H), 4.40 (d, J=6.3 Hz, 2H), 5.06 (d, J=7.4 Hz, 1H), 6.72 (dd, J=12.6 Hz, J=7.4 Hz, 1H), 7.09-7.17 (m, 2H), 7.21-7.32 (m, 2H), 10.00 (s, 1H).

$^{13}$C NMR (75 MHz, CDCl$_3$, δ): 29.2, 46.6, 46.7, 94.7, 115.4, 115.7, 124.5, 124.6, 125.2, 125.4, 129.2, 129.3, 129.6, 129.7, 152.4, 159.0, 162.3, 198.0.

HRMS (ESI$^+$) calcd for [M+H]$^+$ C$_{11}$H$_{13}$NOF m/z 194.0981 found 194.0973.

Step B: synthesis of 2-[[3-acetyl-1-[(2-fluorophenyl)methyl]-4H-pyridin-4-yl]methyl]-6-methoxy-tetralin-1-one (55)

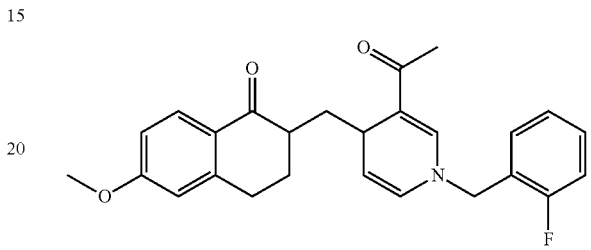

The title compound 55 is prepared according to the procedure reported in step D of Example 8 with aldehyde 54 (100 mg, 0.41 mmol) and enamine 56 (115 mg, 0.59 mmol) as reactants. Purification by column chromatography on SiO$_2$ (Petroleum/EtOAc=2:1) afford the title compound 55 as a yellow solid. (Yield 0.11 g, 65%).

$^1$H NMR (300 MHz, CDCl$_3$, δ): 1.31-1.43 (m, 0.54H), 1.48-1.59 (m, 0.46H), 1.71-1.89 (m, 1H), 1.93-2.37 (m, 2H), 2.15 (s, 1.54H), 2.18 (s, 1.46H), 2.40-2.52 (m, 0.54H), 2.56-2.67 (m, 0.46H), 2.78-2.91 (m, 1.54H), 3.06-3.18 (m, 0.46H), 3.55-3.68 (m, 1H), 3.81 (s, 3H), 4.46 (s, 2H), 4.96-5.06 (m, 1H), 5.89-5.97 (m, 1H), 6.60-6.68 (m, 1H), 6.72-6.80 (m, 1H), 6.99-7.33 (m, 5H), 7.90-7.96 (m, 1H).

$^{13}$C NMR (75 MHz, CDCl$_3$, δ): 24.5, 24.7, 27.1, 27.7, 28.1, 28.4, 29.0, 29.2, 29.3, 37.7, 38.0, 42.8, 43.9, 51.8, 51.9, 52.0, 55.4, 94.7, 108.5, 110.4, 112.4, 113.0, 113.2, 113.7, 114.1, 115.6, 115.9, 123.9, 124.1, 124.5, 124.6, 124.7, 124.8, 124.9, 126.0, 126.3, 127.6, 127.8, 129.2, 129.3, 129.4, 129.7, 129.8, 130.0, 130.2, 142.8, 143.0, 146.6, 146.7, 152.4, 159.1, 162.3, 163.2, 163.3, 195.1, 195.6, 199.8, 199.9.

HRMS (ESI$^+$) calcd for [M+H]$^+$ C$_{26}$H$_{27}$NO$_3$F m/z 420.1975 found 420.1959.

Example 19

Preparation of 2-[[3-acetyl-1-(p-tolylmethyl)-4H-pyridin-4-yl]methyl]-6-methoxy-tetralin-1-one (57)

Step A: synthesis of 4-(p-tolylmethylamino)but-3-en-2-one (58)

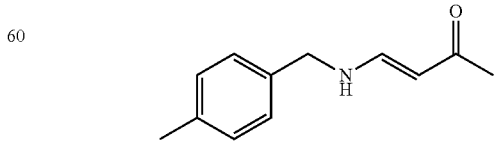

The title compound 58 is prepared according to the procedure reported in step A of Example 18 with 4-methoxy-3- buten-2-one (0.103 g, 1 mmol) and 4-methylbenzylamine (0.125 g, 1 mmol) as reactants. Yellow oil. (Yield 0.19 g, 98%).

$^1$H NMR (300 MHz, CDCl$_3$, δ): 2.06 (s, 3H), 2.33 (s, 3H), 4.32 (d, J=6.1 Hz, 2H), 5.03 (d, J=7.4 Hz, 1H), 6.69 (dd, J=12.7 Hz, J=7.4 Hz, 1H), 7.10-7.14 (m, 4H), 10.03 (s, 1H).

$^{13}$C NMR (75 MHz, CDCl$_3$, δ): 21.2, 29.2, 52.3, 94.4, 127.2, 129.5, 135.0, 137.5, 152.4, 197.8.

HRMS (ESI$^+$) calcd for [M+H]$^+$ C$_{12}$H$_{16}$NO m/z 190.1232 found 190.1228.

Step B: synthesis of 2-[[3-acetyl-1-(p-tolylmethyl)-4H-pyridin-4-yl]methyl]-6-methoxy-tetralin-1-one (57)

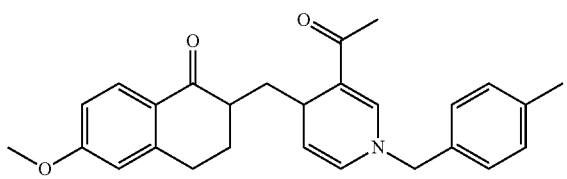

The title compound 57 is prepared according to the procedure reported in step D of Example 8 with aldehyde 54 (100 mg, 0.41 mmol) and enamine 58 (110 mg, 0.57 mmol) as reactants. Purification by column chromatography on SiO$_2$ (Petroleum Ether/EtOAc=2:1) afford the title compound 57 as a yellow oil. (Yield 63.0 mg, 37%).

$^1$H NMR (300 MHz, CDCl$_3$, δ): 1.34-1.44 (m, 0.54H), 1.49-1.60 (m, 0.46H), 1.73-2.38 (m, 3H), 2.15 (s, 1.5H), 2.18 (s, 1.5H), 2.31 (s, 1.5H), 2.33 (s, 1.5H), 2.43-2.55 (m, 0.54H), 2.57-2.69 (m, 0.46H), 2.79-2.93 (m, 1.54H), 3.06-3.20 (m, 0.46H), 3.57-3.72 (m, 1H), 3.82 (s, 3H), 4.38 (s, 2H), 4.96-5.04 (m, 1H), 5.86-5.93 (m, 1H), 6.61-6.68 (m, 1H), 6.72-6.81 (m, 1H), 7.05-7.20 (m, 5H), 7.92-7.99 (m, 1H).

$^{13}$C NMR (75 MHz, CDCl$_3$, δ): 21.2, 24.5, 24.7, 27.1, 27.7, 28.2, 28.4, 29.0, 29.1, 29.3, 29.7, 37.7, 38.0, 42.8, 43.9, 55.4, 57.6, 57.7, 94.3, 108.3, 110.2, 112.4, 113.1, 113.2, 113.3, 113.7, 126.0, 126.3, 127.0, 127.1, 127.2, 127.9, 128.0, 129.5, 129.7, 129.8, 133.7, 137.8, 142.9, 143.1, 146.6, 146.7, 163.2, 163.3, 195.0, 195.6, 199.7, 199.9.

HRMS (ESI$^+$) calcd for [M+H]$^+$ C$_{27}$H$_{30}$NO$_3$ m/z 416.2226 found 416.2233.

Example 20

Preparation of 2-[[3-acetyl-1-(o-tolylmethyl)-4H-pyridin-4-yl]methyl]-6-methoxy-tetralin-1-one (59)

Step A: synthesis of 4-(o-tolylmethylamino)but-3-en-2-one (60)

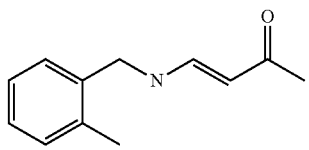

The title compound 60 is prepared according to the procedure reported in step A of Example 18 with 4-methoxy-3-buten-2-one (0.1 g, 1 mmol) and 2-methylbenzylamine (0.125 g, 1 mmol) as reactants. Yellow solid. (Yield 0.19 g, 100%).

$^1$H NMR (300 MHz, CDCl$_3$, δ): 2.06 (s, 3H), 2.31 (s, 3H), 4.35 (d, J=5.9 Hz, 2H), 5.04 (d, J=7.4 Hz, 1H), 6.67 (dd, J=12.7 Hz, J=7.4 Hz, 1H), 7.02-7.24 (m, 4H), 10.05 (s, 1H).

$^{13}$C NMR (75 MHz, CDCl$_3$, δ): 19.2, 29.2, 50.7, 94.5, 126.5, 127.9, 128.0, 130.7, 135.8, 136.0, 152.3, 197.8.

HRMS (ESI$^+$) calcd for [M+H]$^+$ C$_{12}$H$_{16}$NO m/z 190.1232 found 190.1232.

Step B: synthesis of 2-[[3-acetyl-1-(o-tolylmethyl)-4H-pyridin-4-yl]methyl]-6-methoxy-tetralin-1-one (59)

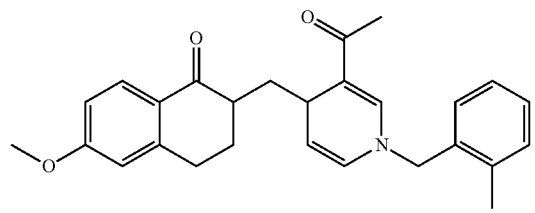 [SMILES: COc1ccc2c(c1)CCC(CC1C=CN(Cc3ccccc3C)C=C1C(C)=O)C2=O]

The title compound 59 is prepared according to the procedure reported in step D of Example 8 with aldehyde 54 (100 mg, 0.41 mmol) and enamine 60 (110 mg, 0.57 mmol) as reactants. Purification by column chromatography on SiO$_2$ (Petroleum Ether/EtOAc=2:1) afford the title compound 59 as a yellow oil. (Yield 100 mg, 59%).

$^1$H NMR (300 MHz, CDCl$_3$, δ): 1.31-1.42 (m, 0.54H), 1.49-1.63 (m, 0.46H), 1.81-1.93 (m, 1H), 2.04-2.41 (m, 2H), 2.11 (s, 1.60H), 2.15 (s, 1.40H), 2.27 (s, 1.60H), 2.28 (s, 1.40H), 2.46-2.57 (m, 0.54H), 2.60-2.72 (m, 0.46H), 2.80-2.95 (m, 1.54H), 3.06-3.23 (m, 0.46H), 3.58-3.71 (m, 1H), 3.83 (s, 3H), 4.39 (s, 1H), 4.42 (s, 1H), 4.97-5.05 (m, 1H), 5.85-5.92 (m, 1H), 6.59-6.71 (m, 1H), 6.63-6.68 (m, 1H), 6.74-6.80 (m, 1H), 7.05-7.25 (m, 4H), 7.91-7.97 (m, 1H).

$^{13}$C NMR (75 MHz, CDCl$_3$, δ): 19.1, 19.2, 24.4, 24.6, 27.0, 27.7, 28.2, 28.4, 29.0, 29.1, 37.9, 38.4, 42.8, 43.9, 50.6, 55.4, 55.9, 56.0, 94.4, 108.2, 110.1, 112.4, 113.0, 113.1, 113.4, 113.8, 126.3, 126.4, 126.5, 126.6, 127.7, 127.8, 127.9, 128.0, 128.1, 128.2, 129.9, 130.6, 130.8, 134.4, 134.5, 135.7, 135.9, 136.0, 142.8, 143.0, 146.6, 146.7, 163.2, 163.3, 195.0, 195.6, 199.7, 199.9.

HRMS (ESI$^+$) calcd for [M+H]$^+$ C$_{27}$H$_{30}$NO$_3$ m/z 416.2226 found 416.2227.

Example 21

Preparation of 2-[[3-acetyl-1-(m-tolylmethyl)-4H-pyridin-4-yl]methyl]-6-methoxy-tetralin-1-one (61)

Step A: synthesis of 4-(m-tolylmethylamino)but-3-en-2-one (62)

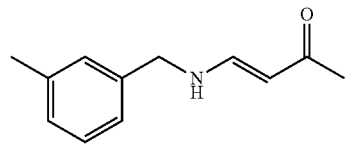

The title compound 62 is prepared according to the procedure reported in step A of Example 18 with 4-methoxy-3- buten-2-one (0.1 g, 1 mmol) and 3-methylbenzylamine (0.125 g, 1 mmol) as reactants. Yellow oil. (Yield 0.19 g, 100%).

$^1$H NMR (300 MHz, CDCl$_3$, δ): 2.06 (s, 3H), 2.34 (s, 3H), 4.33 (d, J=6.1 Hz, 2H), 5.04 (d, J=7.4 Hz, 1H), 6.70 (dd, J=12.7 Hz, J=7.4 Hz, 1H), 6.95-7.14 (m, 3H), 7.22 (t, J=6.0 Hz, 1H), 10.04 (s, 1H).

$^{13}$C NMR (75 MHz, CDCl$_3$, δ): 21.5, 29.2, 52.6, 94.4, 124.3, 128.0, 128.5, 128.8, 138.0, 138.6, 152.5, 197.8.

HRMS (ESI$^+$) calcd for [M+H]$^+$ C$_{12}$H$_{16}$NO m/z 190.1232 found 190.1229.

Step B: synthesis of 2-[[3-acetyl-1-(m-tolylmethyl)-4H-pyridin-4-yl]methyl]-6-methoxy-tetralin-1-one (61)

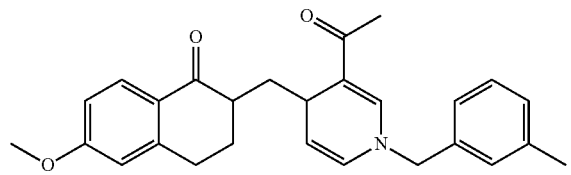

The title compound 61 is prepared according to the procedure reported in step D of Example 8 with aldehyde 54 (100 mg, 0.41 mmol) and enamine 62 (80 mg, 0.42 mmol) as reactants. Purification by column chromatography on SiO$_2$ (Petroleum Ether/EtOAc=2:1) afford the title compound 61 as a yellow solid. (Yield 115 mg, 68%).

$^1$H NMR (300 MHz, CDCl$_3$, δ): 1.21-135 (m, 0.5H), 1.40-1.52 (m, 0.5H), 1.65-2.29 (m, 3H), 2.07 (s, 1.5H), 2.08 (s, 1.5H), 2.22 (s, 1.5H), 2.25 (s, 1.5H), 2.35-2.45 (m, 0.5H), 2.50-2.60 (m, 0.5H), 2.70-2.83 (m, 1.5H), 2.99-3.09 (m, 0.5H), 3.48-3.61 (m, 1H), 3.73 (s, 3H), 4.30 (s, 2H), 4.88-4.97 (m, 1H), 5.76-5.85 (m, 1H), 6.52-6.59 (m, 1H), 6.63-6.70 (m, 1H), 6.88-7.19 (m, 5H), 7.82-7.88 (m, 1H).

$^{13}$C NMR (75 MHz, CDCl$_3$, δ): 21.2, 24.5, 24.7, 27.1, 27.7, 28.2, 28.4, 29.0, 29.1, 29.3, 29.7, 37.7, 38.0, 42.8, 43.9, 55.4, 57.6, 57.7, 94.3, 108.3, 110.2, 112.4, 113.1, 113.2, 113.3, 113.7, 126.0, 126.3, 127.0, 127.1, 127.2, 127.9, 128.0, 129.5, 129.7, 129.8, 133.7, 113.8, 137.8, 142.9, 143.1, 146.6, 146.7, 1632, 163.3, 195.0, 195.6, 199.7, 199.9.

MS (ESI$^+$): 416.22 (M+H$^+$)

Example 22

Preparation of 2-[[3-acetyl-1-[(3-chlorophenyl)methyl]-4H-pyridin-4-yl]methyl]-6-methoxy-tetralin-1-one (63)

Step A: synthesis of 4-[(3-chlorophenyl)methylamino]but-3-en-2-one (64)

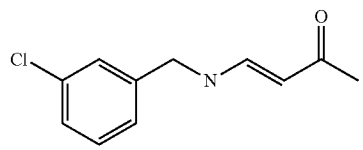

The title compound 64 is prepared according to the procedure reported in step A of Example 18 with 4-methoxy-3-buten-2-one (0.1 g, 1 mmol) and 3-chlorobenzylamine (0.138 g, 1 mmol) as reactants. Yellow oil. (Yield 0.21 g, 100%).

$^1$H NMR (300 MHz, CD$_3$CN, δ): 2.12 (s, 3H), 4.52 (d, J=6.1 Hz, 2H), 5.21 (d, J=7.5 Hz, 1H), 6.97 (dd, J=12.3 Hz, J=7.4 Hz, 1H), 7.46 (m, 4H), 10.08 (s, 1H).

MS (ESI$^+$): 210.06 (M+H$^+$)

Step B: synthesis of 2-[[3-acetyl-1-[(3-chlorophenyl)methyl]-4H-pyridin-4-yl]methyl]-6-methoxy-tetralin-1-one (63)

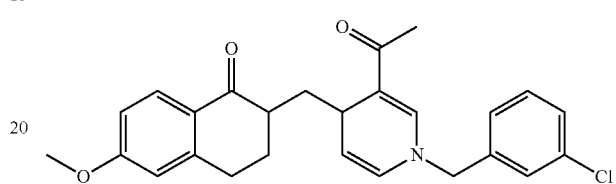

The title compound 63 is prepared according to the procedure reported in step D of Example 8 with aldehyde 54 (100 mg, 0.41 mmol) and enamine 64 (90 mg, 0.42 mmol) as reactants. Purification by column chromatography on SiO$_2$ (Petroleum Ether/EtOAc=2:1) afford the title compound 63 as a yellow solid. (Yield 70 mg, 39%).

$^1$H NMR (300 MHz, CDCl$_3$, δ): 1.27-1.39 (m, 0.54H), 1.42-1.52 (m, 0.46H), 1.67-2.31 (m, 3H), 2.09 (s, 1.60H), 2.12 (s, 1.40H), 2.36-2.49 (m, 0.54H), 2.51-2.62 (m, 0.46H), 2.75-2.85 (m, 1.54H), 3.00-3.10 (m, 0.46H), 3.50-3.65 (m, 1H), 3.75 (s, 3H), 4.32 (s, 1H), 4.34 (s, 1H), 4.93-5.00 (m, 1H), 5.78-5.86 (m, 1H), 6.54-6.63 (m, 1H), 6.67-6.74 (m, 1H), 7.00-7.23 (m, 5H), 7.83-7.90 (m, 1H).

$^{13}$C NMR (75 MHz, CDCl$_3$, δ): 24.6, 24.8, 27.2, 27.7, 28.2, 28.4, 28.9, 29.3, 37.8, 38.2, 42.8, 43.8, 55.4, 57.2, 57.3, 108.6, 110.4, 112.4, 113.0, 113.2, 113.8, 114.3, 125.0, 125.1, 126.0, 126.2, 127.1, 127.7, 127.9, 128.2, 129.8, 130.4, 130.5, 134.9, 139.0, 139.1, 142.6, 142.7, 146.6, 146.7, 163.3, 163.4, 195.1, 195.7, 199.7, 199.9.

MS (ESI$^+$): 436.16 (M+H$^+$)

Example 23

Preparation of 2-[[3-acetyl-1-[[3-(trifluoromethyl)phenyl]methyl]-4H-pyridin-4-yl]methyl]-6-methoxy-tetralin-1-one (65)

Step A: synthesis of 4-[[3-(trifluoromethyl)phenyl]methylamino]but-3-en-2-one (66)

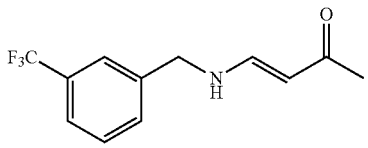 [SMILES: CC(=O)/C=C/NCc1cccc(C(F)(F)F)c1]

The title compound 66 is prepared according to the procedure reported in step A of Example 18 with 4-methoxy-3-buten-2-one (0.2 g, 2 mmol) and 3-trifluoromethylbenzylamine (0.35 g, 2 mmol) as reactants. Yellow oil. (Yield 0.48 g, 100%).

¹H NMR (300 MHz, CDCl₃, δ): 2.07 (s, 3H), 4.41 (d, J=6.2 Hz, 2H), 5.09 (d, J=7.5 Hz, 1H), 6.68 (dd, J=12.5 Hz, J=7.5 Hz, 1H), 7.39-7.54 (m, 4H), 10.04 (s, 1H).
¹³C NMR (75 MHz, CDCl₃, δ): 29.3, 52.1, 95.2, 124.0, 124.1, 124.7, 124.8, 129.5, 130.5, 139.3, 152.2, 198.3.
MS (ESI⁺): 444.09 (M+H⁺)

Step B: synthesis of 2-[[3-acetyl-1-[[3-trifluoromethyl)phenyl]methyl]-4H-pyridin-4-yl]methyl]-6-methoxy-tetralin-1-one (65)

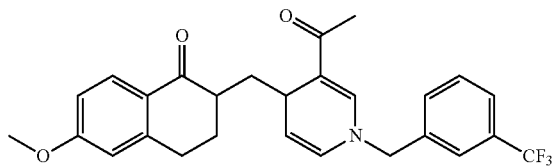 [SMILES: COc1ccc2c(c1)CCC(CC1C=CN(Cc3cccc(C(F)(F)F)c3)C=C1C(C)=O)C2=O]

The title compound 65 is prepared according to the procedure reported in step D of Example 8 with aldehyde 54 (100 mg, 0.41 mmol) and enamine 66 (100 mg, 0.41 mmol) as reactants. Purification by column chromatography on SiO₂ (Petroleum Ether/EtOAc=2:1) afford the title compound 65 as a pale yellow solid. (Yield 65 mg, 39%).
¹H NMR (300 MHz, CDCl₃, δ): 1.34-1.48 (m, 0.54H), 1.51-1.61 (m, 0.46H), 1.78-2.40 (m, 3H), 2.16 (s, 1.5H), 2.19 (s, 1.5H), 2.46-2.56 (m, 0.54H), 2.60-2.70 (m, 0.46H), 2.80-2.95 (m, 1.54H), 3.06-3.18 (m, 0.46H), 3.56-3.71 (m, 1H), 3.83 (s, 3H), 4.50 (s, 2H), 5.02-5.10 (m, 1H), 5.84-5.94 (m, 1H), 6.62-6.69 (m, 1H), 6.74-6.81 (m, 1H), 7.10 (s, 0.46H), 7.16 (s, 0.54H), 7.40-7.60 (m, 4H), 7.90-7.98 (m, 1H).
¹³C NMR (75 MHz, CDCl₃, δ): 24.6, 24.8, 27.3, 27.8, 28.3, 28.5, 29.0, 29.3, 38.0, 38.5, 43.0, 43.9, 55.4, 57.4, 57.5, 108.9, 110.6, 112.5, 113.1, 113.2, 114.2, 114.6, 123.9, 125.0, 126.1, 126.3, 127.7, 127.9, 129.8, 129.9, 130.3, 138.1, 138.2, 142.5, 146.6, 146.7, 163.4, 163.5, 195.1, 195.7, 199.6, 199.8.
MS (ESI⁺): 470.19 (M+H⁺)

Example 24

Preparation of 2-[[3-acetyl-1-[[2-(trifluoromethyl)phenyl]methyl]-4H-pyridin-4-yl]methyl]-6-methoxy-tetralin-1-one (67)

Step A: synthesis of (E)-4-[[2-(trifluoromethyl)phenyl]methylamino]but-3-en-2-one (68)

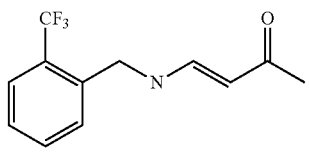 [SMILES: CC(=O)/C=C/NCc1ccccc1C(F)(F)F]

The title compound 68 is prepared according to the procedure reported in step A of Example 17 with 4-methoxy-3-buten-2-one (0.2 g, 2 mmol) and 2-trifluoromethylbenzylamine (0.35 g, 2 mmol) as reactants. Yellow oil. (Yield 0.48 g, 100%).
¹H NMR (300 MHz, CDCl₃, δ): 2.08 (s, 3H), 4.55 (d, J=6.4 Hz, 2H), 5.09 (d, J=7.4 Hz, 1H), 6.67 (dd, J=12.5 Hz, J=7.4 Hz, 1H), 7.38-7.70 (m, 4H), 10.05 (s, 1H).

¹³C NMR (75 MHz, CDCl₃, δ): 29.3, 49.2, 95.1, 126.1, 126.2, 126.3, 127.8, 128.8, 132.5, 136.9, 152.4, 198.3.
MS (ESI⁺): 244.09 (M+H⁺)

Step B: synthesis of 2-[[3-acetyl-1-[[2-(trifluoromethyl)phenyl]methyl]-4H-pyridin-4-yl]methyl]-6-methoxy-tetralin-1-one (67)

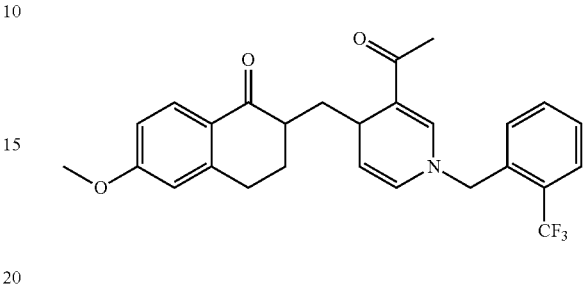

The title compound 67 is prepared according to the procedure reported in step D of Example 8 with aldehyde 54 (100 mg, 0.41 mmol) and enamine 68 (90 mg, 0.37 mmol) as reactants. Purification by column chromatography on SiO₂ (Petroleum Ether/EtOAc=2:1) afford the title compound 67 as a yellow oil. (Yield 35 mg, 20%).
¹H NMR (300 MHz, CDCl₃, δ): 1.37-1.47 (m, 0.5H), 1.53-1.63 (m, 0.5H), 1.75-2.41 (m, 3H), 2.16 (s, 1.5H), 2.19 (s, 1.5H), 2.46-2.56 (m, 0.5H), 2.61-2.72 (m, 0.5H), 2.80-2.93 (m, 1.5H), 3.08-3.20 (m, 0.5H), 3.59-3.70 (m, 1H), 3.83 (s, 3H), 4.51 (s, 1H), 4.52 (s, 1H), 4.98-5.10 (m, 1H), 5.87-5.96 (m, 1H), 6.62-6.69 (m, 1H), 6.73-6.81 (m, 1H), 7.12 (s, 0.5H), 7.18 (s, 0.5H), 7.20-7.43 (m, 4H), 7.92-7.98 (m, 1H).
¹³C NMR (75 MHz, CDCl₃, δ): 24.6, 24.8, 27.1, 27.8, 28.2, 28.4, 29.1, 29.3, 37.9, 38.2, 42.9, 44.0, 55.5, 55.6, 55.7, 108.5, 110.4, 112.4, 113.1, 113.2, 113.8, 114.3, 126.1, 126.4, 127.5, 127.6, 127.9, 128.1, 128.6, 128.8, 129.4, 129.9, 130.0, 133.1, 133.2, 134.5, 142.9, 143.1, 146.7, 146.8, 163.3, 163.4, 195.1, 195.7, 199.7, 199.9.
MS (ESI⁺): 470.20 (M+H⁺)

Example 25

Preparation of methyl 1-benzyl-4-[(6-methoxy-1-oxo-tetralin-2-yl)methyl]-2-methyl-4H-pyridine-3-carboxylate (69)

Step A: synthesis of methyl 3-(benzylamino)but-2-enoate (70)

The title compound 70 is prepared as reported by Liu et al. in *Applied Organometallic Chemistry*, 2010, 685.

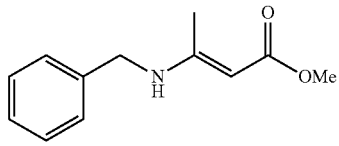

¹H NMR (300 MHz, CDCl₃, δ): 1.92 (s, 3H), 3.63 (s, 3H), 4.43 (d, J=6.3 Hz, 2H), 4.53 (s, 1H), 7.24-7.33 (m, 5H), 8.94 (br s, 1H).
¹³C NMR (75 MHz, CDCl₃, δ): 19.6, 47.0, 50.2, 83.0, 126.9, 127.5, 138.9, 162.1, 171.1.
MS (ESI⁺): 206.12 (M+H⁺)

Step B: synthesis of methyl 1-benzyl-4-[(6-methoxy-1-oxo-tetralin-2-yl)methyl]-2-methyl-4H-pyridine-3-carboxylate (69)

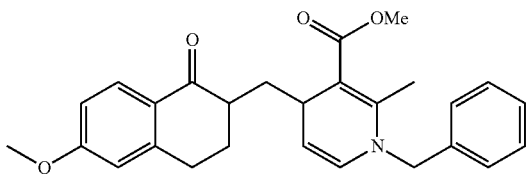 [SMILES: COC(=O)C1=C(C)N(Cc2ccccc2)C=CC1CC1CCc2cc(OC)ccc2C1=O]

The title compound 69 is prepared according to the procedure reported in step D of Example 8 with aldehyde 54 (100 mg, 0.41 mmol) and enamine 70 (90.0 mg, 0.37 mmol) as reactants. Purification by column chromatography on SiO$_2$ (Petroleum Ether/EtOAc=2:1) afford the title compound 69 as a yellow oil. (Yield 80 mg, 45%).

$^1$H NMR (300 MHz, CDCl$_3$, δ): 128-1.51 (m, 1H), 1.77-2.10 (m, 2H), 2.11-2.33 (m, 1H), 2.32 (s, 1.5H), 2.33 (s, 1.5H), 2.55-2.71 (m, 1H), 2.81-3.01 (m, 2H), 3.49-3.59 (m, 1H), 3.58 (s, 1.5H), 3.62 (s, 1.5H), 3.83 (s, 3H), 4.60 (s, 2H), 4.96-5.05 (m, 1H), 5.96-6.01 (m, 1H), 6.65-6.68 (m, 1H), 6.78-6.82 (m, 1H), 7.15-7.37 (m, 5H), 7.97-8.00 (m, 1H).

$^{13}$C NMR (75 MHz, CDCl$_3$, δ): 16.1, 27.2, 28.0, 28.5, 29.4, 29.8, 30.6, 30.9, 38.3, 38.6, 42.7, 43.7, 50.8, 50.9, 53.6, 55.5, 99.4, 99.6, 106.1, 107.8, 112.4, 112.5, 113.0, 126.0, 126.2, 126.3, 126.4, 127.5, 127.7, 128.9, 129.0, 129.9, 130.0, 130.8, 131.2, 138.1, 146.3, 146.4, 150.3, 150.5, 163.3, 163.4, 1693, 169.7, 199.7, 199.9.

MS (ESI$^+$): 432.21 (M+H$^+$)

Example 26

Preparation of 2-[[3-acetyl-2-methyl-1-(o-tolylmethyl)-4H-pyridin-4-yl]methyl]-6-methoxy-tetralin-1-one (71)

Step A: synthesis of 4-(o-tolylmethylamino)pent-3-en-2-one (72)

The title compound 72 is prepared as reported by Liu et al. in *Applied Organometallic Chemistry*, 2010, 685.

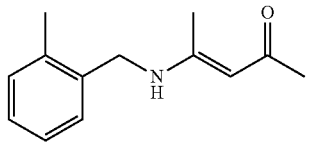

$^1$H NMR (300 MHz, CDCl$_3$, δ): 1.93 (s, 3H), 2.02 (s, 3H), 2.32 (s, 3H), 4.40 (d, J=5.7 Hz, 2H), 5.06 (s, 1H), 7.18-7.25 (m, 4H), 11.1 (br s, 1H).

MS (ESI$^+$): 204.13 (M+H$^+$)

Step B: synthesis of 2-[[3-acetyl-2-methyl-1-(o-tolylmethyl)-4H-pyridin-4-yl]methyl]-6-methoxy-tetralin-1-one (71)

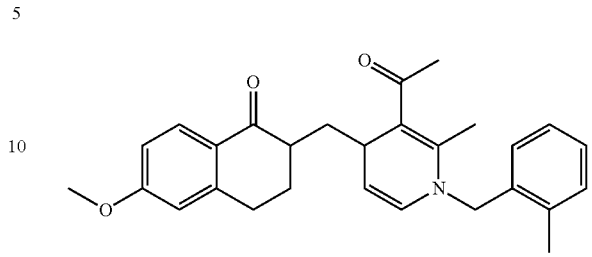

The title compound 71 is prepared according to the procedure reported in step D of Example 8 with aldehyde 54 (60 mg, 0.24 mmol) and enamine 72 (45 mg, 0.22 mmol) as reactants. Purification by column chromatography on SiO$_2$ (Petroleum Ether/EtOAc=2:1) afford the title compound 71 as a yellow solid. (Yield 36 mg, 34%).

$^1$H NMR (300 MHz, CDCl$_3$, δ): 1.24-1.41 (m, 1H), 1.79-1.98 (m, 1.54H), 1.99-2.18 (m, 1.46H), 2.27-2.31 (m, 9H), 2.56-2.71 (m, 1H), 2.87-3.03 (m, 2H), 3.47-3.56 (m, 0.54H), 3.67-3.86 (m, 0.46H), 3.84 (s, 3H), 4.56 (s, 2H), 5.07-5.15 (m, 1H), 5.94-5.98 (m, 1H), 6.65-6.68 (m, 1H), 6.78-6.82 (m, 1H), 6.98-7.04 (m, 1H), 7.15-7.25 (m, 3H), 7.94-7.98 (m, 1H).

$^{13}$C NMR (75 MHz, CDCl$_3$, δ): 16.3, 16.6, 19.0, 27.9, 28.5, 28.7, 29.5, 29.8, 30.5, 31.4, 32.4, 38.5, 40.3, 42.4, 42.6, 51.4, 51.5, 55.5, 106.6, 107.2, 110.2, 110.5, 112.4, 112.5, 113.2, 125.6, 125.7, 126.1, 126.2, 126.5, 126.6, 127.4, 127.7, 129.9, 130.5, 130.8, 130.9, 134.8, 135.4, 135.6, 146.3, 146.4, 1482, 149.2, 163.4, 198.7, 199.5, 199.9, 200.2.

MS (ESI$^+$): 430.23 (M+H$^+$)

Example 27

Preparation of methyl 1-[(2-chlorophenyl)methyl]-4-[(6-methoxy-1-oxo-tetralin-2-yl)methyl]-2-methyl-4H-pyridine-3-carboxylate (73)

This compound was prepared using the method described by Menéndez at al. in *Chemistry an European Journal*, 2013, 13207.

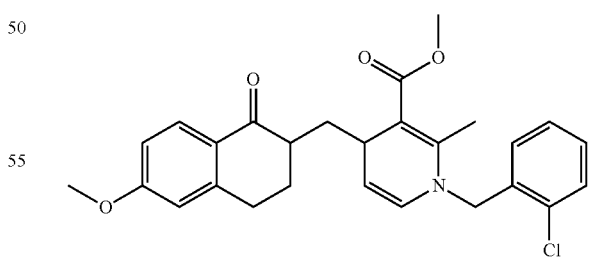

To a solution of 2-chloro-benzylamine (55 mg, 038 mmol) in methanol (3 mL) was added methyl acetoacetate (45 mg, 0.38 mmol) and CAN (11 mg, 5 mol %) at room temperature. The mixture was then heated to reflux for 30 minutes. Aldehyde 54 (100 mg, 0.38 mmol) was then added and the mixture was heated at reflux for further 30 minutes. After cooling to room temperature, the reaction mixture was diluted with dichloromethane and washed with water (3×). The organic layer was then dried over magnesium sulfate and concentrated to dryness. The crude residue was purified by column chromatography on SiO₂ (Petroleum Ether/EtOAc=2:1) to afford the title compound 73 as a yellow solid. (Yield 80 mg, 51%).

¹H NMR (300 MHz, CDCl₃, δ): 1.30-1.54 (m, 1H), 1.93-2.13 (m, 1H), 2.29 (s, 1.5H), 2.31 (s, 1.5H), 2.72-2.93 (m, 2H), 3.59-3.59 (m, 0.5H), 3.64 (s, 1.5H), 3.67 (s, 1.5H), 3.70-3.78 (m, 0.5H), 3.88 (s, 3H), 3.94 (s, 1.5H), 3.95 (s, 1.5H), 4.63-4.66 (m, 2H), 4.95 (dd, 0.5H, J=7.2 Hz, J=6.0 Hz), 5.06 (dd, 0.5H, J=7.5 Hz, J=6.3 Hz), 5.95 (d, 1H, J=7.2 Hz), 6.84-6.91 (m, 1H), 7.09-7.38 (m, 6H).

¹³C NMR (75 MHz, CDCl₃, δ): 14.2, 14.5, 15.8, 16.0, 31.9, 32.2, 32.7, 34.1, 40.5, 41.2, 44.0, 44.7, 50.9, 51.4, 56.1, 56.2, 60.4, 99.4, 99.9, 104.2, 106.3, 107.4, 107.5, 107.7, 127.1, 127.2, 127.4, 127.5, 128.7, 129.4, 129.5, 129.6, 131.0, 131.1, 132.0, 135.2, 135.3, 149.2, 149.3, 149.4, 150.2, 150.3, 155.3, 155.4, 169.1, 169.6, 208.2, 208.3.

Example 28

Preparation of 2-[2-[3-acetyl-1-[(2-chlorophenyl)methyl]-4H-pyridin-4-yl]ethyl]-6-methoxy-tetralin-1-one (74)

Step A: Synthesis of 2-but-3-enyl-6-methoxy-tetralin-1-one (75)

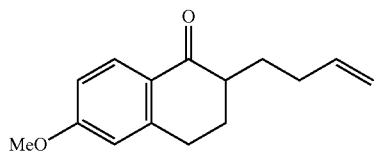

The title compound 75 is prepared according to the procedure reported in step A of Example 17 with 6-methoxy-1-tetralone (0.88 g, 5.0 mmol) and 4-bromo-but-1-ene (5.0 mmol, 1 equiv) as reactants.

Purification by column chromatography on SiO₂ (Petroleum Ether/EtOAc=95:5) afford the title compound 75 as a yellow oil. (Yield 130.0 mg, 11%).

¹H NMR (300 MHz, CDCl₃, δ): 1.42-1.63 (m, 1H), 1.69-1.91 (m, 1H), 1.98-2.22 (m, 4H), 2.35-2.48 (m, 1H), 2.87-2.93 (m, 2H), 3.81 (s, 3H), 4.93-5.06 (m, 2H), 5.71-5.87 (m, 1H), 6.64 (d, 1H, J=2.4 Hz), 6.77 (dd, 1H, J=8.7 Hz, J=2.4 Hz), 7.96 (d, 1H, J=8.7 Hz).

MS (ESI⁺): 231.13 (M+H⁺)

Step B: Synthesis of (E)-5-(6-methoxy-1-oxo-tetralin-2-yl)pent-2-enal (76)

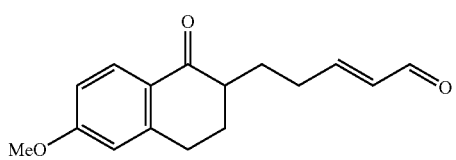 [SMILES: COc1ccc2c(c1)CCC(CC/C=C/C=O)C2=O]

The title compound 76 is prepared according to the procedure reported in step C of Example 8 with tetralone 75 (130 mg, 0.56 mmol) and crotonaldehyde (0.19 mL, 2.24 mmol) as reactants. Purification by column chromatography on SiO₂ (Petroleum/diethyl ether=1:1) afford the title compound 76 as an off-white solid. (Yield 121 mg, 83%).

¹H NMR (300 MHz, CDCl₃, δ): 1.62-1.79 (m, 1H), 1.82-1.93 (m, 1H), 2.07-2.22 (m, 2H), 2.39-2.49 (m, 3H), 2.92-2.96 (m, 2H), 3.82 (s, 3H), 6.07-6.16 (m, 1H), 6.65 (s, 1H), 6.77-6.92 (m, 2H), 7.95 (d, 1H, J=8.7 Hz), 9.48 (d, 1H, J=7.8 Hz).

¹³C NMR (75 MHz, CDCl₃, δ): 27.9, 28.6, 28.9, 30.2, 46.3, 55.4, 112.4, 113.2, 125.9, 129.8, 133.1, 146.3, 158.4, 163.5, 194.1, 198.3.

MS (ESI⁺): 259.13 (M+H⁺)

Step C: Synthesis of 2-[2-[3-acetyl-1-[(2-chlorophenyl)methyl]-4H-pyridin-4-yl]ethyl]-6-methoxy-tetralin-1-one (74)

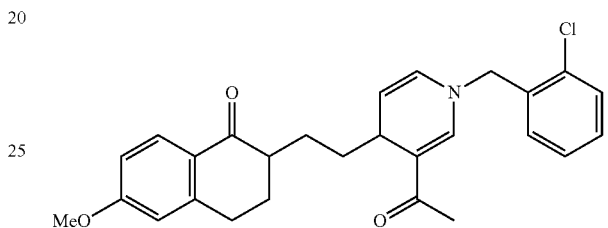

The title compound 73 is prepared according to the procedure reported in step D of Example 8 with aldehyde 76 (121 mg, 0.47 mmol) and enamine 45 (138 mg, 0.56 mmol) as reactants. Purification by column chromatography on SiO₂ (Petroleum Ether/EtOAc=2:1) afford the title compound 74 as a yellow oil. (Yield 67.5 mg, 32%).

¹H NMR (300 MHz, CDCl₃, δ): 1.29-1.61 (m, 2H), 1.58-1.82 (m, 1H), 1.85-2.19 (m, 5H), 2.21-2.38 (m, 1H), 2.77-2.87 (m, 2H), 3.45-3.54 (m, 1H), 3.75 (s, 3H), 4.41 (s, 2H), 4.85-4.91 (m, 1H), 5.77-5.82 (m, 1H), 6.55-6.58 (m, 1H), 6.70-6.73 (m, 1H), 7.05-7.08 (m, 1H), 7.10-7.30 (m, 5H), 7.88-7.92 (m, 1H).

MS (ESI⁺): 450.18 (M+H⁺)

Example 29

Preparation of 2-[[3-acetyl-1-[(3-chlorophenyl)methyl]-4H-pyridin-4-yl]methyl]-5,6-dimethoxy-indan-1-one (77)

Step A: synthesis of 2-allyl-5,6-dimethoxy-indan-1-one (78)

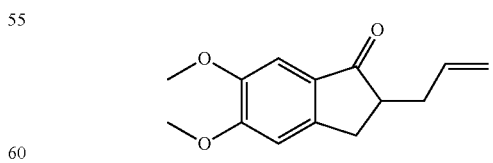

The title compound 78 is prepared according to the procedure reported in step A of Example 17 with 5,6-dimethoxy-1-indanone (1 g, 5.2 mmol) and allyl bromide (0.86 mL, 7.17 mmol) as reactants. Purification by column chromatography on SiO₂ (Petroleum Ether/EtOAc=2:1) afford the title compound 78 as a colorless oil. (Yield 0.5 g, 46%).

¹H NMR (300 MHz, CDCl₃, δ): 2.10-2.29 (m, 1H), 2.57-2.79 (m, 3H), 3.14 (dd, J=17.7 Hz, J=8.0 Hz, 1H), 3.86 (s, 3H), 3.92 (s, 3H), 4.96-5.02 (m, 1H), 5.02-5.14 (m, 1H), 5.75 (ddt, J=16.9 Hz, J=10.1 Hz, J=6.8 Hz, 1H), 6.83 (s, 1H), 7.12 (s, 1H).
¹³C NMR (75 MHz, CDCl₃, δ): 31.8, 35.8, 46.8, 56.1, 56.2, 104.3, 107.4, 116.9, 129.4, 135.6, 149.1, 155.6, 206.9.
HRMS (ESI⁺) calcd for [M+H]⁺ C₁₄H₁₇O₃ m/z 233.1178 found 233.1175.

Step B: synthesis of (E)-4-(5,6-dimethoxy-1-oxo-indan-2-yl)but-2-enal (79)

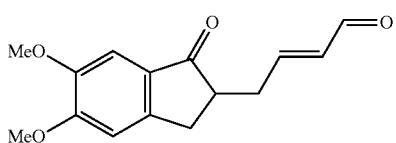 [SMILES: COc1cc2c(cc1OC)C(=O)C(C/C=C/C=O)C2]

The title compound 79 is prepared according to the procedure reported in step C of Example 8 with indanone 78 (0.5 g, 2.1 mmol) and crotonaldehyde (0.75 mL) as reactants. Purification by column chromatography on SiO₂ (Petroleum Ether/EtOAc=1:1) afford the title compound 79 as a white solid. (Yield 0.5 g, 91%).
¹H NMR (300 MHz, CDCl₃, δ): 2.50-2.58 (m, 1H), 2.70 (dd, 1H, J=17.1 Hz, J=3.3 Hz), 2.83-2.98 (m, 2H), 3.26 (dd, 1H, J=16.8 Hz, J=7.5 Hz), 3.90 (s, 3H), 3.95 (s, 3H), 6.13-6.22 (m, 1H), 6.81-6.90 (m, 2H), 7.17 (s, 1H), 9.49 (d, 1H, J=7.8 Hz).
¹³C NMR (75 MHz, CDCl₃, δ): 32.1, 34.7, 45.9, 56.2, 56.4, 104.5, 107.5, 129.0, 134.5, 148.6, 149.8, 155.2, 156.0, 193.8, 205.4.
MS (ESI⁺): 261.11 (M+H⁺)

Step C: synthesis of 2-[[3-acetyl-1-[(3-chlorophenyl)methyl]-4H-pyridin-4-yl]methyl]-5,6-dimethoxy-indan-1-one (77)

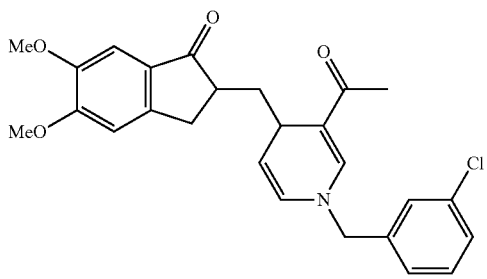 [SMILES: COc1cc2c(cc1OC)C(=O)C(CC1C=CN(Cc3cccc(Cl)c3)C=C1C(C)=O)C2]

The title compound 77 is prepared according to the procedure reported in step D of Example 8 with aldehyde 79 (158 mg, 0.35 mmol) and enamine 45 (73 mg, 0.35 mmol) as reactants. Purification by column chromatography on SiO₂ (Petroleum DCM/EtOAc=2:1) afford the title compound 77 as a yellow oil. (Yield 80 mg, 48%).
¹H NMR (300 MHz, CDCl₃, δ): 1.33-1.64 (m, 1H), 1.89-1.96 (m, 1H), 2.17 (s, 1.5H), 2.23 (s, 1.5H), 2.63-2.87 (m, 1.5H), 3.05-3.32 (m, 1.5H), 3.57-3.68 (m, 0.5H), 3.71-3.80 (m, 0.5H), 3.90 (s, 3H), 3.96 (s, 3H), 4.56 (s, 2H), 4.97 (dd, 0.5H, J=8.4 Hz, J=5.4 Hz), 5.14 (dd, 0.51, J=7.5 Hz, J=5.1 Hz), 5.92-5.98 (m, 1H), 6.85 (s, 0.5H), 6.89 (s, 0.5H), 7.11-7.46 (m, 6H).
¹³C NMR (75 MHz, CDCl₃, δ): 24.5, 24.7, 29.1, 29.2, 32.6, 33.9, 40.2, 41.2, 44.1, 45.1, 55.6, 56.1, 56.3, 104.2, 107.4, 107.6, 108.5, 110.1, 113.5, 114.1, 127.5, 127.6, 128.1, 128.6, 128.8, 129.4, 130.0, 133.1, 134.3, 134.4, 142.9, 143.4, 149.3, 149.7, 155.3, 155.4, 195.0, 195.5, 208.3, 208.4.
MS (ESI⁺): 452.16 (M+H⁺)

Example 30

Preparation of 1-benzyl-4-[(5,6-dimethoxy-1-oxo-indan-2-yl)methyl]-N,2-dimethyl-4H-pyridine-3-sulfonamide (80)

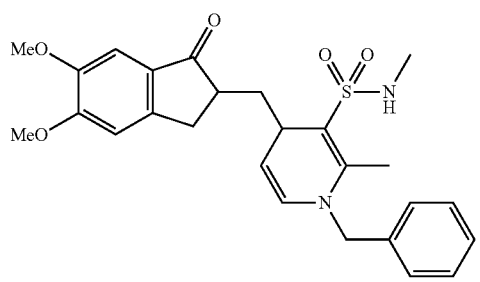 [SMILES: CNS(=O)(=O)C1=C(C)N(Cc2ccccc2)C=CC1CC1Cc2cc(OC)c(OC)cc2C1=O]

The title compound 80 is prepared according to the procedure reported in Example 27 with aldehyde 79 (104.4 mg, 0.40 mmol), N-methyl-2-oxo-propane-1-sulfonamide [prepared as described by Buiila et al in *Tetrahedron* 1998, 3589] (60.4 mg, 0.40 mmol) and benzylamine (42.8 mg, 0.40 mmol) as reactants. Purification by column chromatography on SiO₂ (gradient of EtOAc in Petroleum Ether) afford the title compound 80 as a yellow solid. (Yield 77.1 mg, 40%).
MS (ESI⁺): 483.19 (M+H⁺)

Example 31

Preparation of 2-[(1-benzyl-2-methyl-3-methylsulfonyl-4H-pyridin-4-yl)methyl]-6-methoxy-tetralin-1-one (81)

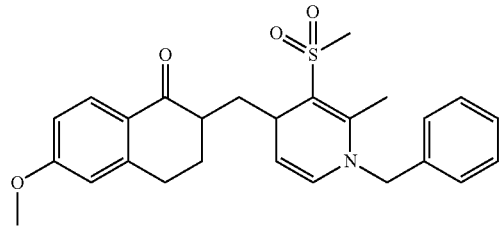 [SMILES: COc1ccc2c(c1)CCC(CC1C=CN(Cc3ccccc3)C(C)=C1S(C)(=O)=O)C2=O]

The title compound 81 is prepared according to the procedure reported in Example 27 with aldehyde 54 (60.9 mg, 0.25 mmol), commercial 1-methylsulfonylpropan-2-one (34.0 mg, 0.25 mmol) and benzylamine (26.8 mg, 0.25 mmol) as reactants. Purification by column chromatography on SiO₂ (gradient of EtOAc in Petroleum Ether) afford the title compound 81 as a pale yellow solid. (Yield 32.8 mg, 29%).
MS (ESI⁺): 452.19 (M+H⁺)

Example 32

Preparation of 2-[(3-acetyl-1-benzyl-pyridin-1-ium-4-yl)methyl]-6-methoxy-tetralin-1-one chloride (82)

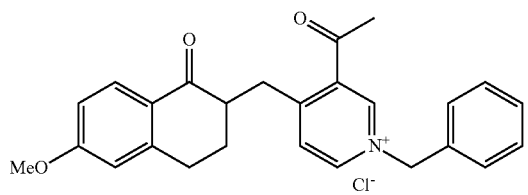

To a solution of compound 52 (80.2 mg, 0.2 mmol) in acetonitrile (2 mL) was added sublimed iodine (1 equiv) in one portion at room temperature. After 30 minutes, the solvent was removed and the residue was taken up in dichloromethane. The organic layer was successively washed with 10% aqueous solution sodium bisulfite and brine, dried over magnesium sulfate, filtered and concentrated to dryness. The obtained solid was placed in presence of anion exchange resin (Amberlyst C) in acetonitrile for 24 h. After filtration and concentration, the title compound 82 was obtained as a white solid (Yield 75 mg, 86%).

$^1$H NMR (300 MHz, CDCl$_3$, δ): 1.98-2.04 (m, 1H), 2.17-2.35 (m, 1H), 2.84-3.18 (m, 4H), 2.98 (s, 3H), 3.46-3.57 (m, 1H), 3.84 (s, 3H), 6.39 (s, 2H), 6.67 (d, 1H, J=2.8 Hz), 6.79 (dd, 1H, J=8.7 Hz, J=2.1 Hz), 7.41 (br s, 3H), 7.67 (br s, 2H), 7.84 (d, 1H, J=8.7 Hz), 8.09 (d, 1H, J=6.6 Hz), 8.89 (br s, 1H), 10.44 (br s, 1H).

MS (ESI$^+$): 400.19 (M$^+$)

Example 33

Preparation of 2-[[3-acetyl-1-[[2-(trifluoromethyl)phenyl]methyl]pyridin-1-ium-4-yl]methyl]-methoxy-tetralin-1-one chloride (83)

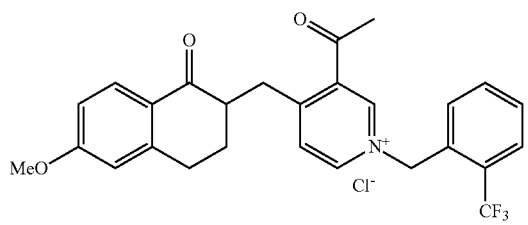 [SMILES: COc1ccc2c(c1)CCC(Cc1cc[n+](Cc3ccccc3C(F)(F)F)cc1C(C)=O)C2=O ; [Cl-]]

To a solution of compound 67 (30.0 mg, 0.064 mmol) in acetonitrile (1 mL) was added DDQ (1 equiv) in one portion at room temperature. After completion of the reaction, acetonitrile was removed under reduced pressure and the residue was taken up in dichloromethane (10 mL). The organic layer was successively washed with aqueous solution of HCl 1M and brine, dried over magnesium sulfate, filtered and concentrated to dryness. The obtained solid was placed in presence of anion exchange resin (Amberlyst Cl$^-$) in acetonitrile for 24 h. After filtration and concentration, the title compound 83 was obtained as a yellow solid (Yield 19.3 mg, 60%).

$^1$H NMR (300 MHz, CD$_3$CN, δ): 1.86-1.99 (m, 1H), 2.04-2.18 (m, 1H), 2.68 (s, 3H), 2.87-3.09 (m, 4H), 3.62-3.73 (m, 1H), 3.80 (s, 3H), 5.85 (s, 2H), 6.68-6.81 (m, 2H), 7.37-7.58 (m, 4H), 7.76 (d, 1H, J=8.4 Hz), 8.01 (d, 1H, J=6.6 Hz), 8.63 (d, 1H, J=6.3 Hz), 9.06 (br s, 1H).

MS (ESI$^+$): 468.17 (M$^+$)

Example 34

Synthesis of 2-[(3-substituted-4-pyridyl)methylene]-tetralone derivatives

Example 34.1

Synthesis of (2E)-2-[(3-bromo-4-pyridyl)methylene]-6,7-dimethoxy-tetralin-1-one (84)

This compound was prepared using the method described by Potter et al. in *J. Med Chem.*, 2006, 1325.

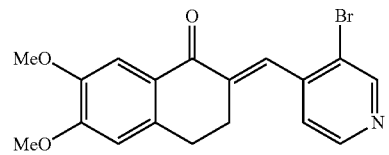 [SMILES: COc1cc2c(cc1OC)C(=O)/C(=C/c1ccncc1Br)CC2]

To a solution of (i-Pr)$_2$NH (0.3 mL, 2.2 mmol) at 0° C. in dry THF (15 mL) was added n-BuLi (1.22 M solution in hexane, 2.7 mL, 2.2 mmol), the mixture was stirred for 15 min at this temperature, after which the 6,7-dimethoxy-1-tetralone (0.412 g, 2 mmol) in dry THF (7 mL) was slowly added at −78° C. After 30 min at this temperature, 3-bromo-4-pyridinecarboxaldehyde (0.446 g, 2.4 mmol) in dry THF (7 mL) was slowly added and the solution was stirred for 30 min at −78° C. before allowed to reach room temperature and being stirred for a night. Then, the mixture was hydrolyzed by HCl 1N and extracted by AcOEt to eliminate the possible excess of tetralone. The aqueous layer was neutralized by NaHCO$_3$ and the compound was extracted by CH$_2$Cl$_2$ three times. The combined organic layers were dried over MgSO$_4$ and concentrated to dryness. The residue was purified by column chromatography on SiO$_2$ (gradient of EtOAc in petroleum ether) to afford the expected product 84 (Yield 598.7 mg, 80%).

$^1$H NMR (300 MHz, CDCl$_3$, δ): 2.87-2.93 (m, 4H), 3.95 (s, 6H), 6.68 (s, 1H), 7.20 (d, 1H, J=4.8 Hz), 7.64 (s, 2H), 8.54 (d, 1H, J=5.1 Hz), 8.79 (s, 1H).

$^{13}$C NMR (75 MHz, CDCl$_3$, δ): 27.8, 28.7, 56.2, 56.3, 109.7, 110.1, 122.6, 124.6, 126.9, 131.6, 138.8, 144.6, 147.6, 148.6, 151.7, 152.4, 154.2, 185.7.

MS (ESI$^+$): 374.03 (M+H$^+$)

Example 34.2

Synthesis of (2E)-2-[(3-chloro-4-pyridyl)methylene]-6,7-dimethoxy-tetralin-1-one (85)

This compound was prepared using the method described by Potter et al. in *J. Med Chem.*, 2006, 1325.

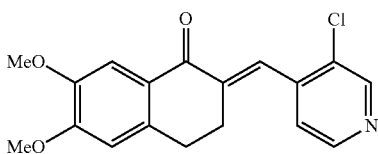 [SMILES: COc1cc2c(cc1OC)C(=O)/C(=C/c1ccncc1Cl)CC2]

At room temperature, a mixture of 6,7-dimethoxy-1-tetralone (1.44 g, 7 mmol) and 3-chloro-4-pyridinecarboxaldehyde (1.0 g, 7 mmol) was added in one portion to a solution of sodium hydroxide (280 mg, 1 equiv) in ethanol (7 mL). After being stirred at room temperature for 4 h, the solid obtained was filtered and rinsed with ethanol then diethyl ether to give the title compound 85 (Yield 932 mg, 44%).

$^1$H NMR (300 MHz, CDCl$_3$, δ): 2.87-2.95 (m, 4H), 3.95 (s, 6H), 6.68 (s, 1H), 7.21 (d, 1H, J=5.1 Hz), 7.63 (s, 1H), 7.70 (s, 1H), 8.54 (d, 1H, J=4.8 Hz), 8.66 (s, 1H).

MS (ESI$^+$): 330.09 (M+H$^+$)

Example 34.3

Synthesis of (2E)-2-[(3-fluoro-4-pyridyl)methylene]-6,7-dimethoxy-tetralin-1-one (86)

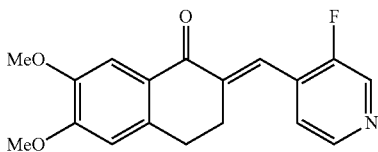 [SMILES: COc1cc2c(cc1OC)C(=O)/C(=C/c1ccncc1F)CC2]

The title compound 86 was prepared according to the procedure reported in Example 34.2 with 6,7-dimethoxy-1-tetralone (1.65 g, 8 mmol) and 3-fluoro-4-pyridinecarboxaldehyde (1.0 g, 8 mmol) as reactants. White solid. (Yield 2.24 g, 89%).

$^1$H NMR (300 MHz, CDCl$_3$, δ): 2.94 (s, 3H), 3.95 (s, 6H), 6.68 (s, 1H), 7.24-7.28 (m, 2H), 7.63 (d, 2H, J=3.0 Hz), 8.44 (d, 1H, J=4.8 Hz), 8.52 (d, 1H, J=1.5 Hz).

$^{13}$C NMR (75 MHz, CDCl$_3$, δ): 28.0, 28.5, 56.1, 56.2, 109.5, 109.9, 124.4, 125.2, 125.3, 126.0, 131.4, 131.6, 138.6, 138.7, 138.9, 140.8, 145.4, 145.5, 148.4, 154.0, 155.1, 158.6, 185.5.

MS (ESI$^+$): 314.13 (M+H$^+$)

Example 34.4

Synthesis of (2E)-2-[(3-bromo-4-pyridyl)-methylene]-6-methoxy-tetralin-1-one (87)

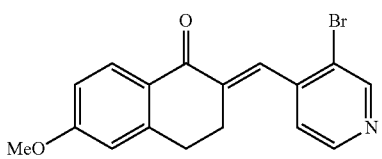 [SMILES: COc1ccc2c(c1)CC/C(=C\c1ccncc1Br)C2=O]

The title compound 87 is prepared according to the procedure reported in Example 34.2 with 6-methoxy-1-tetralone (4.74 g, 26.9 mmol) and 3-bromo-4-pyridinecarboxaldehyde (5.0 g, 26.9 mmol) as reactants. White solid. (Yield 7.0 g, 76%).

$^1$H NMR (300 MHz, CDCl$_3$, δ): 2.84-2.96 (m, 4H), 3.87 (s, 3H), 6.70 (d, 1H, J=1.8 Hz), 6.89 (dd, 1H, J=8.7 Hz, J=2.1 Hz), 7.19 (d, 1H, J=4.8 Hz), 7.64 (s, 1H), 8.13 (d, 1H, J=8.7 Hz), 8.53 (d, 1H, J=4.8 Hz), 8.78 (s, 1H).

$^{13}$C NMR (75 MHz, CDCl$_3$, δ): 27.5, 29.2, 55.6, 112.5, 113.8, 122.6, 124.5, 126.5, 131.1, 131.7, 139.7, 144.5, 146.0, 148.0, 152.4, 164.0, 185.7.

HRMS (ESI$^+$) calcd for [M+H]$^+$ C$_{17}$H$_{15}$NO$_2$Br m/z 344.0286 found 344.0279.

Example 34.5

Synthesis of (2E)-2-[(3-iodo-4-pyridyl)methylene]-6-methoxy-tetralin-1-one (88)

This compound was prepared using the method described by Buchwald in *J. Am. Chem. Soc.*, 2002, 14844.

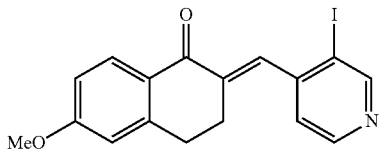 [SMILES: COc1ccc2c(c1)CC/C(=C\c1ccncc1I)C2=O]

In a Schlenk tube, N,N'-dimethyl-1,2-cyclohexanediamine 85% (32 μL, 0.20 mmol) and dioxane (2 mL) were added to a mixture of CuI (19.2 mg, 0.1 mmol), compound 87 (688 mg, 2.0 mmol) and NaI (600 mg, 4.00 mmol). The Schlenk tube was sealed with a Teflon cap and the reaction mixture was stirred at 110° C. for 24 h. After cooling, the resulting suspension was poured into water (20 mL), and extracted with dichloromethane (3×). The combined organic phases were dried over magnesium sulfate and concentrated to dryness. The product was allowed to crystallize at room temperature. The residue was purified by column chromatography on SiO$_2$ (gradient of EtOAc in petroleum ether) to afford the title compound 88 as a yellow solid (Yield 703.8 mg, 90%).

$^1$H NMR (300 MHz, CDCl$_3$, δ): 2.84-2.96 (m, 4H), 3.87 (s, 3H), 6.70 (d, 1H, J=2.4 Hz), 6.89 (dd, 1H, J=8.7 Hz, J=2.4 Hz), 7.17 (d, 1H, J=4.8 Hz), 7.52 (s, 1H), 8.14 (d, 1H, J=8.7 Hz), 8.55 (d, 1H, J=4.8 Hz), 8.99 (s, 1H).

$^{13}$C NMR (75 MHz, CDCl$_3$, δ): 27.4, 29.3, 55.6, 99.1, 112.5, 113.8, 124.4, 126.6, 131.1, 135.7, 139.1, 146.0, 148.3, 148.6, 157.7, 164.1, 185.8.

Example 35

Synthesis of 2-[(3-substituted-4-pyridyl)methylene]-indanonone derivatives

Example 35.1

Synthesis of (2E)-2-[(3-bromo-4-pyridyl)methylene]-5,6-dimethoxy-indan-1-one (89)

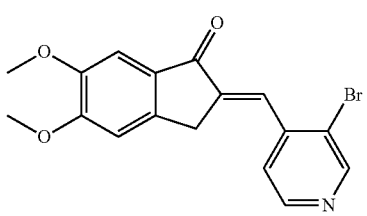 [SMILES: COc1cc2c(cc1OC)C(=O)/C(=C/c1ccncc1Br)C2]

The title compound 89 is prepared according to the procedure reported in Example 34.1 with 5,6-dimethoxy-1-indanone (1.92 g, 10 mmol) and 3-bromo-4-pyridinecarboxaldehyde (2.3 g, 10 mmol) as reactants. White solid. (Yield 2.34 g, 65%).

$^1$H NMR (300 MHz, CDCl$_3$, δ): 3.87-3.88 (m, 2H), 3.95 (s, 3H), 3.99 (s, 3H), 6.93 (s, 1H), 7.34 (s, 1H), 7.49 (d, 1H, J=5.1 Hz), 7.72 (s, 1H), 8.57 (d, 1H, J=5.1 Hz), 8.81 (s, 1H).

$^{13}$C NMR (75 MHz, CDCl$_3$, δ): 31.4, 563, 56.5, 105.2, 107.2, 123.5, 123.6, 127.9, 130.8, 141.3, 143.1, 145.0, 148.3, 150.0, 153.0, 156.1, 191.7.

MS (ESI$^+$): 360.02 (M+H$^+$)

Example 35.2

Synthesis of (2E)-2-[(3-bromo-4-pyridyl)methylene]-5-methyl-indan-1-one (90)

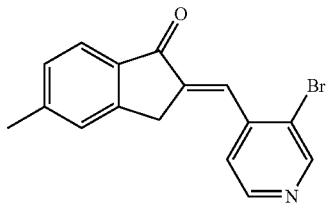 [SMILES: Cc1ccc2c(c1)C/C(=C\c1ccncc1Br)C2=O]

The title compound 90 is prepared according to the procedure reported in Example 34.1 with 5-methyl-1-indanone (0.73 g, 5 mmol) and 3-bromo-4-pyridinecarboxaldehyde (0.93 g, 5 mmol) as reactants. White solid. (Yield 1.24 g, 79%).

$^1$H NMR (300 MHz, CDCl$_3$, δ): 2.46 (s, 3H), 3.90 (s, 2H), 7.23-7.30 (m, 2H), 7.50 (d, 1H, J=5, 1 Hz), 7.76-7.81 (m, 2H), 8.58 (d, 1H, J=5.1 Hz), 8.80 (s, 1H).

$^{13}$C NMR (75 MHz, CDCl$_3$, δ): 22.3, 31.4, 123.4, 123.6, 124.5, 126.5, 128.6, 129.2, 135.1, 140.9, 142.6, 146.8, 148.8, 149.8, 152.8, 192.5.

MS (ESI+): 314.01 (M+H$^+$)

Example 35.3

Synthesis of (2E)-2-[(3-bromo-4-pyridyl)methylene]-5-methoxy-indan-1-one (91)

This compound was prepared using the method described by Li et al. in *Bioorganic & Medicinal Chemistry Letters*, 2012, 4462.

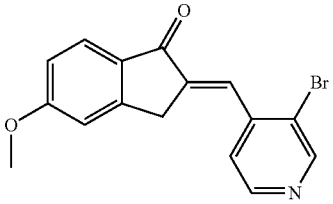 [SMILES: COc1ccc2c(c1)C/C(=C\c1ccncc1Br)C2=O]

To a solution of 5-methoxy-1-indanone (0.32 mmol) and 3-bromo-4-pyridinecarboxaldehyde (0.36 g, 2 mmol) in toluene (30 mL) was added p-toluenesulfonic acid (0.45 g, 2.4 mmol). After heated at reflux using a Dean-Stark for 4 h, the mixture was cooled to room temperature and the solvent was removed in vacuum, then 5% sodium bicarbonate solution was added until pH=8. After extraction with dichloromethane (4×), the organic layer was dried over magnesium sulfate and concentrated to dryness. The residue was taken up with EtOAc and the solid was filtered, rinsed with EtOAc to afford the title compound 91 as a yellow solid (Yield 330 mg, 50%).

$^1$H NMR (300 MHz, CDCl$_3$, δ): 3.91 (br s, 5H), 6.96-7.00 (m, 2H), 7.49 (d, 1H, J=5, 1 Hz), 7.74 (t, 1H, J=2.4 Hz), 7.87 (d, 1H, J=8.4 Hz), 8.58 (d, 1H, J=5.1 Hz), 8.82 (s, 1H).

$^{13}$C NMR (75 MHz, CDCl$_3$, δ): 31.7, 55.8, 109.8, 115.8, 123.5, 126.7, 128.2, 131.1, 141.2, 143.1, 148.3, 152.3, 153.0, 165.8, 191.3.

Example 35.4

Synthesis of (2E)-2-[(3-bromo-4-pyridyl)methylene]-5,6-dimethyl-indan-1-one (92)

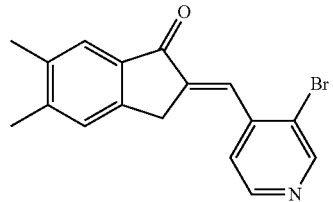 [SMILES: Cc1cc2c(cc1C)C(=O)/C(=C/c1ccncc1Br)C2]

The title compound 92 is prepared according to the procedure reported in Example 35.3 with 5,6-dimethyl-1-indanone (0.40 g, 2.5 mmol) and 3-bromo-4-pyridinecarboxaldehyde (0.45 g, 2.5 mmol) as reactants. Yellow solid. (Yield 0.48 g, 58%).

$^1$H NMR (300 MHz, CDCl$_3$, δ): 2.31 (s, 3H), 2.35 (s, 3H), 3.84 (s, 2H), 7.26 (s, 1H), 7.50 (s, 1H), 7.63 (s, 1H), 7.72 (s, 1H), 8.57 (br s, 1H), 8.80 (br s, 1H).

$^{13}$C NMR (75 MHz, CDCl$_3$, δ): 19.9, 21.0, 31.2, 125.2, 127.0, 128.5, 135.8, 137.1, 141.3, 143.0, 146.0, 147.6, 148.3, 152.9, 192.8.

Example 35.5

Synthesis of (6E)-6-[(3-bromo-4-pyridyl)methylene]-5H-cyclopenta[f][1,3]benzo-dioxol-7-one (93)

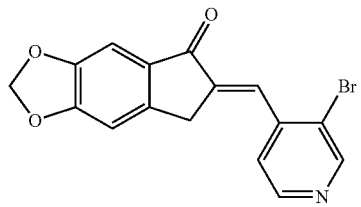 [SMILES: O=C1/C(=C/c2ccncc2Br)Cc2cc3c(cc21)OCO3]

The title compound 93 is prepared according to the procedure reported in Example 35.3 with 5,6-methylenedioxy-1-indanone (0.50 g, 2.87 mmol) and 3-bromo-4-pyridinecarboxaldehyde (0.54 g, 3 mmol) as reactants. Yellow solid. (Yield 0.35 g, 35%).

$^1$H NMR (300 MHz, CDCl$_3$, δ): 3.85 (d, 2H, J=1, 8 Hz), 6.11 (s, 2H), 6.89 (s, 1H), 7.28 (s, 1H), 7.49 (d, 1H, J=5, 1 Hz), 7.71 (t, 1H, J=2.1 Hz), 8.59 (br s, 1 Hz), 8.82 (s, 1H).

MS (ESI$^+$): 344.00 (M+H$^+$)

Example 35.6

Synthesis of (2E)-2-[(3-bromo-4-pyridyl)methylene]-5-chloro-indan-1-one (94)

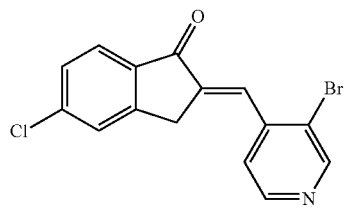 [SMILES: O=C1/C(=C/c2ccncc2Br)Cc2cc(Cl)ccc21]

The title compound 94 is prepared according to the procedure reported in Example 35.3 with 5-chloro-1-indanone (0.83 g, 5 mmol) and 3-bromo-4-pyridinecarboxaldehyde (0.93 g, 5 mmol) as reactants. White solid. (Yield 0.44 g, 26%).

$^1$H NMR (300 MHz, CDCl$_3$, δ): 3.95 (s, 2H), 7.43-7.52 (m, 3H), 7.82 (d, 1H, J=2, 1 Hz), 7.87 (d, 1H, J=5, 1 Hz), 8.61 (d, 1H, J=4.8 Hz), 8.83 (s, 1H).

$^{13}$C NMR (75 MHz, CDCl$_3$, δ): 31.4, 123.4, 123.60, 126.0, 126.5, 129.0, 130.0, 136.0, 139.8, 141.8, 142.6, 148.4, 150.8, 153.0, 191.7.

Example 35.7

Synthesis of (2,4,6-trichlorophenyl) 4-[(E)-(5,6-dimethoxy-1-oxo-indan-2-ylidene-methyl]pyridine-3-carboxylate (95)

This compound was prepared using the method described by Manabe et al in *Organic Letters*, 2002, 14844.

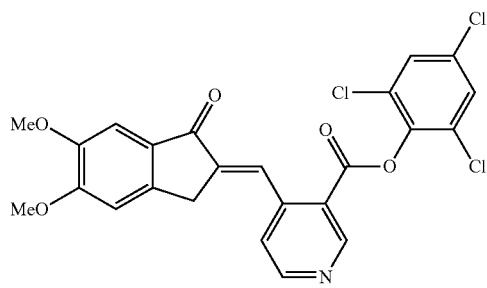 [SMILES: COc1cc2c(cc1OC)C(=O)/C(=C/c1ccncc1C(=O)Oc1c(Cl)cc(Cl)cc1Cl)C2]

In a Schlenk tube under argon atmosphere, n-tributylamine (0.48 mL, 0.20 mmol) in anhydrous toluene (1.2 mL) was added to a mixture of Xantphos (35 mg, 0.06 mmol), compound 89 (360 mg, 1.0 mmol) and Pd(OAc)$_2$ (7 mg, 0.03 mmol). The Schlenk tube was sealed with a Teflon cap and the reaction mixture was stirred at 100° C. for 5 minutes. Then, a degassed solution of 2,4,6-trichlorophenyl-formate (0.27 g, 1.2 mmol) in anhydrous toluene (2.4 mL) were added to the reaction mixture and heated to 100° C. for additional 3 hours. After cooling, the resulting suspension was filtered on Celite and the filtrate was concentrated to dryness. The residue was purified by column chromatography on SiO$_2$ (gradient of EtOAc in petroleum ether) to afford the title compound 95 as a pale yellow solid (Yield 98.0 mg, 19%).

$^1$H NMR (300 MHz, CDCl$_3$, δ): 3.82 (s, 2H), 3.93 (s, 3H), 3.98 (s, 3H), 6.90 (s, 1H), 7.32 (s, 1H), 7.42 (s, 2H), 7.58 (d, 1H, J=5.1 Hz), 8.12 (s, 1H), 8.89 (d, 1H, J=5.1 Hz), 9.48 (s, 1H).

$^{13}$C NMR (75 MHz, CDCl$_3$, δ): 31.0, 56.3, 56.4, 105.3, 107.1, 123.6, 127.9, 128.8, 129.7, 131.0, 132.6, 140.8, 142.7, 144.9, 146.4, 149.9, 152.8, 153.8, 156.0, 161.7, 191.5.

Example 35.8

Synthesis of methyl 4-[(E)-(5,6-dimethoxy-1-oxo-indan-2-ylidene)methyl]pyridine-3-carboxylate (96)

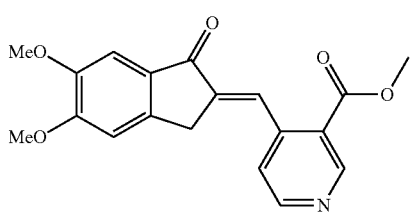 [SMILES: COC(=O)c1cnccc1/C=C1\Cc2cc(OC)c(OC)cc2C1=O]

In a Schlenk tube under argon atmosphere, n-triethylamine (0.13 mL, 0.96 mmol) was added to a solution of compound 95 (93 mg, 0.184 mmol) in anhydrous methanol (1 mL). The tube was sealed with a Teflon cap and the reaction mixture was stirred at 70° C. for 20 h. After cooling, the resulting suspension was filtered on Celite and the filtrate was concentrated to dryness. The residue was purified by column chromatography on SiO$_2$ (gradient of EtOAc in petroleum ether) to afford the title compound 96 as a white solid (Yield 49 mg, 78%).

$^1$H NMR (300 MHz, CDCl$_3$, δ): 3.78 (s, 2H), 3.94 (s, 6H), 3.98 (s, 3H), 6.90 (s, 1H), 734 (s, 1H), 7.48 (d, 1H, J=5.1 Hz), 8.07 (s, 1H), 8.77 (d, 1H, J=4.8 Hz), 9.20 (s, 1H).

MS (ESI$^+$): 340.13 (M+H$^+$)

Example 35.9

Synthesis of (2E)-2-[(3-acetyl-4-pyridyl)methylene]-5,6-dimethoxy-indan-1-one (97)

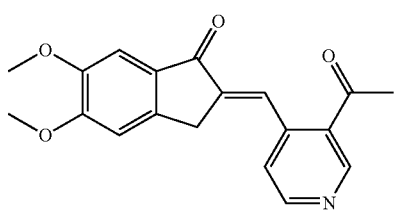 [SMILES: COc1cc2c(cc1OC)C(=O)/C(=C/c1ccncc1C(C)=O)C2]

A toluene solution (3 mL) of compound 89 (0.4 g, 1.1 mmol), Pd(dba)$_2$ (25.3 mg, 0.044 mmol) and PPh$_3$ (23.1 mg, 0.088 mmol) was stirred at room temperature under argon for 15 min. Then, (1-ethoxyvinyl)tri(n-butyl)stannane (0.38 mL, 1.1 mmol) in toluene (3 mL) was added and the resulting mixture was stirred overnight at 110° C., cooled to room temperature and filtered on Celite, washed with EtOAc and concentrated under reduced pressure. Purification on silica gel (gradient of EtOAc in Petroleum ether) afford the product which was placed in presence of an aqueous solution of HCl 1M for 30 minutes at room temperature. After neutralization with a saturated aqueous solution of NaHCO$_3$, aqueous phase was extracted with dichloromethane and the combined organic layers were dried over magnesium sulfate to afford the title compound 97 (Yield 288.1 mg, 81%) which was used without further purification.

¹H NMR (300 MHz, CDCl₃, δ): 2.65 (s, 3H), 3.76 (d, 21, J=2.1 Hz), 3.95 (s, 3H), 3.97 (s, 3H), 6.89 (s, 1H), 7.34 (s, 1H), 7.48 (d, 1H, J=5.1 Hz), 7.85 (s, 1H), 8.76 (d, 1H, J=5.1 Hz), 9.03 (s, 1H).
MS (ESI⁺): 324.12 (M+H⁺)

Example 35.10

Synthesis of 4-[(E)-(5,6-dimethoxy-1-oxo-indan-2-ylidene)methyl]-N-methyl-pyridine-3-carboxamide (98)

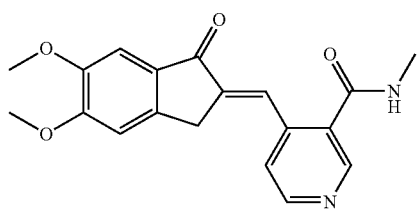

In a Schlenk tube under argon atmosphere, n-triethylamine (5 equiv) was added to a solution of compound 95 (100 mg, 0.198 mmol) and methylamine (4 equiv) in anhydrous THF (1 mL). The tube was sealed with a Teflon cap and the reaction mixture was stirred at 70° C. for 24 h. After cooling, the resulting yellow suspension was filtered on Celite and rinsed with diethylether to afford the title compound 98 as a yellow solid (Yield 61.6 mg, 92%).
¹H NMR (300 MHz, CDCl₃, δ): 3.03 (d, 3H, J=4.8 Hz), 3.85 (s, 2H), 3.93 (s, 3H), 3.98 (s, 3H), 6.02 (br s, 1H), 6.91 (s, 1H), 7.30 (s, 1H), 7.48 (d, 1H, J=3.9 Hz), 7.70 (s, 1H), 8.70 (br s, 1H), 8.80 (br s, 1H).
¹³C NMR (75 MHz, DMSO-D6, δ): 26.2, 31.0, 55.7, 56.1, 104.6, 108.0, 122.7, 126.0, 129.6, 132.9, 140.4, 140.7, 145.6, 148.5, 149.4, 150.6, 155.7, 166.5, 191.3.
MS (ESI⁺): 339.13 (M+H⁺)

Example 36

Synthesis of 2-[(3-substituted-4-pyridyl)methyl]-tetralone derivatives

Example 36.1

Synthesis of 2-[(3-bromo-4-pyridyl)methyl]-6-methoxy-tetralin-1-one (99)

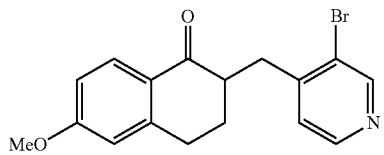 [SMILES: COc1ccc2c(c1)CCC(Cc1ccncc1Br)C2=O]

Pt/C (5 wt % loading, 200 mg) was added to a stirred solution of the compound 87 (2.0 g, 5.81 mmol) in EtOH (58 mL) at room temperature. The resulting suspension was stirred for 4 hours under H₂ atmosphere (1 atm) then filtered over Celite, rinsed with dichloromethane and concentrated to dryness. The crude residue was purified by column chromatography on SiO₂ (gradient of EtOAc in petroleum ether) to afford the title compound 99 (Yield 2.0 g, 99%).
¹H NMR (300 MHz, CDCl₃, δ): 1.80-1.94 (m, 1H), 2.02-2.11 (m, 1H), 2.70-2.95 (m, 4H), 3.65 (dd, 1H, J=13.5 Hz, J=4.5 Hz), 3.85 (s, 3H), 6.67 (d, 1H, J=2.4 Hz), 6.84 (dd, 1H, J=8.7 Hz, J=2.4 Hz), 7.24 (d, 1H, J=5.1 Hz), 8.03 (d, 1H, J=8.7 Hz), 8.41 (d, 1H, J=4.8 Hz), 8.68 (s, 1H).
¹³C NMR (75 MHz, CDCl₃, δ): 28.3, 29.3, 35.5, 47.0, 55.4, 112.4, 113.3, 123.5, 125.7, 126.4, 129.9, 1463, 148.0, 149.0, 151.9, 163.6, 196.9.

Example 36.2

Synthesis of 2-[(3-bromo-4-pyridyl)methyl]-6,7-dimethoxy-tetralin-1-one (100)

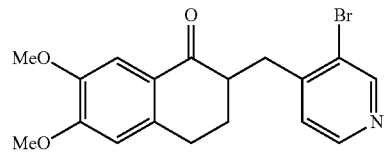 [SMILES: COc1cc2c(cc1OC)C(=O)C(Cc1ccncc1Br)CC2]

The title compound 100 is prepared according to the procedure reported in Example 36.1 with compound 84 (374 mg, 1.0 mmol) and Pt/C (5 wt % loading, 38 mg) as reactants. White solid. (Yield 0.251 g, 99%).
¹H NMR (300 MHz, CDCl₃, δ): 1.88-1.94 (m, 1H), 2.03-2.11 (m, 1H), 2.69-2.92 (m, 4H), 3.63 (dd, 1H, J=13.5 Hz, J=4.5 Hz), 3.90 (s, 3H), 3.92 (s, 3H), 6.63 (s, 1H), 7.24 (d, 1H, J=5.1 Hz), 7.51 (s, 1H), 8.41 (d, 1H, J=4.5 Hz), 8.67 (s, 1H).
¹³C NMR (75 MHz, CDCl₃, δ): 28.7, 35.6, 46.7, 56.0, 56.1, 108.7, 110.0, 123.5, 125.3, 126.4, 138.6, 148.0, 149.0, 152.0, 153.6, 197.1.
HRMS (ESI+): calcd. For C₁₈H₁₉NO₃Br, 376.0548. found 376.0560.

Example 36.3

Synthesis of 2-[(3-chloro-4-pyridyl)methyl]-6,7-dimethoxy-tetralin-1-one (101)

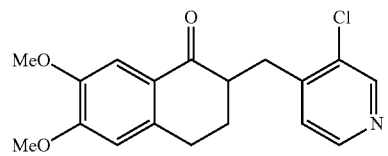

The title compound 101 is prepared according to the procedure reported in Example 36.1 with compound 85 (93 mg, 2.83 mmol) and Pt/C (5 wt/o loading, 93 mg) as reactants. White solid. (Yield 0.47 g, 51%).
¹H NMR (300 MHz, CDCl₃, δ): 1.88-1.93 (m, 1H), 2.03-2.11 (m, 1H), 2.71-2.93 (m, 4H), 3.63 (dd, 1H, J=12.6 Hz, J=3.9 Hz), 3.91 (s, 3H), 3.92 (s, 3H), 6.64 (s, 1H), 7.24 (d, 1H, J=5.7 Hz), 7.52 (s, 1H), 8.40 (d, 1H, J=4.8 Hz), 8.55 (s, 1H).
¹³C NMR (75 MHz, CDCl₃, δ): 28.7, 28.8, 33.2, 46.7, 56.0, 56.1, 108.6, 110.1, 125.3, 126.1, 132.5, 138.7, 147.3, 147.5, 148.0, 149.5, 153.6, 197.2.

HRMS (ESI+) calcd for [M+H]+ C18H19NO3Cl m/z 332.1053 found 332.1042.

Example 36.4

Synthesis of 2-[(3-fluoro-4-pyridyl)methyl]-6,7-dimethoxy-tetralin-1-one (102)

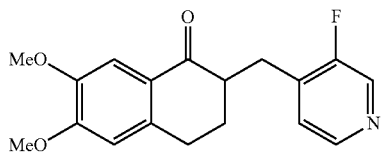 [SMILES: COc1cc2c(cc1OC)C(=O)C(Cc1ccncc1F)CC2]

The title compound 102 is prepared according to the procedure reported in Example 36.1 with compound 86 (313 mg, 1 mmol) and Pt/C (5 wt % loading, 93 mg) as reactants. White solid. (Yield 188 mg, 60%).

1H NMR (300 MHz, CDCl3, δ): 1.73-1.86 (m, 1H), 2.00-2.08 (m, 1H), 2.71-2.76 (m, 2H), 2.79-2.90 (m, 2H), 3.43 (dd, 1H, J=18.0 Hz, J=9.0 Hz), 3.88 (s, 3H), 3.89 (s, 3H), 6.61 (s, 1H), 7.20-7.26 (m, 1H), 7.48 (s, 1H), 8.29 (d, 1H, J=4.8 Hz), 8.36 (d, 1H, J=1.2 Hz).

13C NMR (75 MHz, CDCl3, δ): 28.6, 28.7, 28.8, 47.2, 56.1, 56.2, 108.8, 110.1, 125.4, 126.3, 136.3, 136.5, 137.7, 138.0, 138.8, 145.6, 145.7, 148.1, 153.7, 197.2.

Example 36.5

Synthesis of 2-[(3-acetyl-4-pyridyl)methyl]-6-methoxy-tetralin-1-one (103)

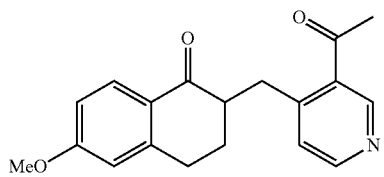 [SMILES: COc1ccc2c(c1)CCC(Cc1ccncc1C(C)=O)C2=O]

A toluene solution (9 mL) of compound 99 (1.0 g, 2.89 mmol), Pd(dba)2 (70 mg, 0.12 mmol) and PPh3 (30 mg, 0.12 mmol) was stirred at room temperature under argon for 15 min. Then, (1-ethoxyvinyl)tri(n-butyl)stannane (1.08 mL, 3.18 mmol) in toluene (6 mL) was added and the resulting mixture was stirred overnight at 110° C., cooled to room temperature and filtered on Celite, washed with EtOAc and concentrated under reduced pressure. Purification on silica gel (Petroleum ether 100% to EtOAc 100%) afford the product which was placed in presence of an aqueous solution of HCl 1M for 30 minutes at room temperature. After neutralization with a saturated aqueous solution of NaHCO3, aqueous phase was extracted with dichloromethane and the combined organic layers were dried over magnesium sulfate to afford the title compound 103 (Yield 475 mg, 96%) which was used without further purification.

1H NMR (300 MHz, CDCl3, δ): 1.69-1.83 (m, 1H), 1.92-2.03 (m, 1H), 2.54 (s, 3H), 2.69-2.82 (m, 4H), 3.55 (dd, 1H, J=12.6 Hz, J=5.4 Hz), 3.71 (s, 3H), 6.53 (d, 1H, J=2.1 Hz), 6.68 (dd, 1H, J=8.7 Hz, J=2.4 Hz), 7.22 (d, 1H, J=4.8 Hz), 7.84 (d, 1H, J=8.7 Hz), 8.48 (d, 1H, J=4.8 Hz), 8.85 (s, 1H).

13C NMR (75 MHz, CDCl3, δ): 28.7, 29.1, 29.6, 33.6, 48.2, 55.2, 112.1, 113.0, 125.6, 126.9, 129.5, 133.3, 146.1, 150.2, 150.4, 151.5, 163.2, 197.3, 199.8.

HRMS (ESI+): calcd. For C19H20NO3 310.1443. found 310.1438.

Example 36.6

Synthesis of 2-[(3-acetyl-4-pyridyl)methyl]-6,7-dimethoxy-tetralin-1-one (104)

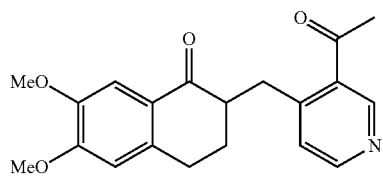 [SMILES: COc1cc2c(cc1OC)C(=O)C(Cc1ccncc1C(C)=O)CC2]

The title compound 104 is prepared according to the procedure reported in Example 36.5 with compound 100 (175 mg, 0.47 mmol) and (1-ethoxyvinyl)tri(n-butyl)stannane (0.16 mL, 0.47 mmol) as reactants. White solid. (Yield 93.2 g, 58%).

1H NMR (300 MHz, CDCl3, δ): 1.93-1.99 (m, 1H), 2.09-2.17 (m, 1H), 2.65 (s, 3H), 2.75-2.96 (m, 4H), 3.62 (dd, 1H, J=13.2 Hz, J=6.3 Hz), 3.89 (s, 3H), 3.91 (s, 3H), 6.62 (s, 1H), 7.34 (d, 1H, J=5.1 Hz), 7.48 (s, 1H), 8.59 (d, 1H, J=5.1 Hz), 8.95 (s, 1H).

13C NMR (75 MHz, CDCl3, δ): 28.8, 29.4, 29.9, 34.0, 48.2, 56.0, 56.1, 108.7, 110.1, 125.5, 127.2, 133.5, 138.7, 148.0, 150.6, 150.7, 151.8, 153.5, 197.9, 200.1.

Example 37

Synthesis of 2-[(3-substituted-4-pyridyl)methyl]-indanone Derivatives

Example 37.1

Synthesis of 2-[(3-bromo-4-pyridyl)methyl]-5,6-dimethoxy-indan-1-one (19)

This compound was prepared using the method described by Lam et al. in *Synlett*, 2010, 2415.

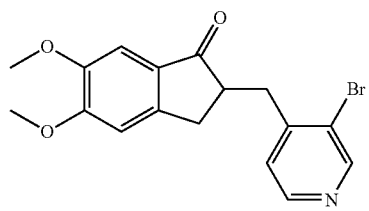 [SMILES: COc1cc2c(cc1OC)C(=O)C(Cc1ccncc1Br)C2]

To the α,β-unsaturated ketone 89 (0.72 g, 2 mmol) in dry THF (10 mL) was added HEH (0.76 g, 3 mmol) and TiCl4 (2.4 mL of 1 M TiCl4 in CH2Cl2, 2.4 mmol). The reaction mixture was stirred at room temperature for 3 h. Thereafter, the mixture was concentrated and dissolved in the minimum of CH2Cl2 before selective precipitation with Et2O. After filtration, the precipitate was dissolved in a mixture of CH2Cl2 and Et$_3$N (10:1) and washed with brine. The organic layer was filtered on silica and concentrated to afford the title product 19 (0.56 g, 77%).

$^1$H NMR (300 MHz, CDCl$_3$, δ): 2.74-2.87 (m, 2H), 3.06-3.17 (m, 2H), 0.13-3.17 (m, 1H), 3.92 (s, 3H), 3.95 (s, 3H), 6.83 (s, 1H), 7.20 (s, 1H), 7.22 (d, 1H, J=5.1 Hz), 8.42 (d, 1H, J=4.8 Hz), 8.70 (s, 1H).

$^{13}$C NMR (75 MHz, CDCl$_3$, δ): 31.8, 36.3, 46.6, 56.1, 56.2, 104.3, 107.3, 123.4, 125.4, 128.8, 148.2, 148.4, 149.6, 152.0, 155.7, 205.0.

HRMS (ESI$^+$): calcd. For C$_{17}$H$_{17}$NO$_3$Br, 362.0392. found 362.0393.

Example 37.2

Synthesis of 2-[(3-bromo-4-pyridyl)methyl]-5-methyl-indan-1-one (105)

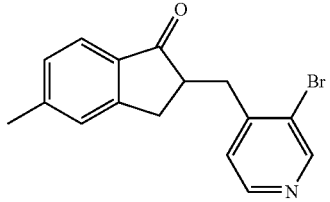 [SMILES: Cc1ccc2c(c1)CC(Cc1ccncc1Br)C2=O]

Pt/C (5 wt % loading, 125 mg) was added to a stirred solution of the compound 90 (1.24 g, 4 mmol) in EtOH (40 mL) at room temperature. The resulting suspension was stirred for 3 hours under H$_2$ atmosphere (1 atm) then filtered over Celite, rinsed with dichloromethane and concentrated to dryness. The crude residue was purified by column chromatography on SiO$_2$ (gradient of EtOAc in petroleum ether) to afford the title compound 105 as a white solid (Yield 0.75 g, 59%).

$^1$H NMR (300 MHz, CDCl$_3$, δ): 2.41 (s, 3H), 2.75-2.85 (m, 2H), 3.04-3.20 (m, 2H), 3.42-3.48 (m, 1H), 7.17-7.22 (m, 3H), 8.42 (d, 2H, J=5.1 Hz), 8.68 (s, 1H).

$^{13}$C NMR (75 MHz, CDCl$_3$, δ): 21.68, 31.57, 35.77, 46.02, 122.96, 123.35, 125.09, 126.47, 128.45, 133.35, 145.82, 147.73, 147.83, 151.48, 153.05, 205.21.

Example 37.3

Synthesis of 2-[(3-bromo-4-pyridyl)methyl]-5-methoxy-indan-1-one (106)

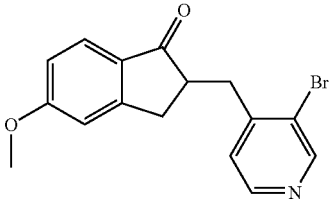 [SMILES: COc1ccc2c(c1)CC(Cc1ccncc1Br)C2=O]

The title compound 106 is prepared according to the procedure reported in Example 37.2 with compound 91 (0.25 g, 0.757 mmol) and Pt/C (5 wt % loading, 25 mg) as reactants. White solid. (Yield 0.251 g, 99%).

$^1$H NMR (300 MHz, CDCl$_3$, δ): 2.72-2.82 (m, 2H), 3.03-3.16 (m, 2H), 3.40 (dd, 1H, J=14.4 Hz, J=4.5 Hz), 3.82 (s, 3H), 6.80 (s, 1H), 6.86 (dd, 1H, J=8.4 Hz, J=2.1 Hz), 7.19 (d, 1H, J=5, 1 Hz), 7.65 (d, 1H, J=8.4 Hz), 838 (d, 1H, J=5.1 Hz), 8.64 (s, 1H).

$^{13}$C NMR (75 MHz, CDCl$_3$, δ): 32.1, 36.3, 46.6, 55.7, 109.6, 115.7, 123.4, 125.5, 125.8, 129.3, 148.2, 1483, 152.0, 156.0, 165.6, 204.5.

Example 37.4

Synthesis of 2-[(3-bromo-4-pyridyl)methyl]-5,6-dimethyl-indan-1-one (107)

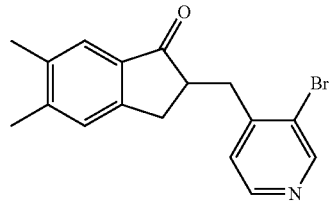 [SMILES: Cc1cc2c(cc1C)C(=O)C(Cc1ccncc1Br)C2]

The title compound 107 is prepared according to the procedure reported in Example 37.2 with compound 92 (0.44 g, 1.35 mmol) and Pt/C (5 wt % loading, 44 mg) as reactants. White solid. (Yield 0.39 g, 89%).

$^1$H NMR (300 MHz, CDCl$_3$, δ): 2.29 (s, 3H), 2.32 (s, 3H), 2.72-2.84 (m, 2H), 3.02-3.16 (m, 2H), 3.44 (dd, 1H, J=14.1 Hz, J=7.2 Hz), 7.17 (s, 1H), 7.21 (d, 1H, J=4.8 Hz), 7.53 (s, 1H), 8.41 (d, 1H, J=4.8 Hz), 8.67 (s, 1H).

$^{13}$C NMR (75 MHz, CDCl$_3$, δ): 19.8, 20.8, 31.6, 36.2, 46.6, 123.5, 124.4, 125.5, 127.2, 134.2, 136.6, 145.5, 148.2, 148.3, 151.2, 152.0, 206.2.

Example 37.5

Synthesis of 6-[(3-bromo-4-pyridyl)methyl]-5,6-dihydrocyclopenta[f][1,3]benzo-dioxol-7-one (108)

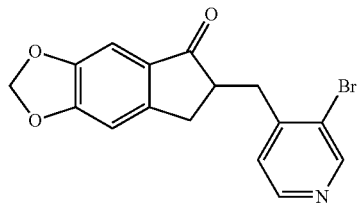 [SMILES: O=C1c2cc3c(cc2CC1Cc1ccncc1Br)OCO3]

The title compound 108 is prepared according to the procedure reported in Example 372 with compound 93 (0.25 g, 0.726 mmol) and Pt/C (5 wt % loading, 25 mg) as reactants. White solid. (Yield 0.25 g, 99%).

$^1$H NMR (300 MHz, CDCl$_3$, δ): 2.61-2.81 (m, 2H), 2.96-3.09 (m, 2H), 3.38 (dd, 1H, J=14.4 Hz, J=4.2 Hz), 6.01 (s, 2H), 6.72 (s, 1H), 7.03 (s, 1H), 7.17 (d, 1H, J=5, 1 Hz), 8.36 (d, 1H, J=5.1 Hz), 8.61 (s, 1H).

¹³C NMR (75 MHz, CDCl₃, δ): 32.0, 363, 46.8, 102.3, 102.4, 105.6, 123.4, 125.4, 130.5, 148.1, 148.2, 148.4, 150.6, 152.0, 154.6, 2043.

Example 37.6

Synthesis of 2-[(3-bromo-4-pyridyl)methyl-]5-chloro-indan-1-one (109)

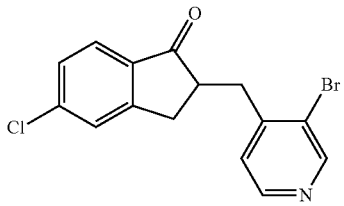 [SMILES: O=C1c2ccc(Cl)cc2CC1Cc1ccncc1Br]

The title compound 109 is prepared according to the procedure reported in Example 37.2 with compound 94 (67 mg, 0.2 mmol) and Pt/C (5 wt % loading, 6.7 mg) as reactants. White solid. (Yield 67 mg, 99%).

¹H NMR (300 MHz, CDCl₃, δ): 2.79-2.87 (m, 2H), 3.07-3.23 (m, 2H), 3.45 (dd, 1H, J=14.1 Hz, J=4.5 Hz), 7.21 (d, 1H, J=4.8 Hz), 7.35 (dd, 1H, J=8.4 Hz, J=1.8 Hz), 7.40 (d, 1H, J=0.6 Hz), 7.69 (d, 1H, J=8.1 Hz), 8.42 (d, 1H, J=4.8 Hz), 8.68 (s, 1H).

¹³C NMR (75 MHz, CDCl₃, δ): 31.9, 36.1, 46.7, 123.4, 125.3, 125.6, 126.8, 128.6, 134.6, 141.7, 147.9, 1483, 152.1, 154.4, 205.0.

Example 37.7

Synthesis of 2-[(3-acetyl-4-pyridyl)methyl]-5-chloro-indan-1-one (110)

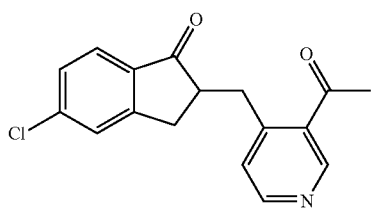 [SMILES: CC(=O)c1cnccc1CC1Cc2cc(Cl)ccc2C1=O]

The title compound 110 is prepared according to the procedure reported in Example 36.5 with compound 109 (317 mg, 0.94 mmol) and (1-ethoxyvinyl)tri(n-butyl)stannane (0.31 mL, 0.94 mmol) as reactants. White solid. (Yield 221 mg, 78%).

¹H NMR (300 MHz, CDCl₃, δ): 2.66 (s, 3H), 2.85 (dd, 1H, J=16.8 Hz, J=3.3 Hz), 3.06-3.25 (m, 3H), 3.46-3.55 (m, 1H), 7.28-7.40 (m, 3H), 7.68 (d, 1H, J=8.1 Hz), 8.61 (d, 1H, J=5, 1 Hz), 8.99 (s, 1H).

Example 37.8

Synthesis of 2-[(3-acetyl-4-pyridyl)methyl]-5,6-dimethyl-indan-1-one (111)

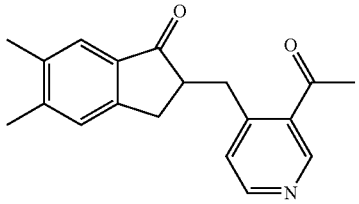 [SMILES: CC(=O)c1cnccc1CC1Cc2cc(C)c(C)cc2C1=O]

The title compound 111 is prepared according to the procedure reported in Example 36.5 with compound 107 (235 mg, 0.71 mmol) and (1-ethoxyvinyl)tri(n-butyl)stannane (0.24 mL, 0.71 mmol) as reactants. White solid. (Yield 125.0 mg, 60%).

¹H NMR (300 MHz, CDCl₃, δ): 2.27 (s, 3H), 2.29 (s, 3H), 2.63 (s, 3H), 2.74 (dd, 1H, J=16.8 Hz, J=3.0 Hz), 2.96-3.16 (m, 3H), 3.49 (dd, 1H, J=12.3 Hz, J=4.5 Hz), 7.14 (s, 1H), 7.27 (d, 1H, J=5.1 Hz), 7.48 (s, 1H), 8.57 (d, 1H, J=5.1 Hz), 8.94 (s, 1H).

¹³C NMR (75 MHz, CDCl₃, δ): 19.8, 20.8, 29.9, 32.0, 34.2, 47.9, 124.3, 126.3, 127.2, 133.5, 134.4, 136.5, 145.3, 149.7, 150.7, 151.4, 200.0, 206.8.

HRMS (ESI⁺): calcd. For C₁₉H₂₀NO₂ 294.1494. found 294.1486.

Example 37.9

Synthesis of 6-[(3-acetyl-4-pyridyl)methyl]-5,6-dihydrocyclopenta[f][1,3]benzo-dioxol-7-one (112)

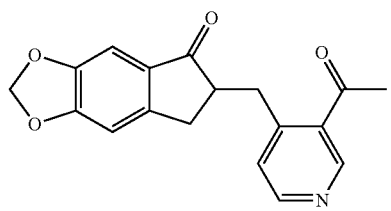 [SMILES: CC(=O)c1cnccc1CC1Cc2cc3c(cc2C1=O)OCO3]

The title compound 112 is prepared according to the procedure reported in Example 36.5 with compound 108 (235 mg, 0.68 mmol) and (1-ethoxyvinyl)tri(n-butyl)stannane (0.32 mL, 0.95 mmol) as reactants. White solid. (Yield 135.0 mg, 64%).

¹H NMR (300 MHz, CDCl₃, δ): 2.61 (s, 3H), 2.63-2.71 (m, 1H), 2.98-3.11 (m, 3H), 3.40 (dd, 1H, J=17.1 Hz, J=63 Hz), 6.01 (s, 2H), 6.71 (s, 1H), 7.02 (s, 1H), 7.25 (d, 1H, J=5, 1 Hz), 8.55 (d, 1H, J=5.1 Hz), 8.91 (s, 1H).

¹³C NMR (75 MHz, CDCl₃, δ): 29.9, 32.4, 34.2, 48.1, 102.2, 102.5, 105.6, 126.3, 130.7, 133.4, 148.3, 149.6, 150.7, 150.8, 152.0, 154.4, 200.0, 204.8.

MS (ESI⁺): 310.20 (M+H⁺)

Example 37.10

Synthesis of 2-[(3-acetyl-4-pyridyl)methyl]-5-methoxy-indan-1-one (113)

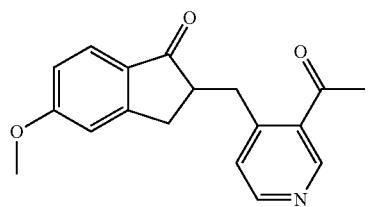 [SMILES: COc1ccc2c(c1)CC(Cc1ccncc1C(C)=O)C2=O]

The title compound 113 is prepared according to the procedure reported in Example 36.5 with compound 106 (235 mg, 0.71 mmol) and (1-ethoxyvinyl)tri(n-butyl)stannane (0.34 mL, 0.99 mmol) as reactants. White solid. (Yield 135 mg, 64%).

$^1$H NMR (300 MHz, CDCl$_3$, δ): 2.61 (s, 3H), 2.76 (dd, 1H, J=16.8 Hz, J=3.0 Hz), 2.99-3.17 (m, 3H), 3.39-3.49 (m, 1H), 3.82 (s, 3H), 6.79 (s, 1H), 6.85 (dd, 1H, J=8.4 Hz, J=2.1 Hz), 7.27 (d, 1H, J=4.8 Hz), 7.63 (d, 1H, J=8.4 Hz), 8.55 (d, 1H, J=4.8 Hz), 8.92 (s, 1H).

$^{13}$C NMR (75 MHz, CDCl$_3$, δ): 29.9, 32.4, 34.2, 47.8, 55.6, 109.6, 115.5, 125.7, 1263, 129.4, 133.5, 149.6, 150.6, 151.9, 156.2, 165.5, 200.0, 205.1.

MS (ESI$^+$): 296.12 (M+H$^+$)

Example 37.11

Synthesis of Synthesis of 2-[(3-acetyl-4-pyridyl)methyl]-5-methyl-indan-1-one (114)

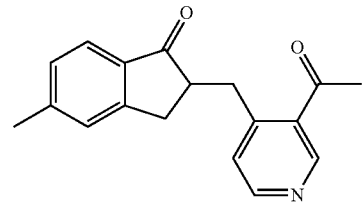 [SMILES: CC(=O)c1cnccc1CC1Cc2cc(C)ccc2C1=O]

The title compound 114 is prepared according to the procedure reported in Example 36.5 with compound 105 (750 mg, 2.38 mmol) and (1-ethoxyvinyl)tri(n-butyl)stannane (0.8 mL, 238 mmol) as reactants. White solid. (Yield 398.8 mg, 60%).

$^1$H NMR (300 MHz, CDCl$_3$, δ): 2.43 (s, 3H), 2.67 (s, 3H), 2.83 (dd, 1H, J=16.5 Hz, J=3 Hz), 3.02-3.23 (m, 3H), 3.49-3.58 (m, 1H), 7.17-7.21 (m, 2H), 7.31-7.33 (m, 1H), 7.65 (d, 1H, J=7.5 Hz), 8.61 (d, 1H, J=5.1 Hz), 8.99 (s, 1H).

$^{13}$C NMR (75 MHz, CDCl$_3$, δ): 22.0, 29.8, 32.2, 34.1, 47.7, 123.8, 126.2, 126.8, 128.8, 133.3, 133.9, 146.1, 149.5, 150.6, 151.9, 153.6, 199.9, 206.4.

MS (ESI$^+$): 280.13 (M+H$^+$)

Example 37.12

Synthesis of 2-[(3-acetyl-4-pyridyl)methyl]-5,6-dimethoxy-indan-1-one (32)

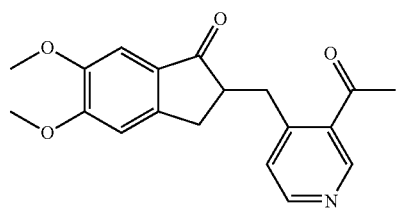 [SMILES: COc1cc2c(cc1OC)C(=O)C(Cc1ccncc1C(C)=O)C2]

The title compound 32 is prepared according to the procedure reported in Example 36.5 with compound 19 (120 mg, 0.33 mmol) and (1-ethoxyvinyl)tri(n-butyl)stannane (0.12 mL, 0.46 mmol) as reactants. White solid. (Yield 94 mg, 87%).

$^1$H NMR (300 MHz, CDCl$_3$, δ): 2.67 (s, 3H), 2.74-2.80 (m, 1H), 3.05-3.18 (m, 3H), 3.48-3.53 (m, 1H), 3.91 (s, 3H), 3.95 (s, 3H), 6.82 (s, 1H), 7.18 (s, 1H), 730 (d, 1H, J=5.1 Hz), 8.60 (d, 1H, J=5.1 Hz), 8.97 (s, 1H).

$^{13}$C NMR (75 MHz, CDCl$_3$, δ): 29.8, 32.0, 34.2, 47.7, 56.0, 56.1, 104.2, 107.2, 126.2, 128.8, 133.3, 148.5, 149.4, 149.6, 150.6, 151.9, 155.5, 199.9, 205.5.

MS (ESI$^+$): 326.14 (M+H$^+$)

Example 37.13

Synthesis of (2,4,6-trichlorophenyl) 4-[(5,6-dimethoxy-1-oxo-indan-2-yl)methyl]pyridine-3-carboxylate (115)

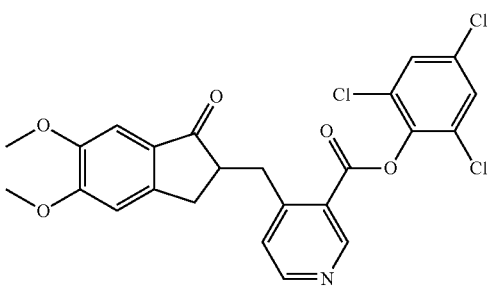 [SMILES: COc1cc2c(cc1OC)C(=O)C(Cc1ccncc1C(=O)Oc1c(Cl)cc(Cl)cc1Cl)C2]

The title compound 115 is prepared according to the procedure reported in Example 35.7 with compound 19 (92.6 mg, 0.26 mmol) and 2,4,6-trichlorophenyl-formate (70 mg, 0.31 mmol) as reactants. Yellow solid. (Yield 41 mg, 31%).

$^1$H NMR (300 MHz, CDCl$_3$, δ): 2.74-2.82 (m, 1H), 3.05-3.29 (m, 3H), 3.62-3.68 (m, 1H), 3.89 (s, 3H), 3.93 (s, 3H) 6.78 (s, 1H), 7.15 (s, 1H), 7.39 (d, 1H, J=5.1 Hz), 7.42 (s, 2H), 8.72 (d, 1H, J=5.1 Hz), 9.42 (s, 1H).

MS (ESI$^+$): 506.03 (M+H$^+$)

Example 37.14

Synthesis of 4-[(5,6-dimethoxy-1-oxo-indan-2-yl)methyl]-N-methyl-pyridine-3-carboxamide (116)

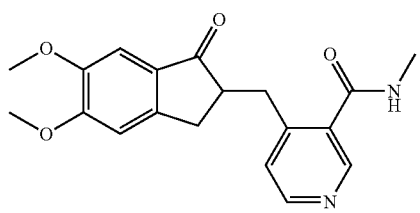

The title compound 116 is prepared according to the procedure reported in Example 37.2 with compound 98 (60 mg, 0.176 mmol) as reactants. White solid. (Yield 55.3 mg, 92%).

MS (ESI$^+$): 341.15 (M+H$^+$)

Example 38

Synthesis of Quaternized Forms (Route C)

Example 38.1

Synthesis of 2-[(1-benzyl-3-bromo-pyridin-1-ium-4-yl)methyl]-6-methoxy-tetralin-1-one bromide (117)

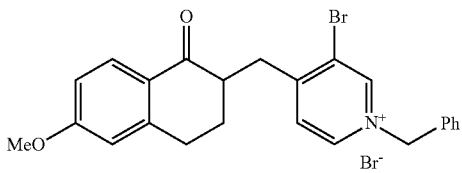 [SMILES: COc1ccc2c(c1)CCC(Cc1cc[n+](Cc3ccccc3)cc1Br)C2=O ; [Br-]]

Compound 99 (69.2 mg, 0.2 mmol) was dissolved in dichloromethane (2 mL). Benzyl bromide (48 μL, 0.4 mmol) was then added and the solution was heated under reflux for 12 h in a sealed tube. After concentration under reduced pressure, the solid was triturated with diethylether, filtered and washed (3×) with n-pentane to afford the title product 117 as a pale brown powder (Yield 82 mg, 80%).

$^1$H NMR (300 MHz, CDCl$_3$, δ): 1.92-2.01 (m, 1H), 2.15-2.22 (m, 1H), 2.84-3.11 (m, 4H), 3.59 (dd, 1H, J=14.1 Hz, J=6.6 Hz), 3.83 (s, 3H), 6.31 (s, 2H), 6.66 (d, 1H, J=1.8 Hz), 6.79 (dd, 1H, J=8.7 Hz, J=2.4 Hz), 7.37-7.39 (m, 3H), 7.68-7.70 (m, 2H), 7.88 (d, 1H, J=5.7 Hz), 8.02 (d, 1H, J=6.3 Hz), 9.52 (d, 1H, J=6.3 Hz), 9.56 (s, 1H).

$^{13}$C NMR (75 MHz, CDCl$_3$, δ): 29.4, 37.0, 46.8, 55.5, 63.1, 112.4, 113.6, 125.2, 125.3, 129.4, 129.6, 129.8, 129.9, 132.8, 142.7, 145.5, 146.4, 161.3, 163.9, 196.3.

HERMS (ESI$^+$): calcd. For C$_{24}$H$_{23}$NO$_2$Br, 436.0912. found 436.0919.

Example 38.2

Synthesis of 2-[[3-bromo-1-(m-tolylmethyl)pyridin-1-ium-4-yl]methyl]-6-methoxy-tetralin-1-one bromide (118)

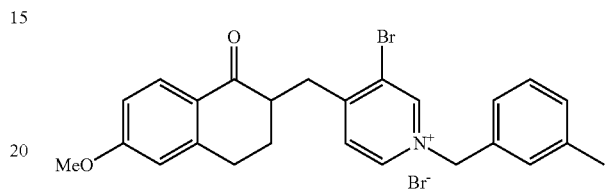

The title compound 118 is prepared according to the procedure reported in Example 38.1 with compound 99 (67 mg, 0.2 mmol) and 3-methylbenzyl bromide as reactants. White solid. (Yield 82.5 mg, 56%).

$^1$H NMR (300 MHz, CDCl$_3$, δ): 1.94-2.04 (m, 1H), 2.16-2.24 (m, 1H), 2.35 (s, 3H), 2.86-3.13 (m, 4H), 3.61 (dd, 1H, J=14.1 Hz, J=6.9 Hz), 3.84 (s, 3H), 6.23 (s, 2H), 6.78 (d, 1H, J=3.3 Hz), 6.80 (dd, 1H, J=8.7 Hz, J=2.4 Hz), 7.20-7.30 (m, 2H), 7.32-7.46 (m, 2H), 7.89 (d, 1H, J=8.7 Hz), 8.03 (d, 1H, J=63 Hz), 9.44 (s, 1H), 9.49 (d, 1H, J=6.3 Hz).

$^{13}$C NMR (75 MHz, CDCl$_3$, δ): 21.3, 29.5, 29.6, 37.1, 46.8, 55.5, 63.4, 112.5, 113.6, 125.2, 127.0, 129.3, 129.5, 129.9, 130.4, 130.9, 132.5, 139.6, 142.8, 145.4, 146.4, 161.3, 163.9, 196.3.

Example 38.3

Synthesis of 2-[(3-acetyl-1-benzyl-pyridin-1-ium-4-yl)methyl]-6-methoxy-tetralin-1-one bromide (119)

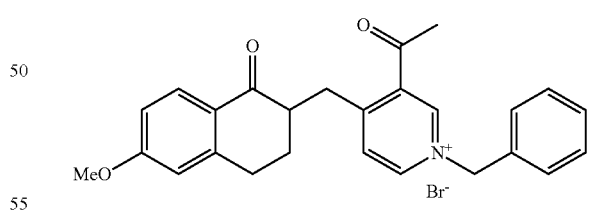

The title compound 119 is prepared according to the procedure reported in Example 38.1 with compound 103 (67 mg, 0.2 mmol) and benzyl bromide as reactants. White solid. (Yield 34.5 mg, 80%).

$^1$H NMR (300 MHz, CDCl$_3$, δ): 1.98-2.04 (m, 1H), 2.17-2.35 (m, 1H), 2.84-3.18 (m, 4H), 2.98 (s, 3H), 3.46-3.57 (m, 1H), 3.84 (s, 3H), 6.39 (s, 2H), 6.67 (d, 1H, J=2.8 Hz), 6.79 (dd, 1H, J=8.7 Hz, J=2.1 Hz), 7.41 (br s, 3H), 7.67 (br s, 2H), 7.84 (d, 1H, J=8.7 Hz), 8.09 (d, 1H, J=6.6 Hz), 8.89 (br s, 1H), 10.44 (br s, 1H).

¹³C NMR (75 MHz, CDCl₃, δ): 29.8, 30.4, 31.5, 35.5, 49.0, 55.6, 63.6, 112.6, 113.6, 125.4, 129.5, 129.8, 129.9, 131.6, 132.7, 136.4, 143.8, 145.8, 146.5, 162.6, 164.0, 164.2, 197.0, 197.5.

Example 38.4

Synthesis of 2-[[3-acetyl-1-(m-tolylmethyl)pyridin-1-ium-4-yl]methyl]-6-methoxy-tetralin-1-one bromide (120)

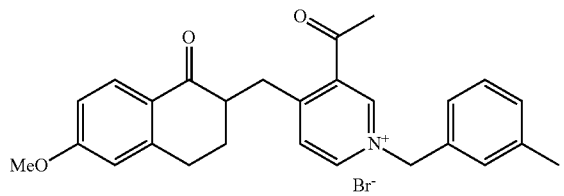 [SMILES: COc1ccc2c(c1)CCC(Cc1cc[n+](Cc3cccc(C)c3)cc1C(C)=O)C2=O ; [Br-]]

The title compound 120 is prepared according to the procedure reported in Example 38.1 with compound 103 (62 mg, 0.2 mmol) and 3-methylbenzyl bromide (46 µL, 0.34 mmol) as reactants. White solid. (Yield 79.3 mg, 80%).

¹H NMR (300 MHz, CDCl₃, δ): 1.94-2.06 (m, 1H), 2.25-2.34 (m, 1H), 2.31 (s, 3H), 2.87-3.18 (m, 4H), 3.05 (s, 3H), 3.46-3.56 (m, 1H), 3.84 (s, 3H), 6.32 (s, 2H), 6.67 (d, 1H, J=2.1 Hz), 6.78 (dd, 1H, J=9.0 Hz, J=2.4 Hz), 7.20-7.32 (m, 2H), 7.43-7.46 (m, 2H), 7.84 (d, 1H, J=8.7 Hz), 8.08 (d, 1H, J=6.6 Hz), 8.86 (d, 1H, J=6.3 Hz), 10.43 (br s, 1H).

¹³C NMR (75 MHz, CDCl₃, δ): 21.3, 29.6, 30.1, 31.3, 35.1, 48.8, 55.5, 63.2, 112.4, 113.5, 1253, 126.8, 129.5, 129.7, 130.3, 130.8, 131.3, 132.9, 136.4, 139.6, 144.2, 145.4, 146.4, 162.1, 163.8, 197.0, 197.3.

Example 38.5

Synthesis of 2-[[3-acetyl-1-(o-tolylmethyl)pyridin-1-ium-4-yl]methyl]-6-methoxy-tetralin-1-one bromide (121)

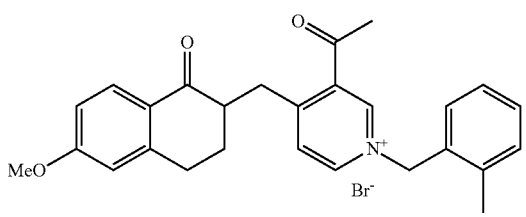 [SMILES: COc1ccc2c(c1)CCC(Cc1cc[n+](Cc3ccccc3C)cc1C(C)=O)C2=O ; [Br-]]

The title compound 121 is prepared according to the procedure reported in Example 38.1 with compound 103 (62 mg, 0.2 mmol) and 2-methylbenzyl bromide (45 µL, 0.34 mmol) as reactants. White solid. (Yield 73.9 mg, 75%).

¹H NMR (300 MHz, CDCl₃, δ): 1.91-2.04 (m, 1H), 2.22-2.31 (m, 1H), 2.35 (s, 3H), 2.87-3.18 (m, 4H), 2.98 (s, 3H), 3.54 (dd, 1H, J=13.2 Hz, J=8.7 Hz), 3.83 (s, 3H), 6.42 (s, 2H), 6.66 (s, 1H), 6.78 (dd, 1H, J=8.7 Hz, J=1.8 Hz), 7.22-7.36 (m, 3H), 7.56 (d, 1H, J=7.2 Hz), 7.83 (d, 1H, J=9.0 Hz), 8.09 (d, 1H, J=6.6 Hz), 8.73 (d, 1H, J=6.3 Hz), 10.28 (br s, 1H).

¹³C NMR (75 MHz, CDCl₃, δ): 19.1, 29.7, 30.4, 31.3, 35.6, 49.0, 55.6, 62.4, 112.5, 113.6, 125.4, 127.4, 129.8, 1303, 130.7, 131.4, 131.5, 131.7, 136.0, 138, 143.1, 146.0, 146.5, 162.7, 164.0, 196.9, 197.6.

Example 38.6

Synthesis of 2-[[3-acetyl-1-[(3-chlorophenyl)methyl]pyridin-1-ium-4-yl]methyl]-6-methoxy-tetralin-1-one bromide (122)

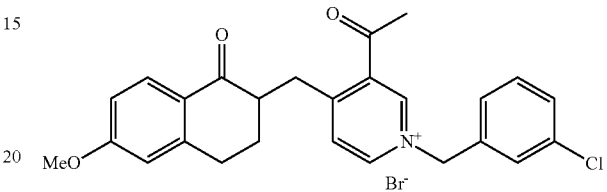

The title compound 122 is prepared according to the procedure reported in Example 38.1 with compound 103 (62 mg, 0.2 mmol) and 3-chlorobenzyl bromide (39 µL, 0.3 mmol) as reactants. White solid. (Yield 75.0 mg, 73%).

¹H NMR (300 MHz, CDCl₃, δ): 1.92-2.05 (m, 1H), 2.25-2.31 (m, 1H), 2.85-3.14 (m, 4H), 2.96 (s, 3H), 3.56 (dd, 1H, J=13.2 Hz, J=8.4 Hz), 3.83 (s, 3H), 6.49 (d, 2H, J=2.4 Hz), 6.65 (d, 1H, J=2.4 Hz), 6.77 (dd, 1H, J=8.7 Hz, J=2.4 Hz), 7.32-7.34 (m, 2H), 7.68 (s, 1H), 7.73-7.76 (m, 1H), 7.82 (d, 1H, J=8.7 Hz), 8.11 (d, 1H, J=6.6 Hz), 9.19 (d, 1H, J=6.3 Hz), 10.43 (br s, 1H).

¹³C NMR (75 MHz, CDCl₃, δ): 29.7, 30.3, 31.4, 35.4, 49.0, 55.6, 62.3, 112.6, 113.6, 125.4, 128.2, 129.6, 129.9, 130.3, 131.1, 131.6, 134.8, 135.4, 136.6, 144.2, 145.5, 146.5, 162.8, 164.0, 196.9, 197.4.

Example 38.7

Synthesis of 2-[[3-acetyl-1-[(3-nitrophenyl)methyl]pyridin-1-ium-4-yl]methyl]-6-methoxy-tetralin-1-one bromide (123)

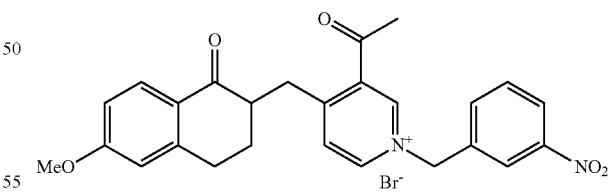

The title compound 123 is prepared according to the procedure reported in Example 38.1 with compound 103 (62 mg, 0.2 mmol) and 3-nitrobenzyl bromide (73 mg, 0.34 mmol) as reactants. White solid. (Yield 85.1 mg, 81%).

¹H NMR (300 MHz, CD₃OD, δ): 1.83-1.92 (m, 1H), 2.00-2.07 (m, 1H), 2.75 (s, 3H), 2.93-3.11 (m, 4H), 3.65 (dd, 1H, J=12.3 Hz, J=5.7 Hz), 3.81 (s, 3H), 5.98 (s, 2H), 6.86-6.89 (m, 2H), 7.73-7.79 (m, 2H), 8.07 (d, 1H, J=7.8 Hz), 8.20 (d, 1H, J=6.6 Hz), 8.29 (dd, 1H, J=8.1 Hz, J=1.5 Hz), 8.58 (s, 1H), 9.17 (d, 1H, J=6.3 Hz), 9.67 (br s, 1H).

$^{13}$C NMR (75 MHz, DMSO-D6, δ): 28.8, 30.4, 33.5, 47.6, 55.5, 61.5, 112.5, 113.5, 124.3, 124.5, 125.0, 129.0, 130.6, 130.7, 135.7, 135.9, 136.9, 144.6, 145.3, 146.8, 148.0, 161.1, 163.3, 196.7, 197.6.

Example 38.8

Synthesis of 2-[[3-acetyl-1-[[3-(trifluoromethyl)phenyl]methyl]pyridin-1-ium-4-yl]methyl]-6-methoxy-tetralin-1-one bromide (124)

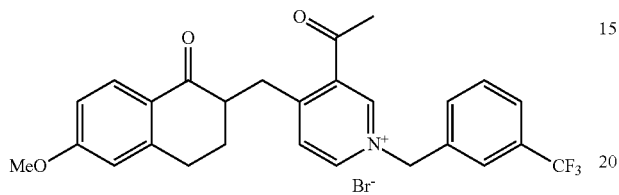

The title compound 124 is prepared according to the procedure reported in Example 38.1 with compound 103 (62 mg, 0.2 mmol) and 3-trifluoromethylbenzyl bromide (52 μL, 0.34 mmol) as reactants. White solid. (Yield 89.9 mg, 82%).

$^1$H NMR (300 MHz, CD$_3$OD, δ): 1.92-2.05 (m, 1H), 2.25-2.38 (m, 1H), 2.85-3.19 (m, 4H), 3.01 (s, 3H), 3.54 (dd, 1H, J=13.2 Hz, J=8.7 Hz), 3.83 (s, 3H), 6.58-6.79 (m, 4H), 7.54-7.68 (m, 2H), 7.80-7.87 (m, 2H), 8.13 (d, 2H, J=6.6 Hz), 9.01 (d, 1H, J=6.3 Hz), 10.52 (br s, 1H).

$^{13}$C NMR (75 MHz, CD$_3$OD, δ): 30.3, 30.4, 31.1, 35.7, 56.0, 64.2, 113.5, 114.6, 123.4, 126.5, 127.1, 127.2, 127.7, 131.6, 132.5, 132.6, 132.9, 134.1, 135.7, 138.9, 145.5, 146.2, 148.5, 164.2, 165.6, 198.0, 199.2.

$^{19}$F NMR (282 MHz, CD$_3$OD, 8): −62.57

Example 38.9

Synthesis of 2-[[3-acetyl-1-[(2-nitrophenyl)methyl]pyridin-1-ium-4-yl]methyl]-6-methoxy-tetralin-1-one bromide (125)

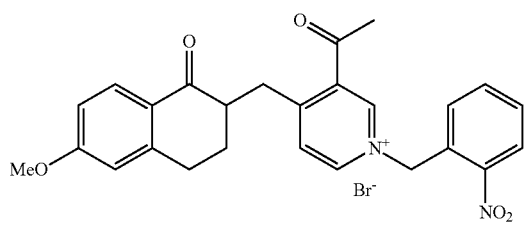 [SMILES: COc1ccc2c(c1)CCC(Cc1cc[n+](Cc3ccccc3[N+](=O)[O-])cc1C(C)=O)C2=O ; [Br-]]

The title compound 125 is prepared according to the procedure reported in Example 38.1 with compound 103 (62 mg, 0.2 mmol) and 2-nitrobenzyl bromide (73 mg, 0.34 mmol) as reactants. White solid. (Yield 87.1 mg, 82%).

$^1$H NMR (300 MHz, CDCl$_3$, δ): 1.97-2.05 (m, 1H), 2.25-234 (m, 1H), 2.89-3.19 (m, 4H), 2.95 (s, 3H), 3.61 (dd, 1H, J=13.2 Hz, J=8.4 Hz), 3.83 (s, 3H), 6.65-6.69 (m, 3H), 6.77 (dd, 1H, J=8.7 Hz, J=2.4 Hz), 7.66 (t, 1H, J=7.5 Hz), 7.81-7.85 (m, 2H), 8.13-8.17 (m, 2H), 8.42 (d, 1H, J=7.5 Hz), 9.05 (d, 1H, J=6.3 Hz), 10.04 (br s, 1H).

$^{13}$C NMR (75 MHz, CDCl$_3$, δ): 29.7, 30.3, 31.0, 35.5, 48.9, 55.5, 60.4, 112.5, 113.5, 125.4, 126.0, 127.4, 129.8, 131.1, 131.7, 134.6, 135.6, 135.9, 144.5, 146.0, 146.5, 148.0, 163.2, 163.9, 196.7, 197.4.

Example 38.10

Synthesis of 2-[[3-acetyl-1-[(2-chlorophenyl)methyl]pyridin-1-ium-4-yl]methyl]-6-methoxy-tetralin-1-one bromide (126)

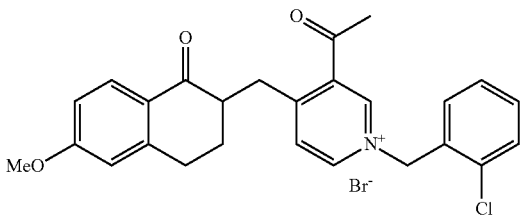 [SMILES: COc1ccc2c(c1)CCC(Cc1cc[n+](Cc3ccccc3Cl)cc1C(C)=O)C2=O ; [Br-]]

The title compound 126 is prepared according to the procedure reported in Example 38.1 with compound 103 (62 mg, 0.2 mmol) and 2-chlorobenzyl bromide (39 μL, 0.3 mmol) as reactants. White solid. (Yield 72.3 mg, 70%).

$^1$H NMR (300 MHz, CDCl$_3$, δ): 1.94-2.07 (m, 1H), 2.29-2.36 (m, 1H), 2.87-3.20 (m, 4H), 3.00 (s, 3H), 3.55 (dd, 1H, J=13.2 Hz, J=8.7 Hz), 3.83 (s, 3H), 6.47 (s, 2H), 6.67 (d, 1H, J=2.4 Hz), 6.78 (dd, 1H, J=8.7 Hz, J=2.4 Hz), 7.40-7.46 (m, 3H), 7.85 (d, 1H, J=9.0 Hz), 8.11 (d, 1H, J=6.6 Hz), 8.30-8.33 (m, 1H), 8.73 (d, 1H, J=6.3 Hz), 10.28 (br s, 1H).

$^{13}$C NMR (75 MHz, CDCl$_3$, δ): 29.7, 30.2, 31.2, 35.4, 48.9, 55.5, 61.2, 112.5, 113.5, 125.4, 128.5, 129.8, 130.3, 130.4, 131.2, 132.0, 133.7, 134.9, 136.0, 144.2, 145.9, 146.5, 162.8, 163.9, 196.8, 197.5.

HRMS (ESI$^+$): calcd. For C$_{26}$H$_{25}$NO$_3$Cl, 434.1523. found 434.1537.

Example 38.11

Synthesis of 2-[[3-acetyl-1-[(2-fluorophenyl)methyl]pyridin-1-ium-4-yl]methyl]-6-methoxy-tetralin-1-one bromide (127)

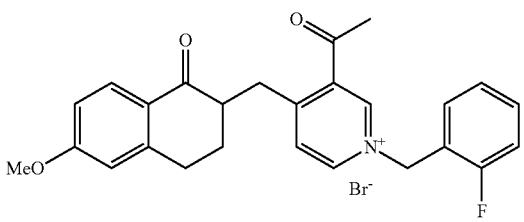 [SMILES: COc1ccc2c(c1)CCC(Cc1cc[n+](Cc3ccccc3F)cc1C(C)=O)C2=O ; [Br-]]

The title compound 127 is prepared according to the procedure reported in Example 38.1 with compound 103 (62 mg, 0.2 mmol) and 2-fluorobenzyl bromide (36 μL, 0.3 mmol) as reactants. White solid. (Yield 70.3 mg, 70%).

$^1$H NMR (300 MHz, CDCl$_3$, δ): 1.89-2.06 (m, 1H), 2.26-2.37 (m, 1H), 2.86-3.20 (m, 4H), 3.02 (s, 3H), 3.55 (dd, 1H, J=13.2 Hz, J=9.0 Hz), 3.83 (s, 3H), 6.46 (d, 2H, J=7.2 Hz), 6.66 (d, 1H, J=2.1 Hz), 6.79 (dd, 1H, J=9.0 Hz, J=2.7 Hz), 7.10 (t, 1H, J=8.7 Hz), 7.24-7.27 (m, 1H), 7.29-7.45 (m, 1H), 7.83 (d, 1H, J=9.0 Hz), 8.14 (d, 1H, J=6.6 Hz), 8.22-8.32 (m, 1H), 8.90 (d, 1H, J=6.6 Hz), 10.44 (br s, 1H).

$^{13}$C NMR (75 MHz, CDCl$_3$, δ): 29.8, 30.4, 31.1, 35.6, 49.1, 55.6, 58.0, 112.6, 113.6, 115.9, 116.2, 120.1, 120.3, 125.4, 125.9, 129.9, 131.6, 132.6, 132.7, 133.1, 136.4, 143.9, 146.0, 146.5, 163.0, 164.0, 196.8, 197.6.

Example 38.12

Synthesis of 2-[[3-acetyl-1-[(3-fluorophenyl)methyl]pyridin-1-ium-4-yl]methyl]-6-methoxy-tetralin-1-one bromide (128)

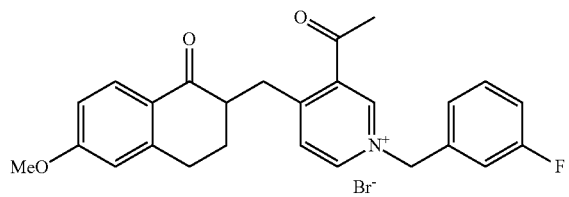 [SMILES: COc1ccc2c(c1)CCC(Cc1cc[n+](Cc3cccc(F)c3)cc1C(C)=O)C2=O ; [Br-]]

The title compound 128 is prepared according to the procedure reported in Example 38.1 with compound 103 (62 mg, 0.2 mmol) and 3-fluorobenzyl bromide (37 μL, 0.3 mmol) as reactants. White solid. (Yield 83.1 mg, 83%).

$^1$H NMR (300 MHz, CDCl$_3$, δ): 1.97-2.06 (m, 1H), 2.24-2.32 (m, 1H), 2.98 (s, 3H), 2.87-3.12 (m, 4H), 3.57 (dd, 1H, J=13.2 Hz, J=8.7 Hz), 3.82 (s, 3H), 6.49 (d, 2H, J=3.3 Hz), 6.64 (d, 1H, J=3.3 Hz), 6.76 (dd, 1H, J=8.7 Hz, J=2.4 Hz), 6.96-7.05 (m, 1H), 7.28-7.39 (m, 1H), 7.51-7.55 (m, 1H), 7.57 (d, 1H, J=7.8 Hz), 7.79 (d, 1H, J=9.0 Hz), 8.10 (d, 1H, J=6.3 Hz), 9.35 (dd, 1H, J=6.3 Hz, J=0.9 Hz), 10.44 (d, 1H, J=0.9 Hz).

$^{13}$C NMR (75 MHz, CDCl$_3$, δ): 29.7, 30.3, 31.4, 35.5, 49.0, 55.6, 62.3, 112.6, 113.6, 116.6, 116.9, 117.1, 117.4, 125.4, 125.7, 129.9, 131.5, 131.6, 136.6, 144.1, 145.6, 146.5, 161.3, 162.9, 164.0, 164.6, 196.9, 197.4.

Example 38.13

Synthesis of 2-[[3-acetyl-1-[(4-fluorophenyl)methyl]pyridin-1-ium-4-yl]methyl]-6-methoxy-tetralin-1-one bromide (129)

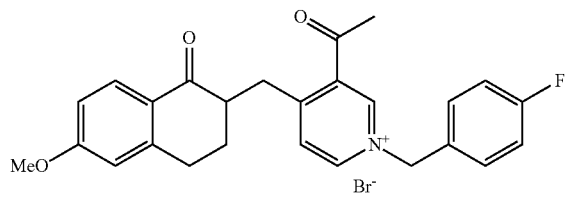 [SMILES: COc1ccc2c(c1)CCC(Cc1cc[n+](Cc3ccc(F)cc3)cc1C(C)=O)C2=O ; [Br-]]

The title compound 129 is prepared according to the procedure reported in Example 38.1 with compound 103 (110 mg, 0.36 mmol) and 4-fluorobenzyl bromide (76 μL, 0.61 mmol) as reactants. White solid. (Yield 149 mg, 83%).

$^1$H NMR (300 MHz, CDCl$_3$, δ): 1.94-2.05 (m, 1H), 2.25-2.33 (m, 1H), 2.82-3.13 (m, 4H), 2.99 (s, 3H), 3.57 (dd, 1H, J=12.9 Hz, J=8.5 Hz), 3.83 (s, 3H), 6.45 (d, 2H, J=1.9 Hz), 6.65 (d, 1H, J=2.1 Hz), 6.77 (dd, 1H, J=8.7 Hz, J=2.4 Hz), 7.05 (t, 2H, J=8.7 Hz), 7.26 (s, 1H), 7.80-7.85 (m, 3H), 8.08 (d, 1H, J=6.6 Hz), 9.21 (d, 1H, J=6.6 Hz).

$^{13}$C NMR (75 MHz, CDCl$_3$, δ): 29.7, 30.2, 31.4, 35.2, 48.9, 55.5, 62.0, 112.5, 113.6, 116.5, 116.8, 125.3, 129.1, 129.2, 129.8, 131.4, 132.1, 132.2, 136.7, 144.3, 145.2, 146.4, 161.9, 162.5, 164.0, 165.2, 196.9, 197.2.

Example 38.14

Synthesis of 2-[[3-acetyl-1-(p-tolylmethyl)pyridin-1-ium-4-yl]methyl]-6-methoxy-tetralin-1-one bromide (130)

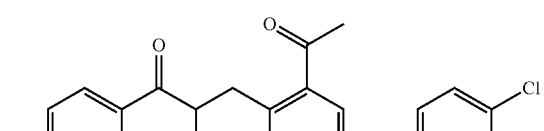

The title compound 130 is prepared according to the procedure reported in Example 38.1 with compound 103 (120 mg, 0.387 mmol) and 4-methylbenzyl bromide (122 mg, 0.66 mmol) as reactants. White solid. (Yield 181.7 mg, 95%).

$^1$H NMR (300 MHz, CDCl$_3$, δ): 1.92-2.07 (m, 1H), 2.30-2.38 (m, 1H), 2.35 (s, 3H), 2.80-3.12 (m, 3H), 3.03 (s, 3H), 3.18 (dd, 1H, J=13.2 Hz, J=4.0 Hz), 3.51 (dd, 1H, J=13.2 Hz, J=8.7 Hz), 3.84 (s, 3H), 6.30 (s, 2H), 6.67 (d, 2H, J=2.1 Hz), 6.79 (dd, 1H, J=8.7 Hz, J=2.4 Hz), 7.21-7.30 (m, 2H), 7.53 (d, 2H, J=8.7 Hz), 7.83 (d, 1H, J=8.7 Hz), 8.09 (d, 1H, J=6.3 Hz), 10.45 (s, 1H).

$^{13}$C NMR (75 MHz, CDCl$_3$, δ): 21.2, 29.5, 30.0, 31.3, 35.0, 48.8, 55.5, 62.8, 112.4, 113.4, 125.3, 129.7, 129.8, 130.0, 130.2, 131.3, 136.4, 140.1, 144.2, 145.1, 146.4, 162.1, 163.8, 197.0, 197.2.

Example 38.15

Synthesis of 2-[[3-acetyl-1-[(4-chlorophenyl)methyl]pyridin-1-ium-4-yl]methyl]-6-methoxy-tetralin-1-one bromide (131)

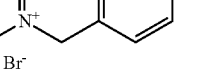

The title compound 131 is prepared according to the procedure reported in Example 38.1 with compound 103 (120 mg, 0.387 mmol) and 4-chlorobenzyl bromide (135.5 mg, 0.66 mmol) as reactants. White solid. (Yield 176.6 mg, 90%).

$^1$H NMR (300 MHz, CD$_3$OD, δ): 1.81-2.03 (m, 1H), 2.13-2.31 (m, 1H), 2.84 (s, 3H), 2.89-3.12 (m, 4H), 3.67-3.78 (m, 1H), 3.83 (s, 3H), 5.97 (s, 2H), 6.76-6.81 (m, 2H), 7.46 (d, 2H, J=8.4 Hz), 7.66 (d, 2H, J=8.4 Hz), 7.75 (d, 1H, J=8.7 Hz), 8.22 (d, 1H, J=6.6 Hz), 9.02 (d, 1H, J=7.2 Hz), 9.66 (s, 1H).

¹³C NMR (75 MHz, CD₃OD, δ): 30.4, 30.6, 30.9, 35.6, 56.1, 64.1, 113.5, 114.6, 126.5, 130.5, 130.7, 1322, 132.6, 133.3, 137.0, 138.7, 145.5, 146.2, 148.4, 163.9, 165.4, 198.2, 199.0.

Example 38.16

Synthesis of 2-[(3-actyl-1-benzyl-pyridin-1-ium-4-yl)methyl]-6,7-dimethoxy-tetralin-1-one bromide (132)

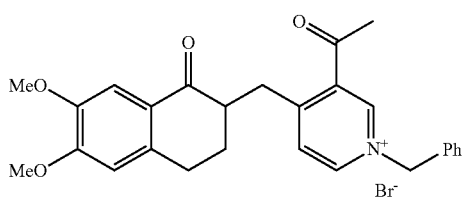 [SMILES: COc1cc2c(cc1OC)C(=O)C(Cc1cc[n+](Cc3ccccc3)cc1C(C)=O)CC2 ; [Br-]]

The title compound 132 is prepared according to the procedure reported in Example 38.1 with compound 104 (93 mg, 0.27 mmol) and benzyl bromide (66 μL, 0.54 mmol) as reactants. White solid. (Yield 117.1 mg, 85%).

¹H NMR (300 MHz, CDCl₃, δ): 1.83-1.99 (m, 1H), 2.12-2.27 (m, 1H), 2.77-2.86 (m, 2H), 2.94 (s, 3H), 2.91-3.08 (m, 2H), 3.48 (dd, 1H, J=13.2 Hz, J=8.7 Hz), 3.79 (s, 3H), 3.85 (s, 3H), 6.35 (s, 2H), 6.56 (s, 1H), 7.31-7.36 (m, 4H), 7.65-7.69 (m, 2H), 8.07 (d, 1H, J=6.0 Hz), 9.02 (d, 1H, J=6.0 Hz), 10.3 (s, 1H).

Example 38.17

Synthesis of 2[(1-benzyl-3-fluoro-pyridin-1-ium-4-yl)methyl]-6,7-dimethoxy-tetralin-1-one bromide (133)

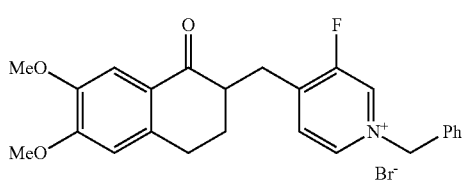 [SMILES: COc1cc2c(cc1OC)C(=O)C(Cc1cc[n+](Cc3ccccc3)cc1F)CC2 ; [Br-]]

The title compound 133 is prepared according to the procedure reported in Example 38.1 with compound 102 (135.8 mg, 0.43 mmol) and benzyl bromide (87 μL, 0.73 mmol) as reactants. White solid. (Yield 152.1 mg, 72%).

¹H NMR (300 MHz, CDCl₃, δ): 1.86-1.99 (m, 1H), 2.21-2.27 (m, 1H), 2.86-3.12 (m, 4H), 3.38-3.47 (m, 1H), 3.85 (s, 3H), 3.91 (s, 3H), 6.35 (s, 2H), 6.63 (s, 1H), 7.35-7.40 (m, 4H), 7.69-7.72 (m, 2H), 8.10 (t, 1H, J=6.6 Hz), 9.36 (d, 1H, J=3.3 Hz), 9.45 (d, 1H, J=6.0 Hz).

¹⁹F NMR (300 MHz, CDCl₃, δ): −117.5.

Example 38.18

Synthesis of 2-[(1-benzyl-3-chloro-pyridin-1-ium-4-yl)methyl]-6,7-dimethoxy-tetralin-1-one bromide (134)

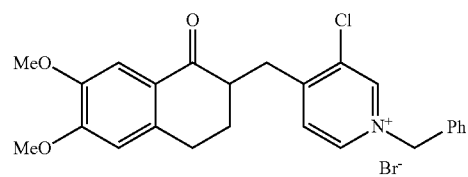 [SMILES: COc1cc2c(cc1OC)C(=O)C(Cc1cc[n+](Cc3ccccc3)cc1Cl)CC2 ; [Br-]]

The title compound 134 is prepared according to the procedure reported in Example 38.1 with compound 101 (132.4 mg, 0.4 mmol) and benzyl bromide (95 μL, 2 equiv) as reactants. White solid. (Yield 133.4 mg, 79%).

MS (ESI⁺): 422.15 (M⁺)

Example 38.19

Synthesis of 2-[(3-acetyl-1-propyl-pyridin-1-ium-4-yl)methyl]-6-methoxy-tetralin-1-one iodide (135)

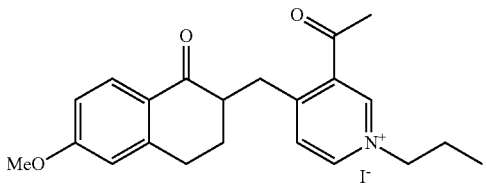 [SMILES: CCC[n+]1ccc(CC2CCc3cc(OC)ccc3C2=O)c(C(C)=O)c1 ; [I-]]

The title compound 135 is prepared according to the procedure reported in Example 38.1 with compound 103 (100.0 mg, 0.323 mmol) and propyl iodide (63 μL, 2 equiv) as reactants. Yellow solid. (Yield 116.2 mg, 75%).

¹H NMR (300 MHz, CDCl₃, δ): 1.06 (t, 3H, J=7.2 Hz), 1.91-2.18 (m, 3H), 2.28-2.38 (m, 1H), 2.90-3.19 (m, 4H), 3.03 (s, 3H), 3.58-3.65 (m, 1H), 3.84 (s, 3H), 4.95-5.10 (m, 2H), 6.66 (s, 1H), 6.78 (dd, 1H, J=8.7 Hz, J=2.4 Hz), 7.84 (d, 1H, J=8.7 Hz), 8.20 (d, 1H, J=63 Hz), 9.04 (d, 1H, J=63 Hz), 9.93 (s, 1H).

¹³C NMR (75 MHz, CD3OD, δ): 10.6, 25.4, 29.7, 30.4, 31.9, 35.4, 49.1, 55.6, 62.7, 112.6, 113.7, 125.4, 129.8, 131.6, 137.0, 144.1, 144.5, 146.6, 162.6, 164.0, 196.8, 197.5.

Example 38.20

Synthesis of 2-[[3-acetyl-1-(o-tolylmethyl)pyridin-1-ium-4-yl]methyl]-5-chloro-indan-1-one bromide (136)

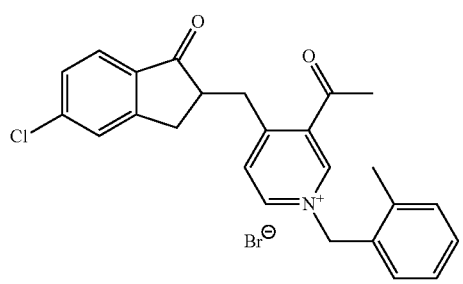 [SMILES: CC(=O)c1c[n+](Cc2ccccc2C)ccc1CC1Cc2cc(Cl)ccc2C1=O ; [Br-]]

The title compound 136 is prepared according to the procedure reported in Example 38.1 with compound 110 (90 mg, 0.3 mmol) and 2-methylbenzyl bromide (68 μL, 0.51 mmol) as reactants. White solid. (Yield 119.2 mg, 82%).

$^1$H NMR (300 MHz, CD3OD, δ): 2.29-2.36 (m, 1H), 2.37 (s, 3H), 2.72 (s, 3H), 2.97 (dd, 1H, J=17.1 Hz, J=3.9 Hz), 3.21-3.50 (m, 2H), 3.63 (dd, 1H, J=13.5 Hz, J=7.8 Hz), 5.97 (s, 2H), 7.23-7.47 (m, 5H), 7.59 (s, 1H), 7.65 (d, 1H, J=8.4 Hz), 8.18 (d, 1H, J=6.6 Hz), 8.79 (d, 1H, J=6.6 Hz), 9.47 (s, 1H).

$^{13}$C NMR (75 MHz, CD$_3$OD, δ): 19.2, 29.9, 33.6, 35.9, 63.4, 126.1, 128.0, 128.3, 129.5, 131.0, 131.4, 132.1, 132.3, 132.5, 135.7, 1382, 138.9, 142.8, 145.7, 146.6, 156.5, 162.5, 197.6, 206.8.

Example 38.21

Synthesis of 2-[[(3-acetyl-1-(o-tolylmethyl)pyridin-1-ium-4-yl]methyl]-5-methyl-indan-1-one bromide (137)

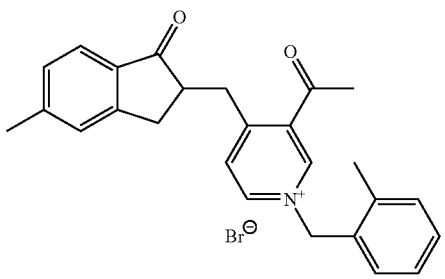 [SMILES: CC(=O)c1c[n+](Cc2ccccc2C)ccc1CC1Cc2cc(C)ccc2C1=O ; [Br-]]

The title compound 137 is prepared according to the procedure reported in Example 38.1 with compound 114 (55.8 mg, 02 mmol) and 2-methylbenzyl bromide (45 μL, 0.34 mmol) as reactants. White solid. (Yield 78.9 mg, 85%).

$^1$H NMR (300 MHz, CDCl$_3$, δ): 2.36 (s, 3H), 2.43 (s, 3H), 2.83 (dd, 1H, J=17.1 Hz, J=4.2 Hz), 2.97 (s, 3H), 3.03-3.10 (m, 1H), 3.35-3.50 (m, 3H), 6.44 (s, 2H), 7.17-7.39 (m, 5H), 7.54-7.58 (m, 2H), 7.95 (d, 1H, J=6.3 Hz), 8.73 (d, 1H, J=5.7 Hz), 10.28 (s, 1H).

HRMS (ESI$^+$): calc for C$_{26}$H$_{26}$NO$_2$. found 384.1963 calc 384.1964.

Example 38.22

Synthesis of 2-[[3-acetyl-1-(o-tolylmethyl)pyridin-1-ium-4-yl]methyl]-5-methoxy-indan-1-one bromide (138)

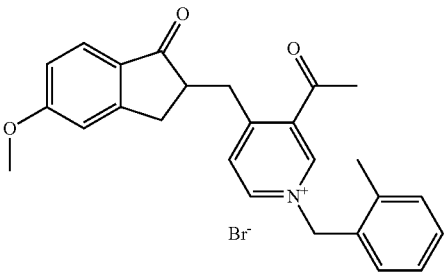 [SMILES: COc1ccc2c(c1)CC(Cc1cc[n+](Cc3ccccc3C)cc1C(C)=O)C2=O ; [Br-]]

The title compound 138 is prepared according to the procedure reported in Example 38.1 with compound 113 (111 mg, 0.37 mmol) and 2-methylbenzyl bromide (84 μL, 0.63 mmol) as reactants. White solid. (Yield 145.2 mg, 81%).

$^1$H NMR (300 MHz, CDCl$_3$, δ): 2.35 (s, 3H), 2.80 (dd, 1H, J=17.1 Hz, J=3.9 Hz), 2.94 (s, 3H), 2.97-3.12 (m, 1H), 3.30-3.48 (m, 3H), 3.86 (s, 3H), 6.45 (s, 2H), 6.82-6.91 (m, 2H), 7-17-7.38 (m, 3H), 7.51-7.65 (m, 2H), 7.99 (d, 1H, J=6.6 Hz), 8.87 (d, 1H, J=6.6 Hz), 10.25 (s, 1H).

$^{13}$C NMR (75 MHz, CDCl$_3$, δ): 19.9, 31.2, 33.1, 35.4, 47.2, 55.8, 62.3, 109.6, 116.1, 125.7, 127.3, 128.8, 130.5, 130.6, 130.8, 131.3, 131.6, 135.7, 138.1, 144.1, 146.0, 156.0, 161.2, 165.9, 196.7, 204.3.

Example 38.23

Synthesis of 6-[[3-acetyl-1-(o-tolylmethyl)pyridin-1-ium-4-yl]methyl]-5,6-dihydrocyclopenta[f][1,3]benzodioxol-7-one bromide (139)

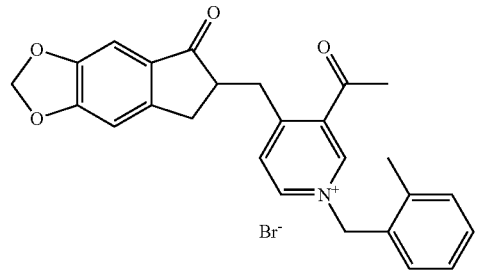 [SMILES: CC(=O)c1c[n+](Cc2ccccc2C)ccc1CC1Cc2cc3c(cc2C1=O)OCO3 ; [Br-]]

The title compound 139 is prepared according to the procedure reported in Example 38.1 with compound 112 (110.1 mg, 0.35 mmol) and 2-methylbenzyl bromide (80 μL, 0.60 mmol) as reactants. White solid. (Yield 135 mg, 77%).

$^1$H NMR (300 MHz, CDCl$_3$, δ): 2.37 (s, 3H), 2.75 (dd, 1H, J=16.8 Hz, J=3.6 Hz), 2.97 (s, 3H), 2.99-3.12 (m, 1H), 3.30-3.50 (m, 3H), 6.07 (s, 2H), 6.46 (s, 2H), 6.80 (s, 1H), 6.98 (s, 1H), 7.24-7.39 (m, 3H), 7.58 (d, 1H, J=7.2 Hz), 7.95 (d, 1H, J=6.3 Hz), 8.77 (d, 1H, J=6.0 Hz), 1032 (s, 1H).

$^{13}$C NMR (75 MHz, CDCl$_3$, δ): 19.9, 31.2, 33.1, 35.6, 47.6, 62.6, 102.5, 105.8, 130.2, 130.3, 130.7, 130.8, 131.4, 131.7, 135.8, 138.2, 143.6, 1462, 148.7, 150.6, 155.0, 161.2, 196.7, 204.1.

Example 38.24

Synthesis of 2-[[3-bromo-1-[(2-chlorophenyl)methyl]pyridin-1-ium-4-yl]methyl]-5,6-dimethoxy-indan-1-one bromide (140)

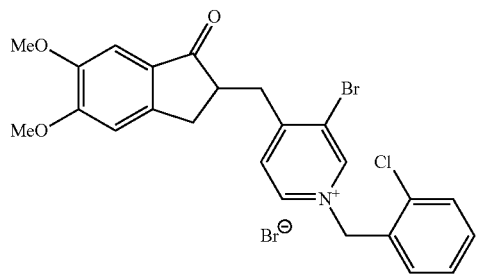 [SMILES: COc1cc2c(cc1OC)C(=O)C(Cc1cc[n+](Cc3ccccc3Cl)cc1Br)C2 ; [Br-]]

The title compound 140 is prepared according to the procedure reported in Example 38.1 with compound 19 (72 mg, 0.2 mmol) and 2-chlorobenzyl bromide (44 µL, 0.34 mmol) as reactants. Brown solid. (Yield 85.0 mg, 75%).

$^1$H NMR (300 MHz, CDCl$_3$, δ): 2.77 (dd, 1H, J=19.8 Hz, J=3.0 Hz), 3.07-3.17 (m, 2H), 3.35 (dd, 1H, J=16.8 Hz, J=7.2 Hz), 3.43-3.52 (m, 1H), 3.89 (s, 3H), 3.96 (s, 3H), 6.40 (s, 2H), 6.87 (s, 1H), 7.13 (s, 1H), 7.41-7.45 (m, 3H), 8.03 (d, 1H, J=6.3 Hz), 8.24-8.28 (m, 1H), 9.30 (s, 1H), 9.42 (dd, 1H, J=6.3 Hz, J=1.2 Hz).

$^{13}$C NMR (75 MHz, CDCl$_3$, δ): 32.4, 37.6, 45.7, 56.1, 56.4, 61.7, 104.3, 107.6, 125.0, 128.1, 128.4, 128.9, 129.9, 130.3, 132.1, 133.8, 134.9, 143.7, 145.4, 148.5, 149.7, 156.1, 160.7, 204.0.

Example 38.25

Synthesis of 2-[[3-bromo-1-(o-tolylmethyl)pyridin-1-ium-4-yl]methyl]-5,6-dimethoxy-indan-1-one bromide (141)

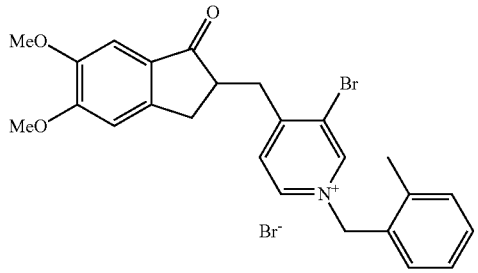 [SMILES: COc1cc2c(cc1OC)C(=O)C(Cc1cc[n+](Cc3ccccc3C)cc1Br)C2 ; [Br-]]

The title compound 141 is prepared according to the procedure reported in Example 38.1 with compound 19 (72 mg, 0.2 mmol) and 2-methylbenzyl bromide (45 µL, 0.34 mmol) as reactants. Brown solid. (Yield 88.7 mg, 81%).

$^1$H NMR (300 MHz, CDCl$_3$, δ): 236 (s, 3H), 2.78 (dd, 1H, J=16.8 Hz, J=2.7 Hz), 3.07-3.18 (m, 2H), 3.33-3.50 (m, 2H), 3.90 (s, 3H), 3.96 (s, 3H), 6.32 (s, 2H), 6.87 (s, 1H), 7.12 (s, 1H), 7.28-7.38 (m, 3H), 7.57 (d, 1H, J=4.5 Hz), 8.04 (d, 1H, J=6.3 Hz), 9.18 (s, 1H), 9.41 (dd, 1H, J=6.3 Hz, J=1.2 Hz).

$^{13}$C NMR (75 MHz, CDCl$_3$, δ): 19.9, 32.5, 37.8, 45.8, 56.2, 56.5, 62.7, 104.2, 107.6, 125.3, 127.4, 128.2, 128.8, 130.0, 130.8, 131.7, 138.2, 143.3, 145.0, 148.4, 149.9, 1563, 160.5, 203.9.

Example 38.26

Synthesis of 2-[(3-acetyl-1-benzyl-pyridin-1-ium-4-yl)methyl]-5,6-dimethoxy-indan-1-one bromide (33)

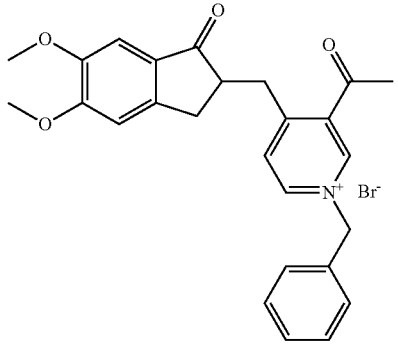 [SMILES: COc1cc2c(cc1OC)C(=O)C(Cc1cc[n+](Cc3ccccc3)cc1C(C)=O)C2 ; [Br-]]

The title compound 33 is prepared according to the procedure reported in Example 38.1 with compound 32 (46 mg, 0.14 mmol) and benzyl bromide (34 µL, 0.28 mmol) as reactants. White solid. (Yield 62.3 mg, 91%).

$^1$H NMR (300 MHz, CDCl$_3$, δ): 2.72-2.79 (m, 1H), 3.01-3.07 (m, 4H), 3.30-3.47 (m, 3H), 3.88 (s, 3H), 3.96 (s, 3H), 6.46 (s, 2H), 6.84 (s, 1H), 7.06 (s, 1H), 7.39-7.41 (m, 3H), 7.72-7.75 (m, 2H), 7.96 (d, 1H, J=6.4 Hz), 9.18 (d, 1H, J=6.2 Hz), 10.4 (s, 1H).

HRMS (ESI$^+$): calcd. For C$_{26}$H$_{26}$NO$_4$ 416.1862. found 416.1865.

Example 38.27

Synthesis of 2-[[3-acetyl-1-(o-tolylmethyl)pyridin-1-ium-4-yl]methyl]-5,6-dimethoxy-indan-1-one bromide (142)

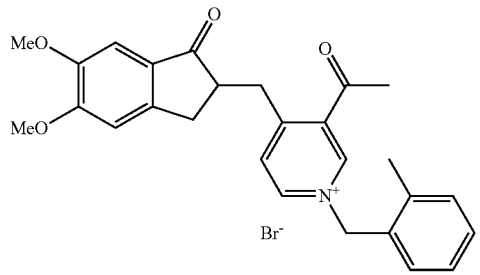 [SMILES: COc1cc2c(cc1OC)C(=O)C(Cc1cc[n+](Cc3ccccc3C)cc1C(C)=O)C2 ; [Br-]]

The title compound 142 is prepared according to the procedure reported in Example 38.1 with compound 32 (130.1 mg, 0.4 mmol) and 2-methylbenzyl bromide (90 µL, 0.68 mmol) as reactants. White solid. (Yield 130 mg, 63%).

$^1$H NMR (300 MHz, CDCl$_3$, δ): 2.35 (s, 3H), 2.76 (dd, 1H, J=16.8 Hz, J=3.9 Hz), 2.95 (s, 3H), 3.00-3.09 (m, 1H), 3.31-3.50 (m, 3H), 3.87 (s, 3H), 3.95 (s, 3H), 6.44 (s, 2H), 6.84 (s, 1H), 7.05 (s, 1H), 7.22-7.36 (m, 3H), 7.57 (dd, 1H, J=6.3 Hz, J=1.2 Hz), 7.95 (d, 1H, J=6.6 Hz), 8.81 (dd, 1H, J=6.6 Hz, J=1.2 Hz), 10.20 (s, 1H).

$^{13}$C NMR (75 MHz, CDCl$_3$, δ): 19.9, 31.2, 32.9, 35.6, 47.4, 56.2, 56.4, 62.5, 104.3, 107.5, 127.4, 128.3, 130.5, 130.6, 130.8, 131.4, 131.7, 135.8, 138.2, 143.8, 146.2, 148.4, 149.8, 156.2, 161.3, 196.7, 204.7.

Example 38.28

Synthesis of 4-[(5,6-dimethoxy-1-oxo-indan-2-yl)methyl]-N-methyl-1-(o-tolylmethyl)pyridin-1-ium-3-carboxamide bromide (143)

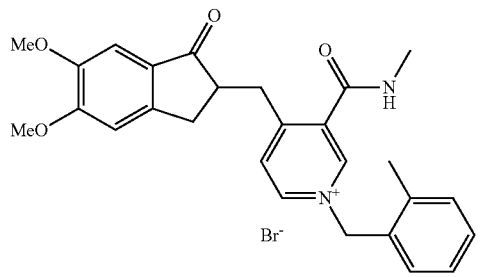 [SMILES: CNC(=O)c1c[n+](Cc2ccccc2C)ccc1CC1Cc2cc(OC)c(OC)cc2C1=O ; [Br-]]

The title compound 143 is prepared according to the procedure reported in Example 38.1 with compound 116 (51.1 mg, 0.15 mmol) and 2-methylbenzyl bromide (40 µL, 0.3 mmol) as reactants. Yellow solid. (Yield 47.5 mg, 71%).

¹H NMR (300 MHz, CDCl₃, δ): 2.29 (s, 3H), 2.768 (dd, 1H, J=16.8 Hz, J=3.6 Hz), 2.95 (d, 3H, J=4.5 Hz), 3.10-3.16 (m, 1H), 3.29-3.48 (m, 4H), 3.86 (s, 3H), 3.92 (s, 3H), 5.95 (s, 2H), 6.82 (s, 1H), 7.06 (s, 1H), 7.25-7.40 (m, 3H), 7.50 (d, 1H, J=7.2 Hz), 7.89 (d, 1H, J=6.3 Hz), 8.54 (d, 1H, J=6.3 Hz), 9.22 (br s, 2H).
¹³C NMR (75 MHz, CDCl₃, δ): 15.3, 19.7, 26.8, 32.4, 34.7, 47.7, 56.2, 56.4, 62.7, 65.9, 104.3, 107.5, 127.5, 128.4, 129.4, 129.5, 130.9, 131.5, 131.7, 135.4, 137.9, 141.6 144.2, 148.6, 149.8, 156.1, 161.0, 163.7, 204.7.
MS (ESI⁺): 445.20 (M⁺)

Example 38.29

Synthesis of 2-[[3-acetyl-1-[(3-chlorophenyl)methyl]pyridin-1-ium-4-yl]methyl]-5,6-dimethoxy-indan-1-one bromide (144)

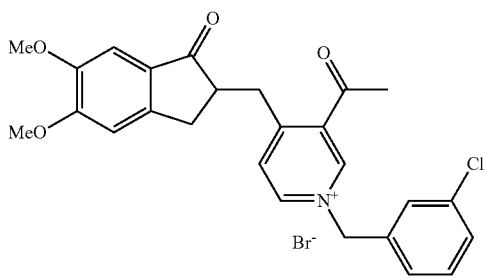 [SMILES: COc1cc2c(cc1OC)C(=O)C(Cc1cc[n+](Cc3cccc(Cl)c3)cc1C(C)=O)C2 ; [Br-]]

The title compound 144 is prepared according to the procedure reported in Example 38.1 with compound 32 (95.1 mg, 0.29 mmol) and 3-chlorobenzyl bromide (65 μL, 0.49 mmol) as reactants. White solid. (Yield 108 mg, 70%).
¹H NMR (300 MHz, DMSO-D6, δ): 2.76-2.83 (m, 3H), 3.16-3.21 (m, 1H), 3.39 (s, 3H), 3.55-3.64 (m, 1H), 3.82 (s, 3H), 3.89 (s, 3H), 5.97 (s, 2H), 7.09 (s, 1H), 7.13 (s, 1H), 7.51-7.67 (m, 3H), 7.84 (s, 1H), 8.31 (d, 1H, J=6.3 Hz), 9.28 (dd, 1H, J=6.3 Hz, J=1.2 Hz), 9.82 (s, 1H).
¹³C NMR (75 MHz, DMSO-D6, δ): 30.4, 31.7, 34.2, 46.5, 55.6, 56.0, 61.9, 103.9, 108.1, 127.7, 127.8, 128.9, 129.4, 130.3, 131.1, 133.6, 136.3, 136.6, 144.9, 145.5, 148.5, 149.2, 155.5, 160.2, 197.3, 204.2.

Example 38.30

Synthesis of 2-[(1-benzyl-3-bromo-pyridin-1-ium-4-yl)methyl]-5,6-dimethoxy-indan-1-one bromide (145)

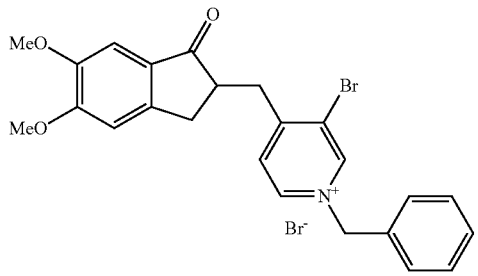 [SMILES: COc1cc2c(cc1OC)C(=O)C(Cc1cc[n+](Cc3ccccc3)cc1Br)C2 ; [Br-]]

The title compound 145 is prepared according to the procedure reported in Example 38.1 with compound 19 (72 mg, 0.2 mmol) and benzyl bromide (40 μL, 0.34 mmol) as reactants. Brown solid. (Yield 75.7 mg, 71%).

¹H NMR (300 MHz, CDCl₃, δ): 2.75 (dd, 1H, J=16.5 Hz, J=3.0 Hz), 3.01-3.15 (m, 2H), 3.33 (dd, 1H, J=16.5 Hz, J=7.2 Hz), 3.45 (dd, 1H, J=13.2 Hz, J=4.2 Hz), 3.89 (s, 3H), 3.95 (s, 3H), 6.29 (s, 2H), 6.87 (s, 1H), 7.12 (s, 1H), 7.40-7.43 (m, 3H), 7.66-7.69 (m, 2H), 8.02 (d, 1H, J=6.3 Hz), 9.43 (s, 1H), 9.56 (d, 1H, J=5.1 Hz).
¹³C NMR (75 MHz, CDCl₃, δ): 32.3, 37.6, 45.6, 56.1, 56.4, 63.4, 104.2, 107.5, 125.2, 128.1, 129.0, 129.6, 129.9, 130.0, 132.7, 143.3, 145.4, 148.4, 149.7, 156.1, 160.2, 203.9.
HRMS (ESI⁺) calcd for [M⁺] C₂₄H₂₃NO₃Br m/z 452.0861 found 452.0841.

Example 38.31

Synthesis of 2-[[3-bromo-1-(m-tolylmethyl)pyridin-1-ium-4-yl]methyl]-5,6-dimethoxy-indan-1-one bromide (146)

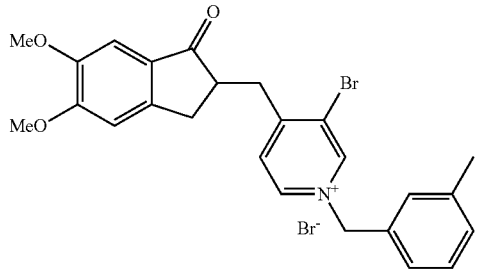 [SMILES: COc1cc2c(cc1OC)C(=O)C(Cc1cc[n+](Cc3cccc(C)c3)cc1Br)C2 ; [Br-]]

The title compound 146 is prepared according to the procedure reported in Example 38.1 with compound 19 (72 mg, 02 mmol) and 3-methylbenzyl bromide (45 μL, 0.34 mmol) as reactants. White solid. (Yield 81.1 mg, 74%).
¹H NMR (300 MHz, CDCl₃, δ): 237 (s, 3H), 2.77 (dd, 1H, J=16.5 Hz, J=2.7 Hz), 3.04-3.15 (m, 2H), 3.31-3.50 (m, 2H), 3.90 (s, 3H), 3.97 (s, 3H), 6.24 (s, 2H), 6.88 (s, 1H), 7.13 (s, 1H), 7.23-7.36 (m, 2H), 7.43 (br s, 2H), 8.01 (d, 1H, J=6.3 Hz), 9.34 (s, 1H), 9.56 (d, 1H, J=6.0 Hz).
¹³C NMR (75 MHz, CDCl₃, δ): 21.4, 32.4, 37.7, 45.7, 56.2, 56.5, 63.8, 104.3, 107.6, 125.3, 127.0, 128.2, 128.9, 129.6, 130.4, 131.0, 132.4, 139.7, 143.4, 145.4, 148.4, 149.8, 156.2, 160.3, 203.9.
HRMS (ESI⁺) calcd for [M⁺] C₂₅H₂₅NO₃Br m/z 466.1012 found 466.1018.

Example 38.32

Synthesis of 4-[3-bromo-4-[(5,6-dimethoxy-1-oxo-indan-2-yl)methyl]pyridin-1-ium-1-yl]butane-1-sulfonate (147)

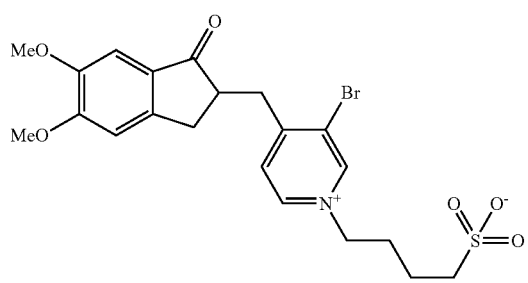 [SMILES: COc1cc2c(cc1OC)C(=O)C(Cc1cc[n+](CCCCS(=O)(=O)[O-])cc1Br)C2]

Compound 19 (72 mg, 0.2 mmol) was dissolved in acetonitrile (2 mL). Then, 1,4-butanesultone (0.5 mL) was then added and the solution was heated at 100° C. for 24 h in a sealed tube. After concentration under reduced pressure, the solid was triturated, filtered and washed (3×) with diethyl ether to afford the title product 147 as a white powder (Yield 40.2 mg, 40%).

$^1$H NMR (300 MHz, DMSO-D6, δ): 1.58-1.63 (m, 2H), 1.97-2.07 (m, 2H), 2.40-2.51 (m, 2H), 2.76-2.85 (m, 1H), 2.99-3.07 (m, 1H), 3.12-3.33 (m, 2H), 3.42 (dd, 1H, J=14.4 Hz, J=4.2 Hz), 3.80 (s, 3H), 3.86 (s, 3H), 4.57 (t, 2H, J=6.9 Hz), 7.11-7.13 (m, 2H), 8.24 (d, 1H, J=6.3 Hz), 9.07 (d, 1H, J=6.3 Hz), 9.51 (s, 1H).

HRMS (ESI$^+$) calcd for [M+H]$^+$ C$_{21}$H$_{25}$NSO$_6$Br m/z 498.0586 found 498.0580.

Example 38.33

Synthesis of 3-[3-bromo-4-[(5,6-dimethoxy-1-oxo-indan-2-yl)methyl]pyridin-1-ium-1-yl]propane-1-sulfonate (148)

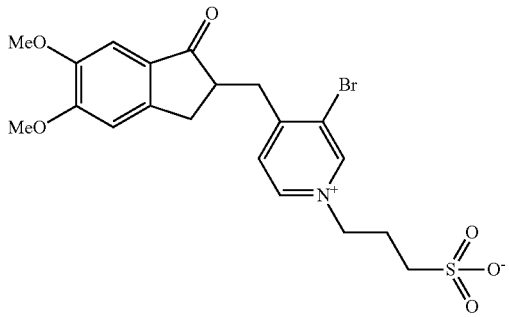 [SMILES: COc1cc2c(cc1OC)C(=O)C(Cc1cc[n+](CCCS(=O)(=O)[O-])cc1Br)C2]

The title compound 148 is prepared according to the procedure reported in Example 38.32 with compound 19 (72 mg, 0.2 mmol) and 1,3-propanesultone (37.5 mg, 0.3 mmol) as reactants. White solid. (Yield 55.5 mg, 57%).

$^1$H NMR (300 MHz, DMSO-D6, δ): 2.20-2.29 (m, 2H), 2.41-2.46 (m, 2H), 2.76-2.85 (m, 1H), 2.98-3.23 (m, 3H), 3.42 (dd, 1H, J=14.4 Hz, J=4.2 Hz), 3.80 (s, 3H), 3.86 (s, 3H), 4.68 (t, 2H, J=6.6 Hz), 7.11-7.13 (m, 2H), 8.22 (d, 1H, J=6.6 Hz), 9.06 (d, 1H, J=5.4 Hz), 9.49 (s, 1H).

$^{13}$C NMR (75 MHz, DMSO-D6, δ): 27.0, 31.4, 36.6, 45.1, 46.9, 55.6, 56.0, 59.2, 104.0, 108.1, 124.3, 146.1, 148.6, 149.2, 155.6, 159.3, 203.7.

Example 38.34

Synthesis of (2E)-2-[(3-actyl-1-benzyl-pyridin-1-ium-4-yl)methylene]-5,6-dimethoxy-indan-1-one bromide (149)

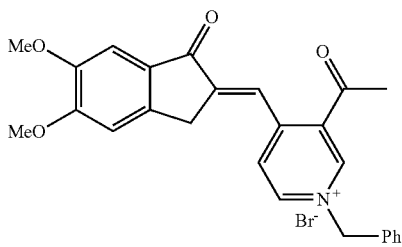

The title compound 149 is prepared according to the procedure reported in Example 38.1 with compound 97 (83 mg, 0.26 mmol) and benzyl bromide (64 μL, 0.52 mmol) as reactants. White solid. (Yield 101.1 mg, 78%).

$^1$H NMR (300 MHz, DMSO-D6, δ): 2.74 (s, 3H), 3.84 (s, 3H), 3.90 (s, 3H), 3.99 (s, 2H), 5.94 (s, 2H), 7.16 (s, 1H), 726 (s, 1H), 7.46-7.51 (m, 3H), 7.61-7.64 (m, 2H), 7.73 (s, 1H), 8.49 (d, 1H, J=6.6 Hz), 9.29 (d, 1H, J=6.6 Hz), 9.81 (s, 1H).

$^{13}$C NMR (75 MHz, DMSO-D6, δ): 29.8, 30.4, 55.7, 56.2, 63.1, 104.7, 107.9, 125.3, 128.3, 128.8, 129.4, 129.5, 134.1, 1363, 144.6, 145.7, 145.9, 149.6, 151.3, 156.2, 190.5, 196.5.

Example 38.35

Synthesis of methyl 1-benzyl-4-[(E)-(5,6-dimethoxy-1-oxo-indan-2-ylidene)methyl]pyridin-1-ium-3-carboxylate bromide (150)

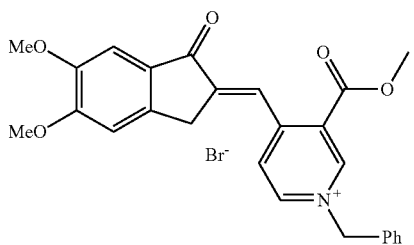

The title compound 150 is prepared according to the procedure reported in Example 38.1 with compound 96 (34 mg, 0.10 mmol) and benzyl bromide (25 μL, 0.21 mmol) as reactants. White solid. (Yield 46.1 mg, 90%).

MS (ESI$^+$): 430.1 (M$^+$)

Example 38.36

Synthesis of 1-benzyl-4-[(E)-(5,6-dimethoxy-1-oxo-indan-2-ylidene)methyl]-N-methyl-pyridin-1-ium-3-carboxamide bromide (151)

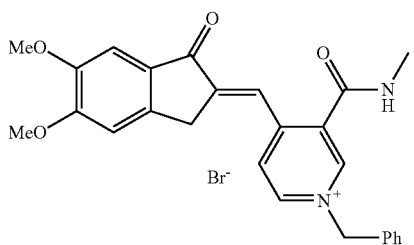

The title compound 151 is prepared according to the procedure reported in Example 38.1 with compound 98 (50 mg, 0.148 mmol) and benzyl bromide (36 μL, 2 equiv) as reactants. Pale yellow solid. (Yield 55.2 mg, 87%).

MS (ESI$^+$): 429.19 (M$^+$)

Example 38.37

Synthesis of 2-[[3-acetyl-1-(o-tolylmethyl)pyridin-1-ium-4-yl]methyl]-5,6-dimethyl-indan-1-one bromide (152)

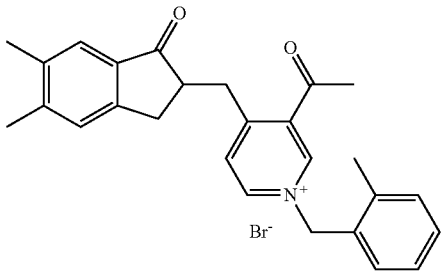

The title compound 152 is prepared according to the procedure reported in Example 38.1 with compound 111 (41.1 mg, 0.14 mmol) and 2-methylbenzyl bromide (32 µL, 0.24 mmol) as reactants. Pale yellow solid. (Yield 66 mg, 97%).

$^1$H NMR (300 MHz, CD$_3$OD, δ): 2.31 (s, 3H), 2.37 (s, 6H), 2.71 (s, 3H), 2.87 (dd, 1H, J=16.8 Hz, J=3.3 Hz), 3.10-3.15 (m, 1H), 3.30-3.41 (m, 2H), 3.60 (dd, 1H, J=13.5 Hz, J=7.8 Hz), 5.96 (s, 2H), 7.26-7.47 (m, 6H), 8.17 (d, 1H, J=63 Hz), 8.77 (d, 1H, J=6.0 Hz), 9.46 (s, 1H).

$^{13}$C NMR (75 MHz, CD$_3$OD, δ): 19.2, 19.7, 20.8, 29.9, 33.4, 36.1, 63.3, 124.9, 128.2, 128.4, 131.0, 131.3, 132.1, 132.5, 135.0, 138.1, 1383, 138.8, 145.6, 146.5, 147.4, 153.1, 162.7, 197.6, 208.2.

HRMS (ESI$^+$): calcd. For CH$_{27}$NO$_{28}$NO$_2$ 398.2120. found 398.2120.

Example 39

Reduction of Quaternized Forms (Route C)

Example 39.1

Synthesis of 2-[[3-acetyl-1-[(4-chlorophenyl)methyl]-4H-pyridin-4-yl]methyl]-6-methoxy-tetralin-1-one (153)

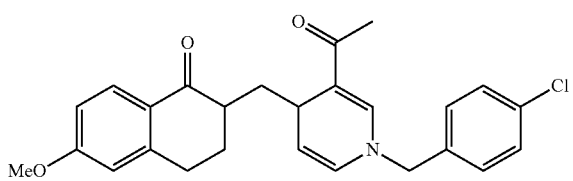 [SMILES: COc1ccc2c(c1)CCC(CC1C=CN(Cc3ccc(Cl)cc3)C=C1C(C)=O)C2=O]

To a solution of pyridinium salt 131 (75 mg, 0.15 mmol) in dry and degassed dichloromethane (2.5 mL) was added at once N-benzyl-1,4-dihydronicotinamide (BNAH) (32 mg, 1 equiv) at 25° C. under Argon. The reaction was monitored by TLC until the starting material has disappeared (48 h). Then, water and dichloromethane were added. The organic layer was washed twice with water and once with brine, dried over magnesium sulfate and concentrated to dryness. The crude residue was purified by column chromatography (gradient of EtOAc in petroleum ether) to afford the title compound 153 as a yellow solid (Yield 29 mg, 44%).

$^1$H NMR (300 MHz, CDCl$_3$, δ): 1.20-1.45 (m, 1.5H), 1.48-1.59 (m, 0.5H), 1.73-2.39 (m, 2H), 2.18 (s, 1.5H), 2.21 (s, 1.5H), 2.40-2.52 (m, 0.5H), 2.57-2.68 (m, 0.5H), 2.78-2.95 (m, 1.5H), 3.06-3.17 (m, 0.5H), 3.57-3.70 (m, 1H), 3.82 (s, 3H), 4.37-4.47 (m, 2H), 4.99-5.08 (m, 1H), 5.82-5.92 (m, 1H), 6.62-6.70 (m, 1H), 6.73-6.82 (m, 1H), 7.08-7.21 (m, 4H), 7.27-7.37 (m, 1H), 7.92-7.95 (m, 1H).

$^{13}$C NMR (75 MHz, CDCl$_3$, δ): 24.5, 24.7, 27.2, 27.8, 28.2, 283, 29.0, 29.3, 29.7, 37.7, 38.1, 42.8, 43.8, 53.5, 55.4, 57.2, 57.3, 108.7, 110.6, 112.4, 113.1, 113.2, 113.6, 114.2, 126.0, 126.2, 127.7, 127.9, 128.3, 128.4, 129.2, 129.3, 129.8, 129.9, 133.9, 135.3, 135.4, 142.7, 142.9, 146.6, 146.7, 163.3, 163.4, 195.2, 195.8, 199.7, 199.9.

Example 39.2

Synthesis of 2-[[3-acetyl-1-(p-tolylmethyl)-4H-pyridin-4-yl]methyl]-6-methoxy-tetralin-1-one (154)

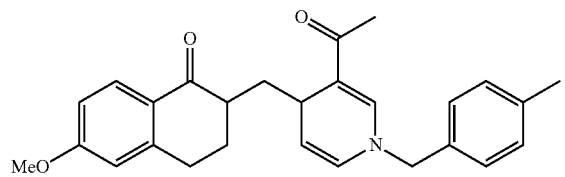 [SMILES: COc1ccc2c(c1)CCC(CC1C=CN(Cc3ccc(C)cc3)C=C1C(C)=O)C2=O]

The title compound 154 is prepared according to the procedure reported in Example 39.1 with compound 130 (75 mg, 0.154 mmol) and BNAH (33 mg, 1 equiv) as reactants. Yellow solid. (Yield 32.9 mg, 51%).

$^1$H NMR (300 MHz, CDCl$_3$, δ): 1.31-1.45 (m, 0.5H), 1.49-1.62 (m, 0.5H), 1.76-2.39 (m, 3H), 2.15 (s, 1.5H), 2.18 (s, 1.5H), 2.32 (s, 1.5H), 2.33 (s, 1.5H), 2.44-2.69 (m, 1H), 2.79-2.93 (m, 1.5H), 3.07-3.20 (m, 0.5H), 3.55-3.71 (m, 1H), 3.87 (s, 3H), 4.39 (s, 2H), 4.98-5.06 (m, 1H), 5.85-5.95 (m, 1H), 6.62-6.71 (m, 1H), 6.74-6.84 (m, 1H), 7.05-7.21 (m, 5H), 7.92-8.00 (m, 1H).

$^{13}$C NMR (75 MHz, CDCl$_3$, δ): 21.2, 21.3, 24.5, 24.7, 25.9, 26.3, 27.0, 27.7, 28.2, 28.4, 29.0, 29.2, 29.7, 37.7, 38.1, 42.8, 43.9, 53.5, 55.4, 57.7, 57.8, 108.3, 110.2, 112.4, 113.0, 113.1, 1133, 113.8, 126.0, 126.3, 127.0, 127.1, 127.8, 128.1, 129.7, 129.8, 133.7, 133.8, 137.9, 142.9, 143.1, 146.6, 146.7, 163.2, 1633, 195.0, 195.6, 199.8, 200.0.

HRMS (ESI) calcd for [M+H]$^+$ C$_{27}$H$_{30}$NO$_3$ m/z 416.2226 found 416.2233.

Example 39.3

Synthesis of 2-[[3-acetyl-1-[(4-fluorophenyl)methyl]-4H-pyridin-4-yl]methyl]-6-methoxy-tetralin-1-one (155)

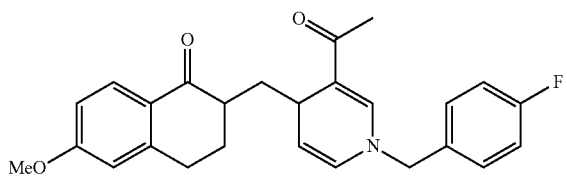 [SMILES: COc1ccc2c(c1)CCC(CC1C=CN(Cc3ccc(F)cc3)C=C1C(C)=O)C2=O]

The title compound 155 is prepared according to the procedure reported in Example 39.1 with compound 129 (75 mg, 0.15 mmol) and BNAH (32 mg, 1 equiv) as reactants. Yellow solid. (Yield 31.4 mg, 50%).

¹H NMR (300 MHz, CDCl₃, δ): 1.31-1.43 (m, 0.5H), 1.49-1.60 (m, 0.5H), 1.85-2.10 (m, 2H), 2.15 (s, 1.5H), 2.18 (s, 1.5H), 2.12-2.40 (m, 1H), 2.42-2.53 (m, 0.5H), 2.59-2.70 (m, 0.5H), 2.78-2.95 (m, 1.5H), 3.06-3.18 (m, 0.5H), 3.58-3.70 (m, 1H), 3.83 (s, 3H), 4.39-4.43 (m, 2H), 4.99-5.06 (m, 1H), 5.84-5.92 (m, 1H), 6.62-6.71 (m, 1H), 6.74-6.82 (m, 1H), 6.97-7.23 (m, 5H), 7.90-7.99 (m, 1H).

¹³C NMR (75 MHz, CDCl₃, δ): 24.5, 24.7, 27.2, 27.8, 28.2, 28.4, 29.0, 29.3, 37.8, 38.2, 42.9, 43.9, 53.5, 55.4, 57.2, 57.3, 108.6, 110.4, 112.4, 113.1, 113.2, 113.7, 114.2, 115.9, 116.0, 116.1, 116.2, 126.1, 126.3, 127.7, 127.9, 128.7, 128.8, 128.9, 129.8, 129.9, 132.5, 132.6, 132.7, 142.6, 142.7, 146.6, 146.7, 160.9, 163.3, 163.4, 164.2, 195.0, 195.6, 199.7, 199.9.

Example 39.4

Synthesis of 2-[[3-acetyl-1-[(3-fluorophenyl)methyl]-4H-pyridin-4-yl]methyl]-6-methoxy-tetralin-1-one (156)

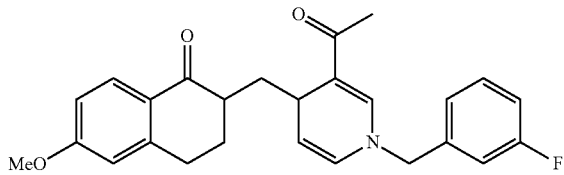 [SMILES: COc1ccc2c(c1)CCC(CC1C=CN(Cc3cccc(F)c3)C=C1C(C)=O)C2=O]

The title compound 156 is prepared according to the procedure reported in Example 39.1 with compound 128 (70 mg, 0.14 mmol) and BNAH (30 mg, 1 equiv) as reactants. Yellow solid. (Yield 17 mg, 29%).

¹H NMR (300 MHz, CDCl₃, δ): 1.38-1.43 (m, 0.5H), 1.52-1.61 (m, 0.5H), 1.84-1.92 (m, 1H), 1.99-2.39 (m, 2H), 2.16 (s, 1.5H), 2.19 (s, 1.5H), 2.47-2.57 (m, 0.5H), 2.59-2.71 (m, 0.5H), 2.82-2.95 (m, 1.5H), 3.08-3.21 (m, 0.5H), 3.59-3.71 (m, 1H), 3.83 (s, 3H), 4.43-4.45 (m, 2H), 5.02-5.08 (m, 1H), 5.85-5.93 (m, 1H), 6.59-6.69 (m, 1H), 6.75-6.82 (m, 1H), 6.90-7.14 (m, 4H), 7.25-7.35 (m, 1H), 7.92-7.97 (m, 1H).

¹³C NMR (75 MHz, CDCl₃, δ): 24.6, 24.8, 27.2, 27.8, 28.2, 28.4, 29.0, 37.9, 383, 42.9, 43.9, 55.5, 57.3, 108.6, 110.5, 112.4, 113.1, 113.2, 113.8, 113.9, 114.1, 114.4, 115.0, 115.2, 122.5, 126.1, 126.3, 127.8, 127.9, 129.9, 130.7, 130.8, 130.9, 139.4, 139.5, 139.7, 142.5, 142.7, 146.6, 146.7, 161.6, 163.3, 163.4, 164.8, 195.0, 195.7, 199.7, 199.9.

¹⁹F NMR (282 MHz, CDCl₃, δ): −111.75, −111.76.

Example 39.5

Synthesis of 2-[[3-acetyl-1-[(2-chlorphenyl)methyl]-4H-pyridin-4-yl]methyl]-6-methoxy-tetralin-1-one (157)

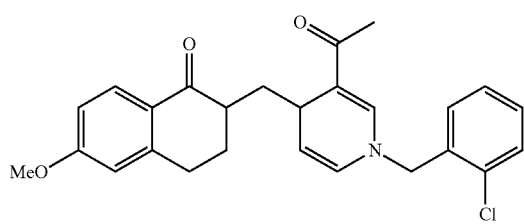 [SMILES: COc1ccc2c(c1)CCC(CC1C=CN(Cc3ccccc3Cl)C=C1C(C)=O)C2=O]

The title compound 157 is prepared according to the procedure reported in Example 39.1 with compound 126 (60 mg, 0.12 mmol) and BNAH (25 mg, 1 equiv) as reactants. Yellow solid. (Yield 25 mg, 49%).

¹H NMR (300 MHz, CDCl₃, δ): 1.39-1.44 (m, 0.5H), 1.54-1.62 (m, 0.5H), 1.84-1.92 (m, 1H), 1.98-2.42 (m, 2H), 2.16 (s, 1.5H), 2.18 (s, 1.5H), 2.46-2.57 (m, 0.5H), 2.62-2.71 (m, 0.5H), 2.82-2.95 (m, 1.5H), 3.09-3.21 (in, 0.5H), 3.61-3.72 (m, 1H), 3.83 (s, 3H), 4.52-4.53 (m, 2H), 5.01-5.08 (m, 1H), 5.89-5.94 (m, 1H), 6.64-6.68 (m, 1H), 6.75-6.80 (m, 1H), 7.12-7.40 (m, 5H), 7.93-7.97 (n, 1H).

¹³C NMR (75 MHz, CDCl₃, δ): 24.6, 24.8, 27.1, 27.7, 28.2, 28.4, 29.0, 292, 37.8, 38.2, 42.9, 44.0, 55.5, 55.6, 108.5, 110.4, 112.4, 113.0, 113.2, 113.8, 114.2, 126.1, 126.3, 127.5, 127.6, 129.8, 128.0, 128.6, 128.8, 129.4, 129.9, 130.0, 133.1, 133.2, 134.5, 142.9, 143.1, 146.6, 146.7, 163.3, 163.4, 195.1, 195.7, 199.7, 199.9.

Example 39.6

Synthesis of 2-[[3-actyl-1-[(2-nitrophenyl)methyl]-4H-pyridin-4-yl]methyl]-6-methoxy-tetralin-1-one (158)

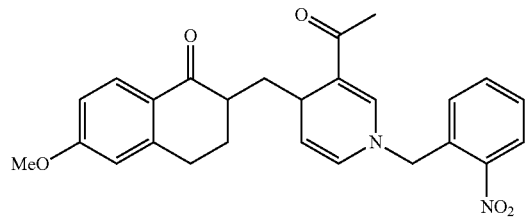 [SMILES: COc1ccc2c(c1)CCC(CC1C=CN(Cc3ccccc3[N+](=O)[O-])C=C1C(C)=O)C2=O]

The title compound 158 is prepared according to the procedure reported in Example 39.1 with compound 125 (80 mg, 0.16 mmol) and BNAH (34 mg, 1 equiv) as reactants. Yellow solid. (Yield 28 mg, 40%).

HRMS (ESI⁺) calcd for [M+H]⁺ C₂₆H₂₇N₂O₅ m/z 447.1919 found 447.1225.

Example 39.7

Synthesis of 2-[[3-acetyl-1-[(3-nitrophenyl)methyl]-4H-pyridin-4-yl]methyl]-6-methoxy-tetralin-1-one (159)

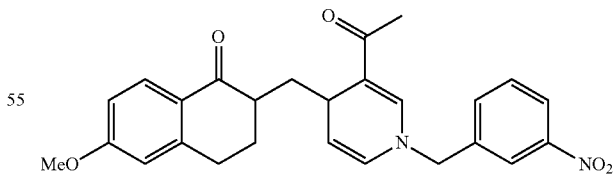

The title compound 159 is prepared according to the procedure reported in Example 39.1 with compound 123 (60 mg, 0.12 mmol) and BNAH (25 mg, 1 equiv) as reactants. Yellow solid. (Yield 20.8 mg, 39%).

¹H NMR (300 MHz, CDCl₃, δ): 1.35-1.46 (m, 0.5H), 1.49-1.61 (m, 0.5H), 1.75-2.13 (m, 2H), 2.17 (s, 1.5H), 2.19 (s, 1.5H), 2.21-2.39 (m, 1H), 2.45-2.55 (m, 0.5H), 2.59-2.68 (m, 0.5H), 2.81-2.96 (m, 1.5H), 3.06-3.17 (m, 0.5H), 3.58-3.70

(m, 1H), 3.83 (s, 3H), 4.54 (s, 1H), 4.55 (s, 1H), 5.02-5.13 (m, 1H), 5.85-5.93 (m, 1H), 6.61-6.69 (m, 1H), 6.73-6.81 (m, 1H), 7.11 (s, 1H), 7.16 (s, 1H), 7.54-7.63 (m, 2H), 7.89-7.95 (m, 1H), 8.07-8.19 (m, 1H).

$^{13}$C NMR (75 MHz, CDCl$_3$, δ): 24.6, 24.9, 27.2, 27.8, 28.2, 28.3, 28.9, 29.3, 37.9, 38.4, 42.9, 43.7, 51.5, 55.5, 57.1, 57.3, 109.1, 110.8, 112.4, 113.1, 113.2, 114.4, 114.8, 121.9, 122.0, 122.1, 122.8, 123.1, 123.2, 126.0, 126.2, 127.5, 127.7, 129.8, 129.9, 130.3, 130.4, 132.8, 132.9, 133.1, 139.2, 139.3, 142.2, 142.3, 146.5, 146.6, 148.6, 163.3, 163.4, 195.1, 195.7, 199.6, 199.8.

Example 39.8

Synthesis of 2-[[3-acetyl-1-(o-tolylmethyl)-4H-pyridin-4-yl]methyl]-6-methoxy-tetralin-1-one (160)

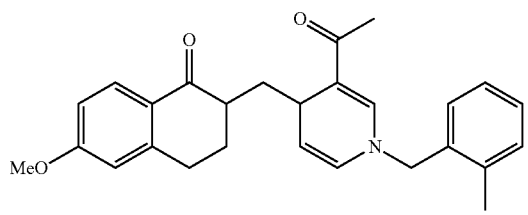 [SMILES: COc1ccc2c(c1)CCC(CC1C=CN(Cc3ccccc3C)C=C1C(C)=O)C2=O]

The title compound 160 is prepared according to the procedure reported in Example 39.1 with compound 121 (500 mg, 1 mmol) and BNAH (214 mg, 1 equiv) as reactants. Yellow solid. (Yield 150 mg, 36%).

The separation of enantiomers of racemic 2-[[3-acetyl-1-(o-tolylmethyl)-4H-pyridin-4-yl]methyl]-6-methoxy-tetralin-1-one 160 (140 mg) was accomplished by chromatography under supercritical fluid chromatography (SFC), eluting with carbon dioxide as the carrier and 15% ethanol (IA column), to give enantiomers 160-A (31 mg), 160-B (30 mg), 160-C (38 mg, %), 160-D (38 mg).

Enantiomers 160-A/160-B:

$^1$H NMR (300 MHz, CDCl$_3$, δ): 135-1.46 (m, 2H), 1.77-1.90 (m, 1H), 2.05-2.13 (m, 1H), 2.16 (s, 3H), 2.29 (s, 3H), 2.34-2.57 (m, 2H), 2.88-2.96 (m, 1H), 3.65-3.73 (m, 1H), 3.84 (s, 3H), 4.44 (s, 2H), 5.03 (dd, 1H, J=7.5 Hz, J=4.4 Hz), 5.91 (dd, 1H, J=7.5 Hz, J=1.2 Hz), 6.66 (d, 1H, J=2.1 Hz), 6.79 (dd, 1H, J=9.0 Hz, J=2.7 Hz), 7.12-7.31 (m, 5H), 7.97 (d, 1H, J=9.0 Hz).

$^{13}$C NMR (75 MHz, CDCl$_3$, δ): 19.2, 24.7, 28.4, 29.0, 29.2, 38.4, 43.9, 55.4, 56.0, 110.2, 112.4, 113.0, 113.4, 126.3, 126.5, 127.9, 128.2, 129.8, 130.8, 134.5, 136.1, 143.0, 146.6, 163.3, 195.6, 199.8.

Enantiomers 160-C/160-D:

$^1$H NMR (300 MHz, CDCl$_3$, δ): 1.48-1.55 (m, 1H), 1.75-1.85 (m, 1H), 1.90-2.05 (m, 1H), 2.13 (s, 3H), 2.17-2.34 (m, 1H), 2.29 (s, 3H), 2.61-2.72 (m, 1H), 2.83-2.95 (m, 1H), 3.10-3.22 (m, 1H), 3.61-3.69 (m, 1H), 3.84 (s, 3H), 4.43 (s, 2H), 5.05 (dd, 1H, J=7.5 Hz, J=4.8 Hz), 5.89 (dd, 1H, J=7.5 Hz, J=1.2 Hz), 6.68 (d, 1H, J=2.4 Hz), 6.78 (dd, 1H, J=8.4 Hz, J=2.4 Hz), 7.05 (s, 1H), 7.13-7.29 (m, 4H), 7.95 (d, 1H, J=8.4 Hz).

$^{13}$C NMR (75 MHz, CDCl$_3$, δ): 19.2, 24.4, 27.0, 27.6, 28.2, 37.9, 42.8, 55.4, 55.9, 108.2, 112.4, 113.2, 113.9, 126.0, 126.6, 127.6, 128.0, 128.2, 129.8, 130.8, 134.4, 136.0, 142.8, 146.7, 163.3, 195.0, 200.0.

Example 39.9

Synthesis of 2-[(3-acetyl-1-propyl-4H-pyridin-4-yl)methyl]-6-methoxy-tetralin-1-one

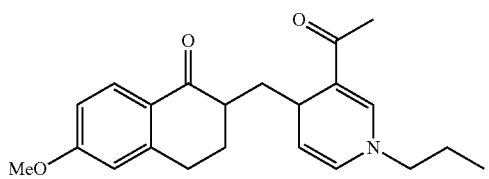 [SMILES: CCCN1C=CC(CC2CCc3cc(OC)ccc3C2=O)C(C(C)=O)=C1]

The title compound 161 is prepared according to the procedure reported in Example 39.1 with compound 135 (100.0 mg, 0.21 mmol) and BNAH (1 equiv) as reactants. Yellow oil. (Yield 26.1 mg, 35%).

MS (ESI$^+$): 354.21 (M+H$^+$)

Example 39.10

Synthesis of 2-[(3-acetyl-1-benzyl-4H-pyridin-4-yl)methyl]-6,7-dimethoxy-tetralin-1-one (162)

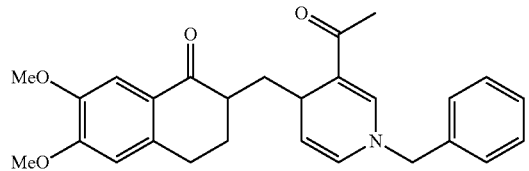 [SMILES: COc1cc2c(cc1OC)C(=O)C(CC1C=CN(Cc3ccccc3)C=C1C(C)=O)CC2]

The title compound 162 is prepared according to the procedure reported in Example 39.1 with compound 132 (51 mg, 0.1 mmol) and BNAH (21.4 mg, 1 equiv) as reactants. Yellow solid. (Yield 20.3 mg, 50%).

$^1$H NMR (300 MHz, CDCl$_3$, δ): 1.30-1.90 (m, 2H), 1.92-239 (m, 2H), 2.15 (s, 1.5H), 2.19 (s, 1.5H), 2.45-2.54 (m, 0.5H), 2.57-2.68 (m, 0.5H), 2.74-2.89 (m, 1.5H), 3.05-3.17 (m, 0.5H), 3.60-3.70 (m, 1H), 3.88-3.92 (m, 6H), 4.44 (s, 2H), 5.01-5.06 (m, 1H), 5.90-5.94 (m, 1H), 6.62-6.65 (m, 1H), 7.10-7.48 (m, 7H).

Example 39.11

Synthesis of 2-[[3-acetyl-1-(o-tolylmethyl)-4H-pyridin-4-yl]methyl]-5-methyl-indan-1-one (163)

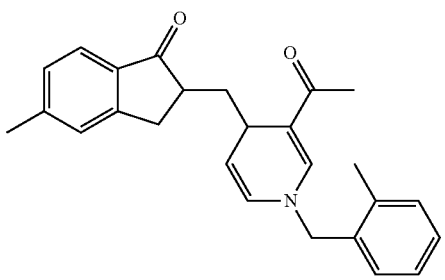 [SMILES: CC(=O)C1=CN(Cc2ccccc2C)C=CC1CC1Cc2cc(C)ccc2C1=O]

The title compound 163 is prepared according to the procedure reported in Example 39.1 with compound 137 (150 mg, 0.32 mmol) and BNAH (69 mg, 1 equiv) as reactants. Yellow solid. (Yield 43.5 mg, 35%).

$^1$H NMR (300 MHz, CDCl$_3$, δ): 1.38-1.58 (m, 056H), 1.89-1.96 (m, 0.44H), 2.12 (s, 1.6H), 2.17 (s, 1.4H), 2.30 (s, 3H), 2.41 (s, 3H), 2.62-2.71 (m, 0.44H), 2.72-2.88 (m, 1H), 3.05-3.45 (m, 1.56H), 3.56-3.66 (m, 0.56H), 3.72-3.76 (m, 0.44H), 4.44 (s, 2H), 4.95 (dd, 0.44H, J=7.8 Hz, J=5.7 Hz), 5.10 (dd, 0.56H, J=7.5 Hz, J=5.1 Hz), 5.90-5.94 (m, 1H), 7.07-7.28 (m, 7H), 7.58-7.61 (m, 1H).

$^{13}$C NMR (75 MHz, CDCl$_3$, δ): 19.2, 19.3, 22.1, 24.5, 24.6, 29.2, 29.3, 32.7, 34.0, 40.3, 41.0, 44.0, 45.0, 56.0, 108.2, 109.9, 113.2, 113.8, 123.6, 126.6, 126.7, 126.9, 127.1, 127.6, 128.2, 128.5, 130.9, 134.4, 134.5, 136.1, 142.7, 143.3, 145.7, 145.8, 154.9, 155.0, 194.9, 195.4, 209.3, 209.4.

Example 39.12

Synthesis of 2-[[3-acetyl-1-(o-tolylmethyl)-4H-pyridin-4-yl]methyl]-5-methoxy-indan-1-one (164)

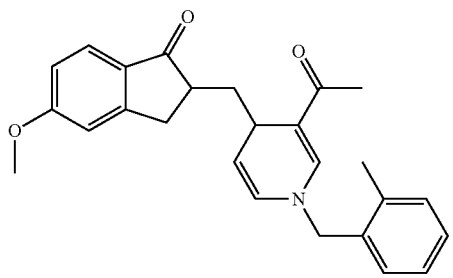 [SMILES: COc1ccc2c(c1)CC(CC1C=CN(Cc3ccccc3C)C=C1C(C)=O)C2=O]

The title compound 164 is prepared according to the procedure reported in Example 39.1 with compound 138 (100 mg, 0.21 mmol) and BNAH (45 mg, 1 equiv) as reactants. Yellow solid. (Yield 34.5 mg, 41%).

$^1$H NMR (300 MHz, CDCl$_3$, δ): 1.38-1.59 (m, 0.54H), 1.83-2.03 (m, 0.46H), 2.12 (s, 1.6H), 2.17 (s, 1.4H), 2.29 (2s, 3H), 2.61-2.88 (m, 1.46H), 3.12 (dd, 0.54H, J=17.4 Hz, J=3.6 Hz), 3.19-3.39 (m, 1H), 3.56-3.66 (m, 0.54H), 3.72-3.88 (m, 0.46H), 3.86 (s, 3H), 4.43 (s, 2H), 4.95 (dd, 0.44H, J=7.8 Hz, J=5.7 Hz), 5.10 (dd, 0.56H, J=7.8 Hz, J=5.4 Hz), 5.89-5.94 (m, 1H), 6.84-6.88 (m, 2H), 7.07-7.28 (m, 5H), 7.61-7.65 (m, 1H).

$^{13}$C NMR (75 MHz, CDCl$_3$, δ): 19.2, 24.5, 24.6, 29.2, 29.3, 32.9, 34.2, 40.4, 41.2, 44.0, 45.0, 55.6, 56.0, 108.3, 109.6, 109.7, 109.9, 113.1, 113.8, 1152, 115.4, 125.4, 126.6, 126.7, 127.6, 127.7, 128.2, 130.0, 130.1, 134.4, 136.0, 142.8, 143.3, 157.4, 157.5, 165.2, 165.3, 194.9, 195.5, 207.8, 207.9.

Example 39.13

Synthesis of 6-[[3-acetyl-1-(o-tolylmethyl)-4H-pyridin-4-yl]methyl]-5,6-dihydrocyclopenta[f][1,3]benzodioxol-7-one (165)

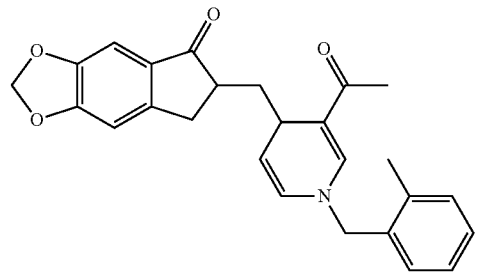 [SMILES: CC(=O)C1=CN(Cc2ccccc2C)C=CC1CC1Cc2cc3c(cc2C1=O)OCO3]

The title compound 165 is prepared according to the procedure reported in Example 39.1 with compound 139 (100 mg, 0.20 mmol) and BNAH (43 mg, 1 equiv) as reactants. Yellow solid. (Yield 32.1 mg, 38%).

$^1$H NMR (300 MHz, CDCl$_3$, δ): 1.34-1.59 (m, 0.54H), 1.86-2.00 (m, 0.46H), 2.13 (s, 1.6H), 2.18 (s, 1.4H), 2.31 (2s, 3H), 2.64-2.86 (m, 1.46H), 3.03 (dd, 0.54H, J=17.1 Hz, J=3.3 Hz), 3.15-3.32 (m, 1H), 3.56-3.65 (m, 0.54H), 3.70-3.79 (m, 0.46H), 4.43 (s, 2H), 4.96 (dd, 0.44H, J=7.5 Hz, J=5.6 Hz), 5.10 (dd, 0.56H, J=7.5 Hz, J=5.1 Hz), 5.91-5.96 (m, 1H), 6.04 (brs, 2H), 6.79 (s, 0.46H), 6.82 (s, 0.54H), 7.05-7.28 (m, 6H).

$^{13}$C NMR (75 MHz, CDCl$_3$, δ): 192, 19.3, 24.5, 24.6, 29.2, 29.3, 32.8, 34.1, 40.5, 41.1, 44.3, 45.3, 56.0, 102.1, 102.3, 105.7, 105.9, 108.2, 109.9, 113.1, 113.8, 126.6, 126.7, 127.6, 127.7, 128.2, 130.9, 131.2, 134.4, 136.1, 142.7, 143.3, 148.1, 151.8, 151.9, 154.2, 154.3, 194.9, 195.4, 207.5, 207.6.

Example 39.14

Synthesis of 2-[[3-acetyl-1-(o-tolylmethyl)-4H-pyridin-4-yl]methyl]-5,6-dimethyl-indan-1-one (166)

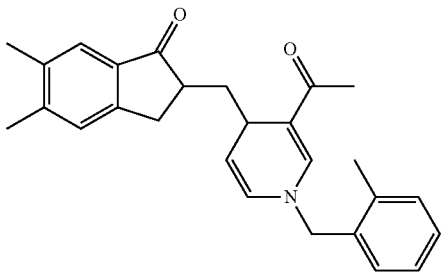 [SMILES: CC(=O)C1=CN(Cc2ccccc2C)C=CC1CC1Cc2cc(C)c(C)cc2C1=O]

The title compound 166 is prepared according to the procedure reported in Example 39.1 with compound 152 (62.0 mg, 0.13 mmol) and BNAH (33 mg, 1 equiv) as reactants. Yellow solid. (Yield 20.0 mg, 38%).

$^1$H NMR (300 MHz, CDCl$_3$, δ): 1.37-1.61 (m, 0.55H), 1.89-1.99 (m, 0.45H), 2.12 (s, 1.6H), 2.18 (s, 1.4H), 2.25-2.36 (m, 9H), 2.61-2.86 (m, 1.45H), 3.05 (dd, 0.55H, J=17.1 Hz, J=3.3 Hz), 3.17-3.37 (m, 1H), 3.59-3.66 (m, 0.55H), 3.72-3.79 (m, 0.45H), 4.44 (s, 2H), 4.95 (dd, 0.45H, J=7.5

J=5.4 Hz), 5.10 (dd, 0.55H, J=7.5 Hz, J=5.1 Hz), 5.89-5.95 (m, 1H), 7.07 (s, 0.55H), 7.12-7.45 (m, 5.45H), 7.50 (s, 1H).
$^{13}$C NMR (75 MHz, CDCl$_3$, δ): 19.2, 19.3, 19.8, 20.8, 24.5, 24.6, 29.3, 29.4, 32.4, 33.7, 40.4, 41.0, 44.0, 45.1, 56.0, 108.2, 109.9, 113.2, 113.9, 124.1, 126.6, 127.3, 127.5, 127.6, 128.2, 130.9, 134.4, 134.9, 136.1, 142.7, 143.2, 144.7, 144.8, 152.5, 152.6, 194.9, 195.4, 209.5, 209.6.

Example 39.15

Synthesis of 2-[[3-acetyl-1-(o-tolylmethyl)-4H-pyridin-4-yl]methyl]-5-chloro-indan-1-one (167)

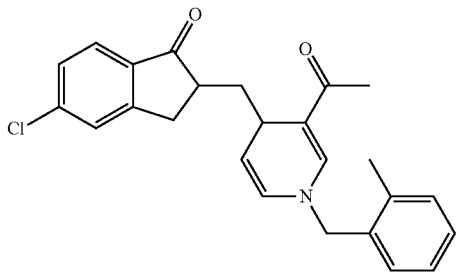 [SMILES: CC(=O)C1=CN(Cc2ccccc2C)C=CC1CC1Cc2cc(Cl)ccc2C1=O]

The title compound 167 is prepared according to the procedure reported in Example 39.1 with compound 136 (42 mg, 0.08 mmol) and BNAH (19 mg, 1 equiv) as reactants. Yellow solid. (Yield 17.5 mg, 50%).
$^1$H NMR (300 MHz, CDCl$_3$, δ): 1.38-1.59 (m, 1.54H), 1.88-2.01 (m, 1.46H), 2.13 (s, 1.6H), 2.17 (s, 1.4H), 2.29 (s, 3H), 2.64-2.75 (m, 1.46H), 3.12 (dd, 0.54H, J=17.7 Hz, J=3.9 Hz), 3.20-3.43 (m, 1H), 3.58-3.66 (m, 0.54H), 3.71-3.79 (m, 0.46H), 4.44 (s, 2H), 4.94 (dd, 0.44H, J=7.5 Hz, J=5.4 Hz), 5.08 (dd, 0.56H, J=7.8 Hz, J=5.1 Hz), 5.89-5.97 (m, 1H), 7.08-7.28 (m, 5H), 7.41-7.44 (m, 1H), 7.61-7.66 (m, 1H).
$^{13}$C NMR (75 MHz, CDCl$_3$, δ): 19.2, 19.3, 24.5, 24.6, 29.1, 29.2, 29.8, 32.7, 33.9, 40.2, 40.9, 44.1, 45.1, 56.0, 108.1, 113.0, 109.9, 113.7, 124.9, 126.6, 126.7, 126.8, 127.6, 127.0, 127.6, 127.7, 128.0, 128.1, 128.3, 128.4, 130.9, 134.3, 135.2, 136.1, 141.0, 141.2, 142.8, 143.3, 155.8, 155.9, 194.9, 195.5, 208.2, 208.3.

Example 39.16

Synthesis of 4-[(5,6-dimethoxy-1-oxo-indan-2-yl)methyl]-N-methyl-1-(o-tolylmethyl)-4H-pyridine-3-carboxamide (168)

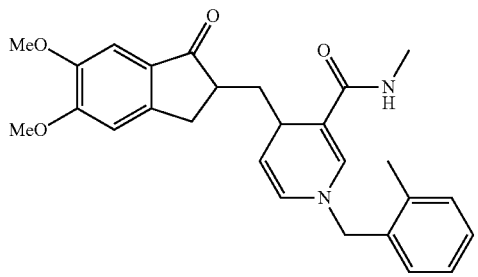 [SMILES: CNC(=O)C1=CN(Cc2ccccc2C)C=CC1CC1Cc2cc(OC)c(OC)cc2C1=O]

The title compound 168 is prepared according to the procedure reported in Example 39.1 with compound 143 (89.1 mg, 0.2 mmol) and BNAH (1 equiv) as reactants. Pale yellow solid. (Yield 35.7 mg, 40%).
MS (ESI$^+$): 447.23 (M+H$^+$)

Example 39.17

Synthesis of 2-[[3-acetyl-1-(o-tolylmethyl)-4H-pyridin-4-yl]methyl]-5,6-dimethoxy-indan-1-one (169)

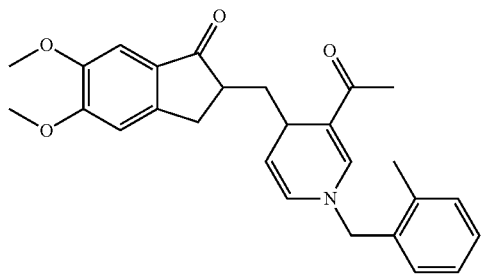 [SMILES: COc1cc2c(cc1OC)C(=O)C(CC1C=CN(Cc3ccccc3C)C=C1C(C)=O)C2]

The title compound 169 is prepared according to the procedure reported in Example 39.1 with compound 142 (74.2 mg, 0.15 mmol) and BNAH (35 mg, 1 equiv) as reactants. Yellow solid. (Yield 32.3 mg, 50%).
$^1$H NMR (300 MHz, CDCl$_3$, δ): 1.35-1.46 (m, 0.55H), 1.48-1.60 (m, 0.45H), 1.88-2.09 (m, 1H), 2.12 (s, 1.65H), 2.18 (s, 1.35H), 2.29 (s, 3H), 2.63-2.85 (m, 1.45H), 3.07 (dd, 0.55H, J=17.1 Hz, J=3.3 Hz), 3.17-3.35 (m, 1H), 3.58-3.66 (m, 0.55H), 3.69-3.79 (m, 0.45H), 3.88 (s, 3H), 3.94-3.95 (m, 3H), 4.44 (s, 2H), 4.95 (dd, 0.45H, J=7.8 Hz, J=5.4 Hz), 5.12 (dd, 0.55H, J 7.8 Hz, J=5.1 Hz), 5.89-5.96 (m, 1H), 6.84 (s, 0.45H), 6.88 (s, 0.55H), 7.06-7.28 (n, 6H).
$^{13}$C NMR (75 MHz, CDCl$_3$, δ): 19.2, 24.5, 24.6, 29.2, 29.4, 32.6, 33.8, 40.5, 41.4, 44.1, 45.2, 56.0, 56.1, 104.2, 107.4, 107.6, 108.3, 110.0, 113.1, 113.8, 126.6, 127.6, 128.2, 129.4, 130.9, 134.4, 136.1, 142.7, 143.3, 149.3, 149.7, 149.8, 155.3, 155.4, 194.9, 195.5, 208.4, 208.5.

Example 39.18

Synthesis of 2-[[3-bromo-1-(o-tolylmethyl)-2H-pyridin-4-yl]methyl]-5,6-dimethoxy-indan-1-one (168)

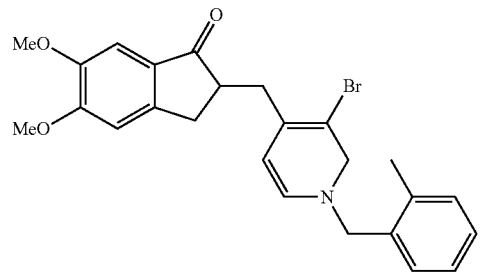 [SMILES: COc1cc2c(cc1OC)C(=O)C(CC1=C(Br)CN(Cc3ccccc3C)C=C1)C2]

To a solution of compound 146 (45 mg, 0.08 mmol) in a mixture of methanol and THF (5 mL, respectively 1:4) was added sodium borohydride (3 mg, 1 equiv) in one portion at 0° C. The reaction mixture was then stirred at this temperature for 1 h and quenched with 35% aqueous ammonia solution (3 mL). The mixture was extracted with dichloromethane (3×) and the organic phase was dried over magnesium sulfate, filtered and concentrated to dryness. The crude residue was purified by column chromatography on silica gel (petroleum ether/EtOAc: 2/3) to afford the title compound 168 as a yellow solid (Yield 21.9 mg, 60%).

MS (ESI+): 447.23 (M+H+).

The invention claimed is:

1. A pyridine compound represented by formula (I):

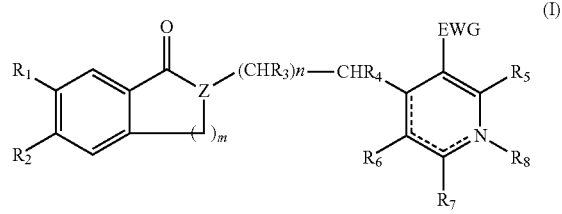

wherein:
the dotted lines in the pyridine cycle indicate the presence of at least one double bond, $R_1$ and $R_2$ are independently chosen between a hydrogen atom, a halogen atom, hydroxy, CN, CF3, a (C1-C8) alkyl, an aryl, a (C1-C8) alkoxy or $R_1$ and $R_2$ form together a dioxolyl group;

n is an integer from 0 to 4; and $R_3$ and $R_4$ are a hydrogen atom, or n=1 and $R_3$ and $R_4$ can also form together a double bond between the carbon atoms to which they are attached so that the radical $CHR_3$—$CHR_4$ form a vinylenyl group —CH=CH—, and either m is 0, 1 or 2, and Z is CH or N; or >Z—$(CHR_3)_n$—$CHR_4$— is >C=CH—$(CH_2)_n$—;

or --(--)$_m$--- is absent and

Z is NH, >N-alkyl ($C_1$-$C_8$), >N-phenyle, >N-benzyle or >N heteroaryle;

$R_5$ is chosen from a hydrogen atom, a halogen atom, hydroxy, CN, CF3, a ($C_1$-$C_8$) alkyl, an aryl, a (C1-C8) alkoxy; and $R_6$ and $R_7$ which may be identical or different are hydrogen, OH, (C1-C8) alkyl, aryl, heteroaryl, (C1-C8) alkylaryl, aryl (C1-C8) alkyl, (C1-C8) alkoxy, hydroxyl (C1-C8) alkyl, (C1-C8) alkoxy (C1-C8) alkyl, —$(CH_2)_q$-COOH wherein q is comprised between 1 and 4, Z', $Z_1$; or $R_6$ and $R_7$ taken together with the carbon atoms to which they are attached form a (C5-C10) cycloalkenyl, a 6-membered aromatic ring or a 5- or 10-membered heterocyclic ring comprising 1 to 4 heteroatoms identical or different chosen between N, S and O, being optionally substituted by one or more identical or different group defined as OH, ($C_1$-$C_8$) alkyl, aryl, heteroaryl, ($C_1$-$C_8$) alkyl-aryl, aryl ($C_1$-$C_8$) alkyl, ($C_1$-$C_8$) alkoxy, hydroxyl ($C_1$-$C_8$) alkyl, ($C_1$-$C_8$) alkoxy ($C_1$-$C_8$) alkyl, $(CH_2)_q$—COOH wherein q is comprised between 1 and 4, Z', $Z_1$;

Z' is a group defined by formula -(L)p-$Z_1$, L is ($C_1$-$C_8$) alkyl, an aryl, ($C_5$-$C_{10}$)heteroaryl, ($C_1$-$C_8$)alkyl-aryl, aryl-($C_1$-$C_8$)alkyl and p is comprised between 1 and 6;

$Z_1$ is defined by formula: —X—C($Y_1$)—$NR_9R_{10}$ wherein X and $Y_1$ are O or S, $R_9$ and $R_{10}$ may be identical or different and represent hydrogen, ($C_1$-$C_8$)alkyl, an aryl, ($C_5$-$C_{10}$)heteroaryl, ($C_1$-$C_8$)alkyl-aryl, cyclopropyl, —$(CH_2)p'$-COOH; and wherein p' is comprised between 1 and 4;

$R_8$ is a (C1-C8)alkyl, an aryl, ($C_5$-$C_{10}$)heteroaryl, an aryl-($C_1$-$C_8$)alkyl or a ($C_1$-$C_8$)alkyl-aryl radical, which can be optionally substituted by at least one group from OH, $NO_2$, $CF_3$, halogen, ($C_1$-$C_8$)alkyl, ($C_1$-$C_8$)alkoxy, or ($C_1$-$C_8$)alkoxy-aryl or sulfonyle;

EWG represents an electron withdrawing group selected from the group comprising COOR, COSR, CONRR', CN, COR, $CF_3$, SOR, $SO_2R$, SONRR', $SO_2NRR'$, $NO_2$, halogen, heteroaryl, wherein R and R' are independently chosen from H, alkyl, cycloalkyl, arylalkyl, heteroarylalkyl, hydroxyalkyl, alkoxyalkyl, aryloxyalkyl, alkylaminoalkyl, aminoalkyl, heteroaryloxyalkyl, halogenoalkyl, mercaptoalkyle HS-alk, alkylthioalkyl, aryl, alkylaryl, hydroxyaryl, alkoxyaryl, aryloxyaryl, aminoaryl, alkylaminoaryl, halogenoaryl, heteroaryl, alkylheteroaryl, alkoxyheteroaryl, aminoheteroaryl, alkylaminoheteroaryl, halogenoheteroaryl, or R and R' taken together with the nitrogen atom to which they are attached either form an heterocyclic ring of at least 3 members, chosen from a 5 or 6 membered heterocyclic ring, optionally substituted by one or more groups being as defined for $R_5$, or form a fused polyheterocyclic system, chosen from tetrahydroisoquinoline, indoline, isoindoline, optionally substituted by one or more group being as defined for $R_5$, or the pharmaceutical salts and stereoisomers thereof if any, or the quaternarized oxidized forms of said pyridine derivatives, it being understood that when the nitrogen atom of formula (I) is quaternarized, there is a counter ion X⁻ chosen from a halogen atom, a sulfate ion, a triflate ion, a carboxylate ion, a tosylate ion or a mesylate ion.

2. A compound represented by the formula (I+)

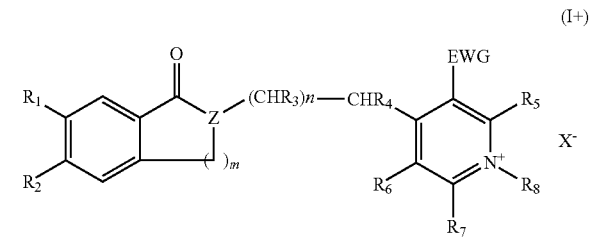

in which $R_1$ and $R_2$ are independently chosen between a hydrogen atom, a halogen atom, hydroxy, CN, CF3, a (C1-C8) alkyl, an aryl, a (C1-C8) alkoxy or $R_1$ and $R_2$ form together a dioxolyl group;

n is an integer from 0 to 4; and $R_2$ and $R_4$ are a hydrogen atom, or n=1 and $R_3$ and $R_4$ can also form together a double bond between the carbon atoms to which the are attached so that the radical $CHR_3$—$CHR_4$ form a vinylenyl group —CH=CH—, and either m is 0, 1 or 2, and Z is CH or N; or >Z—$(CHR_3)_n$—$CHR_4$— is >C=CH—$(CH_2)_n$—;

or -(--)--- is absent and

Z is NH, >N-alkyl ($C_1$-$C_8$), >N-phenyle, >N-benzyle or >N heteroaryle;

$R_5$ is chosen from a hydrogen atom, a halogen atom, hydroxy, CN, CF3, a ($C_1$-$C_8$) alkyl, an aryl, a (C1-C8) alkoxy; and $R_6$ and $R_7$ which may be identical or different are hydrogen, OH, (C1-C8) alkyl, aryl, heteroaryl, (C1-C8)

alkylaryl, aryl (C1-C8) alkyl, (C1-C8) alkoxy, hydroxyl (C1-C8) alkyl, (C1-C8) alkoxy (C1-C8) alkyl, —(CH$_2$)q-COOH wherein q is comprised between 1 and 4, Z', Z$_1$; or $R_6$ and $R_7$ taken together with the carbon atoms to which they are attached form a (C5-C10) cycloalkenyl, a 6-membered aromatic ring or a 5- or 10-membered heterocyclic ring comprising 1 to 4 heteroatoms identical or different chosen between N, S and O, being optionally substituted by one or more identical or different group defined as OH, (C$_1$-C$_8$) alkyl, aryl, heteroaryl, (C$_1$-C$_8$) alkyl-aryl, aryl (C$_1$-C$_8$) alkyl, (C$_1$-C$_8$) alkoxy, hydroxyl (C$_1$-C$_8$) alkyl, (C$_1$-C$_8$) alkoxy (C$_1$-C$_8$) alkyl, (CH$_2$)$_q$—COOH wherein q is comprised between 1 and 4, Z', Z$_1$;

Z' is a group defined by formula -(L)p-Z$_1$, L is (C$_1$-C$_8$) alkyl, an aryl, (C$_5$-C$_{10}$)heteroaryl, (C$_1$-C$_8$)alkyl-aryl, aryl-(C$_1$-C$_8$)alkyl and p is comprised between 1 and 6;

Z$_1$ is defined by formula: —X—C(Y$_1$)—NR$_9$R$_{10}$ wherein X and Y$_1$ are O or S, R$_9$ and R$_{10}$ may be identical or different and represent hydrogen, (C$_1$-C$_8$) alkyl, an aryl, (C$_5$-C$_{10}$)heteroaryl, (C$_1$-C$_8$)alkyl-aryl, cyclopropyl, —(CH$_2$)p'-COOH; and wherein p' is comprised between 1 and 4;

R$_8$ is a (C$_1$-C$_8$)alkyl, an aryl, (C$_5$-C$_{10}$)heteroaryl, an aryl-(C$_1$-C$_8$)alkyl or a (C$_1$-C$_8$)alkyl-aryl radical, which can be optionally substituted by at least one group from OH, NO$_2$, CF$_3$ halogen, (C$_1$-C$_8$)alkyl, (C$_1$-C$_8$)alkoxy, or (C$_1$-C$_8$)alkoxy-aryl or sulfonyle;

EWG represents an electron withdrawing group selected from the group comprising COOR, COSR, CONRR', CN, COR, CF$_3$, SOR, SO$_2$R, SONRR', SO$_2$NRR', NO$_2$, halogen, heteroaryl, wherein R and R' are independently chosen from H, alkyl, cycloalkyl, arylalkyl, heteroarylalkyl, hydroxyalkyl, alkoxyalkyl, aryloxyalkyl, alkylaminoalkyl, aminoalkyl, heteroaryloxyalkyl, halogenoalkyl, mercaptoalkyle HS-alk, alkylthioalkyl, aryl, alkylaryl, hydroxyaryl, alkoxyaryl, aryloxyaryl, aminoaryl, alkylaminoaryl, halogenoaryl, heteroaryl, alkylheteroaryl, alkoxyheteroaryl, aminoheteroaryl, alkylaminoheteroaryl, halogenoheteroaryl, or R and R' taken together with the nitrogen atom to which they are attached either form an heterocyclic ring of at least 3 members, preferably a 5 or 6 membered heterocyclic ring, optionally substituted by one or more groups being as defined for R$_5$, or form a fused polyheterocyclic system, chosen from tetrahydroisoquinoline, indoline, isoindoline, and X$^-$ represents a counter ion chosen from a halogen atom, a sulfate ion, a triflate ion, a carboxylate ion, a tosylate ion or a mesylate ion.

3. A compound represented by formula (Ia) or (Ib),

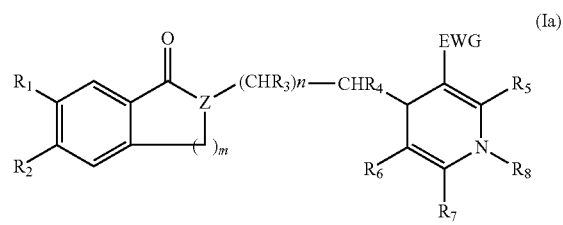

(Ia)

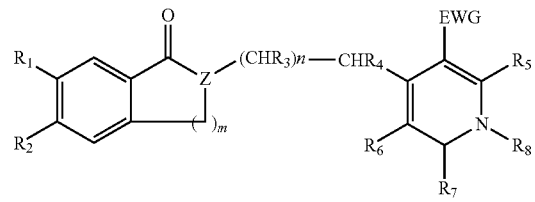

(Ib)

wherein

R$_1$ and R$_2$ are independently chosen between a hydrogen atom, a halogen atom, hydroxy, CN, CF3, a (C1-C8) alkyl, an aryl, a (C1-C8) alkoxy or R$_1$ and R$_2$ form to ether a dioxolyl group;

n is an integer from 0 to 4; and

R$_3$ and R$_4$ are a hydrogen atom, or n=1 and R$_3$ and R$_4$ can also form together a double bond between the carbon atoms to which they are attached so that the radical CHR$_3$—CHR$_4$ form a vinylenyl group —CH═CH—, and either m is 0, 1 or 2, and Z is CH or N; or >Z—(CHR$_3$)$_n$—CHR$_4$— is >C═CH—(CH$_2$)$_n$—;

or --(--)$_m$--- is absent and

Z is NH, >N-alkyl (C$_1$-C$_8$), >N-phenyle, >N-benzyle or >N heteroaryle;

R$_5$ is chosen from a hydrogen atom, a halogen atom, hydroxy, CN, CF$_3$, a (C$_1$-C$_8$) alkyl, an aryl, a (C1-C8) alkoxy; and R$_6$ and R$_7$ which may be identical or different are hydrogen, OH, (C1-C8) alkyl, aryl, heteroaryl, (C1-C8) alkylaryl, aryl (C1-C8) alkyl, (C1-C8) alkoxy, hydroxyl (C1-C8) alkyl, (C1-C8 alkoxy (C1-C8) alkyl, —(CH$_2$)q-COOH wherein q is comprised between 1 and 4 Z' Z$_1$; or R$_6$ and R$_7$ taken together with the carbon atoms to which they are attached form a (C5-C10) cycloalkenyl, a 6-membered aromatic ring or a 5- or 10-membered heterocyclic ring comprising 1 to 4 heteroatoms identical or different chosen between N, S and O, being optionally substituted by one or more identical or different group defined as OH, (C$_1$-C$_8$) alkyl, aryl, heteroaryl, (C$_1$-C$_8$) alkyl-aryl, aryl (C$_1$-C$_8$) alkyl, (C$_1$-C$_8$) alkoxy, hydroxyl (C$_1$-C$_8$) alkyl, (C$_1$-C$_8$) alkoxy (C$_1$-C$_8$) alkyl, (CH$_2$)$_q$—COOH wherein q is comprised between 1 and 4 Z' Z$_1$;

Z' is a group defined by formula -(L)p-Z$_1$, L is (C$_1$-C$_8$) alkyl, an aryl, (C$_5$-C$_{10}$)heteroaryl, (C$_1$-C$_8$)alkyl-aryl, aryl-(C$_1$-C$_8$)alkyl and p is comprised between 1 and 6;

Z$_1$ is defined by formula: —X—C(Y$_1$)—NR$_9$R$_{10}$ wherein X and Y$_1$ are O or S, R$_9$ and R$_{10}$ may be identical or different and represent hydrogen, (C$_1$-C$_8$)alkyl, an aryl, (C$_5$-C$_{10}$)heteroaryl, (C$_1$-C$_8$)alkyl-aryl, cyclopropyl, —(CH$_2$)p'-COOH; and wherein p' is comprised between 1 and 4;

R$_8$ is a (C1-C8 alkyl, an aryl, (C$_5$-C$_{10}$)heteroaryl, an aryl-(C$_1$-C$_8$)alkyl or a (C$_1$-C$_8$)alkyl-aryl radical, which can be optionally substituted by at least one group from OH, NO$_2$, CF$_3$, halogen, (C$_1$-C$_8$)alkyl, (C$_1$-C$_8$)alkoxy, or (C$_1$-C$_8$)alkoxy-aryl or sulfonyle;

EWG represents an electron withdrawing group selected from the group comprising COOR, COSR, CONRR', CN, COR, CF$_3$, SOR, SO$_2$R, SONRR', SO$_2$NRR', NO$_2$, halogen, heteroaryl, wherein R and R' are independently chosen from H, alkyl, cycloalkyl, arylalkyl, heteroarylalkyl, hydroxyalkyl, alkoxyalkyl, aryloxyalkyl, alkylaminoalkyl, aminoalkyl, heteroaryloxyalkyl, halogenoalkyl, mercaptoalkyle HS-alk, alkylthioalkyl, aryl, alkylaryl, hydroxyaryl, alkoxyaryl, aryloxyaryl, aminoaryl, alkylaminoaryl, halogenoaryl, heteroaryl, alkylheteroaryl, alkoxyheteroaryl, aminoheteroaryl, alkylaminoheteroaryl, halogenoheteroaryl, or R and R' taken together with the nitrogen atom to which they are attached either form an heterocyclic ring of at least 3 members, chosen from a 5 or 6 membered heterocyclic ring, optionally substituted by one or more groups being as defined for R$_5$, or form a fused polyheterocyclic system, chosen from tetrahydroisoquinoline, indoline, isoindoline, optionally substituted by one or more group being as defined for R$_5$, or the pharmaceutical salts and stereoisomers thereof if any, or the quaternarized oxidized forms of said pyridine derivatives, it being understood that when the nitrogen atom of formula (I) is quaternarized, there is a counter ion X$^-$ chosen from a halogen atom, a sulfate ion, a triflate ion, a carboxylate ion, a tosylate ion or a mesylate ion.

4. A compound according to claim 1, in which R$_1$ and R$_2$ are independently a (C$_1$-C$_8$)alkoxy, chosen from a (C$_1$-C$_4$) alkoxy, ethoxy or methoxy.

5. A compound according to claim 1, in which R$_8$ is an aryl-(C$_1$-C$_8$)alkyl, chosen from an aryl-(C$_1$-C$_4$)alkyl, phenyl-(C$_1$-C$_4$)alkyl, or benzyl-(C$_1$-C$_4$)alkyl.

6. A compound according to formula (I):

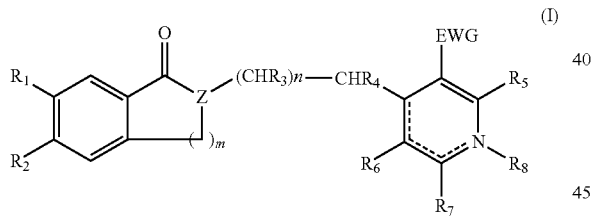

wherein:
the dotted lines in the pyridine cycle indicate the presence of at least one double bond, R$_1$ and R$_2$ are independently chosen between a hydrogen atom, a halogen atom, hydroxy, CN, CF3, a (C1-C8)alkyl, an aryl, a (C1-C8) alkoxy or R$_1$ d R$_2$ form m together a dioxol 1 group;
n is an integer from 0 to 4; and
R$_3$ and R$_4$ are a hydrogen atom, or
n=1 and R$_3$ and R$_4$ can also form together a double bond between the carbon atoms to which they are attached so that the radical CHR$_3$—CHR$_4$ form a vinylenyl group —CH=CH—, and
either m is 0, 1 or 2, and
Z is CH or N; or >Z—(CHR$_3$)$_n$—CHR$_4$— is >C=CH—(CH$_2$)$_n$—;
or --(--)$_m$--- is absent and
Z is NH, >N-alkyl (C$_1$-C$_8$), >N-phenyle, >N-benzyle or >N heteroaryle;

R$_5$ is chosen from a hydrogen atom, a halogen atom, hydroxy, CN, CF$_3$, a (C$_1$-C$_8$) alkyl, an aryl, a (C1-C8) alkoxy; and R$_6$ and R$_7$ which may be identical or different are hydrogen, OH, (C1-C8) alkyl, aryl, heteroaryl, (C1-C8) alkylaryl, aryl (C1-C8) alkyl, (C1-C8) alkoxy, hydroxyl (C1-C8) alkyl, (C1-C8) alkoxy (C1-C8) alkyl, —(CH$_2$)q-COOH wherein q is comprised between 1 and 4, Z', Z$_1$; or R$_6$ and R$_7$ taken to ether with the carbon atoms to which the are attached form a (C5-C10) cycloalkenyl, a 6-membered aromatic ring or a 5- or 10-membered heterocyclic ring comprising 1 to 4 heteroatoms identical or different chosen between N, S and O, being optionally substituted by one or more identical or different group defined as OH, (C$_1$-C$_8$) alkyl, aryl, heteroaryl, (C$_1$-C$_8$) alkyl-aryl, aryl (C$_1$-C$_8$) alkyl, (C$_1$-C$_8$) alkoxy, hydroxyl (C$_1$-C$_8$) alkyl, (C$_1$-C$_8$) alkoxy (C$_1$-C$_8$) alkyl, (CH$_2$)$_q$—COOH wherein q is comprised between 1 and 4 Z' Z$_1$;

Z' is a group defined by -(L)p-Z$_1$, L is (C$_1$-C$_8$)alkyl, an aryl, (C$_5$-C$_{10}$)heteroaryl, (C$_1$-C$_8$)alkyl-aryl, aryl-(C$_1$-C$_8$) alkyl and p is comprised between 1 and 6;

Z$_1$ is defined by formula: —X—C(Y$_1$)—NR$_9$R$_{10}$ wherein X and Y$_1$ are O or S, R$_9$ and R$_{10}$ may be identical or different and represent hydrogen, (C$_1$-C$_8$)alkyl, an aryl, (C$_5$-C$_{10}$)heteroaryl, (C$_1$-C$_8$)alkyl-aryl, cyclopropyl, —(CH$_2$)p'-COOH; and wherein p' is comprised between 1 and 4;

R$_8$ is a (C1-C8)alkyl, an aryl, (C$_5$-C$_{10}$)heteroaryl, an aryl-(C$_1$-C$_8$)alkyl or a (C$_1$-C$_8$)alkyl-aryl radical, which can be optionally substituted by at least one group from OH, NO$_2$, CF$_3$, halogen, (C$_1$-C$_8$)alkyl, (C$_1$-C$_8$)alkoxy, or (C$_1$-C$_8$)alkoxy-aryl or sulfonyle;

EWG represents an electron withdrawing group selected from the group comprising COOR, COSR, CONRR', CN, wherein R and R' are independently chosen from H, alkyl, cycloalkyl, arylalkyl, heteroarylalkyl, hydroxyalkyl, alkoxyalkyl, aryloxyalkyl, alkylaminoalkyl, aminoalkyl, heteroaryloxyalkyl, halogenoalkyl, mercaptoalkyle HS-alk, alkylthioalkyl, aryl, alkylaryl, hydroxyaryl, alkoxyaryl, aryloxyaryl, aminoaryl, alkylaminoaryl, halogenoaryl, heteroaryl, alkylheteroaryl, alkoxyheteroaryl, aminoheteroaryl, alkylaminoheteroaryl, halogenoheteroaryl, or R and R' taken together with the nitrogen atom to which they are attached either form an heterocyclic ring of at least 3 members, chosen from a 5 or 6 membered heterocyclic ring, optionally substituted by one or more groups being as defined for R$_5$, or form a fused polyheterocyclic system, chosen from tetrahydroisoquinoline, indoline, isoindoline, optionally substituted by one or more group being as defined for R$_5$, or the pharmaceutical salts and stereoisomers thereof if any, or the quaternarized oxidized forms of said pyridine derivatives, it being understood that when the nitrogen atom of formula (I) is quaternarized, there is a counter ion X$^-$ chosen from a halogen atom, a sulfate ion, a triflate ion, a carboxylate ion, a tosylate ion or a mesylate ion.

7. A compound according to formula (IIa):

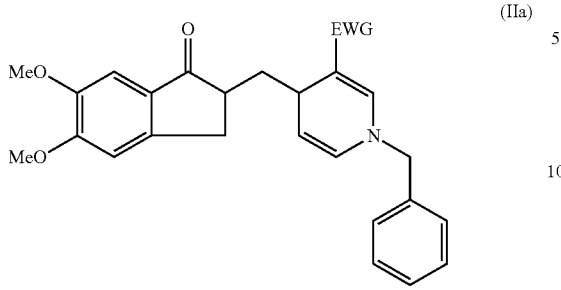

in which EWG
represents an electron withdrawing group selected from the group comprising COOR, COSR, CONRR', CN, COR, $CF_3$, SOR, $SO_2R$, SONRR', $SO_2NRR'$, $NO_2$ halogen, heteroaryl, wherein R and R' are independently chosen from H, alkyl, cycloalkyl, arylalkyl, heteroarylalkyl, hydroxyalkyl, alkoxyalkyl, aryloxyalkyl, alkylaminoalkyl, aminoalkyl, heteroaryloxyalkyl, halogenoalkyl, mercaptoalkyle HS-alk, alkylthioalkyl, aryl, alkylaryl, hydroxyaryl, alkoxyaryl, aryloxyaryl, aminoaryl, alkylaminoaryl, halogenoaryl, heteroaryl, alkylheteroaryl, alkoxyheteroaryl, aminoheteroaryl, alkylaminoheteroaryl, halogenoheteroaryl, or R and R' taken together with the nitrogen atom to which they are attached either form an heterocyclic ring of at least 3 members, chosen from a 5 or 6 membered heterocyclic ring, optionally substituted by one or more groups being as defined for $R_5$, or form a fused polyheterocyclic system, chosen from tetrahydroisoquinoline, indoline, isoindoline, optionally substituted by one or more group being as defined for $R_5$, or the pharmaceutical salts and stereoisomers thereof if any, or the quaternarized oxidized forms of said pyridine derivatives, it being understood that when the nitrogen atom of formula (I) is quaternarized, there is a counter ion $X^-$ chosen from a halogen atom, a sulfate ion, a triflate ion, a carboxylate ion, a tosylate ion or a mesylate ion.

8. A compound according to claim 2, of the formula ($II^+$):

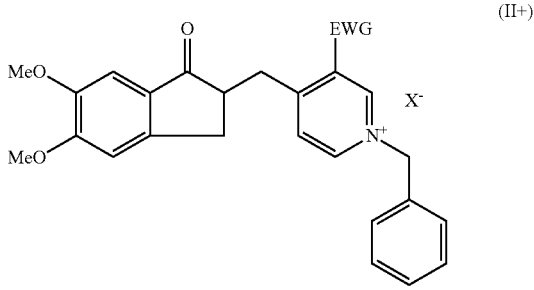

in which
EWG represents an electron withdrawing group selected from the group comprising COOR, COSR, CONRR', CN, COR, $CF_3$, SOR, $SO_2R$, SONRR', $SO_2NRR'$, $NO_2$, halogen, heteroaryl, wherein R and R' are independently chosen from H, alkyl, cycloalkyl, arylalkyl, heteroarylalkyl, hydroxyalkyl, alkoxyalkyl, aryloxyalkyl, alkylaminoalkyl, aminoalkyl, heteroaryloxyalkyl, halogenoalkyl, mercaptoalkyle HS-alk, alkylthioalkyl, aryl, alkylaryl, hydroxyaryl, alkoxyaryl, aryloxyaryl, aminoaryl, alkylaminoaryl, halogenoaryl, heteroaryl, alkylheteroaryl, alkoxyheteroaryl, aminoheteroaryl, alkylaminoheteroaryl, halogenoheteroaryl, or R and R' taken together with the nitrogen atom to which they are attached either form an heterocyclic ring of at least 3 members, chosen from a 5 or 6 membered heterocyclic ring, optionally substituted by one or more groups being as defined for $R_5$ or form a fused polyheterocyclic system, chosen from tetrahydroisoquinoline, indoline, isoindoline, optionally substituted by one or more group being as defined for $R_5$, or the pharmaceutical salts and stereoisomers thereof if any, or the quaternarized oxidized forms of said pyridine derivatives, it being understood that when the nitrogen atom of formula (I) is quaternarized, there is a counter ion $X^-$ chosen from a halogen atom, a sulfate ion, a triflate ion, a carboxylate ion, a tosylate ion or a mesylate ion.

9. A compound of formula (I) according to claim 1, wherein the dotted lines in the pyridine cycle indicate the presence of at least one double bond, $R_1$ and $R_2$ are independently chosen between a hydrogen atom, a halogen atom, a (C1-C8) alkyl, a (C1-C8) alkoxy or $R_1$ and $R_2$ form together a dioxolyl group;

n is an integer from 0 to 2; and $R_3$ and $R_4$ are a hydrogen atom, and either m is 1 or 2, and Z is CH or N; or >Z—$(CHR_3)_n$—$CHR_4$— is >C=CH—$(CH_2)_n$—;

or --(--)$_m$--- is absent and Z is >N-phenyle;

$R_5$ is chosen from a hydrogen atom, a ($C_1$-$C_8$) alkyl; and $R_6$ and $R_7$ are hydrogen;

$R_8$ is a (C1-C8)alkyl or an aryl-($C_1$-$C_8$)alkyl radical, which can be optionally substituted by at least one group from $NO_2$, $CF_3$, halogen, ($C_1$-$C_8$)alkyl or sulfonyle;

EWG represents an electron withdrawing group selected from the group comprising COOR, COSR, CONRR', CN, COR, $CF_3$, SOR, $SO_2R$, SONRR', $SO_2NRR'$, $NO_2$, halogen, wherein R and R' are independently chosen from H, alkyl, and the pharmaceutical salts and stereoisomers thereof if any, or the quaternarized oxidized forms of said pyridine derivatives, it being understood that when the nitrogen atom of formula (I) is quaternarized, there is a counter ion $X^-$.

10. A compound of formula (I) according to claim 1, wherein the dotted lines in the pyridine cycle indicate the presence of at least one double bond, $R_1$ and $R_2$ are independently chosen between a hydrogen atom, a halogen atom, a methyl, a methoxy radical or $R_1$ and $R_2$ form together a dioxolyl group;

n is an integer from 0 to 2; and $R_3$ and $R_4$ are a hydrogen atom, and either m is 1 or 2, and Z is CH or N; or >Z—$(CHR_3)_n$—$CHR_4$— is >C=CH—;

or --(--)$_m$--- is absent and Z is >N-phenyle;

$R_5$ is chosen from a hydrogen atom, a methyl; and $R_6$ and $R_7$ are hydrogen;

$R_8$ is a $(C_1\text{-}C_4)$alkyl or a benzyl radical, which can be optionally substituted by a group chosen from $NO_2$, $CF_3$, chloro, fluoro, methyl or sulfonyle;

EWG represents an electron withdrawing group selected from the group comprising COOR, CONRR', CN, COMe, $SO_2$Me, $SO_2$NRR', fluoro, chloro, bromo, wherein R and R' are independently chosen from H, $(C_1\text{-}C_3)$alkyl, and the pharmaceutical salts and stereoisomers thereof if any, or the quaternarized oxidized forms of said pyridine derivatives, it being understood that when the nitrogen atom of formula (I) is quaternarized, there is a counter ion $X^-$.

11. A compound of formula (Ia) according to claim 1, wherein

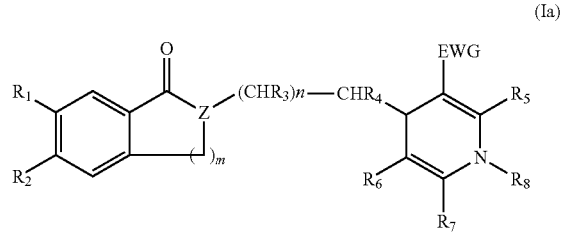

(Ia)

where $R_3$ and $R_4$ are hydrogen, $R_5$ is chosen from a hydrogen atom, $CF_3$, a $(C_1\text{-}C_8)$ alkyl, a $(C_1\text{-}C_8)$ alkoxy;

$R_6$ and $R_7$ are hydrogen;

$R_8$ is a $(C_1\text{-}C_8)$alkyl, an aryl-$(C_1\text{-}C_8)$alkyl or a $(C_1\text{-}C_8)$ alkyl-aryl radical which can be optionally substituted by at least one group from OH, $NO_2$, halogen, $(C_1\text{-}C_8)$ alkyl, $(C_1\text{-}C_8)$alkoxy, or $(C_1\text{-}C_8)$alkoxy-aryl;

Z and m are defined as above for formula (I) and when $-(-)_m$- is absent, Z is NH, >N-alkyl$(C_1\text{-}C_8)$, or >N-phenyle;

$R_1$, $R_2$, n and EWG are defined as in claim 1;

and the pharmaceutical salts thereof and stereoisomers thereof if any.

12. A compound according to claim 4, in which $R_1$ and $R_2$ are a $(C_1\text{-}C_4)$alkoxy.

13. A compound according to claim 4, in which $R_1$ and $R_2$ are an ethoxy radical.

14. A compound according to claim 4, in which $R_1$ and $R_2$ are a methoxy radical.

15. A compound according to claim 5, in which $R_8$ is an aryl-$(C_1\text{-}C_4)$alkyl.

16. A compound according to claim 5, in which $R_8$ is a phenyl-$(C_1\text{-}C_4)$alkyl.

17. A compound according to claim 5, in which $R_8$ is a benzyl-$(C_1\text{-}C_4)$alkyl.

18. A pharmaceutical composition comprising at least one compound according to formula (I):

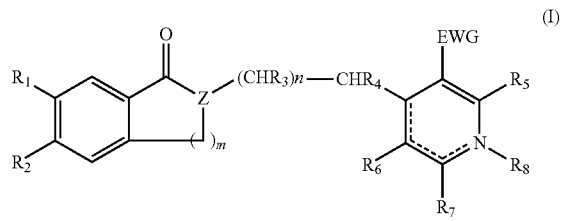

(I)

wherein:

the dotted lines in the pyridine cycle indicate the presence of at least one double bond, $R_1$ and $R_2$ are independently chosen between a hydrogen atom, a halogen atom, hydroxy, CN, CF3, a (C1-C8) alkyl, an aryl, a (C1-C8) alkoxy or $R_1$ and $R_2$ form together a dioxolyl group;

n is an integer from 0 to 4; and $R_3$ and $R_4$ are a hydrogen atom, or n=1 and $R_3$ and $R_4$ can also form together a double bond between the carbon atoms to which they are attached so that the radical $CHR_3$—$CHR_4$ form a vinylenyl group —CH=CH—, and either m is 0, 1 or 2, and Z is CH or N; or >Z—$(CHR_3)_n$—$CHR_4$— is >C=CH—$(CH_2)_n$—;

or --(--)$_m$--- is absent and

Z is NH, >N-alkyl $(C_1\text{-}C_8)$, >N-phenyle, >N-benzyle or >N heteroaryle;

$R_5$ is chosen from a hydrogen atom, a halogen atom, hydroxy, CN, $CF_3$, a $(C_1\text{-}C_8)$ alkyl, an aryl, a (C1-C8) alkoxy; and $R_6$ and $R_7$ which may be identical or different are hydrogen, OH, (C1-C8) alkyl, aryl, heteroaryl, (C1-C8) alkylaryl, aryl (C1-C8) alkyl, (C1-C8) alkoxy, hydroxyl (C1-C8) alkyl, (C1-C8) alkoxy (C1-C8) alkyl, —$(CH_2)$q-COOH wherein q is comprised between 1 and 4, Z', $Z_1$; or $R_6$ and $R_7$ taken to ether with the carbon atoms to which the are attached form a (C5-C10) cycloalkenyl, a 6-membered aromatic ring or a 5- or 10-membered heterocyclic ring comprising 1 to 4 heteroatoms identical or different chosen between N, S and O, being optionally substituted by one or more identical or different group defined as OH, $(C_1\text{-}C_8)$ alkyl, aryl, heteroaryl, $(C_1\text{-}C_8)$ alkyl-aryl, aryl $(C_1\text{-}C_8)$ alkyl, $(C_1\text{-}C_8)$ alkoxy, hydroxyl $(C_1\text{-}C_8)$ alkyl, $(C_1\text{-}C_8)$ alkoxy $(C_1\text{-}C_8)$ alkyl, $(CH_2)_q$—COOH wherein q is comprised between 1 and 4, Z', $Z_1$;

Z' is a group defined by formula -(L)p-$Z_1$, L is $(C_1\text{-}C_8)$ alkyl, an aryl, $(C_5\text{-}C_{10})$heteroaryl, $(C_1\text{-}C_8)$alkyl-aryl, aryl-$(C_1\text{-}C_8)$alkyl and p is comprised between 1 and 6;

$Z_1$ is defined by formula: —X—C($Y_1$)—$NR_9R_{10}$ wherein X and $Y_1$ are O or S, $R_9$ and $R_{10}$ may be identical or different and represent hydrogen, $(C_1\text{-}C_8)$alkyl, an aryl, $(C_5\text{-}C_{10})$heteroaryl, $(C_1\text{-}C_8)$alkyl-aryl, cyclopropyl, —$(CH_2)$p'-COOH; and where p' is comprised between 1 and 4;

$R_8$ is a (C1-C8)alkyl, an aryl, $(C_5\text{-}C_{10})$heteroaryl, an aryl-$(C_1\text{-}C_8)$alkyl or a $(C_1\text{-}C_8)$alkyl-aryl radical, which can be optionally substituted by at least one group from OH, $NO_2$, $CF_3$, halogen, $(C_1\text{-}C_8)$alkyl, $(C_1\text{-}C_8)$alkoxy, or $(C_1\text{-}C_8)$alkoxy-aryl or sulfonyle;

EWG represents an electron withdrawing group selected from the group comprising COOR, COSR, CONRR', CN, COR, CF$_3$, SOR, SO$_2$R, SONRR', SO$_2$NRR', NO$_2$, halogen, heteroaryl, wherein R and R' are independently chosen from H, alkyl, cycloalkyl, arylalkyl, heteroarylalkyl, hydroxyalkyl, alkoxyalkyl, aryloxyalkyl, alkylaminoalkyl, aminoalkyl, heteroaryloxyalkyl, halogenoalkyl, mercaptoalkyle HS-alk, alkylthioalkyl, aryl, alkylaryl, hydroxyaryl, alkoxyaryl, aryloxyaryl, aminoaryl, alkylaminoaryl, halogenoaryl, heteroaryl, alkylheteroaryl, alkoxyheteroaryl, aminoheteroaryl, alkylaminoheteroaryl, halogenoheteroaryl, or R and R' taken together with the nitrogen atom to which they are attached either form an heterocyclic ring of at least 3 members, chosen from a 5 or 6 membered heterocyclic ring, optionally substituted by one or more groups being as defined for R$_5$, or forma fused polyheterocyclic system, chosen from tetrahydroisoquinoline, indoline, isoindoline, optionally substituted by one or more group being as defined for R$_5$, or the pharmaceutical salts and stereoisomers thereof if any, or the quaternarized oxidized forms of said pyridine derivatives, it being understood that when the nitrogen atom of formula (I) is quaternarized, there is a counter ion X$^-$ chosen from a halogen atom, a sulfate ion, a triflate ion, a carboxylate ion, a tosylate ion or a mesylate ion in the pure state or in a combined form with one or more compatible and pharmaceutically acceptable diluents or adjuvants.

19. A process for the preparation of a compound according to claim 1, where Z is a C atom, which comprises the quaternization of the nitrogen atom of a compound of formula (I'):

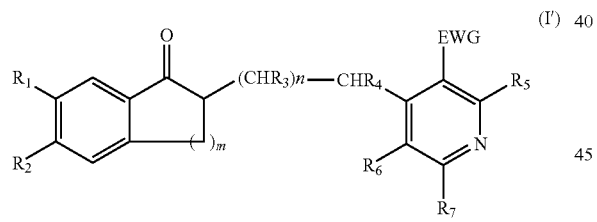

(I')

where radicals R$_1$ to R$_7$, m, n and EWG are as defined in claim 1, by an alkylating agent, followed if desired by regioselective reduction, for the preparation of compounds of formula (I).

20. The process according to claim 19, according to the scheme:

Route A

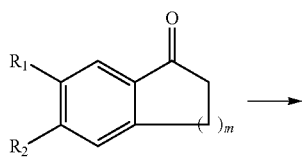

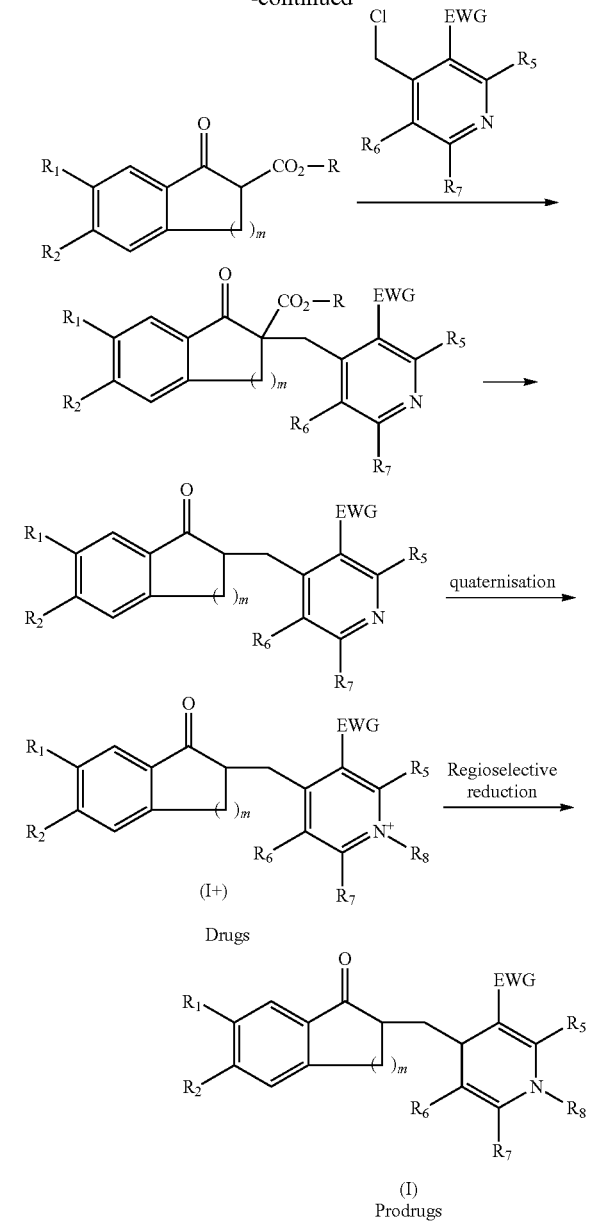

Drugs (I+)

Prodrugs (I)

in which the group "—CH$_2$—" between the indanone and the pyridine means indifferently —CH$_2$— (when n=0) or —(CHR$_3$)$_n$CHR$_4$—and where radicals R$_1$ and R$_2$ are independently chosen between a hydrogen atom, a halogen atom, hydroxy, CN, CF3, a (C1-C8) alkyl, an aryl, a (C1-C8) alkoxy or R$_1$ and R$_2$ form together a dioxolyl group;

n is an integer from 0 to 4; and

R$_3$ and R$_4$ are a hydro en atom, or n=1 and R$_3$ and R$_4$ can also form together a double bond between the carbon atoms to which the are attached so that the radical CHR$_3$—CHR$_4$ form a vinylenyl group —CH=CH—, and either m is 0, 1 or 2, and R$_5$ is chosen from a hydrogen atom, a halogen atom, hydroxy, CN, CF$_3$, a (C$_1$-C$_8$) alkyl, an aryl, a (C1-C8) alkoxy; and R$_6$ and R$_7$ which may be identical or different are hydrogen, OH, (C1-C8) alkyl, aryl, heteroaryl, (C1-C8) alkylaryl, aryl (C1-C8) alkyl, (C1-C8) alkoxy, hydroxyl (C1-C8) alkyl, (C1-C8 alkoxy (C1-C8)alkyl, —(CH$_2$)$_q$—COOH wherein q is comprised between 1 and 4, Z', Z$_1$; or R$_6$ and R$_7$ taken together with the carbon atoms to which they are attached form a (C5-C10) cycloalkenyl, a 6-membered aromatic ring or a 5- or 10-membered heterocyclic ring comprising 1 to 4 heteroatoms identical or different chosen between N, S and O, being optionally substituted by one or more identical or different group defined as OH, (C$_1$-C$_8$) alkyl, aryl, heteroaryl, (C$_1$-C$_8$) alkyl-aryl, aryl (C$_1$-C$_8$) alkyl, (C$_1$-C$_8$) alkoxy, hydroxyl (C$_1$-C$_8$) alkyl, (C$_1$-C$_8$)alkoxy (C$_1$-C$_8$)alkyl, (CH$_2$)$_q$—COOH wherein q is comprised between 1 and 4;

R$_8$ is a (C$_1$-C$_8$)alkyl, an aryl, (C$_5$-C$_{10}$)heteroaryl, an aryl-(C$_1$-C$_8$)alkyl or a (C$_1$-C$_8$)alkyl-aryl radical, which can be optionally substituted by at least one group from OH, NO$_2$, CF$_3$, halogen, (C$_1$-C$_8$)alkyl, (C$_1$-C$_8$)alkoxy, or (C$_1$-C$_8$)alkoxy-aryl or sulfonyle;

EWG represents an electron withdrawing group selected from the group comprising COOR, COSR, CONRR', CN, COR, CF$_3$, SOR, SO$_2$R, SONRR', SO$_2$NRR', NO$_2$ halogen, heteroaryl, wherein R and R' are independently chosen from H, alkyl, cycloalkyl, arylalkyl, heteroarylalkyl, hydroxyalkyl, alkoxyalkyl, aryloxyalkyl, alkylaminoalkyl, aminoalkyl, heteroaryloxyalkyl, halogenoalkyl, mercaptoalkyle HS-alk, alkylthioalkyl, aryl, alkylaryl, hydroxyaryl, alkoxyaryl, aryloxyaryl, aminoaryl, alkylaminoaryl, halogenoaryl, heteroaryl, alkylheteroaryl, alkoxyheteroaryl, aminoheteroaryl, alkylaminoheteroaryl, halogenoheteroaryl, or R and R' taken together with the nitrogen atom to which they are attached either form an heterocyclic ring of at least 3 members, preferably a 5 or 6 membered heterocyclic ring, optionally substituted by one or more groups being as defined for R$_5$, or form a fused polyheterocyclic system, chosen from tetrahydroisoquinoline, indoline, isoindoline, and X$^-$ represents a counter ion chosen from a halogen atom, a sulfate ion, a triflate ion, a carboxylate ion, a tosylate ion or a mesylate ion.

21. The process according to claim 19, which comprises the step of reduction of a compound of formula (I+) in the presence of a reducing agent.

22. The process for the preparation of a compound according to claim 1, where Z is CH or N, and where a compound of the formula

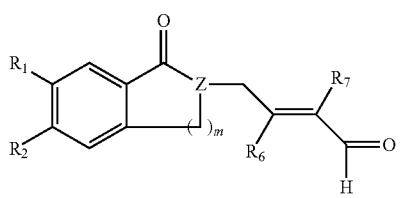

having radicals R$_1$, R$_2$, R$_6$ and R$_7$ and m defined as above, is submitted to a dihydropyridine construction, leading to a compound of formula (I), and if desired, subsequently to the corresponding drug of formula (I+) by oxidation of said compound.

23. The process according to claim 22, which comprise the scheme:

Route B

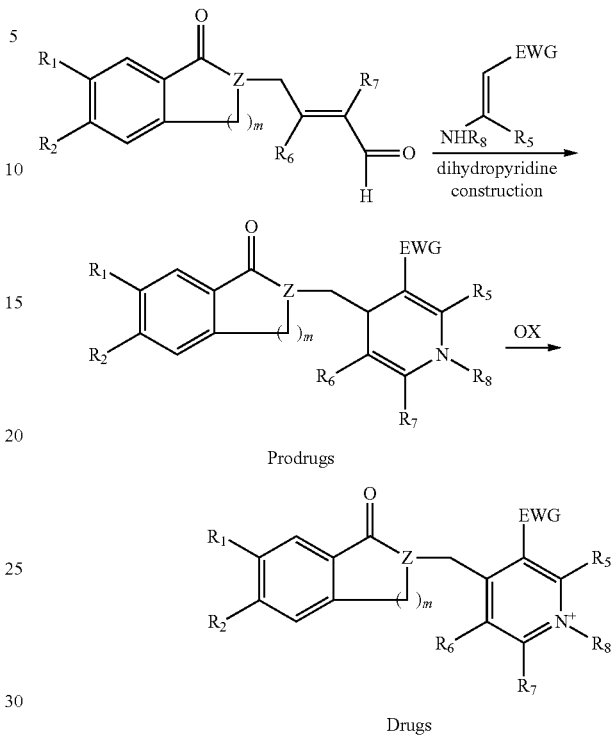

in which the group "—CH$_2$—" between the indanone either the ethylenyle chain or the pyridine group, can be understood as meaning indifferently —CH$_2$— (when n=0) or —(CHR$_3$)$_n$—CHR$_4$—.

24. The process for the preparation of a compound according to claim 1, where Z is CH and n=0, and where radicals R$_1$ to R$_8$, m and EWG are defined as in claim 1, according to the scheme:

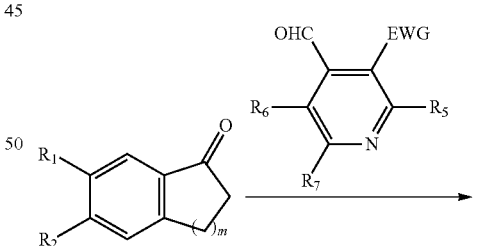

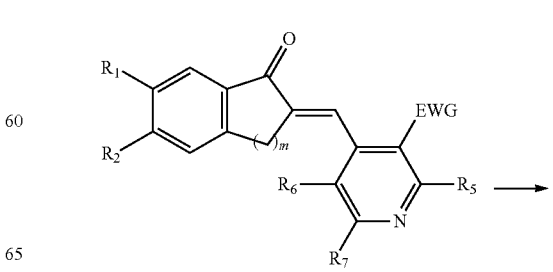

131
-continued
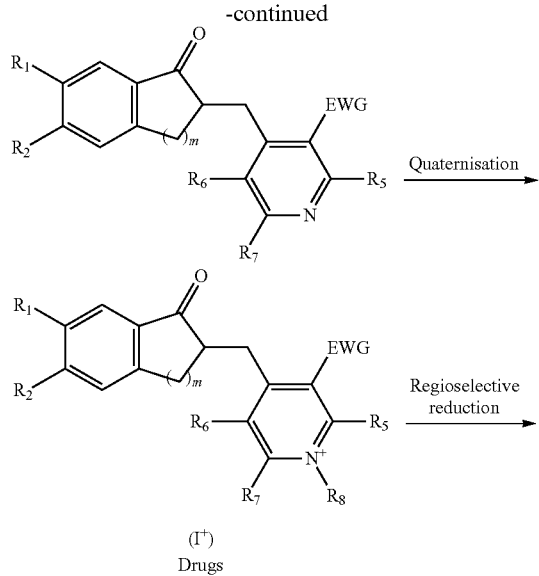
(I⁺)
Drugs
132
-continued
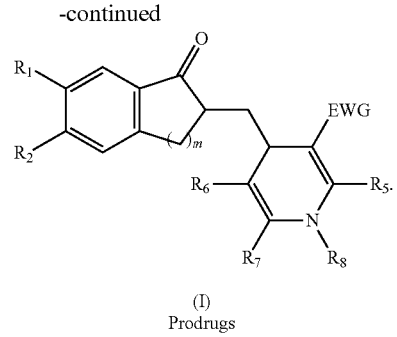
(I)
Prodrugs
25. The process according to claim 24, where a compound having EWG is COOR, COR or CN is intended to be prepared, wherein the corresponding pyridine having EWG=bromo is firstly reacted and before the step of quaternisation, the intermediate compound is converted into a compound having EWG=COOR, COR or CN.
* * * * *